United States Patent
Curtiss, III et al.

(10) Patent No.: US 11,000,583 B2
(45) Date of Patent: May 11, 2021

(54) **FOOD SAFETY VACCINE TO CONTROL *SALMONELLA ENTERICA* AND REDUCE CAMPYLOBACTER IN POULTRY**

(71) Applicant: UNIVERSITY OF FLORIDA RESEARCH FOUNDATION, INCORPORATED, Gainesville, FL (US)

(72) Inventors: Roy Curtiss, III, Gainesville, FL (US); Soo-Young Wanda, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/480,904

(22) PCT Filed: Jan. 26, 2018

(86) PCT No.: PCT/US2018/015438
§ 371 (c)(1),
(2) Date: Jul. 25, 2019

(87) PCT Pub. No.: WO2018/140717
PCT Pub. Date: Aug. 2, 2018

(65) Prior Publication Data
US 2020/0009240 A1    Jan. 9, 2020

Related U.S. Application Data

(60) Provisional application No. 62/451,146, filed on Jan. 27, 2017.

(51) Int. Cl.
| | | |
|---|---|---|
| *A61K 39/02* | (2006.01) | |
| *A61K 39/112* | (2006.01) | |
| *A61K 39/205* | (2006.01) | |
| *C07K 14/205* | (2006.01) | |
| *C12N 1/36* | (2006.01) | |
| *C12N 15/74* | (2006.01) | |
| *A61K 39/00* | (2006.01) | |

(52) U.S. Cl.
CPC ........ *A61K 39/0275* (2013.01); *A61K 39/105* (2013.01); *A61K 39/205* (2013.01); *C07K 14/205* (2013.01); *C12N 1/36* (2013.01); *C12N 15/74* (2013.01); *A61K 2039/522* (2013.01); *A61K 2039/523* (2013.01); *A61K 2039/58* (2013.01); *A61K 2039/70* (2013.01)

(58) Field of Classification Search
None
See application file for complete search history.

(56) References Cited

U.S. PATENT DOCUMENTS

| | | | | |
|---|---|---|---|---|
| 8,465,755 | B2 * | 6/2013 | Curtiss, III | C12N 15/74 424/258.1 |
| 2011/0033501 | A1 * | 2/2011 | Curtiss, III | A61K 39/025 424/258.1 |
| 2013/0266604 | A1 | 10/2013 | Szymanski et al. | |
| 2014/0273163 | A1 | 9/2014 | Fisher et al. | |
| 2016/0184422 | A1 | 6/2016 | Joens et al. | |
| 2016/0199467 | A1 * | 7/2016 | Curtiss, III | A61K 35/74 424/200.1 |
| 2016/0326563 | A1 * | 11/2016 | Aebi | A61P 31/00 |
| 2019/0382717 | A1 * | 12/2019 | Curtiss, III | A61P 31/04 |

FOREIGN PATENT DOCUMENTS

| | | |
|---|---|---|
| WO | 2010/108682 A1 | 9/2010 |
| WO | 2011/091291 A1 | 7/2011 |
| WO | 2012/027850 A1 | 3/2012 |

OTHER PUBLICATIONS

Curtiss et al. 2010 (New Technologies in Using Recombinant Attenuated *Salmonella* Vaccine Vectors; Crit Rev Immunol. 30(3):255-270). (Year: 2010).*
International Search Report and Written Opinion for Application No. PCT/US2018/015438, dated May 8, 2018, 11 pages.
International Preliminary Report on Patentability for Application No. PCT/US2018/015438, dated Aug. 8, 2019, 9 pages.
Laniewski et al., Evaluation of the immunogenicity of Campylobacter jejuni CjaA protein delivered by *Salmonella enterica* sv. Typhimurium strain with regulated delayed attenuation in chickens. World J Microbiol Biotechnol. Jan. 2014;30(1):281-92.

* cited by examiner

*Primary Examiner* — Mary Maille Lyons
(74) *Attorney, Agent, or Firm* — McCarter & English, LLP; Marcie B. Clarke

(57) ABSTRACT

Described herein are compositions and methods for making and using recombinant bacteria that are capable of regulated attenuation, regulated expression of one or more antigens of interest, and/or N-glycan modification of secreted/surface antigens.

Figure 1B:
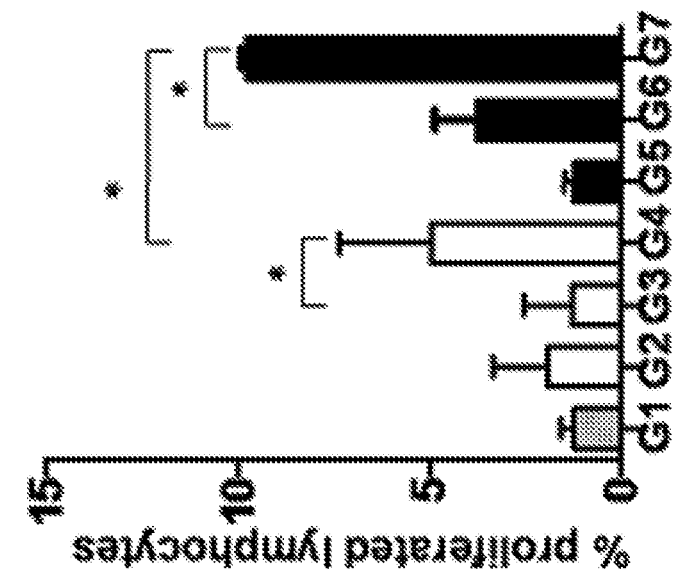

17 Claims, 12 Drawing Sheets
Specification includes a Sequence Listing.

G1- BSG
G2-χ11840(pYA3342) non-lysis ΔsifA strain
G3-χ11442(pYA5301) non-lysis strain + SO7
G4-χ11840(pYA5301) non-lysis ΔsifA strain + SO7
G5-χ11791(pYA3681) lysis ΔsifA strain
G6-χ11730(pYA5293) lysis strain + SO7
G7-χ11791(pYA5293) ) lysis ΔsifA strain + SO7

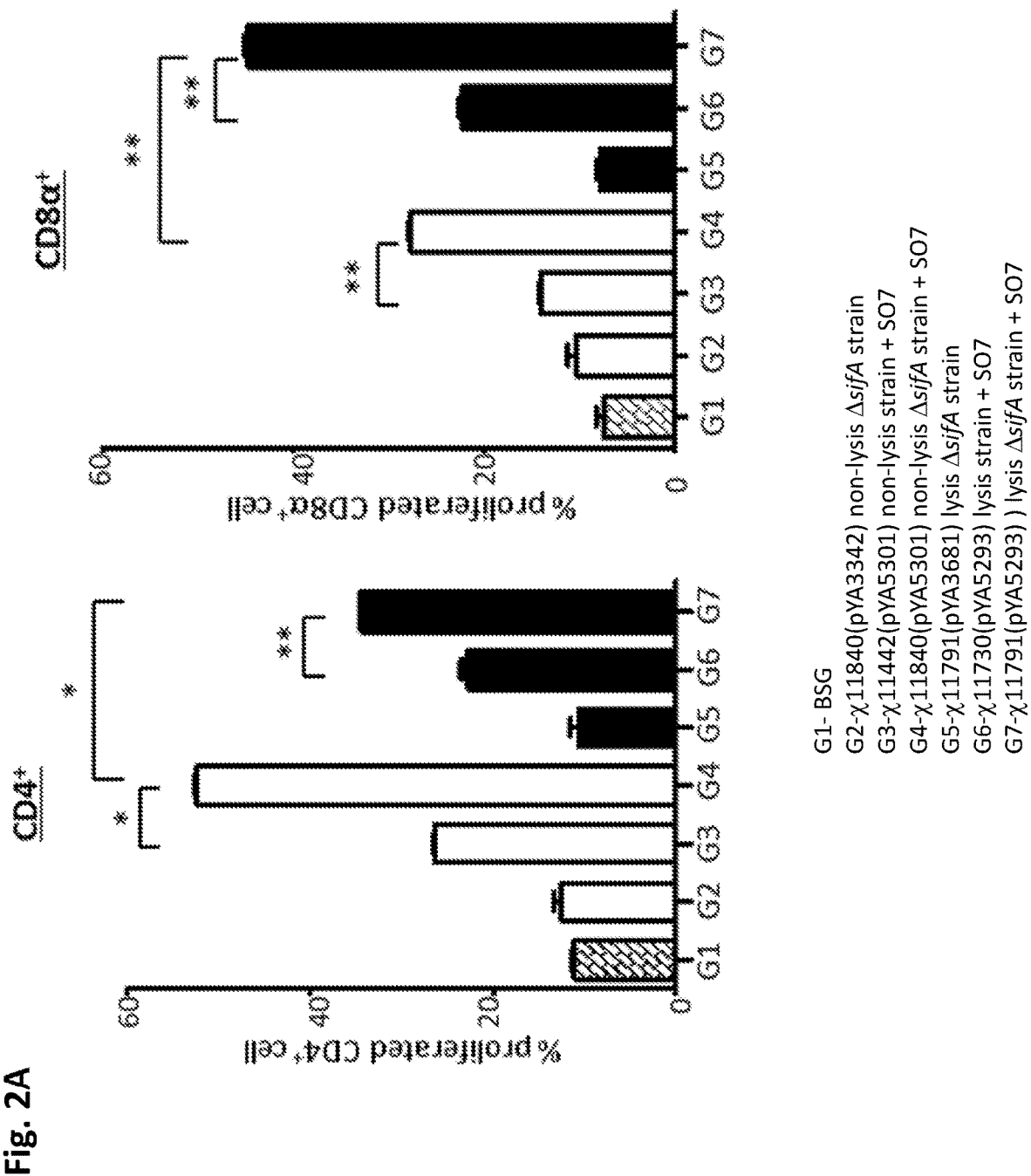

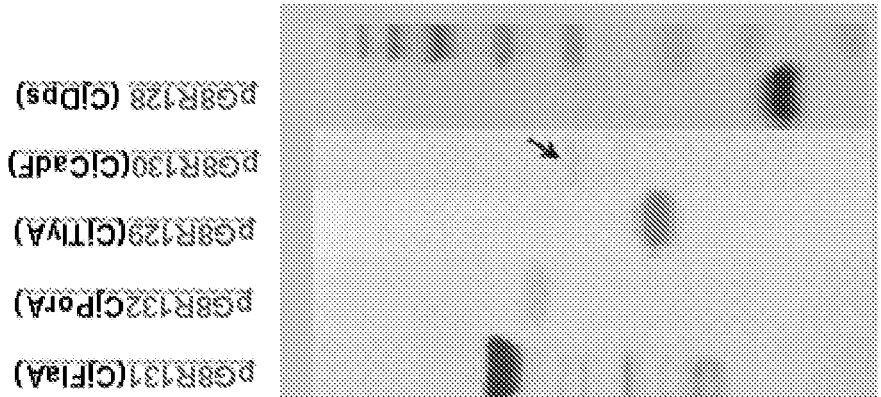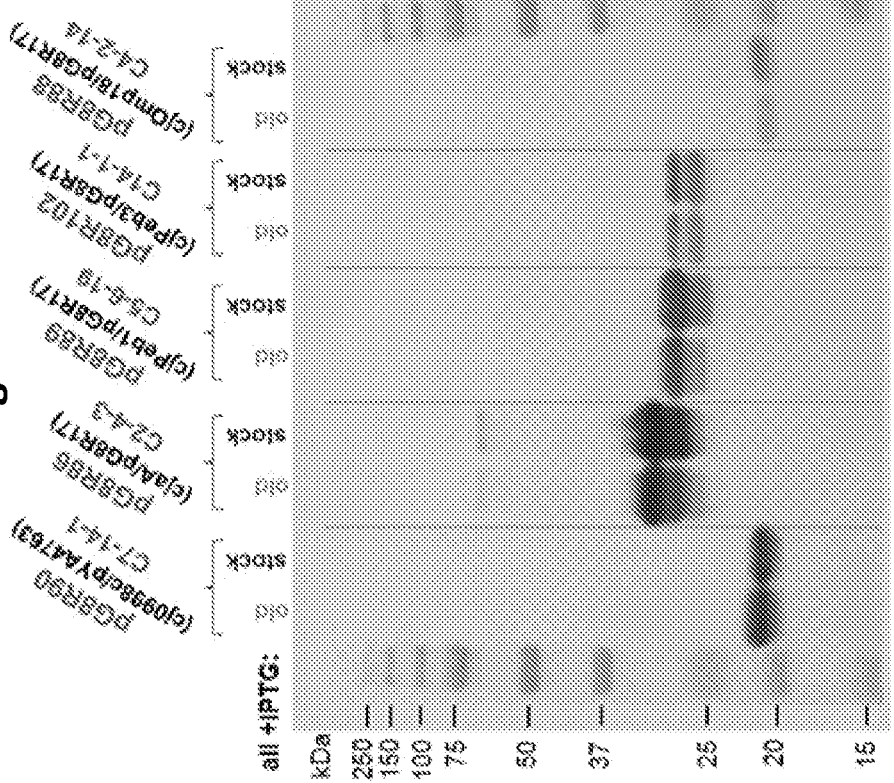

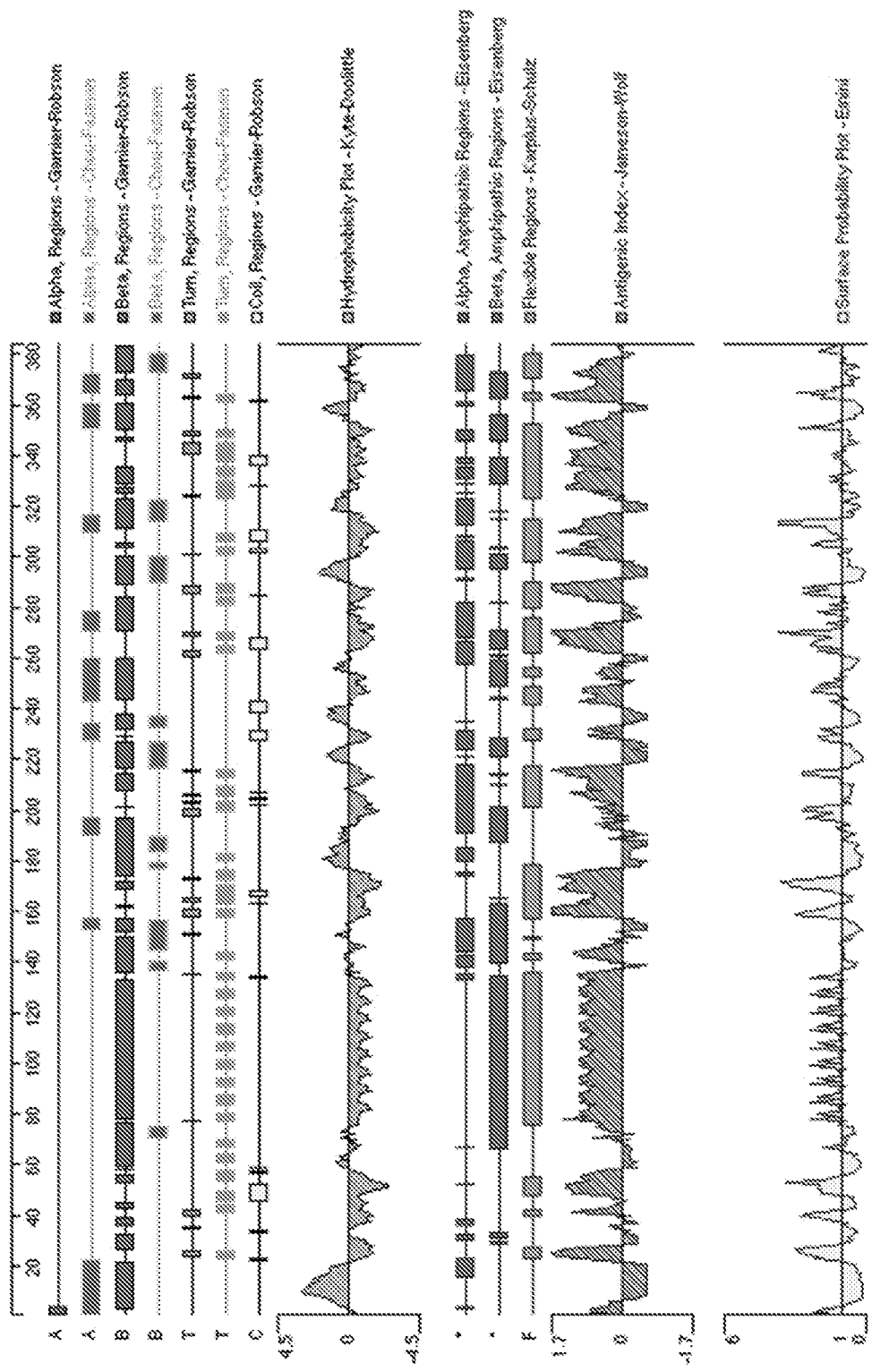
Fig. 8A: OmpA Δaa70-107 + Cj1443c (aa21-86) insertion 2 beta barrels (3 and 4) of OmpA deleted Predicted Structural Class of the Whole Protein: Alpha
Deléage & Roux Modification of Nishikawa & Ooi 1987

| Analysis | Whole Protein |
|---|---|
| Molecular Weight | 41323.30 m.w. |
| Length | 382 |
| 1 microgram = | 24.199 pMoles |
| Molar Extinction coefficient | 38640±5% |
| 1 A(280) = | 1.07 mg/ml |
| Isoelectric Point | 5.45 |
| Charge at pH 7 | -5.31 |

Whole Protein Composition Analysis

| Amino Acid(s) | Number count | % by weight | % by frequency |
|---|---|---|---|
| Charged (RKHYCDE) | 100 | 31.66 | 26.18 |
| Acidic (DE) | 44 | 12.63 | 11.52 |
| Basic (KR) | 38 | 12.53 | 9.95 |
| Polar (NCQSTY) | 113 | 30.88 | 29.58 |
| Hydrophobic (AILFWV) | 128 | 32.32 | 33.51 |
| A Ala | 32 | 5.50 | 8.38 |
| C Cys | 2 | 0.50 | 0.52 |
| D Asp | 33 | 9.19 | 8.64 |
| E Glu | 11 | 3.44 | 2.88 |
| F Phe | 9 | 3.21 | 2.36 |
| G Gly | 31 | 4.28 | 8.12 |
| H His | 5 | 1.66 | 1.31 |
| I Ile | 26 | 7.12 | 6.81 |
| K Lys | 27 | 8.37 | 7.07 |
| L Leu | 30 | 8.22 | 7.85 |
| M Met | 3 | 0.95 | 0.79 |
| N Asn | 34 | 9.39 | 8.90 |
| P Pro | 20 | 4.70 | 5.24 |
| Q Gln | 17 | 5.27 | 4.45 |
| R Arg | 11 | 4.16 | 2.88 |
| S Ser | 18 | 3.79 | 4.71 |
| T Thr | 31 | 7.58 | 8.12 |
| V Val | 27 | 6.48 | 7.07 |
| W Trp | 4 | 1.80 | 1.05 |
| Y Tyr | 11 | 4.34 | 2.88 |
| B Asx | 0 | 0.00 | 0.00 |
| Z Glx | 0 | 0.00 | 0.00 |
| X Xxx | 0 | 0.00 | 0.00 |
| . Ter | 1 | 0.00 | 0.26 |

Fig. 8B

SEQUENCE LISTING

<160> NUMBER OF SEQ ID NOS: 82

<210> SEQ ID NO 1
<211> LENGTH: 5
<212> TYPE: PRT
<213> ORGANISM: Campylobacter jejuni
<220> FEATURE:
<221> NAME/KEY: MOD_RES
<222> LOCATION: (1)..(1)
<223> OTHER INFORMATION: Asp or Glu
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)

<223> OTHER INFORMATION: Ser or Thr

<400> SEQUENCE: 1

Xaa Xaa Asn Tyr Xaa
1               5

<210> SEQ ID NO 2
<211> LENGTH: 4
<212> TYPE: PRT
<213> ORGANISM: Campylobacter jejuni

<400> SEQUENCE: 2

Asp Gly Gly Lys
1

<210> SEQ ID NO 3
<211> LENGTH: 702
<212> TYPE: DNA
<213> ORGANISM: Campylobacter jejuni

<400> SEQUENCE: 3

```
atgaaaacaa ataatatctt tatggcttta gccatagttt tggcaagttt gattctagct    60
tttggattta caaggctttt aagtgatttt aaaacacttg aaagaagtgt aagtgtaaag   120
ggtttaagtc aaaagaagt cgaagcggat actttgatac ttcctataaa attcacaaga   180
tcaaacaaca atcttacaaa tttatacgaa gaactagaac aagataaaga aaatatcatc   240
aaatttttag aaaaacaagg cataaaagaa gatgagatca gctacaactc gccaaatatc   300
atagatcgtt taagcgatcc ttatagcaac gacactcaag ctgcataccg atacataggc   360
actgcgaatt tactcatcta tactcaaaat gtaaagcttg aaaaagcat actagaaaac    420
atttcaagtc ttgcaaaatt tggtatagta acaaaaatcg atgattatga tatagaatac   480
ctttacacca agctaaatga tataaaacca caaatgatag aagaagcaac gctcaatgct   540
agaaatgcag cgataaaatt cgcacaagac tcaaacagcc atctaggcaa gataaaaaag   600
gcttctcaag gacaatttag cattagcaac agagataaaa acacccctta tatcaaaacc   660
ataagagtgg tttctactat agaatactac ttaaaagact ga                      702
```

<210> SEQ ID NO 4
<211> LENGTH: 233
<212> TYPE: PRT
<213> ORGANISM: Campylobacter jejuni

<400> SEQUENCE: 4

Met Lys Thr Asn Asn Ile Phe Met Ala Leu Ala Ile Val Leu Ala Ser
1               5                   10                  15

Leu Ile Leu Ala Phe Gly Phe Asn Lys Ala Leu Ser Asp Phe Lys Thr
            20                  25                  30

Leu Glu Arg Ser Val Ser Val Lys Gly Leu Ser Gln Lys Glu Val Glu
        35                  40                  45

Ala Asp Thr Leu Ile Leu Pro Ile Lys Phe Thr Arg Ser Asn Asn Asn
    50                  55                  60

Leu Thr Asn Leu Tyr Glu Glu Leu Glu Gln Asp Lys Glu Asn Ile Ile
65                  70                  75                  80

Lys Phe Leu Glu Lys Gln Gly Ile Lys Glu Asp Glu Ile Ser Tyr Asn
                85                  90                  95

Ser Pro Asn Ile Ile Asp Arg Leu Ser Asp Pro Tyr Ser Asn Asp Thr
            100                 105                 110

```
Gln Ala Ala Tyr Arg Tyr Ile Gly Thr Ala Asn Leu Leu Ile Tyr Thr
            115                 120                 125

Gln Asn Val Lys Leu Gly Lys Ser Ile Leu Glu Asn Ile Ser Ser Leu
130                 135                 140

Ala Lys Phe Gly Ile Val Thr Lys Ile Asp Asp Tyr Asp Ile Glu Tyr
145                 150                 155                 160

Leu Tyr Thr Lys Leu Asn Asp Ile Lys Pro Gln Met Ile Glu Glu Ala
                165                 170                 175

Thr Leu Asn Ala Arg Asn Ala Ala Ile Lys Phe Ala Gln Asp Ser Asn
            180                 185                 190

Ser His Leu Gly Lys Ile Lys Lys Ala Ser Gln Gly Gln Phe Ser Ile
            195                 200                 205

Ser Asn Arg Asp Lys Asn Thr Pro Tyr Ile Lys Thr Ile Arg Val Val
210                 215                 220

Ser Thr Ile Glu Tyr Tyr Leu Lys Asp
225                 230
```

<210> SEQ ID NO 5
<211> LENGTH: 573
<212> TYPE: DNA
<213> ORGANISM: Campylobacter jejuni

<400> SEQUENCE: 5

```
atgaaaaaag ttttattgag ttcattggtt gcggtgtctt tgttaagcac aggtttgttt      60
gctaaagaat atactttaga taaagcacat acagatgtag gttttaaaat caaacattta     120
caaattagca atgtaaaagg aaatttcaaa gattattctg cggtgattga ttttgatcct     180
gcgagtgctg aatttaaaaa gcttgatgta actataaaaa tcgcatctgt aaatacagaa     240
aatcaaacaa gagataatca cttacaacaa gatgattttt tcaaagcaaa aaaatatcct     300
gatatgactt ttacaatgaa aaaatatgaa aaaatcgata tgaaaaagg caaaatgaca     360
ggaactttaa ctatagctgg agtttctaaa gatatcgttt tagatgctga atcggcggt     420
gtagctaaag gcaaagatgg aaaagaaaaa ataggatttt ctttaaatgg aaaaatcaaa     480
cgctctgatt ttaaatttgc aacaagtact tcaactatta ctttaagtga tgatattaat     540
ttaaatatcg aagttgaagc gaacgaaaaa taa                                  573
```

<210> SEQ ID NO 6
<211> LENGTH: 190
<212> TYPE: PRT
<213> ORGANISM: Campylobacter jejuni

<400> SEQUENCE: 6

```
Met Lys Lys Val Leu Leu Ser Ser Leu Val Ala Val Ser Leu Leu Ser
1               5                   10                  15

Thr Gly Leu Phe Ala Lys Glu Tyr Thr Leu Asp Lys Ala His Thr Asp
            20                  25                  30

Val Gly Phe Lys Ile Lys His Leu Gln Ile Ser Asn Val Lys Gly Asn
        35                  40                  45

Phe Lys Asp Tyr Ser Ala Val Ile Asp Phe Asp Pro Ala Ser Ala Glu
    50                  55                  60

Phe Lys Lys Leu Asp Val Thr Ile Lys Ile Ala Ser Val Asn Thr Glu
65                  70                  75                  80

Asn Gln Thr Arg Asp Asn His Leu Gln Gln Asp Asp Phe Phe Lys Ala
                85                  90                  95

Lys Lys Tyr Pro Asp Met Thr Phe Thr Met Lys Lys Tyr Glu Lys Ile
```

```
            100                 105                 110
Asp Asn Glu Lys Gly Lys Met Thr Gly Thr Leu Thr Ile Ala Gly Val
            115                 120                 125

Ser Lys Asp Ile Val Leu Asp Ala Glu Ile Gly Gly Val Ala Lys Gly
            130                 135                 140

Lys Asp Gly Lys Glu Lys Ile Gly Phe Ser Leu Asn Gly Lys Ile Lys
145                 150                 155                 160

Arg Ser Asp Phe Lys Phe Ala Thr Ser Thr Ser Thr Ile Thr Leu Ser
                165                 170                 175

Asp Asp Ile Asn Leu Asn Ile Glu Val Glu Ala Asn Glu Lys
            180                 185                 190

<210> SEQ ID NO 7
<211> LENGTH: 168
<212> TYPE: DNA
<213> ORGANISM: Campylobacter jejuni

<400> SEQUENCE: 7
atgaaaaaag ttgtactaat ctcagcatta ctaggtgctt tcgcagctaa tgttttgca        60 gctaatactc aagcgatgt aaatcaaaca catacaaaag ctaaagctga taaaaaacat       120
gaagctaaaa ctcacaaaaa aacaaaagag caaacaccag ctcaataa                   168

<210> SEQ ID NO 8
<211> LENGTH: 55
<212> TYPE: PRT
<213> ORGANISM: Campylobacter jejuni

<400> SEQUENCE: 8

Met Lys Lys Val Val Leu Ile Ser Ala Leu Leu Gly Ala Phe Ala Ala
1               5                   10                  15

Asn Val Phe Ala Ala Asn Thr Pro Ser Asp Val Asn Gln Thr His Thr
            20                  25                  30

Lys Ala Lys Ala Asp Lys Lys His Glu Ala Lys Thr His Lys Lys Thr
        35                  40                  45

Lys Glu Gln Thr Pro Ala Gln
    50                  55

<210> SEQ ID NO 9
<211> LENGTH: 858
<212> TYPE: DNA
<213> ORGANISM: Campylobacter jejuni

<400> SEQUENCE: 9
atgattggag atatgaatga gcttttatta aaaagcgttg aagtattgcc acctttacct        60
gatactgtaa gtaagttaag aaaatatgtg agcgaggcta attcaaatat agaaactatg       120
aaagttgctg aaatcatttc aagcgatccg ttgatgacgg ctaagctttt gcaattagca       180
aattctcctt attatggttt tacaagagaa attacaacca taatcaagt gattacttta       240 ttaggcgttg gtaatatcat caatatagtt atggctgact ccattagaga taattttaaa       300
atagacgttt caccttatgg tttaaatact caaaattttt taaaaacgtg caatgaagag       360
gcaactttta tcgcaaattg gcttaatgat gaagataaaa actttctca tcttttagtt       420 ccttgtgcaa tgcttttaag gcttggtatt gttattttt caatttttct tatacaaaat       480
cataaggata aggattttt agcttttta aataaaaatg aaaatcttgc tttagcggag       540
aatgaatttt taggcgtaga tcatatttct ttcttgggat ttttgttaca tcgttggaat       600
```

-continued

```
tttgatgatg ttttgattga agtatatgt tttgttcgca ctcctcatgc tgctcgcgaa    660
aaagtgaaaa aatccgctta tgctttagca ataacagatc atcttttgc tccgcatgat     720 ggttcttctc catttaacgc aaaagctgca gttgctttac ttaaagaggc aaaaactcaa    780
ggaattaatt ttgatttaaa caatctttta tctaagcttc ctaacaaagc taaggaaaat   840
ttaaacaaag aagattaa                                                  858
```

<210> SEQ ID NO 10
<211> LENGTH: 285
<212> TYPE: PRT
<213> ORGANISM: Campylobacter jejuni

<400> SEQUENCE: 10

```
Met Ile Gly Asp Met Asn Glu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu
        115                 120                 125

Asn Asp Glu Asp Lys Lys Leu Ser His Leu Leu Val Pro Cys Ala Met
    130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Lys Val Lys Lys
    210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Lys Glu
                245                 250                 255

Ala Lys Thr Gln Gly Ile Asn Phe Asp Leu Asn Leu Leu Ser Lys
            260                 265                 270

Leu Pro Asn Lys Ala Lys Glu Asn Leu Asn Lys Glu Asp
        275                 280                 285
```

<210> SEQ ID NO 11
<211> LENGTH: 753
<212> TYPE: DNA
<213> ORGANISM: Campylobacter jejuni

<400> SEQUENCE: 11

-continued

```
atgaaaaaaa ttattacttt atttggtgca tgtgccttag cttttagtat ggcaaatgca      60
gacgtgaacc tgtacggccc gggcggcccg cacacggccc tgaaagacat cgcaaacaaa     120
tatagcgaaa aaaccggcgt gaaagtgaac gtgaactttg ccccgcaggc gacctggttt     180
gaaaaagcga aaaagacgc ggacatcctg tttggcgcgt cagaccagtc cgctctggct     240
atcgcgagcg actttggcaa agactttaac gtgagcaaaa tcaaaccgct gtattttcgt     300
gaagccatca tcctgaccca gaaaggcaac ccgctgaaaa tcaaaggcct gaaagacctg     360
gcgaacaaaa aagtgcgtat cgtggtgccg gaaggcgcgg gcaaaagcaa cacctctggc     420
accggcgtgt gggaagacat gatcggccgt acccaggaca tcaaaaccat ccagaacttt     480
cgtaacaaca tcgtggcctt tgtgccgaac agcggtagcg cgcgtaaact gttcgcgcag     540
gaccaggccg acgcttggat cacttggatc gactggtcaa aaagcaaccc ggacatcggc     600
actgccgtgg ctatcgaaaa agacctggtg gtgtatcgta cttttaacgt gatcgcgaaa     660
gaaggcgcga gcaaagaaac acaggacttt atcgcttatc tgagttctaa agaagcgaaa     720
gaaatctta aaaaatacgg ctggcgtgaa taa                                  753
```

<210> SEQ ID NO 12
<211> LENGTH: 250
<212> TYPE: PRT
<213> ORGANISM: Campylobacter jejuni

<400> SEQUENCE: 12

Met Lys Lys Ile Ile Thr Leu Phe Gly Ala Cys Ala Leu Ala Phe Ser
1               5                   10                  15

Met Ala Asn Ala Asp Val Asn Leu Tyr Gly Pro Gly Gly Pro His Thr
            20                  25                  30

Ala Leu Lys Asp Ile Ala Asn Lys Tyr Ser Glu Lys Thr Gly Val Lys
        35                  40                  45

Val Asn Val Asn Phe Gly Pro Gln Ala Thr Trp Phe Glu Lys Ala Lys
    50                  55                  60

Lys Asp Ala Asp Ile Leu Phe Gly Ala Ser Asp Gln Ser Ala Leu Ala
65                  70                  75                  80

Ile Ala Ser Asp Phe Gly Lys Asp Phe Asn Val Ser Lys Ile Lys Pro
                85                  90                  95

Leu Tyr Phe Arg Glu Ala Ile Ile Leu Thr Gln Lys Gly Asn Pro Leu
            100                 105                 110

Lys Ile Lys Gly Leu Lys Asp Leu Ala Asn Lys Lys Val Arg Ile Val
        115                 120                 125

Val Pro Glu Gly Ala Gly Lys Ser Asn Thr Ser Gly Thr Gly Val Trp
    130                 135                 140

Glu Asp Met Ile Gly Arg Thr Gln Asp Ile Lys Thr Ile Gln Asn Phe
145                 150                 155                 160

Arg Asn Asn Ile Val Ala Phe Val Pro Asn Ser Gly Ser Ala Arg Lys
                165                 170                 175

Leu Phe Ala Gln Asp Gln Ala Asp Ala Trp Ile Thr Trp Ile Asp Trp
            180                 185                 190

Ser Lys Ser Asn Pro Asp Ile Gly Thr Ala Val Ala Ile Glu Lys Asp
        195                 200                 205

Leu Val Val Tyr Arg Thr Phe Asn Val Ile Ala Lys Glu Gly Ala Ser
    210                 215                 220

Lys Glu Thr Gln Asp Phe Ile Ala Tyr Leu Ser Ser Lys Glu Ala Lys
225                 230                 235                 240

Glu Ile Phe Lys Lys Tyr Gly Trp Arg Glu
            245                 250

<210> SEQ ID NO 13
<211> LENGTH: 1479
<212> TYPE: DNA
<213> ORGANISM: Campylobacter jejuni

<400> SEQUENCE: 13

| | | | | |
|---|---|---|---|---|
| atgaataaaa taatttcaat tagtgctata gcaagttta  ctcttttgat  ttcagcttgc | | | | 60 |
| tctttaagtc caaatttaaa tattcccgaa gcaaactata gcattgataa taagcttgga | | | | 120 |
| gccttatctt gggaaaaaga aaacaatagc tctatcacaa aaaattggtg aaagacttt  | | | | 180 |
| gatgatgaaa atttaaataa agtggttgat ttagcactta aaaataataa tgatttaaaa | | | | 240 |
| cttgctttca tacacatgga acaagctgct gctcaattag gtatagattt tagcagtttg | | | | 300 |
| ttgccaaaat ttgatggtag cgcaagcgga agtcgtgcaa aaacagctat aaatgctcca | | | | 360 |
| agcaatcgaa ctggggaagt aagttacggt aatgattta  aaatgggact taatttaagc | | | | 420 |
| tatgaaatcg atctttgggg aaaatatcgc gatacatatc gcgcctcaaa atcaggcttt | | | | 480 |
| aaagcaagtg agtatgatta tgaagctgca agactttctg ttatttcaaa tacagttcaa | | | | 540 |
| acttattta  atcttgtaaa tgcttatgaa aatgaaaatg ctcttaaaga agcctataaa | | | | 600 |
| tctgcaaaag aaatttatag gattaatgat gaaaaattc  aagttggtgc tgtaggtgaa | | | | 660 |
| tatgaacttg ctcaagcaag agccaactta gaaagtatgg ctttgcaata taatgaagca | | | | 720 |
| aagttaaata agaaaatta  ccttaaagct ttaaaaattt taacttcaaa tgatttaaat | | | | 780 |
| gacatacttt acaaaaatca aagctatcaa gttttaatc  ttaaagaatt tgacattcca | | | | 840 |
| actggaattt caagtaccat cttgcttcaa cgtccagata ttggctcttc tttagaaaaa | | | | 900 |
| ttaactcagc aaaattatct tgttggagta gctcgcacgg ctttcttacc tagccttct  | | | | 960 |
| ttaacaggat tattgggatt tgaaagcggg gatttagata ccttggttaa aggaggttct | | | | 1020 |
| aagacttgga atataggtgg aaactttact ctgcctattt ttcattgggg tgaaatttac | | | | 1080 |
| caaaatgtaa atttagccaa gcttaataaa gatgaagctt ttgtaaatta tcaaaatact | | | | 1140 |
| ttgattactg cttttggaga aattcgctat gctttagtag ctagaaaaac tatacgctta | | | | 1200 |
| caatacgata tgcacaagc  aagcgaacaa tcttacaaaa gaatctatga aattgctaaa | | | | 1260 |
| gaacgctatg atataggaga atgtctttg  caagattatt tagaggcacg tcaaaattgg | | | | 1320 |
| cttaatgctg cggttgcttt taataatatt aaatattctt atgccaattc catagtagat | | | | 1380 |
| gtaatcaaag catttggtgg aggatttgag caaagtgaag atacgagtaa aaatatataa | | | | 1440 |
| gaagaatcaa aaaatttaga tatgtctttt agagaatag                         | | | | 1479 |

<210> SEQ ID NO 14
<211> LENGTH: 492
<212> TYPE: PRT
<213> ORGANISM: Campylobacter jejuni

<400> SEQUENCE: 14

Met Asn Lys Ile Ile Ser Ile Ser Ala Ile Ala Ser Phe Thr Leu Leu
1               5                   10                  15

Ile Ser Ala Cys Ser Leu Ser Pro Asn Leu Asn Ile Pro Glu Ala Asn
            20                  25                  30

Tyr Ser Ile Asp Asn Lys Leu Gly Ala Leu Ser Trp Glu Lys Glu Asn
        35                  40                  45

```
Asn Ser Ser Ile Thr Lys Asn Trp Trp Lys Asp Phe Asp Asp Glu Asn
    50                  55                  60
Leu Asn Lys Val Val Asp Leu Ala Leu Lys Asn Asn Asn Asp Leu Lys
65                  70                  75                  80
Leu Ala Phe Ile His Met Glu Gln Ala Ala Gln Leu Gly Ile Asp
                85                  90                  95
Phe Ser Ser Leu Leu Pro Lys Phe Asp Gly Ser Ala Ser Gly Ser Arg
                100                 105                 110
Ala Lys Thr Ala Ile Asn Ala Pro Ser Asn Arg Thr Gly Glu Val Ser
            115                 120                 125
Tyr Gly Asn Asp Phe Lys Met Gly Leu Asn Leu Ser Tyr Glu Ile Asp
    130                 135                 140
Leu Trp Gly Lys Tyr Arg Asp Thr Tyr Arg Ala Ser Lys Ser Gly Phe
145                 150                 155                 160
Lys Ala Ser Glu Tyr Asp Tyr Glu Ala Ala Arg Leu Ser Val Ile Ser
                165                 170                 175
Asn Thr Val Gln Thr Tyr Phe Asn Leu Val Asn Ala Tyr Glu Asn Glu
                180                 185                 190
Asn Ala Leu Lys Glu Ala Tyr Lys Ser Ala Lys Glu Ile Tyr Arg Ile
            195                 200                 205
Asn Asp Glu Lys Phe Gln Val Gly Ala Val Gly Tyr Glu Leu Ala
    210                 215                 220
Gln Ala Arg Ala Asn Leu Glu Ser Met Ala Leu Gln Tyr Asn Glu Ala
225                 230                 235                 240
Lys Leu Asn Lys Glu Asn Tyr Leu Lys Ala Leu Lys Ile Leu Thr Ser
                245                 250                 255
Asn Asp Leu Asn Asp Ile Leu Tyr Lys Asn Gln Ser Tyr Gln Val Phe
                260                 265                 270
Asn Leu Lys Glu Phe Asp Ile Pro Thr Gly Ile Ser Ser Thr Ile Leu
            275                 280                 285
Leu Gln Arg Pro Asp Ile Gly Ser Ser Leu Glu Lys Leu Thr Gln Gln
    290                 295                 300
Asn Tyr Leu Val Gly Val Ala Arg Thr Ala Phe Leu Pro Ser Leu Ser
305                 310                 315                 320
Leu Thr Gly Leu Leu Gly Phe Glu Ser Gly Asp Leu Asp Thr Leu Val
                325                 330                 335
Lys Gly Gly Ser Lys Thr Trp Asn Ile Gly Gly Asn Phe Thr Leu Pro
                340                 345                 350
Ile Phe His Trp Gly Glu Ile Tyr Gln Asn Val Asn Leu Ala Lys Leu
            355                 360                 365
Asn Lys Asp Glu Ala Phe Val Asn Tyr Gln Asn Thr Leu Ile Thr Ala
    370                 375                 380
Phe Gly Glu Ile Arg Tyr Ala Leu Val Ala Arg Lys Thr Ile Arg Leu
385                 390                 395                 400
Gln Tyr Asp Asn Ala Gln Ala Ser Glu Gln Ser Tyr Lys Arg Ile Tyr
                405                 410                 415
Glu Ile Ala Lys Glu Arg Tyr Asp Ile Gly Glu Met Ser Leu Gln Asp
            420                 425                 430
Tyr Leu Glu Ala Arg Gln Asn Trp Leu Asn Ala Ala Val Ala Phe Asn
    435                 440                 445
Asn Ile Lys Tyr Ser Tyr Ala Asn Ser Ile Val Asp Val Ile Lys Ala
450                 455                 460
Phe Gly Gly Gly Phe Glu Gln Ser Glu Asp Thr Ser Lys Asn Ile Lys
```

```
                465                 470                 475                 480
Glu Glu Ser Lys Asn Leu Asp Met Ser Phe Arg Glu
                485                 490

<210> SEQ ID NO 15
<211> LENGTH: 837
<212> TYPE: DNA
<213> ORGANISM: Campylobacter jejuni

<400> SEQUENCE: 15
atggaaaatc aaaaaaatga atttgatgat attattttag aaaaaagtaa taaaagtgaa    60
aaagtaaaaa aaattctttt acgagttatt gctttagtta ttttgttttt agctatcatg   120
atagttatga agcttattaa tggtagtggt gatgaaaata cgcaaaatca agtgtattg    180
ccaagtgaac ctatagcaac tcaagacaat aacaatgata cttcttttga agtatgcca    240
attacagata atacttcagc agaagatcaa tttgaggcat taagaaaaca atttcaagat   300
gaacaaaata caactcaaaa tacaacaacc tctagttcaa ataacaatga tactacaaat   360
tttgctatgc ctgatcaaga agttccagca gaaccaacag caactacttc agcaaatacc   420
actccacaag caagtactcc taaacaagaa gtaacacaaa ctgcaaaatc taagaagaa    480
gcaaaaaaac aaacagctgt aaaaaaagaa aaagaaagtg caaacaaac ccctaaaaaa    540
gaacaaaatg caaatgattt atttaaaaat gttgatgcta aacctgtaca tccaagtggt   600
ttagcatcgg gtatttatgt gcaaattttc tcagtaagta atttggatca aaaatcaaaa   660
gaacttgctt ctgtaaagca aaaaggttat gattataaac tttataaaac tacagttgga   720
agtaaagaaa ttaccaaggt tttaatagga ccatttgaaa aggcagatat tgcagcagaa   780
cttgctaaaa tccgtaagga tattgcaaaa gatgcttttt cttttacttt aaaatga      837

<210> SEQ ID NO 16
<211> LENGTH: 278
<212> TYPE: PRT
<213> ORGANISM: Campylobacter jejuni

<400> SEQUENCE: 16

Met Glu Asn Gln Lys Asn Glu Phe Asp Asp Ile Ile Leu Glu Lys Ser
1               5                   10                  15

Asn Lys Ser Glu Lys Val Lys Lys Ile Leu Leu Arg Val Ile Ala Leu
                20                  25                  30

Val Ile Leu Phe Leu Ala Ile Met Ile Val Met Lys Leu Ile Asn Gly
            35                  40                  45

Ser Gly Asp Glu Asn Thr Gln Asn Gln Ser Val Leu Pro Ser Glu Pro
        50                  55                  60

Ile Ala Thr Gln Asp Asn Asn Asn Asp Thr Ser Phe Glu Ser Met Pro
65                  70                  75                  80

Ile Thr Asp Asn Thr Ser Ala Glu Asp Gln Phe Glu Ala Leu Arg Lys
                85                  90                  95

Gln Phe Gln Asp Glu Gln Asn Thr Thr Gln Asn Thr Thr Thr Ser Ser
                100                 105                 110

Ser Asn Asn Asn Asp Thr Thr Asn Phe Ala Met Pro Asp Gln Glu Val
            115                 120                 125

Pro Ala Glu Pro Thr Ala Thr Thr Ser Ala Asn Thr Thr Pro Gln Ala
        130                 135                 140

Ser Thr Pro Lys Gln Glu Val Thr Gln Thr Ala Lys Ser Lys Glu Glu
145                 150                 155                 160
```

Ala Lys Lys Gln Thr Ala Val Lys Lys Glu Lys Glu Ser Ala Lys Gln
            165                 170                 175

Thr Pro Lys Lys Glu Gln Asn Ala Asn Asp Leu Phe Lys Asn Val Asp
        180                 185                 190

Ala Lys Pro Val His Pro Ser Gly Leu Ala Ser Gly Ile Tyr Val Gln
        195                 200                 205

Ile Phe Ser Val Ser Asn Leu Asp Gln Lys Ser Lys Glu Leu Ala Ser
        210                 215                 220

Val Lys Gln Lys Gly Tyr Asp Tyr Lys Leu Tyr Lys Thr Thr Val Gly
225                 230                 235                 240

Ser Lys Glu Ile Thr Lys Val Leu Ile Gly Pro Phe Glu Lys Ala Asp
                245                 250                 255

Ile Ala Ala Glu Leu Ala Lys Ile Arg Lys Asp Ile Ala Lys Asp Ala
                260                 265                 270

Phe Ser Phe Thr Leu Lys
            275

<210> SEQ ID NO 17
<211> LENGTH: 573
<212> TYPE: DNA
<213> ORGANISM: Campylobacter jejuni

<400> SEQUENCE: 17

```
atgaaaaaag tttattgag ttcattggtt gcggtgtctt tgttaagcac aggtttgttt      60
gctaagaat atactttaga taaagcacat acagatgtag gttttaaaat caaacattta     120
caaattagca atgtaaaagg aaatttcaaa gattattctg cggtgattga ttttgatcct     180
gcgagtgctg aatttaaaaa gcttgatgta actataaaaa tcgcatctgt aaatacagaa     240
aatcaaacaa gagataatca cttacaacaa gatgattttt tcaaagcaaa aaatatcct     300
gatatgactt ttacaatgaa aaatatgaa aaaatcgata tgaaaaagg caaaatgaca     360
ggaacttta ctatagctgg agttttctaaa gatatcgttt tagatgctga atcggcggt     420
gtagctaaag gcaaagatgg aaaagaaaaa ataggatttt ctttaaatgg aaaaatcaaa     480
cgctctgatt ttaaatttgc aacaagtact tcaactatta ctttaagtga tgatattaat     540
ttaaatatcg aagttgaagc gaacgaaaaa taa                                  573
```

<210> SEQ ID NO 18
<211> LENGTH: 190
<212> TYPE: PRT
<213> ORGANISM: Campylobacter jejuni

<400> SEQUENCE: 18

Met Lys Lys Val Leu Leu Ser Ser Leu Val Ala Val Ser Leu Leu Ser
1               5                   10                  15

Thr Gly Leu Phe Ala Lys Glu Tyr Thr Leu Asp Lys Ala His Thr Asp
            20                  25                  30

Val Gly Phe Lys Ile Lys His Leu Gln Ile Ser Asn Val Lys Gly Asn
        35                  40                  45

Phe Lys Asp Tyr Ser Ala Val Ile Asp Phe Asp Pro Ala Ser Ala Glu
    50                  55                  60

Phe Lys Lys Leu Asp Val Thr Ile Lys Ile Ala Ser Val Asn Thr Glu
65                  70                  75                  80

Asn Gln Thr Arg Asp Asn His Leu Gln Gln Asp Asp Phe Phe Lys Ala
                85                  90                  95

Lys Lys Tyr Pro Asp Met Thr Phe Thr Met Lys Lys Tyr Glu Lys Ile 100                 105                 110

Asp Asn Glu Lys Gly Lys Met Thr Gly Thr Leu Thr Ile Ala Gly Val
            115                 120                 125

Ser Lys Asp Ile Val Leu Asp Ala Glu Ile Gly Gly Val Ala Lys Gly
        130                 135                 140

Lys Asp Gly Lys Glu Lys Ile Gly Phe Ser Leu Asn Gly Lys Ile Lys
145                 150                 155                 160

Arg Ser Asp Phe Lys Phe Ala Thr Ser Thr Ser Thr Ile Thr Leu Ser
                165                 170                 175

Asp Asp Ile Asn Leu Asn Ile Glu Val Glu Ala Asn Glu Lys
            180                 185                 190

<210> SEQ ID NO 19
<211> LENGTH: 336
<212> TYPE: DNA
<213> ORGANISM: Campylobacter jejuni

<400> SEQUENCE: 19
atgatggcta aatttagaat tcaatacagc gcaggttttg ggcactatac gcaaaatcac      60
aagggttttg gacctacgat ttatatagaa gaggtcgtag agtttgataa tggcaaggat     120
tattttgact atatagattt ttataaaact tattcaaaga gcgatgatac ttattttcat     180
atcagttttt tagaagatag acctctaagc gataaagaaa tcaccattcg caatgaatac     240
cgcaaaatgc gtgatgaaaa ctgtaaaaaa gccaaggagg aatttatagc caacaatgag     300
cttgatgtgg agcatttgcc tactcaccat gattaa                              336

<210> SEQ ID NO 20
<211> LENGTH: 111
<212> TYPE: PRT
<213> ORGANISM: Campylobacter jejuni

<400> SEQUENCE: 20

Met Met Ala Lys Phe Arg Ile Gln Tyr Ser Ala Gly Phe Gly His Tyr
1               5                   10                  15

Thr Gln Asn His Lys Gly Phe Gly Pro Thr Ile Tyr Ile Glu Glu Val
            20                  25                  30

Val Glu Phe Asp Asn Gly Lys Asp Tyr Phe Asp Tyr Ile Asp Phe Tyr
        35                  40                  45

Lys Thr Tyr Ser Lys Ser Asp Asp Thr Tyr Phe His Ile Ser Phe Leu
    50                  55                  60

Glu Asp Arg Pro Leu Ser Asp Lys Glu Ile Thr Ile Arg Asn Glu Tyr
65                  70                  75                  80

Arg Lys Met Arg Asp Glu Asn Cys Lys Lys Ala Lys Glu Glu Phe Ile
                85                  90                  95

Ala Asn Asn Glu Leu Asp Val Glu His Leu Pro Thr His His Asp
            100                 105                 110

<210> SEQ ID NO 21
<211> LENGTH: 384
<212> TYPE: DNA
<213> ORGANISM: Campylobacter jejuni

<400> SEQUENCE: 21
atgcaggtaa attatagaac gattagctcg tatgaatacg atgctattag tggtcagtat      60
aaacaggtgg ataaacagat tgaagattat tcttcatctg gagattctga ttttatggat     120
atgttaaata aggcggatga aagtcaagc ggagatgctt taaattctag cagtagtttt     180

-continued

```
caaagcaatg cgcaaaactc aaattcaaat ttaagtaatt atgctcaaat gtcaaatgtt    240
tacgcttatc gttttagaca aaatgaaggc gagctgtcta tgagagctca aagtgctagc    300
gttcataatg atcttacaca acaaggtgca aatgaacaaa gtaagaataa tactttgtta    360
aatgatttat tgaacgcaat ttaa                                          384
```

<210> SEQ ID NO 22
<211> LENGTH: 127
<212> TYPE: PRT
<213> ORGANISM: Campylobacter jejuni

<400> SEQUENCE: 22

```
Met Gln Val Asn Tyr Arg Thr Ile Ser Ser Tyr Glu Tyr Asp Ala Ile
1               5                   10                  15

Ser Gly Gln Tyr Lys Gln Val Asp Lys Gln Ile Glu Tyr Ser Ser
            20                  25                  30

Ser Gly Asp Ser Asp Phe Met Asp Met Leu Asn Lys Ala Asp Glu Lys
        35                  40                  45

Ser Ser Gly Asp Ala Leu Asn Ser Ser Ser Phe Gln Ser Asn Ala
    50                  55                  60

Gln Asn Ser Asn Ser Asn Leu Ser Asn Tyr Ala Gln Met Ser Asn Val
65                  70                  75                  80

Tyr Ala Tyr Arg Phe Arg Gln Asn Glu Gly Glu Leu Ser Met Arg Ala
                85                  90                  95

Gln Ser Ala Ser Val His Asn Asp Leu Thr Gln Gln Gly Ala Asn Glu
            100                 105                 110

Gln Ser Lys Asn Asn Thr Leu Leu Asn Asp Leu Leu Asn Ala Ile
        115                 120                 125
```

<210> SEQ ID NO 23
<211> LENGTH: 674
<212> TYPE: DNA
<213> ORGANISM: Campylobacter jejuni

<400> SEQUENCE: 23

```
atgcgtttcg acttcttcgt gtccaaacgt ctgaacatca gccgtaacaa agcgctggag     60
ctgatcgaaa acgaagagat cctgctgaac ggcaaaagct tcaaagcgtc cttcgacgtg    120
aaaaacttcc tggaaaacct gaaaaaaacc caggacctga cccggaagaa catcctgctg    180
gcgaacgagc tgaaactgga cctgctgagc gaaatctacg tgtcccgtgc ggcgctgaaa    240
ctgaaaaaat tcctggaaga aaacgacatc gaaatcaaac acaaaaactg tctggacatc    300
ggctccagca ccggcggctt cgtgcagatc ctgctggaaa accaggcgct gaaaatcacc    360
gcgctggacg tgggcagcaa ccagctgcac ccgagcctgc gtgtgaacga aaaaatcatc    420
ctgcacgaaa acaccgacct gcgtgcgttc aaaagcgaag aaaaattcga actggtgacc    480
tgcgacgtga gcttcatctc cctgatcaac ctgctgtact acatcgacaa cctggcgctg    540
aaagaaatca tcctgctgtt caaaccgcag ttcgaagtgg gcaaaaacat caaacgtgac    600
aaaaaaggcg tgctgaaaga cgacaaagcg atcctgaaag cgcgtatgga cttcgaaaaa    660
gcgtgcgcga aact                                                     674
```

<210> SEQ ID NO 24
<211> LENGTH: 253
<212> TYPE: PRT
<213> ORGANISM: Campylobacter jejuni

<400> SEQUENCE: 24

Met Arg Phe Asp Phe Val Ser Lys Arg Leu Asn Ile Ser Arg Asn
1               5                   10                  15

Lys Ala Leu Glu Leu Ile Glu Asn Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Leu Ala Asn Glu Leu
    50                  55                  60

Lys Leu Asp Leu Leu Ser Glu Ile Tyr Val Ser Arg Ala Ala Leu Lys
65                  70                  75                  80

Leu Lys Lys Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
                100                 105                 110

Glu Asn Gln Ala Leu Lys Ile Thr Ala Leu Asp Val Gly Ser Asn Gln
            115                 120                 125

Leu His Pro Ser Leu Arg Val Asn Glu Lys Ile Ile Leu His Glu Asn
    130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Ile Lys Asn
                245                 250

<210> SEQ ID NO 25
<211> LENGTH: 780
<212> TYPE: DNA
<213> ORGANISM: Campylobacter jejuni

<400> SEQUENCE: 25
atggttttta gaaatctttt gttaaagttg cagttttttg ctctaggtgc ttgtgttgca    60
tttagcaatg ctaatgcagc agaaggcaaa ctggagtcca tcaaatccaa aggccagctg   120
atcgtgggcg tgaaaaacga cgtgccgcac tacgctctgc tggaccaggc aaccggcgaa   180
atcaaaggct cgaagtggac cgtggccaaa ctgctggcta aaagcatcct ggggacgac    240 aaaaaaatca aactggtggc agtgaacgcc aaaacccgtg gcccgctgct ggacaacggc   300
agcgtggacg cggtgatcgc aaccttcacc atcaccccgg agcgcaaacg tatctataac   360
ttctccgagc cgtattatca ggacgctatc ggcctgctgg ttctgaaaga aaaaaaatat   420
aaatctctgg ctgacatgaa aggtgcaaac atcggcgtgg ctcaagctgc aactacaaaa   480
aaagctatcg cgaagctgc taaaaaaatc ggcatcgacg tgaaattcag cgaattcccg   540
gactatccga gcatcaaagc tgctctggac gctaaacgtg tggacgcgtt ctctgtggac   600
aaatccatcc tgctgggcta tgtggacgac aaaagcgaaa tcctgccgga cagcttcgaa   660

```
ccgcagagct atggcatcgt gaccaaaaaa gacgacccgg ctttcgcaaa atatgtggac    720
gacttcgtga aagaacacaa aaacgaaatc gacgctctgg cgaaaaaatg gggcctgtaa   780

<210> SEQ ID NO 26
<211> LENGTH: 259
<212> TYPE: PRT
<213> ORGANISM: Campylobacter jejuni

<400> SEQUENCE: 26

Met Val Phe Arg Lys Ser Leu Leu Lys Leu Ala Val Phe Ala Leu Gly
1               5                   10                  15

Ala Cys Val Ala Phe Ser Asn Ala Asn Ala Ala Glu Gly Lys Leu Glu
            20                  25                  30

Ser Ile Lys Ser Lys Gly Gln Leu Ile Val Gly Val Lys Asn Asp Val
        35                  40                  45

Pro His Tyr Ala Leu Leu Asp Gln Ala Thr Gly Glu Ile Lys Gly Phe
    50                  55                  60

Glu Val Asp Val Ala Lys Leu Leu Ala Lys Ser Ile Leu Gly Asp Asp
65                  70                  75                  80

Lys Lys Ile Lys Leu Val Ala Val Asn Ala Lys Thr Arg Gly Pro Leu
                85                  90                  95

Leu Asp Asn Gly Ser Val Asp Ala Val Ile Ala Thr Phe Thr Ile Thr
            100                 105                 110

Pro Glu Arg Lys Arg Ile Tyr Asn Phe Ser Glu Pro Tyr Tyr Gln Asp
        115                 120                 125

Ala Ile Gly Leu Leu Val Leu Lys Glu Lys Tyr Lys Ser Leu Ala
    130                 135                 140

Asp Met Lys Gly Ala Asn Ile Gly Val Ala Gln Ala Ala Thr Thr Lys
145                 150                 155                 160

Lys Ala Ile Gly Glu Ala Ala Lys Lys Ile Gly Ile Asp Val Lys Phe
                165                 170                 175

Ser Glu Phe Pro Asp Tyr Pro Ser Ile Lys Ala Ala Leu Asp Ala Lys
            180                 185                 190

Arg Val Asp Ala Phe Ser Val Asp Lys Ser Ile Leu Leu Gly Tyr Val
        195                 200                 205

Asp Asp Lys Ser Glu Ile Leu Pro Asp Ser Phe Glu Pro Gln Ser Tyr
    210                 215                 220

Gly Ile Val Thr Lys Lys Asp Asp Pro Ala Phe Ala Lys Tyr Val Asp
225                 230                 235                 240

Asp Phe Val Lys Glu His Lys Asn Glu Ile Asp Ala Leu Ala Lys Lys
                245                 250                 255

Trp Gly Leu

<210> SEQ ID NO 27
<211> LENGTH: 836
<212> TYPE: DNA
<213> ORGANISM: Campylobacter jejuni

<400> SEQUENCE: 27
atgaaaaaaa tacttctaag tgttttaacg gcctttgttg cagtagtatt ggctgcggcg    60
gcaactccga ctccaaaacc ctgaactccc tggacaaaat caaacagaac ggcgtggtgc   120
gtatcggcgt gtttggcgac aaaccgccgt ttggctatgt ggacgaaaaa ggcaacaacc   180
agggctatga catcgctctg gctaaacgta tcgcgaaaga actgtttggc gacgaaaaca   240
```

-continued

```
aagtgcagtt tgtgctggtg gaagctgcga accgtgtgga gtttctgaaa tccaacaaag    300
tggacatcat cctggctaac tttacccaga ccccgcagcg tgcggagcag gtggactttt    360
gctccccgta tatgaaagtg gctctgggcg tggctgtgcc gaaagacagc aacatcacca    420
gcgtggaaga cctgaaagac aaaaccctgc tgctgaacaa aggcaccacc gcggacgctt    480
attttaccca gaactatccg aacatcaaaa ccctgaaata tgaccagaac accgaaacct    540 tgcggctct gatggacaaa cgtggcgacg ctctgagcca cgacaacacc ctgctgtttg    600
cttgggtgaa agaccacccg gactttaaaa tgggcatcaa agagctgggc aacaaagacg    660
tgatcgcgcc ggcggtgaaa aaaggcgaca agaactgaa agaatttatc gacaacctga    720
tcatcaaact gggccaggag cagttttttc acaaagctta tgacgaaacc ctgaaagctc    780
actttggcga cgacgtgaaa gcggacgacg tggtgatcga aggcggcaaa atctaa       836
```

```
<210> SEQ ID NO 28
<211> LENGTH: 279
<212> TYPE: PRT
<213> ORGANISM: Campylobacter jejuni

<400> SEQUENCE: 28

Met Lys Lys Ile Leu Leu Ser Val Leu Thr Ala Phe Val Ala Val Val
1               5                   10                  15

Leu Ala Ala Cys Gly Gly Asn Ser Asp Ser Lys Thr Leu Asn Ser Leu
                20                  25                  30

Asp Lys Ile Lys Gln Asn Gly Val Val Arg Ile Gly Val Phe Gly Asp
            35                  40                  45

Lys Pro Pro Phe Gly Tyr Val Asp Glu Lys Gly Asn Asn Gln Gly Tyr
        50                  55                  60

Asp Ile Ala Leu Ala Lys Arg Ile Ala Lys Glu Leu Phe Gly Asp Glu
65                  70                  75                  80

Asn Lys Val Gln Phe Val Leu Val Glu Ala Ala Asn Arg Val Glu Phe
                85                  90                  95

Leu Lys Ser Asn Lys Val Asp Ile Ile Leu Ala Asn Phe Thr Gln Thr
            100                 105                 110

Pro Gln Arg Ala Glu Gln Val Asp Phe Cys Ser Pro Tyr Met Lys Val
        115                 120                 125

Ala Leu Gly Val Ala Val Pro Lys Asp Ser Asn Ile Thr Ser Val Glu
    130                 135                 140

Asp Leu Lys Asp Lys Thr Leu Leu Leu Asn Lys Gly Thr Thr Ala Asp
145                 150                 155                 160

Ala Tyr Phe Thr Gln Asn Tyr Pro Asn Ile Lys Thr Leu Lys Tyr Asp
                165                 170                 175

Gln Asn Thr Glu Thr Phe Ala Leu Met Asp Lys Arg Gly Asp Ala
            180                 185                 190

Leu Ser His Asp Asn Thr Leu Leu Phe Ala Trp Val Lys Asp His Pro
        195                 200                 205

Asp Phe Lys Met Gly Ile Lys Glu Leu Gly Asn Lys Asp Val Ile Ala
    210                 215                 220

Pro Ala Val Lys Lys Gly Asp Lys Glu Leu Lys Glu Phe Ile Asp Asn
225                 230                 235                 240

Leu Ile Ile Lys Leu Gly Gln Glu Gln Phe Phe His Lys Ala Tyr Asp
                245                 250                 255

Glu Thr Leu Lys Ala His Phe Gly Asp Asp Val Lys Ala Asp Asp Val
            260                 265                 270
```

Val Ile Glu Gly Gly Lys Ile
        275

<210> SEQ ID NO 29
<211> LENGTH: 573
<212> TYPE: DNA
<213> ORGANISM: Campylobacter jejuni

<400> SEQUENCE: 29

| | | | | |
|---|---|---|---|---|
| atgaaaaaaa ttcttgtaag tgttttaagt tcttgcttgt tagcttcggc tttaagtgcg | | | | 60 |
| gtgtccttca aagaagacag cctgaaaatc tccttcgaag ctacaaaac caaagacatg | | | | 120 |
| atcggcacca aaggcgaatt caaaaacgtg aatacaaat tctccaaaaa catcaaagac | | | | 180 |
| ctggcgagct acctgaaagg cgcgaaagcg accatcaaac cgagcaacgc gttcatgggc | | | | 240 |
| gaaggcaacg acatcatcac caacaacatc accaaagtgt tcttcccggc gctgctgggc | | | | 300 |
| gacacggaca tcaaagtggt gtttcaggac gtgatcgcgg gcgaaaacaa aggcgtgatc | | | | 360 |
| tccgcgaaaa tcaccatgga caaaaaaagc accatcgtgc cgctgaccta ccatcaaa | | | | 420 |
| gacaacaaat ttgaagcgaa aggccagctg gacctgcaca cctttaaaaa cggctccaaa | | | | 480 |
| gcgctgaaag cgctgagcga cgtggctgca ggccacggcg gcatctcctg gccgctggtg | | | | 540 |
| gacatcagct ttaacgcgga cctggcgaa taa | | | | 573 |

<210> SEQ ID NO 30
<211> LENGTH: 190
<212> TYPE: PRT
<213> ORGANISM: Campylobacter jejuni

<400> SEQUENCE: 30

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Ile Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
    130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
            180                 185                 190

<210> SEQ ID NO 31
<211> LENGTH: 1275
<212> TYPE: DNA

<213> ORGANISM: Campylobacter jejuni

<400> SEQUENCE: 31

```
atgaaactag ttaaacttag tttagttgca gctcttgctg caggtgcttt ttcagcagct    60
aacgctaccc cgctggaaga agcgatcaaa gacgtggacg tgtccggcgt gctgcgttac   120
cgttacgaca ccggcaactt tgacaaaaac ttcgtgaaca actccaacct gaacaacagc   180
aaacaggacc acaaatatcg tgcacaggtg aacttcagtg ctgctatcgc tgacaacttc   240
aaagcttttg tgcagtttga ctataacgct gctgacggtg gctatggcgc taacggcatc   300
aaaaacgacc agaaaggcct gtttgtgcgt cagctgtacc tgacttatac caacgaagac   360
gtggctacca gtgtgatcgc tggtaaacag cagctgaacc tgatctggac ggacaacgct   420
atcgacggtc tggtgggcac cggtgtgaaa gtggtgaaca acagcatcga cggtctgact   480
ctggctgctt ttgctgtgga cagcttcatg gctgcggagc agggtgcgga cctgctggaa   540
cacagtaaca tctccaccac ctccaaccag gctccgttta agtggactc cgtgggcaac   600
ctgtacggtg ctgctgctgt gggttcttat gacctggctg gtggccagtt caacccgcag   660
ctgtggctgg cttattggga ccaggtggca ttcttctatg ctgtggacgc agcttatagc   720
acaactatct ttgacggcat caactggaca ctggaaggcg cttacctggg aaacagcctg   780
gacagcgaac tggacgacaa acacacgct aacggcaacc tgtttgctct gaaaggcagc   840
atcgaagtga acggctggga cgctagcctg ggtggtctgt actacggcga caagaaaaaa   900
gcttctacag tggtgatcga agaccagggt aacctgggtt ctctgctggc aggtgaggaa   960
atcttctata ctactggctc acgcctgaac ggtgacactg tcgtaacat cttcggttat  1020
gtgactggtg gatatacttt caacgaaaca gtgcgcgtgg gtgctgactt cgtgtatggt  1080
ggaacaaaaa cagaagctgc taaccacctg ggtggtggta aaaaactgga agctgtggca  1140
cgcgtggact acaaatactc tccgaaactg aacttctcag cattctattc ttatgtgaac  1200
ctggaccagg gtgtgaacac taacgaaagt gctgaccaca gcactgtgcg tctgcaggct  1260
ctgtacaaat tctaa                                                  1275
```

<210> SEQ ID NO 32
<211> LENGTH: 424
<212> TYPE: PRT
<213> ORGANISM: Campylobacter jejuni

<400> SEQUENCE: 32

```
Met Lys Leu Val Lys Leu Ser Leu Val Ala Ala Leu Ala Ala Gly Ala
 1               5                  10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Ser Lys Gln Asp His
        50                  55                  60

Lys Tyr Arg Ala Gln Val Asn Phe Ser Ala Ala Ile Ala Asp Asn Phe
 65                  70                  75                  80

Lys Ala Phe Val Gln Phe Asp Tyr Asn Ala Ala Asp Gly Gly Tyr Gly
                85                  90                  95

Ala Asn Gly Ile Lys Asn Asp Gln Lys Gly Leu Phe Val Arg Gln Leu
           100                 105                 110

Tyr Leu Thr Tyr Thr Asn Glu Asp Val Ala Thr Ser Val Ile Ala Gly
           115                 120                 125
```

| | | | | | | | | | | | | |
|---|---|---|---|---|---|---|---|---|---|---|---|---|
|Lys|Gln|Gln|Leu|Asn|Leu|Ile|Trp|Thr|Asp|Asn|Ala|Ile|Asp|Gly|Leu|
| |130| | | |135| | | |140| | | | | | |

Lys Gln Gln Leu Asn Leu Ile Trp Thr Asp Asn Ala Ile Asp Gly Leu
    130             135             140

Val Gly Thr Gly Val Lys Val Val Asn Asn Ser Ile Asp Gly Leu Thr
145             150             155             160

Leu Ala Ala Phe Ala Val Asp Ser Phe Met Ala Ala Glu Gln Gly Ala
            165             170             175

Asp Leu Leu Glu His Ser Asn Ile Ser Thr Thr Ser Asn Gln Ala Pro
            180             185             190

Phe Lys Val Asp Ser Val Gly Asn Leu Tyr Gly Ala Ala Ala Val Gly
        195             200             205

Ser Tyr Asp Leu Ala Gly Gly Gln Phe Asn Pro Gln Leu Trp Leu Ala
    210             215             220

Tyr Trp Asp Gln Val Ala Phe Phe Tyr Ala Val Asp Ala Ala Tyr Ser
225             230             235             240

Thr Thr Ile Phe Asp Gly Ile Asn Trp Thr Leu Glu Gly Ala Tyr Leu
            245             250             255

Gly Asn Ser Leu Asp Ser Glu Leu Asp Asp Lys Thr His Ala Asn Gly
            260             265             270

Asn Leu Phe Ala Leu Lys Gly Ser Ile Glu Val Asn Gly Trp Asp Ala
        275             280             285

Ser Leu Gly Gly Leu Tyr Tyr Gly Asp Lys Glu Lys Ala Ser Thr Val
    290             295             300

Val Ile Glu Asp Gln Gly Asn Leu Gly Ser Leu Leu Ala Gly Glu Glu
305             310             315             320

Ile Phe Tyr Thr Thr Gly Ser Arg Leu Asn Gly Asp Thr Gly Arg Asn
            325             330             335

Ile Phe Gly Tyr Val Thr Gly Tyr Thr Phe Asn Glu Thr Val Arg
            340             345             350

Val Gly Ala Asp Phe Val Tyr Gly Gly Thr Lys Thr Glu Ala Ala Asn
        355             360             365

His Leu Gly Gly Gly Lys Lys Leu Glu Ala Val Ala Arg Val Asp Tyr
    370             375             380

Lys Tyr Ser Pro Lys Leu Asn Phe Ser Ala Phe Tyr Ser Tyr Val Asn
385             390             395             400

Leu Asp Gln Gly Val Asn Thr Asn Glu Ser Ala Asp His Ser Thr Val
            405             410             415

Arg Leu Gln Ala Leu Tyr Lys Phe
            420

<210> SEQ ID NO 33
<211> LENGTH: 1718
<212> TYPE: DNA
<213> ORGANISM: Campylobacter jejuni

<400> SEQUENCE: 33

```
atgggttttc gtatcaacac caacgtggcg gctctgaacg caaaagcaaa cgcggatctg      60
aacagcaaaa gcctggatgc ttctctgagc cgtctgagct ccggcctgcg tatcaactcc     120
gcagcagatg atgcttccgg gatggcgatc gcagatagcc tgcgttctca ggctaacact     180
ctgggccagg ctatctctaa cggcaacgat gctctgggca tcctgcagac tgctgataaa     240
gctatggacg agcagctgaa aatcctggat accatcaaaa ctaaagcaac ccaggcggct     300
caggatggcc agagcctgaa aacccgtacc atgctgcagg cagatatcaa ccgtctgatg     360
gaagaactgg acaacatcgc aaacactact tcctttaacg gtaaacagct gctgagcggc     420
```

-continued

```
aactttatca accaggaatt tcagatcggc gcaagctcca accagactgt gaaagctact    480
atcggcgcaa ctcagtcttc taaaatcggt ctgacccgct ttgaaaccgg cggccgtatc    540
tccactagcg gcgaagtgca gtttactctg aaaaactaca acggtatcga tgattttcag    600
tttcagaaag tggtgatctc cacttccgtg ggcaccggcc tgggcgctct ggcagatgag    660
atcaacaaaa acgctgataa accggtgtg cgtgctactt ttacagtgga aactcgtggt    720
atcgctgcag tgcgtgcagg cgctacttca gatactttg ctatcaacgg ggtgaaaatc    780
ggcaaagtgg attacaaaga tggcgatgct aacggcgccc tggtggctgc aatcaactcg    840
gtgaaagata ccaccggcgt ggaagcttcg atcgatgcta acggccagct gctgctgact    900
tcccgtgaag gccgtggcat caaaatcgat ggtaacatcg tggcggtgc ctttatcaac    960 gctgatatga agaaaaacta tggccgcctg tctctggtga aaacgatgg taaagatatc   1020 ctgatcagcg gtagcaacct gtcttctgca ggttttggtg caacccagtt tatctctcag   1080
gcttctgtgt ctctgcgtga gtccaaaggc cagatcgatg ctaacatcgc tgatgctatg   1140
ggctttggct ctgcaaacaa aggcgtggtg ctgggtggtt attcttctgt gagcgcctat   1200
atgagcagcg caggcagcgg cttttcttcc ggttccggtt attctgtggg tagcggcaaa   1260
aactattcca ccggttttgc aaacgctatc gctatctccg ctgcttcgca gctgtctacg   1320
gtgtataacg tgtctgcagg ctcaggtttt caagcggtt ccaccctgtc tcagtttgcc   1380
actatgaaaa ccactgcttt tggcgtgaaa gatgaaaccg caggtgtgac caccctgaaa   1440
ggcgctatgg ctgtgatgga tatcgctgaa accgctatca ccaacctgga tcagatccgt   1500
gccgacatcg gctcggtgca gaaccaggtg acatccacta tcaacaacat caccgtgact   1560
caggtgaacg tgaaagcagc agaatcgcag atccgtgatg tggactttgc agccgagagc   1620
gcaaactact ctaaagcaaa catcctggct cagagcggct cttatgccat ggcacaggct   1680
aactctgtgc agcagaacgt gctgcgtctg ctgcagta                          1718
```

<210> SEQ ID NO 34
<211> LENGTH: 571
<212> TYPE: PRT
<213> ORGANISM: Campylobacter jejuni

<400> SEQUENCE: 34

```
Met Gly Phe Arg Ile Asn Thr Asn Val Ala Ala Leu Asn Ala Lys Ala
1               5                   10                  15

Asn Ala Asp Leu Asn Ser Lys Ser Leu Asp Ala Ser Leu Ser Arg Leu
            20                  25                  30

Ser Ser Gly Leu Arg Ile Asn Ser Ala Ala Asp Asp Ala Ser Gly Met
        35                  40                  45

Ala Ile Ala Asp Ser Leu Arg Ser Gln Ala Asn Thr Leu Gly Gln Ala
    50                  55                  60

Ile Ser Asn Gly Asn Asp Ala Leu Gly Ile Leu Gln Thr Ala Asp Lys
65                  70                  75                  80

Ala Met Asp Glu Gln Leu Lys Ile Leu Asp Thr Ile Lys Thr Lys Ala
                85                  90                  95

Thr Gln Ala Ala Gln Asp Gly Gln Ser Leu Lys Thr Arg Thr Met Leu
            100                 105                 110

Gln Ala Asp Ile Asn Arg Leu Met Glu Glu Leu Asp Asn Ile Ala Asn
        115                 120                 125

Thr Thr Ser Phe Asn Gly Lys Gln Leu Leu Ser Gly Asn Phe Ile Asn
    130                 135                 140
```

```
Gln Glu Phe Gln Ile Gly Ala Ser Ser Asn Gln Thr Val Lys Ala Thr
145                 150                 155                 160

Ile Gly Ala Thr Gln Ser Ser Lys Ile Gly Leu Thr Arg Phe Glu Thr
            165                 170                 175

Gly Gly Arg Ile Ser Thr Ser Gly Glu Val Gln Phe Thr Leu Lys Asn
        180                 185                 190

Tyr Asn Gly Ile Asp Asp Phe Gln Phe Gln Lys Val Val Ile Ser Thr
    195                 200                 205

Ser Val Gly Thr Gly Leu Gly Ala Leu Ala Asp Glu Ile Asn Lys Asn
210                 215                 220

Ala Asp Lys Thr Gly Val Arg Ala Thr Phe Thr Val Glu Thr Arg Gly
225                 230                 235                 240

Ile Ala Ala Val Arg Ala Gly Ala Thr Ser Asp Thr Phe Ala Ile Asn
                245                 250                 255

Gly Val Lys Ile Gly Lys Val Asp Tyr Lys Asp Gly Asp Ala Asn Gly
            260                 265                 270

Ala Leu Val Ala Ala Ile Asn Ser Val Lys Asp Thr Thr Gly Val Glu
        275                 280                 285

Ala Ser Ile Asp Ala Asn Gly Gln Leu Leu Thr Ser Arg Glu Gly
290                 295                 300

Arg Gly Ile Lys Ile Asp Gly Asn Ile Gly Gly Ala Phe Ile Asn
305                 310                 315                 320

Ala Asp Met Lys Glu Asn Tyr Gly Arg Leu Ser Leu Val Lys Asn Asp
                325                 330                 335

Gly Lys Asp Ile Leu Ile Ser Gly Ser Asn Leu Ser Ser Ala Gly Phe
            340                 345                 350

Gly Ala Thr Gln Phe Ile Ser Gln Ala Ser Val Ser Leu Arg Glu Ser
        355                 360                 365

Lys Gly Gln Ile Asp Ala Asn Ile Ala Asp Ala Met Gly Phe Gly Ser
    370                 375                 380

Ala Asn Lys Gly Val Val Leu Gly Gly Tyr Ser Ser Val Ser Ala Tyr
385                 390                 395                 400

Met Ser Ser Ala Gly Ser Gly Phe Ser Ser Gly Ser Gly Tyr Ser Val
                405                 410                 415

Gly Ser Gly Lys Asn Tyr Ser Thr Gly Phe Ala Asn Ala Ile Ala Ile
            420                 425                 430

Ser Ala Ala Ser Gln Leu Ser Thr Val Tyr Asn Val Ser Ala Gly Ser
        435                 440                 445

Gly Phe Ser Ser Gly Ser Thr Leu Ser Gln Phe Ala Thr Met Lys Thr
    450                 455                 460

Thr Ala Phe Gly Val Lys Asp Glu Thr Ala Gly Val Thr Thr Leu Lys
465                 470                 475                 480

Gly Ala Met Ala Val Met Asp Ile Ala Glu Thr Ala Ile Thr Asn Leu
                485                 490                 495

Asp Gln Ile Arg Ala Asp Ile Gly Ser Val Gln Asn Val Thr Ser
            500                 505                 510

Thr Ile Asn Asn Ile Thr Val Thr Gln Val Asn Val Lys Ala Ala Glu
        515                 520                 525

Ser Gln Ile Arg Asp Val Asp Phe Ala Ala Glu Ser Ala Asn Tyr Ser
    530                 535                 540

Lys Ala Asn Ile Leu Ala Gln Ser Gly Ser Tyr Ala Met Ala Gln Ala
545                 550                 555                 560
```

Ser Val Gln Gln Asn Val Leu Arg Leu Leu Gln
            565                 570

<210> SEQ ID NO 35
<211> LENGTH: 960
<212> TYPE: DNA
<213> ORGANISM: Campylobacter jejuni

<400> SEQUENCE: 35

```
atgaaaaaaa tcttcctgtg tctgggcctg gcgagcgtgc tgtttggcgc tgacaacaac    60
gtgaaatttg aaatcacccc gaccctgaac tataactact ttgaaggcaa cctggacatg   120
gacaaccgtt atgcgccggg gatccgtctg ggctatcact ttgacgactt ttggctggac   180
cagctggaat ttgggctgga gcactattct gacgtgaaat ataccaacac caacaaaacc   240
accgacatca cccgtaccta tctgagcgct atcaaaggca tcgacgtggg tgagaaattt   300
tatttctatg gcctggcagg cggcggctat gaggactttt ccaacgctgc gtatgacaac   360
aaaagcggcg gctttggcca ctatggcgcg ggcgtgaaat ccgtctgag cgactctctg   420
gctctgcgtc tggaaacccg tgaccagatc aacttcaacc acgcaaacca caactgggtg   480
tccactctgg catcagctt tggctttggc ggcaaaaaag aaaaagctgt ggaagaagtg   540
gctgacaccc gtgcaactcc gcaggccaaa tgtccggtgg aaccgcgtga aggcgctctg   600
ctggacgaaa acggctgcga aaaaaccatc tctctggaag ccactttgg ctttgacaaa   660
accaccatca cccgactttt caggaaaaaa atcaagaaa tcgcaaaagt gctggacgaa   720
aacgaacgtt atgacactat cctggaaggc cacaccgaca catcggctc ccgtgcttat   780
aaccagaaac tgtccgaacg tcgtgctaaa agcgtggcta cgaactgga aaaatatggc   840
gtggaaaaaa gccgcatcaa acagtgggc tatggccagg acaacccgcg ctccagcaac   900
gacaccaaag aaggccgcgc ggacaaccgt cgcgtggacg ctaaatttat cctgcgctaa   960
```

<210> SEQ ID NO 36
<211> LENGTH: 319
<212> TYPE: PRT
<213> ORGANISM: Campylobacter jejuni

<400> SEQUENCE: 36

Met Lys Lys Ile Phe Leu Cys Leu Gly Leu Ala Ser Val Leu Phe Gly
1               5                   10                  15

Ala Asp Asn Asn Val Lys Phe Glu Ile Thr Pro Thr Leu Asn Tyr Asn
            20                  25                  30

Tyr Phe Glu Gly Asn Leu Asp Met Asp Asn Arg Tyr Ala Pro Gly Ile
        35                  40                  45

Arg Leu Gly Tyr His Phe Asp Asp Phe Trp Leu Asp Gln Leu Glu Phe
    50                  55                  60

Gly Leu Glu His Tyr Ser Asp Val Lys Tyr Thr Asn Thr Asn Lys Thr
65                  70                  75                  80

Thr Asp Ile Thr Arg Thr Tyr Leu Ser Ala Ile Lys Gly Ile Asp Val
                85                  90                  95

Gly Glu Lys Phe Tyr Phe Tyr Gly Leu Ala Gly Gly Gly Tyr Glu Asp
            100                 105                 110

Phe Ser Asn Ala Ala Tyr Asp Asn Lys Ser Gly Gly Phe Gly His Tyr
        115                 120                 125

Gly Ala Gly Val Lys Phe Arg Leu Ser Asp Ser Leu Ala Leu Arg Leu
    130                 135                 140

Glu Thr Arg Asp Gln Ile Asn Phe Asn His Ala Asn His Asn Trp Val

```
145                 150                 155                 160
Ser Thr Leu Gly Ile Ser Phe Gly Phe Gly Gly Lys Lys Glu Lys Ala
                165                 170                 175

Val Glu Glu Val Ala Asp Thr Arg Ala Thr Pro Gln Ala Lys Cys Pro
                180                 185                 190

Val Glu Pro Arg Glu Gly Ala Leu Leu Asp Glu Asn Gly Cys Glu Lys
                195                 200                 205

Thr Ile Ser Leu Glu Gly His Phe Gly Phe Asp Lys Thr Thr Ile Asn
                210                 215                 220

Pro Thr Phe Gln Glu Lys Ile Lys Glu Ile Ala Lys Val Leu Asp Glu
225                 230                 235                 240

Asn Glu Arg Tyr Asp Thr Ile Leu Glu Gly His Thr Asp Asn Ile Gly
                245                 250                 255

Ser Arg Ala Tyr Asn Gln Lys Leu Ser Glu Arg Ala Lys Ser Val
                260                 265                 270

Ala Asn Glu Leu Glu Lys Tyr Gly Val Glu Lys Ser Arg Ile Lys Thr
                275                 280                 285

Val Gly Tyr Gly Gln Asp Asn Pro Arg Ser Ser Asn Asp Thr Lys Glu
                290                 295                 300

Gly Arg Ala Asp Asn Arg Arg Val Asp Ala Lys Phe Ile Leu Arg
305                 310                 315

<210> SEQ ID NO 37
<211> LENGTH: 450
<212> TYPE: DNA
<213> ORGANISM: Campylobacter jejuni

<400> SEQUENCE: 37
atgtccgtga ccaaacagct gctgcagatg caggcggacg cgcaccacct gtgggtgaaa      60
ttccacaact accactggaa cgtgaaaggc ctgcagttct tctccatcca cgagtacacc     120
gaaaaagcgt acgaagaaat ggcagaactg ttcgacagct gtgcggaacg tgtgctgcag     180
ctgggcgaaa aagcgatcac ctgccagaaa gtgctgatgg aaaacgcgaa aagcccgaaa     240
gtggcgaaag actgcttcac cccgctggaa gtgatcgaac tgatcaaaca ggactacgaa     300
tacctgctgg cggaattcaa aaaactgaac gaagcggcag aaaaagaaag cgacaccacc     360
accgctgctt tcgcgcagga aaacatcgcg aaatatgaaa aagtctgtg atgatcggc       420 gctaccctgc agggcgcttg caaaatgtaa                                      450

<210> SEQ ID NO 38
<211> LENGTH: 149
<212> TYPE: PRT
<213> ORGANISM: Campylobacter jejuni

<400> SEQUENCE: 38

Met Ser Val Thr Lys Gln Leu Leu Gln Met Gln Ala Asp Ala His His
1               5                   10                  15

Leu Trp Val Lys Phe His Asn Tyr His Trp Asn Val Lys Gly Leu Gln
                20                  25                  30

Phe Phe Ser Ile His Glu Tyr Thr Glu Lys Ala Tyr Glu Glu Met Ala
                35                  40                  45

Glu Leu Phe Asp Ser Cys Ala Glu Arg Val Leu Gln Leu Gly Glu Lys
                50                  55                  60

Ala Ile Thr Cys Gln Lys Val Leu Met Glu Asn Ala Lys Ser Pro Lys
65                  70                  75                  80
```

-continued

```
Val Ala Lys Asp Cys Phe Thr Pro Leu Glu Val Ile Glu Leu Ile Lys
                85                  90                  95

Gln Asp Tyr Glu Tyr Leu Leu Ala Glu Phe Lys Lys Leu Asn Glu Ala
            100                 105                 110

Ala Glu Lys Glu Ser Asp Thr Thr Thr Ala Ala Phe Ala Gln Glu Asn
        115                 120                 125

Ile Ala Lys Tyr Glu Lys Ser Leu Trp Met Ile Gly Ala Thr Leu Gln
    130                 135                 140

Gly Ala Cys Lys Met
145

<210> SEQ ID NO 39
<211> LENGTH: 183
<212> TYPE: DNA
<213> ORGANISM: Campylobacter jejuni

<400> SEQUENCE: 39
atggtttcag atgtttctat gggtaatgtt aatttaatga ctgctgttaa tacttcagtt      60
ttgaaaaaat ctatggacac aaacgaggca ttgatgaatg aactcatcga aggtatggaa     120
ggtgtctctc aagcctccgc tccacaagct tctagctcta gtggtttgga tatttacgct     180
taa                                                                    183

<210> SEQ ID NO 40
<211> LENGTH: 60
<212> TYPE: PRT
<213> ORGANISM: Campylobacter jejuni

<400> SEQUENCE: 40

Met Val Ser Asp Val Ser Met Gly Asn Val Asn Leu Met Thr Ala Val
1               5                   10                  15

Asn Thr Ser Val Leu Lys Lys Ser Met Asp Thr Asn Glu Ala Leu Met
            20                  25                  30

Asn Glu Leu Ile Glu Gly Met Glu Gly Val Ser Gln Ala Ser Ala Pro
        35                  40                  45

Gln Ala Ser Ser Ser Ser Gly Leu Asp Ile Tyr Ala
    50                  55                  60

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Ser or Thr

<400> SEQUENCE: 41

Xaa Xaa Asn Xaa Xaa
```

<210> SEQ ID NO 42
<211> LENGTH: 15612
<212> TYPE: DNA
<213> ORGANISM: Campylobacter jejuni

<400> SEQUENCE: 42

| | | | | | |
|---|---|---|---|---|---|
| ggattacaaa | tggcaaaaaa | tgaaggttat | atttgtgttt | ttgattgtga | gagtgtgcca | 60 |
| gatgttgagc | ttatccgcaa | aactttgggt | tttgaaggaa | gtgatttaga | ggtaagttta | 120 |
| aaagcacttc | agtggcaaaa | agaacaaagt | gggagtgagt | ttttgccttt | gccttatcat | 180 |
| aaaattatca | gtatttgtgc | ggttttaagt | gataatttg | gaaaatttat | caaagtgaat | 240 |
| aaaattgatg | gacaaaatga | aaagaaatg | attgagaatt | ttttcaattt | tatagaaaat | 300 |
| tatgagccaa | aattagtcag | ttttaatggt | aaaaatttcg | atatgcctgt | tcttgtttta | 360 |
| agggctttaa | aatacaattt | aaaagcagca | acttatttgg | atactcaaag | tgataaatgg | 420 |
| aataattata | aaacaagatt | ttcagaatta | aaacattgtg | atttattaga | atccttagga | 480 |
| tctaacgggc | gtggaataaa | gcttgataca | ctttgttcta | tggtgggttt | gccaggaaaa | 540 |
| tatgatgtgc | atggcgatga | ggtaatgaaa | cttttttatg | aaaatacaact | tgaaaaaatc | 600 |
| cacgaatatt | gtgaaagtga | tgttttaaac | acctatatgc | ttttttttaaa | atatgaactt | 660 |
| attaaagcta | atgttgatga | agaagattat | gttggttttc | tttcttatat | gagagatttc | 720 |
| ttgtgtgcaa | aaaatcaga | tcgttcttat | acagaagttt | ttgcaaaagc | ttgtgagagt | 780 |
| gaaatttcaa | aagttcgatc | ttaagtattt | aagaaaatat | attaaaattt | attttttgaca | 840 |
| tttttaaaaa | aaggaatgat | gatgaaaatt | cttattagcg | gtggtgcagg | ttatataggt | 900 |
| tctcatactt | taagacaatt | tttaaaaaca | gatcatgaaa | tttgtgtttt | agataatctt | 960 |
| tctaagggtt | ctaaaatcgc | aatagaagat | ttgcaaaaaa | caagagcttt | taaattttc | 1020 |
| gaacaagatt | taagtgattt | tcaaggcgta | aaagcattgt | ttgagagaga | aaaatttgac | 1080 |
| gctattgtgc | attttgcagc | aagcattgaa | gtttttgaaa | gtatgcaaaa | tcctttaaaa | 1140 |
| tattatatga | acaacactgt | taatacgaca | aatctcatcg | aaacttgttt | gcaaactgga | 1200 |
| gtgaataaat | ttatattttc | ttcaacggcg | gccacttatg | gcgaaccaca | aactcccgtt | 1260 |
| gtgagcgaaa | caagtccttt | agcacctatt | aatccttatg | ggcgtagtaa | gcttatgagt | 1320 |
| gaagaagttt | tgcgtgatgc | aagtatggca | atcctgaat | ttaagcattg | tattttaaga | 1380 |
| tattttaatg | ttgcaggtgc | ttgtatggat | tatactttag | gacaacgcta | tccaaaagcg | 1440 |
| actttgctta | taaaagttgc | agctgaatgt | gccgcaggaa | aacgtgataa | acttttcata | 1500 |
| tttggcgatg | attatgatac | aaaagatggt | acttgcataa | gagattttat | ccatgtagat | 1560 |
| gatatttcaa | gtgcacattt | agcggctttg | gattatttaa | aagagaatga | aagcaatgtt | 1620 |
| tttaatgtag | gttatggaca | tggttttagc | gtaaaagaag | tgattgaagc | gatgaaaaaa | 1680 |
| gttagcggag | tggattttaa | agtagaactt | gccccacgcc | gtgcgggtga | tcctagtgta | 1740 |
| ttgatttctg | atgcaagtaa | aatcagaaat | cttacttctt | ggcagcctaa | atatgatgat | 1800 |
| ttagagctta | tttgtaaatc | tgcttttgat | tgggaaaaac | agtgttaaaa | aaactttttt | 1860 |
| ttatttaag | taaggaagat | aaaaattttt | tatttttctt | gcttgttttt | tcagtattta | 1920 |
| tttcttttat | agaaacttttt | gcaatttctt | tggtaatgcc | ttttatcact | ttggctagtg | 1980 |
| atttttctta | ttttgatcgt | aataaatatt | taatcagcct | aaaagaatat | cttaatatcc | 2040 |
| ctgttttttga | aatcattgtt | tattttggag | tggggcttat | tgttttttat | gtgtttagag | 2100 |

```
ctttgttaaa tgcgtattat tttcatctttt tggcaagatt ttctaaaggg cgttatcatg   2160
cgatcgctta taaggttttt tctaaatttt taaatattaa ttatgaaaaa tttactcaaa   2220
aaaatcaatc tgaaatttta aagtccatta caggggaagt ttataatcta agcactatga   2280
tttcatcatt tttactttttg atgagtgaaa tttttgtagt acttttgctt tatgctttaa   2340
tgcttttgat taattataaa atcactttgt ttttaagtat ttttatggtg ttaaatgcct   2400
ttattttagt gaaaatttta agccctatca ttaaaaaagc aggagtaaga cgcgaagaag   2460
cgatgaaaaa tttctttgaa attttaaata caaatttaaa taatttcaaa tttattaagc   2520
ttaaaaccaa agaagatgga gtattaagtc ttttaaagc gcaaagtgaa gcttttcta    2580
aagcaaatat taccaacgaa agcgtagctg cggtgcctag aatttatctt gaaggaatag   2640
gcttttgcgt acttgttttt atcgtggtat ttttggtttt gaaaaatgaa agtgatattt   2700
caggtatttt atccacgatt tctattttgt tttagcgct ttatcgctta atgccaagtg   2760
caaatcgtat tattacaagt tatcatgatt tgctttatta tcattcttct ttggatatta   2820
tttatcaaaa tttaagacaa gaagaagaaa atttgggcga ggaaaaatta agctttaatc   2880
aagagcttaa aatttgcaat cttagctttg gttatgaggg aaaaaaatat ttatttaaaa   2940
atcttaactt aaatattaaa aaaggcgaaa aaatcgcttt tataggggag agtggttgtg   3000
gaaaaagtac cttagtagat cttatcatag gacttttaaa accaaaagaa gggcaaattt   3060
taattgatga gcaagaatta aatgcaaata atacaaaaaa ttatcgccaa aaaataggct   3120
atatcccgca aaatatctat cttttttaatg acagtatagc taaaaatatc acttttggag   3180
atgcggttga tgaagaaaaa cttaataggg ttatcaaaca agcaaattta gagcatttta   3240
taaaaaattt acctcaagga gtgcaaacaa aagtgggcga tggggggagt aatttaagcg   3300
ggggacaaaa acaacgcata gctatagcaa gagctttata tttagagcct gaaatgttag   3360
tgcttgatga agcaacttct gcgcttgata ctcaaagtga agcaaaaatt atggatgaaa   3420
tttataaaat ttctaaagat aaaaccatga ttattatcgc acatcgcctt tctacgataa   3480
cacaatgtga taaggtttat cgtttagaac acggtaagct taaagaggag aaatgatgaa   3540
aataagcttt attatcgcaa cttttaaattc aggaggtgct gagcgtgctt tagtaacctt   3600
agctaatgca ctttgcaaag agcatgaagt aagtattatt aaatttcatg caggagaatc   3660
ttttttataag cttgaaaatg aagttaaagt tacaagtttg gaacaattta gatttgacac   3720
gctttatcat aaaatcgcaa gtcgttttaa gaatttttt gctttaagaa aggctttgaa   3780
agaaagtaag tctgatgttt ttatttcttt tttggatacg actaatattg cttgtattgc   3840
tgcgaaaata gggcttaaaa ctccactcat tataagtgag catagcaatg aagcgtattt   3900
aaaacctaaa atttggcgtt ttaagaag ggtaagctat ccttttttgtg atgctttaag   3960
tgtgcttgga agcagtgata aggtgtatta tgaaagattt gtaaaagggg ttaagctttt   4020
attaaaccct tgtcattta gcgatgaaat ttctttttgat tctagttttg aaaggaaaa   4080
tttggttctt tttataggg gtttagatca caacaaaaac cctgtaatgt tttaaaagc    4140
tatagcgcat ttggataaaa atttacaaga aaattataaa tttgttatag caggagatgg   4200
acagttaaga caagaacttg aatataaggt aaaatcttta ggaataaaag ttgatttttt   4260
aggacgcgtt gaaaatgtca aggctctta tgaaaaagca aaagtgcttt gcctttgttc   4320
ttttgtagag ggtttgccaa cggttttaat tgaaagtttg tattttgagg tttgtagaat   4380
ttcaagttct tattataatg gtgctaagga tttaatcaaa gataatcatg atgggctttt   4440
```

```
ggtaggttgt gatgatgaaa tagcacttgc taaaaaactt gaacttgttt taaatgatga   4500
aaattttaga aaagaacttg taaataatgc caaacaaagg tgtaaagact ttgaaatttc   4560
tcatatcaaa gaagaatggc ttaagcttat agccgaggtt aaaaatgcct aaactttctg   4620
ttatagtacc aactttttaat cgtcaagttt tgttagaaaa ggctattaaa agcatacaaa   4680
atcaagattt taaagattta gaaattattg taagcgatga taattctagc gatgatacta   4740
aaagtgtggt gcaaaattta caaaaagatg atgatcgcat taagtatttt ttaaatcaaa   4800
attacaaaca aggtccaaat ggcaataaaa acaatggctt agatcaagca agtggcgagt   4860
tgtaactttt tttagatgat gatgatgagc ttttatccgg ggctttaagt accttgatgc   4920
aaaaagcaaa tgagggttat gctcatgttt ttggaaattg tttgatagaa aaagaaggaa   4980
atttaagcaa ggaatttagc ggcaagggct tggaaaaaga tagtgaaatt tctaaaaaag   5040
attttttaat ggctaaattt agcggagagt ttttttctgt ttttaaaaaa tccctacttg   5100
aaaataagcg ttttaatgaa gaattttatg gcaatgaagc cacgctttgg gtaaatttat   5160
acaaagaaaa aagttttttat atccataagg cttttaggat ttatagaatt tttaggcaag   5220
atagcgtgac tttaggggcg agtaaaaatg cttataggggt gtatttggga tatttagagc   5280
ttgctaaaat tttagaaaat gaacttagaa tgagtaagga taaagattat aaaaaaactt   5340
gtgcgagtta ttataaaatg gcagcttatt atgcaaaact tgcaaaaaat tataaagccc   5400
tttataaatg tttgttttaaa agcctaagta taaaaatcaa cgctcctgct ttgatattac   5460
tcattttaag tataattcca aataatatga ttgaaaaatt atcaaaaatt cgggtggctt   5520
tatgcaaaaa ttaggcattt ttatttattc tttaggaagt ggtggtgctg aaagagttgt   5580
ggcgacttta ttgcctattt taagtttgaa atttgaagtg catttgatct tgatgaatga   5640 taaaattttct tatgaaattc cagagtgtca aattcattt ttagaatgtt caaaacctag   5700
tgaaaatcct attttgaaat ttttaaaact acctttttg gctttaaaat acaaaaaact   5760
ttgcagaaat ttaggtattg atacagaatt tgttttttta aatcgaccta attatatagc   5820
tttaatggca agaatgtttg gaaacaaaac tcgccttgtg atcaatgaat gcactacgcc   5880
aagtgtgatg tatatgaaaa ataattttaa ttctttggta aataaatttt taatttcttt   5940 gctttacca aaagctgatt taatcttgcc taattctaag ggaaatttag aagatttagt   6000
gcaaaatttt agtataagtc caaaaaaatg tgaaattttta acaatgcca tcgatttaga   6060 aaacataggg caaaaagccc ttgaagacat agctttaaaa gataaattta ttttaagtgt   6120
aggcaggctt gataaaggta aaaatcatgc tttattaatt cgtgcttatg cgagattgaa   6180
aacagattta aagcttgtga ttttaggtga aggtgtgctt aaggatgagc ttttagcttt   6240
gattaaagaa ttaaatttgg aagaaaaggt tttgctttta ggatttgata taatccttta   6300
taaatacatg gctaaatgcg aatttttgc ttttgcttct gtgtttgaag ttttttcaaa   6360
tgttttaatc gaaagtttgg cttgttcttg tgcggtggtt tgcactgatc ataaaagtgg   6420
tgcaagagag cttttttggcg atgatgaatt tggactttta gtagaagtag ataatgaaaa   6480
ctctatgttt cagggtttaa aaactatgct tgaagacgat aaattaagaa agcgtataa   6540 aaacaaagct aaaactaggg ctaaagcctt tgataaagta aaaattgcac gcgatgcttt   6600
gaaatattta ttaggataaa agatgttgaa aaaagagtat ttaaaaaacc cttatttagt   6660
tttgtttgcg atgattgtat tagcttatgt tttagtgta ttttgcaggt tttattgggt   6720
ttggtgggca agtgagttta acgagtattt tttcaataat caattaatga tcatttcaaa   6780
cgatggctat gcttttgctg agggcgcaag agatatgata gcaggttttc atcagcctaa   6840
```

```
tgatttgagt tattatggat cttctttatc tacgcttact tattggcttt ataaaatcac   6900
acctttttct tttgaaagta tcattttata tatgagtact ttttatctt ctttggtggt   6960 gattcctatt attttactag ctaatgaata caaacgccct ttaatgggct ttgtagctgc   7020
tcttttagca agtgtagcaa acagttatta aatcgcact atgagtgggt attatgatac    7080
ggatatgctg gtaattgttt tacctatgtt tattttattt tttatggtaa gaatgatttt   7140
aaaaaaagac tttttttcat tgattgcctt gccattattt ataggaattt atctttggtg   7200
gtatccttca agttatactt taaatgtagc tttaattgga cttttttaa tttatacact    7260 tattttcat agaaaagaaa agattttta tatagctgtg attttgtctt ctcttactct     7320
ttcaaatata gcatggtttt atcaaagtgc cattatagta atactttttg ctttatttgc   7380
tttagagcaa aaacgcttaa attttatgat tataggaatt ttaggtagtg caactttgat   7440 attttgatt ttaagtggtg gggttgatcc catactttat cagcttaaat tttatatttt   7500
tagaagcgat gaaagtgcga atttaacaca gggctttatg tattttaatg ttaatcaaac   7560
catacaagaa gttgaaaatg tagattttag cgaatttatg cgaagaatta gtggtagtga   7620
aattgttttc ttgttttctt tgtttggttt tgtatggctt ttgagaaaac ataaaagtat   7680
gattatggct ttacctatat tggtgcttgg gttttagcc ttaaaaggag gacttagatt    7740
taccatttat tctgtacctg taatggcttt aggatttggt tttttattga gcgagtttaa   7800
ggctatattg gttaaaaaat atagccaatt aacttcaatg tttgtattgt ttttgcaact   7860
attttgactt tggctccagt atttatccat atttacaact ataaagcgcc aacagttttt   7920
tctcaaaatg aagcatcatt attaaatcaa ttaaaaaata tagccaatag agaagattat   7980
gtggtaactt ggtgggatta tggttatcct gtgcgttatt atagcgatgt gaaaactta    8040 gtagatggtg gaaagcattt aggtaaggat aattttttcc cttctttttc tttaagtaaa   8100
gatgaacaag ctgcagctaa tatggcaaga cttagtgtag aatatacaga aaaaagcttt   8160
tatgctccgc aaaatgatat tttaaaatca gacattttac aagccatgat gaaagattat   8220
aatcaaagca atgtggattt atttctagct tcattatcaa aacctgattt taaaatcgat   8280
acaccaaaaa ctcgtgatat ttatctttat atgcccgcta gaatgtcttt gattttttct   8340
acggtggcta gttttttctt tattaattta gatacaggag ttttggataa accttttacc   8400
tttagcacag cttatccact tgatgttaaa aatggagaaa tttatcttag caacggagtg   8460 gtttaagcg atgattttag aagtttttaaa ataggtgata atgtggtttc tgtaaatagt   8520
atcgtagaga ttaattctat taaacaaggt gaatacaaaa tcactccaat cgatgataag   8580
gctcagtttt atattttta tttaaaggat agtgctattc cttacgcaca atttatttta    8640
atggataaaa ccatgtttaa tagtgcttat gtgcaaatgt tttttttggg aaattatgat   8700
aagaatttat ttgacttggt gattaattct agagatgcta agttttaa acttaaaatt     8760 taagggttga aaatgagaat aggattttta tcacatgcag gagcgagtat ttatcatttt   8820
agaatgccta ttataaaagc gttaaaagat agaaaagacg aagttttgt tatagtgccg    8880 caagatgaat acacgcaaaa acttagagat cttggcttaa aagtaattgt ttatgagttt   8940
tcaagagcta gtttaaatcc ttttgtggtt ttaagaatt ttttttatct tgctaaggtt    9000
ttgaaaaatt taaatcttga ttttattcaa agtgcggcac acaaaagcaa tacttttgga   9060
attttagcag caaaatgggc aaaaattcct tatcgttttg ccttagtaga aggcttggga   9120 tcttttata tagatcaagg ttttaaggca aatttagtgc gttttgttat taatagtctt   9180
```

```
tataaattaa gttttaaatt tgcacaccaa tttattttg tcaatgaaag taatgctgag      9240
tttatgcgga atttaggact taaagaaaat aaaatttgcg tgataaaatc tgtagggatc      9300
aatttaaaaa aattttttcc tatttatgta gaatcggaaa aaaagagct tttttggaaa      9360 aatttaaaca tagataaaaa acccattgtg cttatgatag caagagcttt atggcataag      9420
ggtgtaaaag aattttatga aagtgctact atgctaaaag acaaagcaaa ttttgtttta      9480
gttggtggaa gagatgaaaa tccttcttgt gcaagtttgg agtttttaaa ctctggcgcg      9540
gtgcattatt tgggtgctag aagtgatata gtcgagcttt tgcaaaattg tgatattttt      9600
gttttgccaa gctataaaga aggctttcct gtaagtgttt tggaggcaaa agcttgcggt      9660
aaggctatag tggtgagtga ttgtgaaggt tgtgtggagg ctatttctaa tgcttatgat      9720
ggactttggg caaaaacaaa aaatgctaaa gatttaagcg aaaaaatttc acttttatta      9780
gaagatgaaa aattaagatt aaatttagct aaaaatgccg cccaagatgc tttacaatac      9840
gatgaaaata taatcgcaca gcgttattta aaacttatg ataggtaat taagaatgta      9900 tgaaaaagtt tttaaaagaa ttttttgattt tatttagct ttagtgcttt tagtgctttt      9960
ttctccggtg attttaatca ctgctttact tttaaaaatc actcaaggaa gtgtgatttt      10020
tacccaaaat cgtcccgggt tagataaaa aattttaaa atttataaat ttaaaaccat      10080
gagcgatgaa agagatgaaa agggtgagtt attaagcgat gaattgcgtt tgaaagcttt      10140
tggaaaaatc gttagaagct taagtttgga tgagcttttg caacttttta atgttttaaa      10200
aggggatatg agttttgttg gacctagacc tcttttggtt gagtatttgc ctctttacaa      10260
taaagagcaa aaattgcgtc ataaagtgcg tccaggtata acaggatggg cgcaggtaaa      10320
tggtagaaat gctatttctt ggcagaaaaa attcgaactt gatgtgtatt atgtgaaaaa      10380
tatttctttt ttgcttgatt taaaaatcat gtttttaaca gctttaaagg ttttaaaacg      10440 aagtgggta agcaaagaag gccatgttac aacagagaaa tttaatggca agaactgaaa      10500
aaatttatat ttatggtgct agtggtcatg ggcttgtttg tgaagatgtg gctaaaaata      10560
tgggttataa agaatgtatt tttttagatg attttaaagg aatgaaattt gaaagtacct      10620
tacctaaata tgatttttt atagccatag gaaacaatga aattcgaaaa aagatttatc      10680 aaaaaattc agaaaatggc tttaaaattg tcaatcttat ccataaaagc gcgcttataa      10740
gtcctagcgc aatcgtggaa gaaaatgcag gaattttaat catgccttat gtagtgatta      10800
acgctaaagc taaaatagaa aaaggtgtga ttttaaatac ttcaagcgta attgagcatg      10860
aatgtgtgat agggaattt tctcatgtga gtgtgggagc taaatgtgcg ggtaatgtaa      10920
aaattggtaa aaattgtttt ttagggatta attcttgtgt tttgcctaat ttaagtttgg      10980
cagatgatag tattttaggt ggtggagcaa ctttagttaa aaatcaagat gaaaaaggtg      11040
tttttgtggg agtacctgca aaaaggatgt aaattgcatt ttaataacaa tcttgttgtt      11100
cactatatag taaatccttc gcctttgggg tggattgtca ttaatttact aaccatatgt      11160
ctaatatgct acatatttcc tttgaaaaat tctttaaaac acaaaaaact ttttagtctt      11220
aaagcaaatg taaattctaa aaatagtagg attataaaat atacaggtat tgctgctttt      11280
ttgggtggat taataggaat ttggtataat tttgaaggtt tttatcaact tctttttttc      11340
tttgaattag aaaatgaaaa tttaaaaaca ctttggagtt tgcaagtatc agtttcttct      11400
gtgataacag gtatgttatt attgttgata tatgttataa atttagcaat ggtttgtgaa      11460
aatgaaattt atatagttag taaatttaat cttttttata tgtatttat aaaacgagaa      11520 gatttggaaa ttgttaaaat agaaaaaatg aaattttaa atcaagttga agtttgtttt      11580
```

```
gttatcaaaa caaaaaataa aatactcctt aaatgctttg aaagtattta taaaaaagaa    11640
gacttagaaa agcttaaaaa ttggtatgaa aacaagcttt gactataaaa agaatttaaa    11700
tatttgaatc tttgtaaatt tttttaggta aaatagagtc aatttataaa aattttgttt    11760
tacacaaagg ataaatcatg agattttttc tttctcctcc gcatatgggt ggtaatgaat    11820
taaaatacat agaagaagtt ttcaaaagca attatatagc acctttgggt gaatttgtaa    11880
atcgctttga acaaagtgtc aaggcttaca gtaaaagtga aaatgcctta gctttaaatt    11940
cagccacagc ggctttgcat ttagctttaa gggtggcagg ggtaaaacaa gatgatattg    12000
ttttggcttc ttcttttact tttatcgctt cagtagcacc tatttgttat cttaaagcaa    12060
aacctgtatt tatagattgt gatgaaactt ataatatcga tgtagattta ttaaagcttg    12120
ctattaaaga atgtgaaaaa aaaccaaaag cattgatttt aactcatctt tatggcaatg    12180
cggctaaaat ggatgaaatt gttgaaattt gcaaagaaaa tgaaattgtt ttaatcgaag    12240
atgctgctga agcttaggaa agtttttata agaataaagc tttaggaact tttggagaat    12300
ttggagctta ttcttataat ggcaataaaa ttatcaccac ttcaggtgga ggtatgctta    12360
taggaaaaaa taagaaaaag attgaaaaag caagattta tagcactcaa gctagggaaa     12420
attgtttgca ttatgaacat ttagattatg gttataatta ccgcttaagc aatgttttag    12480
gagctattgg cgtagcgcaa atggaggttt tagaacaaag agtgcttaaa aaaagagaaa    12540
tttatgagtg gtataaagaa ttttttaggag agtgttttag cttttagat gaattagaaa     12600 attcaagaag caatcgctgg ttaagtacag ctttgattga ttttgataaa aatgaactta    12660
attcttgtca aaagatata aatatcagtc aaaaaaatat tactttgcat ccaaaaattt      12720
caaaactcat agaagatttg aaaaatgaac aaatagaaac aagaccatta tggaaagcta    12780
tgcacgctca agaagtattt aaaggagcta aggcttatct taatggcaat agtgagttat    12840
ttttccaaaa aggaatttgt ttgccaagtg gcacggcgat gagtaaagat gatgtttatg    12900
aaatttcaaa actgatctta aagagcataa aggcttaaaa tgatttttta taaaagcaaa    12960
agattagcat ttttttttaac ttcagatatt gttttaattt tacttagcgt ttatctggct   13020
ttttctttga gatttagtgg agatattccg agtattttt atcatggtat gatggtttct    13080
gctattattt tgcttgtttt aaaactttca tttttgtttg tttttagaat ttataaagta    13140
gcttggagat ttttttctct caatgaagca agaaagattt ttatcgcttt gcttttagct   13200
gagttttgtt ttttttcttat ttttttatttt tttagtgatt ttttaatcc tttttccaaga   13260 agtgctattg tgatagattt tgttctttct tatatgttta taggtacttt aagaattagc    13320
aaaagaatgc ttgtggattt taaaccttct agaatgaaag aagaagaaac tccttgtatt    13380
gtagtagggg caacttctaa ggctttgcat ttgttaaaag gtgcaaaaga aggttcttta    13440 gggcttttc ctgtaggcgt agttgatgcg agaaaagagc ttatagggac ttattgtgat    13500
aaatttattg tagaagaaaa agaaaaaata aaatcttatg tagaacaagg ggtaaaaact   13560
gccattattg ctttaagact tgaacaagaa gagcttaaaa aactttttga agaacttgta    13620
gcttatggta tttgcgatgt aaaaatattt tcttttacaa gaaacgaagc aagagatatc    13680
agtatagaag acttgcttgc tagaaaacca aaagatttag atgatagtgc tgtggcggct    13740
tttttaaaag ataaggtagt tttggtaagt ggagcaggtg gaactatagg cagtgaactt    13800
tgtaagcaat gtattaaatt tggtgctaag catcttatca tggttgatca tagtgagtat    13860
aatctttata agatcaatga tgatttaaat ttatataaag aaaaaattac tcctatttta    13920
```

```
ctgagtattt tagataagca aagtttagat gaggtattaa aaacttataa acccgagctt    13980
attttacatg cagccgctta taaacatgtg cctctttgcg aacaaaatcc acattcagca    14040
gtaatcaata atattttagg aactaaaatt ttatgcgaca gtgctaaaga aaacaaagta    14100
gctaaatttg tgatgataag tacagataaa gcagtacgac caacaaatat tatgggttgc    14160
actaagagag tttgcgagct ttatacttta agtatgagtg atgaaaattt tgaagttgct    14220
tgtgtgcgtt ttggtaatgt tttaggttct agtggtagtg tgataccgaa atttaaagca    14280
caaattgcca ataatgagcc tttaacttta acgcaccctg atatagtgcg ttattttatg    14340
cttgtggctg aggcagtgca acttgtttta caagctggag ctatcgcaaa aggggggagaa    14400 cttttttgttt tggatatggg taagcctgtg aaaatcatag atttagctaa aaaaatgctt    14460
ttactttcta atcgcaatga tttagaaatt aaaatcacag cttaagaaa aggtgagaag    14520 ctttatgaag agcttttgat tgatgaaaat gatgctaaaa cacaatatga gagtattttt    14580
gtagcaaaga atgagaaggt tgaccttgat tggcttaata aagagataga aaatttacaa    14640
atatgtgaag atatttcaga ggcttttatta aagattgtac ctgaatttaa acacaataaa    14700
gaaggtgtat aatgtatata aaagatatac aaagatttga agataatcgc tatcgtgcta    14760
gagcttatat gagttatatt ttaacaagaa atctgcccaa taaacttcct gacattcacc    14820
ttgaaacgat taaaacagct ttggataaaa tagctcatga agttgttgtt tttgatgctt    14880
tgtatatttt agatatttca ggcatgcaaa tagaaaatgc gatttcctta aataaagctc    14940
atgaaatagg gcagggtgag gatagaagta ctcgttctta ttttttataga gctgtaaaat    15000 taagacgatg tgttttgagc gatcctatc cttcggttt aaataatgag ctttgcgtga    15060
cagcttctat gccaatttac gatgataaaa ataacttgct ttttgttgtt tgtattgata    15120
tcaagcttga agatatttta aagattattc aagcaggaaa atttgaattt gttttttactc    15180 agtttagtcg tttggtatat ttttgcttcg cactggttt atttgtgatt acttgttttt    15240
tatttcaaaa aggttttttt agtcttttg ataatcaagc tataggtata gaacatatgt    15300
ttgaaagtac catcgctata actttggctt tagctatttt tgatttggca aaaactttga    15360
tcgaacaaga agtattagga aggacgaaaa aagaagaagg tggaattcaa aaaactatgg    15420
tgagattttt gggttctatt atcattgctt tagctataga agctttgatg ttggtatta    15480 aacttgctat tggtgatctt tctcagatga tttatgcgat ttatcttatc ggtggagtga    15540
gcttgcttct tttaggttta agtgtatatt tatttacggt taagtataaa aataataata    15600
tttgaactta gt                                                       15612
```

<210> SEQ ID NO 43
<211> LENGTH: 795
<212> TYPE: DNA
<213> ORGANISM: Campylobacter jejuni

<400> SEQUENCE: 43

```
atggcaaaaa atgaaggtta tatttgtgtt tttgattgtg agagtgtgcc agatgttgag     60
cttatccgca aaactttggg ttttgaagga agtgatttag aggtaagttt aaaagcactt    120
cagtggcaaa agaacaaag tgggagtgag ttttgcctt tgccttatca taaaattatc    180
agtatttgtg cggtttaag tgataatttt ggaaaattta tcaaagtgaa taaaattgat    240
ggacaaaatg aaaagaaat gattgagaat ttttcaatt ttatagaaaa ttatgagcca    300
aaattagtca gttttaatgg taaaaatttc gatatgcctg ttcttgtttt aagggcttta    360
aaatacaatt taaaagcagc aacttatttg gatactcaaa gtgataaatg gaataattat    420
```

```
aaaacaagat ttcagaatt aaaacattgt gatttattag aatccttagg atctaacggg      480
cgtggaataa agcttgatac actttgttct atggtgggtt tgccaggaaa atatgatgtg      540
catggcgatg aggtaatgaa acttttttat gaaaataaac ttgaaaaaat ccacgaatat      600
tgtgaaagtg atgttttaaa cacctatatg ctttttttaa aatatgaact tattaaagct      660
aatgttgatg aagaagatta tgttggtttt ctttcttata tgagagattt cttgtgtgca      720
aaaaaatcag atcgttctta tacagaagtt tttgcaaaag cttgtgagag tgaaatttca      780
aaagttcgat cttaa                                                      795
```

<210> SEQ ID NO 44
<211> LENGTH: 264
<212> TYPE: PRT
<213> ORGANISM: Campylobacter jejuni

<400> SEQUENCE: 44

```
Met Ala Lys Asn Glu Gly Tyr Ile Cys Val Phe Asp Cys Glu Ser Val
1               5                   10                  15

Pro Asp Val Glu Leu Ile Arg Lys Thr Leu Gly Phe Glu Gly Ser Asp
            20                  25                  30

Leu Glu Val Ser Leu Lys Ala Leu Gln Trp Gln Lys Glu Gln Ser Gly
        35                  40                  45

Ser Glu Phe Leu Pro Leu Pro Tyr His Lys Ile Ile Ser Ile Cys Ala
    50                  55                  60

Val Leu Ser Asp Asn Phe Gly Lys Phe Ile Lys Val Asn Lys Ile Asp
65                  70                  75                  80

Gly Gln Asn Glu Lys Glu Met Ile Glu Asn Phe Phe Asn Phe Ile Glu
                85                  90                  95

Asn Tyr Glu Pro Lys Leu Val Ser Phe Asn Gly Lys Asn Phe Asp Met
            100                 105                 110

Pro Val Leu Val Leu Arg Ala Leu Lys Tyr Asn Leu Lys Ala Ala Thr
        115                 120                 125

Tyr Leu Asp Thr Gln Ser Asp Lys Trp Asn Asn Tyr Lys Thr Arg Phe
    130                 135                 140

Ser Glu Leu Lys His Cys Asp Leu Leu Glu Ser Leu Gly Ser Asn Gly
145                 150                 155                 160

Arg Gly Ile Lys Leu Asp Thr Leu Cys Ser Met Val Gly Leu Pro Gly
                165                 170                 175

Lys Tyr Asp Val His Gly Asp Glu Val Met Lys Leu Phe Tyr Glu Asn
            180                 185                 190

Lys Leu Glu Lys Ile His Glu Tyr Cys Glu Ser Asp Val Leu Asn Thr
        195                 200                 205

Tyr Met Leu Phe Leu Lys Tyr Glu Leu Ile Lys Ala Asn Val Asp Glu
    210                 215                 220

Glu Asp Tyr Val Gly Phe Leu Ser Tyr Met Arg Asp Phe Leu Cys Ala
225                 230                 235                 240

Lys Lys Ser Asp Arg Ser Tyr Thr Glu Val Phe Ala Lys Ala Cys Glu
                245                 250                 255

Ser Glu Ile Ser Lys Val Arg Ser
            260
```

<210> SEQ ID NO 45
<211> LENGTH: 654
<212> TYPE: DNA
<213> ORGANISM: Campylobacter jejuni

<400> SEQUENCE: 45

```
atgaaaaagg tgtttttgtg ggagtacctg caaaaaggat gtaaattgca tttttaataac    60
aatcttgttg ttcactatat agtaaatcct tcgcctttgg ggtggattgt cattaattta   120
ctaaccatat gtctaatatg ctacatattt cctttgaaaa attctttaaa acacaaaaaa   180
cttttagtc ttaaagcaaa tgtaaattct aaaaatagta ggattataaa atatacaggt    240
attgctgctt ttttgggtgg attaatagga atttggtata attttgaagg ttttatcaa   300
cttctttttt tctttgaatt agaaatgaa aatttaaaaa cactttggag tttgcaagta    360
tcagtttctt ctgtgataac aggtatgtta ttattgttga tatatgttat aaatttagca    420
atggtttgtg aaaatggaat ttatatagtt agtaaattta atcttttta tatgtatttt     480
ataaaacgag aagatttgga aattgttaaa atagaaaaaa tgaaattttt aaatcaagtt    540
gaagtttgtt ttgttatcaa aacaaaaaat aaaatactcc ttaaatgctt tgaaagtatt    600
tataaaaaag aagacttaga aaagcttaaa aattggtatg aaaacaagct ttga         654
```

<210> SEQ ID NO 46
<211> LENGTH: 217
<212> TYPE: PRT
<213> ORGANISM: Campylobacter jejuni

<400> SEQUENCE: 46

```
Met Lys Lys Val Phe Leu Trp Glu Tyr Leu Gln Lys Gly Cys Lys Leu
1               5                   10                  15
His Phe Asn Asn Asn Leu Val Val His Tyr Ile Val Asn Pro Ser Pro
            20                  25                  30
Leu Gly Trp Ile Val Ile Asn Leu Leu Thr Ile Cys Leu Ile Cys Tyr
        35                  40                  45
Ile Phe Pro Leu Lys Asn Ser Leu Lys His Lys Lys Leu Phe Ser Leu
    50                  55                  60
Lys Ala Asn Val Asn Ser Lys Asn Ser Arg Ile Ile Lys Tyr Thr Gly
65                  70                  75                  80
Ile Ala Ala Phe Leu Gly Gly Leu Ile Gly Ile Trp Tyr Asn Phe Glu
                85                  90                  95
Gly Phe Tyr Gln Leu Leu Phe Phe Glu Leu Glu Asn Glu Asn Leu
            100                 105                 110
Lys Thr Leu Trp Ser Leu Gln Val Ser Val Ser Ser Val Ile Thr Gly
        115                 120                 125
Met Leu Leu Leu Ile Tyr Val Ile Asn Leu Ala Met Val Cys Glu
    130                 135                 140
Asn Gly Ile Tyr Ile Val Ser Lys Phe Asn Leu Phe Tyr Met Tyr Phe
145                 150                 155                 160
Ile Lys Arg Glu Asp Leu Glu Ile Val Lys Ile Glu Lys Met Lys Phe
                165                 170                 175
Leu Asn Gln Val Glu Val Cys Phe Val Ile Lys Thr Lys Asn Lys Ile
            180                 185                 190
Leu Leu Lys Cys Phe Glu Ser Ile Tyr Lys Lys Glu Asp Leu Glu Lys
        195                 200                 205
Leu Lys Asn Trp Tyr Glu Asn Lys Leu
    210                 215
```

<210> SEQ ID NO 47
<211> LENGTH: 993
<212> TYPE: DNA

<213> ORGANISM: Campylobacter jejuni

<400> SEQUENCE: 47

```
atgatgatga aaattcttat tagcggtggt gcaggttata taggttctca tactttaaga      60
caattttaa aaacagatca tgaaatttgt gttttagata tctttctaa gggttctaaa       120
atcgcaatag aagatttgca aaaacaaga gcttttaaat ttttcgaaca agatttaagt      180
gattttcaag gcgtaaaagc attgtttgag agagaaaaat ttgacgctat tgtgcatttt      240
gcagcaagca ttgaagtttt tgaaagtatg caaaatcctt aaaatatta tatgaacaac      300
actgttaata cgacaaatct catcgaaact tgtttgcaaa ctggagtgaa taaatttata      360
ttttcttcaa cggcggccac ttatggcgaa ccacaaactc ccgttgtgag cgaaacaagt      420
cctttagcac ctattaatcc ttatgggcgt agtaagctta tgagtgaaga agtttttgcgt      480
gatgcaagta tggcaaatcc tgaatttaag cattgtattt taagatattt taatgttgca      540
ggtgcttgta tggattatac tttaggacaa cgctatccaa aagcgacttt gcttataaaa      600
gttgcagctg aatgtgccgc aggaaaacgt gataaacttt tcatatttgg cgatgattat      660
gatacaaaag atggtacttg cataagagat tttatccatg tagatgatat ttcaagtgca      720
catttagcgg ctttggatta tttaaaagag aatgaaagca atgttttaa tgtaggttat      780
ggacatggtt ttagcgtaaa agaagtgatt gaagcgatga aaaagttag cggagtggat      840
tttaaagtag aacttgcccc acgccgtgcg ggtgatccta tgtattgat ttctgatgca      900
agtaaaatca gaaatcttac ttcttggcag cctaaatatg atgatttaga gcttatttgt      960
aaatctgctt ttgattggga aaaacagtgt taa                                  993
```

<210> SEQ ID NO 48
<211> LENGTH: 330
<212> TYPE: PRT
<213> ORGANISM: Campylobacter jejuni

<400> SEQUENCE: 48

```
Met Met Met Lys Ile Leu Ile Ser Gly Gly Ala Gly Tyr Ile Gly Ser
1               5                   10                  15

His Thr Leu Arg Gln Phe Leu Lys Thr Asp His Glu Ile Cys Val Leu
            20                  25                  30

Asp Asn Leu Ser Lys Gly Ser Lys Ile Ala Ile Glu Asp Leu Gln Lys
        35                  40                  45

Thr Arg Ala Phe Lys Phe Phe Glu Gln Asp Leu Ser Asp Phe Gln Gly
    50                  55                  60

Val Lys Ala Leu Phe Glu Arg Glu Lys Phe Asp Ala Ile Val His Phe
65                  70                  75                  80

Ala Ala Ser Ile Glu Val Phe Glu Ser Met Gln Asn Pro Leu Lys Tyr
                85                  90                  95

Tyr Met Asn Asn Thr Val Asn Thr Thr Asn Leu Ile Glu Thr Cys Leu
            100                 105                 110

Gln Thr Gly Val Asn Lys Phe Ile Phe Ser Ser Thr Ala Ala Thr Tyr
        115                 120                 125

Gly Glu Pro Gln Thr Pro Val Val Ser Glu Thr Ser Pro Leu Ala Pro
    130                 135                 140

Ile Asn Pro Tyr Gly Arg Ser Lys Leu Met Ser Glu Glu Val Leu Arg
145                 150                 155                 160

Asp Ala Ser Met Ala Asn Pro Glu Phe Lys His Cys Ile Leu Arg Tyr
                165                 170                 175
```

-continued

```
Phe Asn Val Ala Gly Ala Cys Met Asp Tyr Thr Leu Gly Gln Arg Tyr
            180                 185                 190

Pro Lys Ala Thr Leu Leu Ile Lys Val Ala Ala Glu Cys Ala Ala Gly
        195                 200                 205

Lys Arg Asp Lys Leu Phe Ile Phe Gly Asp Asp Tyr Asp Thr Lys Asp
    210                 215                 220

Gly Thr Cys Ile Arg Asp Phe Ile His Val Asp Asp Ile Ser Ser Ala
225                 230                 235                 240

His Leu Ala Ala Leu Asp Tyr Leu Lys Glu Asn Glu Ser Asn Val Phe
                245                 250                 255

Asn Val Gly Tyr Gly His Gly Phe Ser Val Lys Glu Val Ile Glu Ala
            260                 265                 270

Met Lys Lys Val Ser Gly Val Asp Phe Lys Val Glu Leu Ala Pro Arg
        275                 280                 285

Arg Ala Gly Asp Pro Ser Val Leu Ile Ser Asp Ala Ser Lys Ile Arg
    290                 295                 300

Asn Leu Thr Ser Trp Gln Pro Lys Tyr Asp Asp Leu Glu Leu Ile Cys
305                 310                 315                 320

Lys Ser Ala Phe Asp Trp Glu Lys Gln Cys
                325                 330

<210> SEQ ID NO 49
<211> LENGTH: 1594
<212> TYPE: DNA
<213> ORGANISM: Campylobacter jejuni
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (182)..(182)
<223> OTHER INFORMATION: a, c, t, g, unknown or other
<220> FEATURE:
<221> NAME/KEY: modified_base
<222> LOCATION: (303)..(303)
<223> OTHER INFORMATION: a, c, t, g, unknown or other
<220> FEATURE:
<221> NAME/KEY: modified_base
<222> LOCATION: (424)..(424)
<223> OTHER INFORMATION: a, c, t, g, unknown or other
<220> FEATURE:
<221> NAME/KEY: modified_base
<222> LOCATION: (545)..(545)
<223> OTHER INFORMATION: a, c, t, g, unknown or other
<220> FEATURE:
<221> NAME/KEY: modified_base
<222> LOCATION: (666)..(666)
<223> OTHER INFORMATION: a, c, t, g, unknown or other
<220> FEATURE:
<221> NAME/KEY: modified_base
<222> LOCATION: (787)..(787)
<223> OTHER INFORMATION: a, c, t, g, unknown or other
<220> FEATURE:
<221> NAME/KEY: modified_base
<222> LOCATION: (908)..(908)
<223> OTHER INFORMATION: a, c, t, g, unknown or other
<220> FEATURE:
<221> NAME/KEY: modified_base
<222> LOCATION: (1029)..(1029)
<223> OTHER INFORMATION: a, c, t, g, unknown or other
<220> FEATURE:
<221> NAME/KEY: modified_base
<222> LOCATION: (1150)..(1150)
<223> OTHER INFORMATION: a, c, t, g, unknown or other
<220> FEATURE:
<221> NAME/KEY: modified_base
<222> LOCATION: (1271)..(1271)
<223> OTHER INFORMATION: a, c, t, g, unknown or other
```

<220> FEATURE:
<221> NAME/KEY: modified_base
<222> LOCATION: (1392)..(1392)
<223> OTHER INFORMATION: a, c, t, g, unknown or other
<220> FEATURE:
<221> NAME/KEY: modified_base
<222> LOCATION: (1513)..(1513)
<223> OTHER INFORMATION: a, c, t, g, unknown or other

<400> SEQUENCE: 49

| | | | | | |
|---|---|---|---|---|---|
| atgccttta | tcactttggc | tagtgatttt | tcttatttg | atcgtaataa | atatttaatc | 60 |
| nagcctaaaa | gaatatctta | atatccctgt | ttttgaaatc | attgttatt | ttggagtggg | 120 |
| gcttattgtt | tttatgtgt | ttagagcttt | gttaaatgcg | tattattttc | atcttttggc | 180 |
| anagattttc | taaagggcgt | tatcatgcga | tcgcttataa | ggttttttct | aaattttaa | 240 |
| atattaatta | tgaaaatt | actcaaaaa | atcaatctga | aatttaaag | tccattacag | 300 |
| ggngaagttt | ataatctaag | cactatgatt | tcatcatttt | tacttttgat | gagtgaaatt | 360 |
| tttgtagtac | ttttgcttta | tgctttaatg | cttttgatta | attataaaat | cactttgttt | 420 |
| ttanagtatt | tttatggtgt | taaatgcctt | tattttagtg | aaaattttaa | gccctatcat | 480 |
| taaaaaagca | ggagtaagac | gcgaagaagc | gatgaaaaat | ttctttgaaa | ttttaaatac | 540 |
| aaatnttaaa | taatttcaaa | tttattaagc | ttaaaaccaa | agaagatgga | gtattaagtc | 600 |
| ttttaaagc | gcaaagtgaa | gctttttcta | aagcaaatat | taccaacgaa | agcgtagctg | 660 |
| cggtgnccta | gaatttatct | tgaaggaata | ggcttttgcg | tacttgtttt | tatcgtggta | 720 |
| ttttggttt | tgaaaaatga | aagtgatatt | tcaggtattt | tatccacgat | ttctattttt | 780 |
| gttttangcg | ctttatcgct | taatgccaag | tgcaaatcgt | attattacaa | gttatcatga | 840 |
| tttgctttat | tatcattctt | ctttggatat | tatttatcaa | aatttaagac | aagaagaaga | 900 |
| aaatttgngg | cgaggaaaaa | ttaagcttta | atcaagagct | taaaatttgc | aatcttagct | 960 |
| ttggttatga | gggaaaaaaa | tatttattta | aaaatcttaa | cttaaatatt | aaaaaaggcg | 1020 |
| aaaaaatcng | cttttatagg | ggagagtggt | tgtggaaaaa | gtaccttagt | agatcttatc | 1080 |
| ataggacttt | taaaaccaaa | agaagggcaa | atttaattg | atgagcaaga | attaaatgca | 1140 |
| aataatacan | aaaaattatc | gccaaaaaat | aggctatatc | ccgcaaaata | tctatctttt | 1200 |
| taatgacagt | atagctaaaa | atatcacttt | tggagatgcg | gttgatgaag | aaaaacttaa | 1260 |
| tagggttatc | naaacaagca | aatttagagc | attttataaa | aaatttaccct | caaggagtgc | 1320 |
| aaacaaaagt | gggcgatggg | gggagtaatt | taagcggggg | acaaaaacaa | cgcatagcta | 1380 |
| tagcaagagc | tnttatattt | agagcctgaa | atgttagtgc | ttgatgaagc | aacttctgcg | 1440 |
| cttgatactc | aaagtgaagc | aaaaattatg | gatgaaattt | ataaaatttc | taaagataaa | 1500 |
| accatgatta | ttnatcgcac | atcgccttc | tacgataaca | caatgtgata | aggtttatcg | 1560 |
| tttagaacac | ggtaagctta | aagaggagaa | atga | | | 1594 |

<210> SEQ ID NO 50
<211> LENGTH: 526
<212> TYPE: PRT
<213> ORGANISM: Campylobacter jejuni

<400> SEQUENCE: 50

Met Pro Phe Ile Thr Leu Ala Ser Asp Phe Ser Tyr Phe Asp Arg Asn
1               5                   10                  15

Lys Tyr Leu Ile Ser Leu Lys Glu Tyr Leu Asn Ile Pro Val Phe Glu
            20                  25                  30

-continued

```
Ile Ile Val Tyr Phe Gly Val Gly Leu Ile Val Phe Tyr Val Phe Arg
            35                  40                  45
Ala Leu Leu Asn Ala Tyr Tyr Phe His Leu Leu Ala Arg Phe Ser Lys
 50                  55                  60
Gly Arg Tyr His Ala Ile Ala Tyr Lys Val Phe Ser Lys Phe Leu Asn
 65                  70                  75                  80
Ile Asn Tyr Glu Lys Phe Thr Gln Lys Asn Gln Ser Glu Ile Leu Lys
                 85                  90                  95
Ser Ile Thr Gly Glu Val Tyr Asn Leu Ser Thr Met Ile Ser Ser Phe
                100                 105                 110
Leu Leu Leu Met Ser Glu Ile Phe Val Val Leu Leu Leu Tyr Ala Leu
                115                 120                 125
Met Leu Leu Ile Asn Tyr Lys Ile Thr Leu Phe Leu Ser Ile Phe Met
    130                 135                 140
Val Leu Asn Ala Phe Ile Leu Val Lys Ile Leu Ser Pro Ile Ile Lys
145                 150                 155                 160
Lys Ala Gly Val Arg Arg Glu Glu Ala Met Lys Asn Phe Phe Glu Ile
                165                 170                 175
Leu Asn Thr Asn Leu Asn Asn Phe Lys Phe Ile Lys Leu Lys Thr Lys
                180                 185                 190
Glu Asp Gly Val Leu Ser Leu Phe Lys Ala Gln Ser Glu Ala Phe Ser
                195                 200                 205
Lys Ala Asn Ile Thr Asn Glu Ser Val Ala Ala Val Pro Arg Ile Tyr
    210                 215                 220
Leu Glu Gly Ile Gly Phe Cys Val Leu Val Phe Ile Val Val Phe Leu
225                 230                 235                 240
Val Leu Lys Asn Glu Ser Asp Ile Ser Gly Ile Leu Ser Thr Ile Ser
                245                 250                 255
Ile Phe Val Leu Ala Leu Tyr Arg Leu Met Pro Ser Ala Asn Arg Ile
                260                 265                 270
Ile Thr Ser Tyr His Asp Leu Leu Tyr Tyr His Ser Ser Leu Asp Ile
    275                 280                 285
Ile Tyr Gln Asn Leu Arg Gln Glu Glu Glu Asn Leu Gly Glu Glu Lys
    290                 295                 300
Leu Ser Phe Asn Gln Glu Leu Lys Ile Cys Asn Leu Ser Phe Gly Tyr
305                 310                 315                 320
Glu Gly Lys Lys Tyr Leu Phe Lys Asn Leu Asn Leu Asn Ile Lys Lys
                325                 330                 335
Gly Glu Lys Ile Ala Phe Ile Gly Glu Ser Gly Cys Gly Lys Ser Thr
    340                 345                 350
Leu Val Asp Leu Ile Ile Gly Leu Leu Lys Pro Lys Glu Gly Gln Ile
    355                 360                 365
Leu Ile Asp Glu Gln Glu Leu Asn Ala Asn Asn Thr Lys Asn Tyr Arg
    370                 375                 380
Gln Lys Ile Gly Tyr Ile Pro Gln Asn Ile Tyr Leu Phe Asn Asp Ser
385                 390                 395                 400
Ile Ala Lys Asn Ile Thr Phe Gly Asp Ala Val Asp Glu Glu Lys Leu
                405                 410                 415
Asn Arg Val Ile Lys Gln Ala Asn Leu Glu His Phe Ile Lys Asn Leu
                420                 425                 430
Pro Gln Gly Val Gln Thr Lys Val Gly Asp Gly Gly Ser Asn Leu Ser
                435                 440                 445
Gly Gly Gln Lys Gln Arg Ile Ala Ile Ala Arg Ala Leu Tyr Leu Glu
```

```
                  450                 455                 460
Pro Glu Met Leu Val Leu Asp Glu Ala Thr Ser Ala Leu Asp Thr Gln
465                 470                 475                 480

Ser Glu Ala Lys Ile Met Asp Glu Ile Tyr Lys Ile Ser Lys Asp Lys
                485                 490                 495

Thr Met Ile Ile Ile Ala His Arg Leu Ser Thr Ile Thr Gln Cys Asp
                500                 505                 510

Lys Val Tyr Arg Leu Glu His Gly Lys Leu Lys Glu Glu Lys
                515                 520                 525

<210> SEQ ID NO 51
<211> LENGTH: 1062
<212> TYPE: DNA
<213> ORGANISM: Campylobacter jejuni

<400> SEQUENCE: 51
aaaataagct ttattatcgc aactttaaat tcaggaggtg ctgagcgtgc tttagtaacc      60
ttagctaatg cactttgcaa agagcatgaa gtaagtatta ttaaatttca tgcaggagaa     120 tcttttttata agcttgaaaa tgaagttaaa gttacaagtt tggaacaatt tagatttgac    180
acgctttatc ataaaatcgc aagtcgtttt aagaaatttt ttgctttaag aaaggctttg     240
aaagaaagta agtctgatgt ttttatttct ttttggata cgactaatat tgcttgtatt      300
gctgcgaaaa tagggcttaa aactccactc attataagtg agcatagcaa tgaagcgtat    360
ttaaaaccta aaatttggcg ttttttaaga agggtaagct atccttttg tgatgcttta     420 agtgtgcttg aagcagtga taaggtgtat tatgaaagat ttgtaaaaag ggttaagctt     480
ttattaaacc cttgtcattt tagcgatgaa atttcttttg attctagttt tgaaaaggaa   540
aatttggttc ttttttatagg gcgtttagat cacaacaaaa accctgtaat gtttttaaaa   600
gctatagcgc atttggataa aaatttacaa gaaaattata aatttgttat agcaggagat    660
ggacagttaa gacaagaact tgaatataag gtaaatcctt taggaataaa agttgatttt    720
ttaggacgcg ttgaaaatgt caaggctctt tatgaaaaag caaagtgct tgcctttgt      780 tcttttgtag aggggttttgcc aacggtttta attgaaagtt tgtatttga ggtttgtaga    840 atttcaagtt cttattataa tggtgctaag gatttaatca agataatca tgatgggctt    900 ttggtaggtt gtgatgatga atagcactt gctaaaaaac ttgaacttgt tttaaatgat    960 gaaaattttta gaaagaact tgtaaataat gccaaacaaa ggtgtaaaga ctttgaaatt  1020
tctcatatca agaagaatg gcttaagctt atagccgagg tt                      1062

<210> SEQ ID NO 52
<211> LENGTH: 354
<212> TYPE: PRT
<213> ORGANISM: Campylobacter jejuni

<400> SEQUENCE: 52

Lys Ile Ser Phe Ile Ile Ala Thr Leu Asn Ser Gly Gly Ala Glu Arg
1               5                   10                  15

Ala Leu Val Thr Leu Ala Asn Ala Leu Cys Lys Glu His Glu Val Ser
                20                  25                  30

Ile Ile Lys Phe His Ala Gly Glu Ser Phe Tyr Lys Leu Glu Asn Glu
                35                  40                  45

Val Lys Val Thr Ser Leu Glu Gln Phe Arg Phe Asp Thr Leu Tyr His
                50                  55                  60

Lys Ile Ala Ser Arg Phe Lys Lys Phe Phe Ala Leu Arg Lys Ala Leu
```

```
              65                  70                  75                  80
Lys Glu Ser Lys Ser Asp Val Phe Ile Ser Phe Leu Asp Thr Thr Asn
                    85                  90                  95
Ile Ala Cys Ile Ala Ala Lys Ile Gly Leu Lys Thr Pro Leu Ile Ile
                100                 105                 110
Ser Glu His Ser Asn Glu Ala Tyr Leu Lys Pro Lys Ile Trp Arg Phe
                115                 120                 125
Leu Arg Arg Val Ser Tyr Pro Phe Cys Asp Ala Leu Ser Val Leu Gly
            130                 135                 140
Ser Ser Asp Lys Val Tyr Tyr Glu Arg Phe Val Lys Arg Val Lys Leu
145                 150                 155                 160
Leu Leu Asn Pro Cys His Phe Ser Asp Glu Ile Ser Phe Asp Ser Ser
                165                 170                 175
Phe Glu Lys Glu Asn Leu Val Leu Phe Ile Gly Arg Leu Asp His Asn
                180                 185                 190
Lys Asn Pro Val Met Phe Leu Lys Ala Ile Ala His Leu Asp Lys Asn
            195                 200                 205
Leu Gln Glu Asn Tyr Lys Phe Val Ile Ala Gly Asp Gly Gln Leu Arg
    210                 215                 220
Gln Glu Leu Glu Tyr Lys Val Lys Ser Leu Gly Ile Lys Val Asp Phe
225                 230                 235                 240
Leu Gly Arg Val Glu Asn Val Lys Ala Leu Tyr Glu Lys Ala Lys Val
                245                 250                 255
Leu Cys Leu Cys Ser Phe Val Glu Gly Leu Pro Thr Val Leu Ile Glu
                260                 265                 270
Ser Leu Tyr Phe Glu Val Cys Arg Ile Ser Ser Ser Tyr Tyr Asn Gly
            275                 280                 285
Ala Lys Asp Leu Ile Lys Asp Asn His Asp Gly Leu Leu Val Gly Cys
            290                 295                 300
Asp Asp Glu Ile Ala Leu Ala Lys Lys Leu Glu Leu Val Leu Asn Asp
305                 310                 315                 320
Glu Asn Phe Arg Lys Glu Leu Val Asn Asn Ala Lys Gln Arg Cys Lys
                325                 330                 335
Asp Phe Glu Ile Ser His Ile Lys Glu Glu Trp Leu Lys Leu Ile Ala
            340                 345                 350
Glu Val

<210> SEQ ID NO 53
<211> LENGTH: 911
<212> TYPE: DNA
<213> ORGANISM: Campylobacter jejuni

<400> SEQUENCE: 53
atgcctaaac tttctgttat agtaccaact tttaatcgtc aagttttgtt agaaaaggct     60
attaaaagca tacaaaatca agattttaaa gatttagaaa ttattgtaag cgatgataat    120
tctagcgatg atactaaaag tgtggtgcaa aatttacaaa aagatgatga tcgcattaag    180
tattttttaa atcaaaatta caacaaggt ccaaatggca ataaaaacaa tggcttagat    240
caagcaagtg gcgagtttgt aactttttta gatgatgatg atgagctttt atccggggct    300
ttaagtacct tgatgcaaaa agcaaatgag ggttatgctc atgttttggg aaattgtttg    360
atagaaaaag aaggaaattt aagcaaggaa tttagcggca agggcttgga aaagatagt    420 gaaatttcta aaaagagttt ttaatggct aaatttagcg gagagttttt ttctgttttt    480
```

```
aaaaaatccc tacttgaaaa taagcgtttt aatgaagaat tttatggcaa tgaagccacg    540
ctttgggtaa atttatacaa agaaaaaagt ttttatatcc ataaggcttt taggattat     600 agaatttta ggcaagatag cgtgactta ggggcgagta aaaatgctta tagggtgtat      660
ttggatattt agagcttgct aaaattttag aaaatgaact tagaatgagt aaggataaag    720
attataaaaa aacttgtgcg agttattata aaatggcagc ttattatgca aaacttgcaa    780
aaaattataa agccctttat aaatgtttgt ttaaaagcct aagtataaaa atcaacgctc    840
ctgctttgat attactcatt ttaagtataa ttccaaataa tatgattgaa aaattatcaa    900
aaattcgggt g                                                        911
```

```
<210> SEQ ID NO 54
<211> LENGTH: 304
<212> TYPE: PRT
<213> ORGANISM: Campylobacter jejuni

<400> SEQUENCE: 54
```

```
Met Pro Lys Leu Ser Val Ile Val Pro Thr Phe Asn Arg Gln Val Leu
1               5                   10                  15

Leu Glu Lys Ala Ile Lys Ser Ile Gln Asn Gln Asp Phe Lys Asp Leu
            20                  25                  30

Glu Ile Ile Val Ser Asp Asp Asn Ser Ser Asp Thr Lys Ser Val
        35                  40                  45

Val Gln Asn Leu Gln Lys Asp Asp Arg Ile Lys Tyr Phe Leu Asn
    50                  55                  60

Gln Asn Tyr Lys Gln Gly Pro Asn Gly Asn Lys Asn Gly Leu Asp
65                  70                  75                  80

Gln Ala Ser Gly Glu Phe Val Thr Phe Leu Asp Asp Asp Glu Leu
                85                  90                  95

Leu Ser Gly Ala Leu Ser Thr Leu Met Gln Lys Ala Asn Glu Gly Tyr
            100                 105                 110

Ala His Val Phe Gly Asn Cys Leu Ile Glu Lys Glu Gly Asn Leu Ser
        115                 120                 125

Lys Glu Phe Ser Gly Lys Gly Leu Glu Lys Asp Ser Glu Ile Ser Lys
    130                 135                 140

Lys Asp Phe Leu Met Ala Lys Phe Ser Gly Glu Phe Phe Ser Val Phe
145                 150                 155                 160

Lys Lys Ser Leu Leu Glu Asn Lys Arg Phe Asn Glu Glu Phe Tyr Gly
                165                 170                 175

Asn Glu Ala Thr Leu Trp Val Asn Leu Tyr Lys Glu Lys Ser Phe Tyr
            180                 185                 190

Ile His Lys Ala Phe Arg Ile Tyr Arg Ile Phe Arg Gln Asp Ser Val
        195                 200                 205

Thr Leu Gly Ala Ser Lys Asn Ala Tyr Arg Val Tyr Leu Gly Tyr Leu
    210                 215                 220

Glu Leu Ala Lys Ile Leu Glu Asn Glu Leu Arg Met Ser Lys Asp Lys
225                 230                 235                 240

Asp Tyr Lys Lys Thr Cys Ala Ser Tyr Tyr Lys Met Ala Ala Tyr Tyr
                245                 250                 255

Ala Lys Leu Ala Lys Asn Tyr Lys Ala Leu Tyr Lys Cys Leu Phe Lys
            260                 265                 270

Ser Leu Ser Ile Lys Ile Asn Ala Pro Ala Leu Ile Leu Leu Ile Leu
        275                 280                 285

Ser Ile Ile Pro Asn Asn Met Ile Glu Lys Leu Ser Lys Ile Arg Val
```

<210> SEQ ID NO 55
<211> LENGTH: 1089
<212> TYPE: DNA
<213> ORGANISM: Campylobacter jejuni

<400> SEQUENCE: 55

```
ttaggcattt ttatttattc tttaggaagt ggtggtgctg aaagagttgt ggcgacttta      60
ttgcctattt taagtttgaa atttgaagtg catttgatct tgatgaatga taaaatttct     120
tatgaaattc cagagtgtca aattcatttt ttagaatgtt caaaacctag tgaaaatcct     180
attttgaaat ttttaaaact accttttttg gctttaaaat acaaaaaact ttgcagaaat     240
ttaggtattg atacagaatt tgttttttta aatcgaccta attatatagc tttaatggca     300
agaatgtttg gaaacaaaac tcgccttgtg atcaatgaat gcactacgcc aagtgtgatg     360
tatatgaaaa ataattttaa ttctttggta ataaaatttt taatttcttt gctttaccca     420
aaagctgatt taatcttgcc taattctaag ggaaatttag aagattagt gcaaaatttt       480
agtataagtc aaaaaaatg tgaaatttta tacaatgcca tcgatttaga aaacataggg     540
caaaaagccc ttgaagacat agctttaaaa gataaattta ttttaagtgt aggcaggctt     600
gataaaggta aaaatcatgc tttattaatt cgtgcttatg cgagattgaa acagattta      660
aagcttgtga tttaggtga aggtgtgctt aaggatgagc tttagccttt gattaaagaa     720
ttaaatttgg aagaaaaggt tttgcttta ggatttgata ataatcctta taaatacatg      780
gctaaatgcg aattttttgc ttttgcttct gtgtttgaag ttttttcaaa tgttttaatc     840
gaaagtttgg cttgttcttg tgcggtggtt tgcactgatc ataaaagtgg tgcaagagag     900
cttttttggcg atgatgaatt tggactttta gtagaagtag ataatgaaaa ctctatgttt     960
cagggtttaa aaactatgct tgaagacgat aaattaagaa aagcgtataa aaacaaagct    1020
aaaactaggg ctaaagcctt tgataaagta aaaattgcac gcgatgcttt gaaatattta    1080
ttaggataa                                                            1089
```

<210> SEQ ID NO 56
<211> LENGTH: 362
<212> TYPE: PRT
<213> ORGANISM: Campylobacter jejuni

<400> SEQUENCE: 56

```
Leu Gly Ile Phe Ile Tyr Ser Leu Gly Ser Gly Gly Ala Glu Arg Val
1               5                  10                  15

Val Ala Thr Leu Leu Pro Ile Leu Ser Leu Lys Phe Glu Val His Leu
            20                  25                  30

Ile Leu Met Asn Asp Lys Ile Ser Tyr Glu Ile Pro Glu Cys Gln Ile
        35                  40                  45

His Phe Leu Glu Cys Ser Lys Pro Ser Glu Asn Pro Ile Leu Lys Phe
    50                  55                  60

Leu Lys Leu Pro Phe Leu Ala Leu Lys Tyr Lys Lys Leu Cys Arg Asn
65                  70                  75                  80

Leu Gly Ile Asp Thr Glu Phe Val Phe Leu Asn Arg Pro Asn Tyr Ile
                85                  90                  95

Ala Leu Met Ala Arg Met Phe Gly Asn Lys Thr Arg Leu Val Ile Asn
            100                 105                 110

Glu Cys Thr Thr Pro Ser Val Met Tyr Met Lys Asn Asn Phe Asn Ser
        115                 120                 125
```

```
Leu Val Asn Lys Phe Leu Ile Ser Leu Leu Tyr Pro Lys Ala Asp Leu
    130                 135                 140

Ile Leu Pro Asn Ser Lys Gly Asn Leu Glu Asp Leu Val Gln Asn Phe
145                 150                 155                 160

Ser Ile Ser Pro Lys Lys Cys Glu Ile Leu Tyr Asn Ala Ile Asp Leu
                165                 170                 175

Glu Asn Ile Gly Gln Lys Ala Leu Glu Asp Ile Ala Leu Lys Asp Lys
                180                 185                 190

Phe Ile Leu Ser Val Gly Arg Leu Asp Lys Gly Lys Asn His Ala Leu
            195                 200                 205

Leu Ile Arg Ala Tyr Ala Arg Leu Lys Thr Asp Leu Lys Leu Val Ile
    210                 215                 220

Leu Gly Glu Gly Val Leu Lys Asp Glu Leu Leu Ala Leu Ile Lys Glu
225                 230                 235                 240

Leu Asn Leu Glu Glu Lys Val Leu Leu Leu Gly Phe Asp Asn Asn Pro
                245                 250                 255

Tyr Lys Tyr Met Ala Lys Cys Glu Phe Ala Phe Ala Ser Val Phe
                260                 265                 270

Glu Gly Phe Ser Asn Val Leu Ile Glu Ser Leu Ala Cys Ser Cys Ala
            275                 280                 285

Val Val Cys Thr Asp His Lys Ser Gly Ala Arg Glu Leu Phe Gly Asp
    290                 295                 300

Asp Glu Phe Gly Leu Leu Val Glu Val Asp Asn Glu Asn Ser Met Phe
305                 310                 315                 320

Gln Gly Leu Lys Thr Met Leu Glu Asp Asp Lys Leu Arg Lys Ala Tyr
                325                 330                 335

Lys Asn Lys Ala Lys Thr Arg Ala Lys Ala Phe Asp Lys Val Lys Ile
                340                 345                 350

Ala Arg Asp Ala Leu Lys Tyr Leu Leu Gly
            355                 360

<210> SEQ ID NO 57
<211> LENGTH: 2142
<212> TYPE: DNA
<213> ORGANISM: Campylobacter jejuni

<400> SEQUENCE: 57
atgttgaaaa aagagtattt aaaaaaccct tatttagttt tgtttgcgat gattgtatta      60
gcttatgttt ttagtgtatt ttgcaggttt tattgggttt ggtgggcaag tgagtttaac     120
gagtattttt tcaataatca attaatgatc atttcaaacg atggctatgc ttttgctgag     180
ggcgcaagag atatgatagc aggttttcat cagcctaatg atttgagtta ttatggatct     240
tctttatcta cgcttactta ttggctttat aaaatcacac cttttctctt tgaaagtatc     300
attttatata tgagtacttt tttatcttct ttggtggtga ttcctattat tttactagct     360
aatgaataca aacgcccttt aatgggcttt gtagctgctc ttttagcaag tgtagcaaac     420
agttattata tcgcactat gagtgggtat tatgatacgg atatgctggt aattgtttta     480
cctatgttta ttttattttt tatggtaaga atgattttaa aaaagactt ttttcattg      540 attgccttgc cattatttat aggaatttat ctttggtggt atccttcaag ttatactta      600 aatgtagctt taattggact ttttttaatt tatacactta ttttcatag aaaagaaaag     660 atttttata tagctgtgat tttgtcttct cttactcttt caaatatagc atggtttat      720 caaagtgcca ttatagtaat acttttttgct ttatttgctt tagagcaaaa acgcttaaat     780
```

```
tttatgatta taggaattttt aggtagtgca actttgatat ttttgatttt aagtggtggg    840
gttgatccca tactttatca gcttaaattt tatattttta gaagcgatga aagtgcgaat    900
ttaacacagg gctttatgta ttttaatgtt aatcaaacca tacaagaagt tgaaaatgta    960
gattttagcg aatttatgcg aagaattagt ggtagtgaaa ttgttttctt gttttctttg   1020
tttggttttg tatggctttt gagaaaacat aaaagtatga ttatggcttt acctatattg   1080
gtgcttgggt tttagccttt aaaaggagga cttagattta ccatttattc tgtacctgta   1140
atggctttag gatttggttt tttattgagc gagtttaagg ctatattggt taaaaaatat   1200
agccaattaa cttcaaatgt ttgtattgtt tttgcaacta ttttgacttt ggctccagta   1260
tttatccata tttacaacta taaagcgcca acagtttttt ctcaaaatga agcatcatta   1320
ttaaatcaat taaaaaatat agccaataga aagattatg tggtaacttg gtgggattat    1380
ggttatcctg tgcgttatta tagcgatgtg aaaactttag tagatggtgg aaagcattta   1440
ggtaaggata atttttcccc ttcttttttct ttaagtaaag atgaacaagc tgcagctaat   1500
atggcaagac ttagtgtaga atatacagaa aaaagctttt atgctccgca aatgatatt   1560
ttaaaatcag acatttttaca agccatgatg aaagattata tcaaagcaa tgtggattta   1620
tttctagctt cattatcaaa acctgatttt aaaatcgata caccaaaaac tcgtgatatt   1680
tatctttata tgcccgctag aatgtctttg attttttcta cggtggctag tttttctttt   1740
attaatttag atacaggagt tttggataaa ccttttacct ttagcacagc ttatccactt   1800
gatgttaaaa atggagaaat ttatcttagc aacggagtgg ttttaagcga tgatttttaga   1860
agttttaaaa taggtgataa tgtggtttct gtaaatagta tcgtagagat taattctatt   1920
aaacaaggtg aatacaaaat cactccaatc gatgataagg ctcagtttta tatttttat   1980
ttaaaggata gtgctattcc ttacgcacaa tttatttttaa tggataaaac catgtttaat   2040
agtgcttatg tgcaaatgtt ttttttggga aattatgata agaatttatt tgacttggtg   2100
attaattcta gagatgctaa agttttttaaa cttaaaattt aa                     2142
```

<210> SEQ ID NO 58
<211> LENGTH: 712
<212> TYPE: PRT
<213> ORGANISM: Campylobacter jejuni

<400> SEQUENCE: 58

```
Met Leu Lys Lys Glu Tyr Leu Lys Asn Pro Tyr Leu Val Leu Phe Ala
1               5                   10                  15

Met Ile Val Leu Ala Tyr Val Phe Ser Val Phe Cys Arg Phe Tyr Trp
            20                  25                  30

Val Trp Trp Ala Ser Glu Phe Asn Glu Tyr Phe Asn Asn Gln Leu
        35                  40                  45

Met Ile Ile Ser Asn Asp Gly Tyr Ala Phe Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Thr Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Ile Ile Leu Leu Ala Asn Glu Tyr Lys Arg Pro Leu Met
        115                 120                 125
```

-continued

```
Gly Phe Val Ala Ala Leu Leu Ala Ser Val Ala Asn Ser Tyr Tyr Asn
            130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                    165                 170                 175

Phe Phe Ser Leu Ile Ala Leu Pro Leu Phe Ile Gly Ile Tyr Leu Trp
                180                 185                 190

Trp Tyr Pro Ser Ser Tyr Thr Leu Asn Val Ala Leu Ile Gly Leu Phe
            195                 200                 205

Leu Ile Tyr Thr Leu Ile Phe His Arg Lys Glu Lys Ile Phe Tyr Ile
210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                    245                 250                 255

Lys Arg Leu Asn Phe Met Ile Ile Gly Ile Leu Gly Ser Ala Thr Leu
                260                 265                 270

Ile Phe Leu Ile Leu Ser Gly Gly Val Asp Pro Ile Leu Tyr Gln Leu
            275                 280                 285

Lys Phe Tyr Ile Phe Arg Ser Asp Glu Ser Ala Asn Leu Thr Gln Gly
290                 295                 300

Phe Met Tyr Phe Asn Val Asn Gln Thr Ile Gln Glu Val Glu Asn Val
305                 310                 315                 320

Asp Phe Ser Glu Phe Met Arg Arg Ile Ser Gly Ser Glu Ile Val Phe
                    325                 330                 335

Leu Phe Ser Leu Phe Gly Phe Val Trp Leu Leu Arg Lys His Lys Ser
                340                 345                 350

Met Ile Met Ala Leu Pro Ile Leu Val Leu Gly Phe Leu Ala Leu Lys
            355                 360                 365

Gly Gly Leu Arg Phe Thr Ile Tyr Ser Val Pro Val Met Ala Leu Gly
370                 375                 380

Phe Gly Phe Leu Leu Ser Glu Phe Lys Ala Ile Leu Val Lys Lys Tyr
385                 390                 395                 400

Ser Gln Leu Thr Ser Asn Val Cys Ile Val Phe Ala Thr Ile Leu Thr
                    405                 410                 415

Leu Ala Pro Val Phe Ile His Ile Tyr Asn Tyr Lys Ala Pro Thr Val
                420                 425                 430

Phe Ser Gln Asn Glu Ala Ser Leu Leu Asn Gln Leu Lys Asn Ile Ala
            435                 440                 445

Asn Arg Glu Asp Tyr Val Val Thr Trp Trp Asp Tyr Gly Tyr Pro Val
450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ser Leu Ser Lys Asp Glu Gln
                    485                 490                 495

Ala Ala Asn Met Ala Arg Leu Ser Val Glu Tyr Thr Glu Lys Ser Phe
                500                 505                 510

Tyr Ala Pro Gln Asn Asp Ile Leu Lys Ser Asp Ile Leu Gln Ala Met
            515                 520                 525

Met Lys Asp Tyr Asn Gln Ser Asn Val Asp Leu Phe Leu Ala Ser Leu
530                 535                 540

Ser Lys Pro Asp Phe Lys Ile Asp Thr Pro Lys Thr Arg Asp Ile Tyr
```

```
                545                 550                 555                 560
Leu Tyr Met Pro Ala Arg Met Ser Leu Ile Phe Ser Thr Val Ala Ser
                        565                 570                 575

Phe Ser Phe Ile Asn Leu Asp Thr Gly Val Leu Asp Lys Pro Phe Thr
                580                 585                 590

Phe Ser Thr Ala Tyr Pro Leu Asp Val Lys Asn Gly Glu Ile Tyr Leu
            595                 600                 605

Ser Asn Gly Val Val Leu Ser Asp Asp Phe Arg Ser Phe Lys Ile Gly
        610                 615                 620

Asp Asn Val Val Ser Val Asn Ser Ile Val Glu Ile Asn Ser Ile Lys
625                 630                 635                 640

Gln Gly Glu Tyr Lys Ile Thr Pro Ile Asp Asp Lys Ala Gln Phe Tyr
                645                 650                 655

Ile Phe Tyr Leu Lys Asp Ser Ala Ile Pro Tyr Ala Gln Phe Ile Leu
                660                 665                 670

Met Asp Lys Thr Met Phe Asn Ser Ala Tyr Val Gln Met Phe Phe Leu
                675                 680                 685

Gly Asn Tyr Asp Lys Asn Leu Phe Asp Leu Val Ile Asn Ser Arg Asp
            690                 695                 700

Ala Lys Val Phe Lys Leu Lys Ile
705                 710

<210> SEQ ID NO 59
<211> LENGTH: 1128
<212> TYPE: DNA
<213> ORGANISM: Campylobacter jejuni

<400> SEQUENCE: 59
atgagaatag atttttatc acatgcagga gcgagtattt atcattttag aatgcctatt      60
ataaaagcgt taaagatag aaaagacgaa gttttgtta tagtgccgca agatgaatac     120
acgcaaaaac ttagagatct tggcttaaaa gtaattgttt atgagttttc aagagctagt     180
ttaaatcctt ttgtggtttt aaagaatttt ttttatcttg ctaaggtttt gaaaaattta     240
aatcttgatt ttattcaaag tgcggcacac aaaagcaata cttttggaat tttagcagca     300
aaatgggcaa aaattcctta tcgttttgcc ttagtagaag gcttgggatc ttttttatata    360 gatcaaggtt ttaaggcaaa tttagtgcgt tttgttatta atagtcttta taaattaagt     420
tttaaatttg cacaccaatt tattttgtc aatgaaagta atgctgagtt tatgcggaat      480
ttaggactta agaaaataa aatttgcgtg ataaaatctg tagggatcaa tttaaaaaaa     540
tttttcccta tttatgtaga atcggaaaaa aaagagcttt tttggaaaaa tttaaacata     600
gataaaaaac ccattgtgct tatgatagca agagctttat ggcataaggg tgtaaaagaa     660
ttttatgaaa gtgctactat gctaaaagac aaagcaaatt ttgttttagt tggtggaaga     720
gatgaaaatc cttcttgtgc aagtttggag tttttaaact ctggcgcggt gcattatttg     780
ggtgctagaa gtgatatagt cgagcttttg caaaattgtg atattttgt tttgccaagc     840 tataaagaag gctttcctgt aagtgttttg gaggcaaaag cttgcggtaa ggctatagtg     900
gtgagtgatt gtgaaggttg tgtggaggct atttctaatg cttatgatgg actttgggca    960
aaaacaaaaa atgctaaaga tttaagcgaa aaaatttcac ttttattaga agatgaaaaa    1020
ttaagattaa atttagctaa aaatgccgcc caagatgctt tacaatacga tgaaaatata    1080
atcgcacagc gttattaaa actttatgat agggtaatta agaatgta                  1128
```

<210> SEQ ID NO 60
<211> LENGTH: 376
<212> TYPE: PRT
<213> ORGANISM: Campylobacter jejuni

<400> SEQUENCE: 60

| Met | Arg | Ile | Gly | Phe | Leu | Ser | His | Ala | Gly | Ala | Ser | Ile | Tyr | His | Phe |
| 1 | | | | 5 | | | | | 10 | | | | | 15 | |

| Arg | Met | Pro | Ile | Ile | Lys | Ala | Leu | Lys | Asp | Arg | Lys | Asp | Glu | Val | Phe |
| | | | 20 | | | | | 25 | | | | | 30 | | |

| Val | Ile | Val | Pro | Gln | Asp | Glu | Tyr | Thr | Gln | Lys | Leu | Arg | Asp | Leu | Gly |
| | | 35 | | | | | 40 | | | | | 45 | | | |

| Leu | Lys | Val | Ile | Val | Tyr | Glu | Phe | Ser | Arg | Ala | Ser | Leu | Asn | Pro | Phe |
| | 50 | | | | | 55 | | | | | 60 | | | | |

| Val | Val | Leu | Lys | Asn | Phe | Phe | Tyr | Leu | Ala | Lys | Val | Leu | Lys | Asn | Leu |
| 65 | | | | | 70 | | | | | 75 | | | | | 80 |

| Asn | Leu | Asp | Phe | Ile | Gln | Ser | Ala | Ala | His | Lys | Ser | Asn | Thr | Phe | Gly |
| | | | | 85 | | | | | 90 | | | | | 95 | |

| Ile | Leu | Ala | Ala | Lys | Trp | Ala | Lys | Ile | Pro | Tyr | Arg | Phe | Ala | Leu | Val |
| | | | 100 | | | | | 105 | | | | | 110 | | |

| Glu | Gly | Leu | Gly | Ser | Phe | Tyr | Ile | Asp | Gln | Gly | Phe | Lys | Ala | Asn | Leu |
| | | 115 | | | | | 120 | | | | | 125 | | | |

| Val | Arg | Phe | Val | Ile | Asn | Ser | Leu | Tyr | Lys | Leu | Ser | Phe | Lys | Phe | Ala |
| | 130 | | | | | 135 | | | | | 140 | | | | |

| His | Gln | Phe | Ile | Phe | Val | Asn | Glu | Ser | Asn | Ala | Glu | Phe | Met | Arg | Asn |
| 145 | | | | | 150 | | | | | 155 | | | | | 160 |

| Leu | Gly | Leu | Lys | Glu | Asn | Lys | Ile | Cys | Val | Ile | Lys | Ser | Val | Gly | Ile |
| | | | | 165 | | | | | 170 | | | | | 175 | |

| Asn | Leu | Lys | Lys | Phe | Phe | Pro | Ile | Tyr | Val | Glu | Ser | Glu | Lys | Lys | Glu |
| | | | 180 | | | | | 185 | | | | | 190 | | |

| Leu | Phe | Trp | Lys | Asn | Leu | Asn | Ile | Asp | Lys | Lys | Pro | Ile | Val | Leu | Met |
| | | 195 | | | | | 200 | | | | | 205 | | | |

| Ile | Ala | Arg | Ala | Leu | Trp | His | Lys | Gly | Val | Lys | Glu | Phe | Tyr | Glu | Ser |
| | 210 | | | | | 215 | | | | | 220 | | | | |

| Ala | Thr | Met | Leu | Lys | Asp | Lys | Ala | Asn | Phe | Val | Leu | Val | Gly | Gly | Arg |
| 225 | | | | | 230 | | | | | 235 | | | | | 240 |

| Asp | Glu | Asn | Pro | Ser | Cys | Ala | Ser | Leu | Glu | Phe | Leu | Asn | Ser | Gly | Ala |
| | | | | 245 | | | | | 250 | | | | | 255 | |

| Val | His | Tyr | Leu | Gly | Ala | Arg | Ser | Asp | Ile | Val | Glu | Leu | Leu | Gln | Asn |
| | | | 260 | | | | | 265 | | | | | 270 | | |

| Cys | Asp | Ile | Phe | Val | Leu | Pro | Ser | Tyr | Lys | Glu | Gly | Phe | Pro | Val | Ser |
| | | 275 | | | | | 280 | | | | | 285 | | | |

| Val | Leu | Glu | Ala | Lys | Ala | Cys | Gly | Lys | Ala | Ile | Val | Val | Ser | Asp | Cys |
| | 290 | | | | | 295 | | | | | 300 | | | | |

| Glu | Gly | Cys | Val | Glu | Ala | Ile | Ser | Asn | Ala | Tyr | Asp | Gly | Leu | Trp | Ala |
| 305 | | | | | 310 | | | | | 315 | | | | | 320 |

| Lys | Thr | Lys | Asn | Ala | Lys | Asp | Leu | Ser | Glu | Lys | Ile | Ser | Leu | Leu | Leu |
| | | | | 325 | | | | | 330 | | | | | 335 | |

| Glu | Asp | Glu | Lys | Leu | Arg | Leu | Asn | Leu | Ala | Lys | Asn | Ala | Ala | Gln | Asp |
| | | | 340 | | | | | 345 | | | | | 350 | | |

| Ala | Leu | Gln | Tyr | Asp | Glu | Asn | Ile | Ile | Ala | Gln | Arg | Tyr | Leu | Lys | Leu |
| | | 355 | | | | | 360 | | | | | 365 | | | |

| Tyr | Asp | Arg | Val | Ile | Lys | Asn | Val |
| | 370 | | | | | 375 | |

<210> SEQ ID NO 61
<211> LENGTH: 597
<212> TYPE: DNA
<213> ORGANISM: Campylobacter jejuni

<400> SEQUENCE: 61

| | | | | | |
|---|---|---|---|---|---|
| gaaaaagttt | ttaaaagaat | ttttgatttt | attttatctt | tagtgctttt | agtgctttt | 60 |
| tctccggtga | ttttaatcac | tgctttactt | ttaaaaatca | ctcaaggaag | tgtgattttt | 120 |
| acccaaaatc | gtcccggggtt | agatgaaaaa | attttttaaaa | tttataaatt | taaaaccatg | 180 |
| agcgatgaaa | gagatgaaaa | gggtgagtta | ttaagcgatg | aattgcgttt | gaaagctttt | 240 |
| ggaaaaatcg | ttagaagctt | aagtttggat | gagcttttgc | aacttttttaa | tgttttaaaa | 300 |
| ggggatatga | gttttgttgg | acctagacct | cttttggttg | agtatttgcc | tcttacaat | 360 |
| aaagagcaaa | aattgcgtca | taaagtgcgt | ccaggtataa | caggatgggc | gcaggtaaat | 420 |
| ggtagaaatg | ctatttcttg | gcagaaaaaa | ttcgaacttg | atgtgtatta | tgtgaaaaat | 480 |
| atttcttttt | tgcttgattt | aaaaatcatg | tttttaacag | ctttaaaggt | tttaaaacga | 540 |
| agtggggtaa | gcaaagaagg | ccatgttaca | acagagaaat | ttaatggcaa | gaactga | 597 |

<210> SEQ ID NO 62
<211> LENGTH: 198
<212> TYPE: PRT
<213> ORGANISM: Campylobacter jejuni

<400> SEQUENCE: 62

Glu Lys Val Phe Lys Arg Ile Phe Asp Phe Ile Leu Ser Leu Val Leu
1               5                   10                  15

Leu Val Leu Phe Ser Pro Val Ile Leu Ile Thr Ala Leu Leu Leu Lys
            20                  25                  30

Ile Thr Gln Gly Ser Val Ile Phe Thr Gln Asn Arg Pro Gly Leu Asp
        35                  40                  45

Glu Lys Ile Phe Lys Ile Tyr Lys Phe Lys Thr Met Ser Asp Glu Arg
    50                  55                  60

Asp Glu Lys Gly Glu Leu Leu Ser Asp Glu Leu Arg Leu Lys Ala Phe
65                  70                  75                  80

Gly Lys Ile Val Arg Ser Leu Ser Leu Asp Glu Leu Leu Gln Leu Phe
                85                  90                  95

Asn Val Leu Lys Gly Asp Met Ser Phe Val Gly Pro Arg Pro Leu Leu
            100                 105                 110

Val Glu Tyr Leu Pro Leu Tyr Asn Lys Glu Gln Lys Leu Arg His Lys
        115                 120                 125

Val Arg Pro Gly Ile Thr Gly Trp Ala Gln Val Asn Gly Arg Asn Ala
    130                 135                 140

Ile Ser Trp Gln Lys Lys Phe Glu Leu Asp Val Tyr Tyr Val Lys Asn
145                 150                 155                 160

Ile Ser Phe Leu Leu Asp Leu Lys Ile Met Phe Leu Thr Ala Leu Lys
                165                 170                 175

Val Leu Lys Arg Ser Gly Val Ser Lys Glu Gly His Val Thr Thr Glu
            180                 185                 190

Lys Phe Asn Gly Lys Asn
        195

<210> SEQ ID NO 63
<211> LENGTH: 588
<212> TYPE: DNA

<213> ORGANISM: Campylobacter jejuni

<400> SEQUENCE: 63

```
atggcaagaa ctgaaaaaat ttatatttat ggtgctagtg gtcatgggct tgtttgtgaa      60
gatgtggcta aaatatgggt tataaagaa tgtattttttt tagatgattt taaaggaatg    120
aaatttgaaa gtaccttacc taaatatgat tttttttatag ccataggaaa caatgaaatt   180
cgaaaaaaga tttatcaaaa aatttcagaa aatggcttta aaattgtcaa tcttatccat   240
aaaagcgcgc ttataagtcc tagcgcaatc gtggaagaaa atgcaggaat tttaatcatg   300
ccttatgtag tgattaacgc taaagctaaa atagaaaaag gtgtgatttt aaatacttca   360
agcgtaattg agcatgaatg tgtgataggg gaattttctc atgtgagtgt gggagctaaa   420
tgtgcgggta atgtaaaaat tggtaaaaat tgttttttag ggattaattc ttgtgttttg   480
cctaatttaa gtttggcaga tgatagtatt ttaggtggtg gagcaacttt agttaaaaat   540
caagatgaaa aaggtgtttt tgtgggagta cctgcaaaaa ggatgtaa                 588
```

<210> SEQ ID NO 64
<211> LENGTH: 195
<212> TYPE: PRT
<213> ORGANISM: Campylobacter jejuni

<400> SEQUENCE: 64

```
Met Ala Arg Thr Glu Lys Ile Tyr Ile Tyr Gly Ala Ser Gly His Gly
1               5                   10                  15
Leu Val Cys Glu Asp Val Ala Lys Asn Met Gly Tyr Lys Glu Cys Ile
            20                  25                  30
Phe Leu Asp Asp Phe Lys Gly Met Lys Phe Glu Ser Thr Leu Pro Lys
        35                  40                  45
Tyr Asp Phe Phe Ile Ala Ile Gly Asn Asn Glu Ile Arg Lys Lys Ile
    50                  55                  60
Tyr Gln Lys Ile Ser Glu Asn Gly Phe Lys Ile Val Asn Leu Ile His
65                  70                  75                  80
Lys Ser Ala Leu Ile Ser Pro Ser Ala Ile Val Glu Glu Asn Ala Gly
                85                  90                  95
Ile Leu Ile Met Pro Tyr Val Val Ile Asn Ala Lys Ala Lys Ile Glu
            100                 105                 110
Lys Gly Val Ile Leu Asn Thr Ser Ser Val Ile Glu His Glu Cys Val
        115                 120                 125
Ile Gly Glu Phe Ser His Val Ser Val Gly Ala Lys Cys Ala Gly Asn
    130                 135                 140
Val Lys Ile Gly Lys Asn Cys Phe Leu Gly Ile Asn Ser Cys Val Leu
145                 150                 155                 160
Pro Asn Leu Ser Leu Ala Asp Asp Ser Ile Leu Gly Gly Gly Ala Thr
                165                 170                 175
Leu Val Lys Asn Gln Asp Glu Lys Gly Val Phe Val Gly Val Pro Ala
            180                 185                 190
Lys Arg Met
        195
```

<210> SEQ ID NO 65
<211> LENGTH: 1161
<212> TYPE: DNA
<213> ORGANISM: Campylobacter jejuni

<400> SEQUENCE: 65

```
atgagattttt tctttctcc tccgcatatg ggtggtaatg aattaaaata catagaagaa      60
gttttcaaaa gcaattatat agcacctttg ggtgaatttg taaatcgctt tgaacaaagt     120
gtcaaggctt acagtaaaag tgaaaatgcc ttagctttaa attcagccac agcggctttg     180
catttagctt taagggtggc aggggtaaaa caagatgata ttgttttggc ttcttctttt     240
acttttatcg cttcagtagc acctatttgt tatcttaaag caaaacctgt atttatagat     300
tgtgatgaaa cttataatat cgatgtagat ttattaaagc ttgctattaa agaatgtgaa     360
aaaaaaccaa aagcattgat tttaactcat ctttatggca atgcggctaa aatggatgaa     420
attgttgaaa tttgcaaaga aaatgaaatt gttttaatcg aagatgctgc tgaagcttta     480
ggaagttttt ataagaataa agctttagga acttttggag aatttggagc ttattcttat     540
aatggcaata aaattatcac cacttcaggt ggaggtatgc ttataggaaa aaataaagaa     600
aagattgaaa aagcaagatt ttatagcact caagctaggg aaaattgttt gcattatgaa     660
catttagatt atggttataa ttaccgctta agcaatgttt taggagctat tggcgtagcg     720
caaatggagg ttttagaaca aagagtgctt aaaaaaagag aaatttatga gtggtataaa     780 gaattttttag gagagtgttt tagctttttta gatgaattag aaaattcaag aagcaatcgc     840
tggttaagta cagctttgat tgattttgat aaaaatgaac ttaattcttg tcaaaaagat     900
ataaatatca gtcaaaaaaa tattactttg catccaaaaa tttcaaaact catagaagat     960
ttgaaaaatg aacaaataga acaagacca ttatggaaag ctatgcacgc tcaagaagta    1020
tttaaaggag ctaaggctta tcttaatggc aatagtgagt tattttttcca aaaaggaatt    1080 tgtttgccaa gtggcacggc gatgagtaaa gatgatgttt atgaaatttc aaaactgatc    1140
ttaaagagca taaaggctta a                                              1161
```

<210> SEQ ID NO 66
<211> LENGTH: 386
<212> TYPE: PRT
<213> ORGANISM: Campylobacter jejuni

<400> SEQUENCE: 66

```
Met Arg Phe Phe Leu Ser Pro Pro His Met Gly Gly Asn Glu Leu Lys
1               5                   10                  15

Tyr Ile Glu Glu Val Phe Lys Ser Asn Tyr Ile Ala Pro Leu Gly Glu
            20                  25                  30

Phe Val Asn Arg Phe Glu Gln Ser Val Lys Ala Tyr Ser Lys Ser Glu
        35                  40                  45

Asn Ala Leu Ala Leu Asn Ser Ala Thr Ala Ala Leu His Leu Ala Leu
    50                  55                  60

Arg Val Ala Gly Val Lys Gln Asp Asp Ile Val Leu Ala Ser Ser Phe
65                  70                  75                  80

Thr Phe Ile Ala Ser Val Ala Pro Ile Cys Tyr Leu Lys Ala Lys Pro
                85                  90                  95

Val Phe Ile Asp Cys Asp Glu Thr Tyr Asn Ile Asp Val Asp Leu Leu
            100                 105                 110

Lys Leu Ala Ile Lys Glu Cys Glu Lys Lys Pro Lys Ala Leu Ile Leu
        115                 120                 125

Thr His Leu Tyr Gly Asn Ala Ala Lys Met Asp Glu Ile Val Glu Ile
    130                 135                 140

Cys Lys Glu Asn Glu Ile Val Leu Ile Glu Asp Ala Ala Glu Ala Leu
145                 150                 155                 160

Gly Ser Phe Tyr Lys Asn Lys Ala Leu Gly Thr Phe Gly Glu Phe Gly
```

```
               165                 170                 175
Ala Tyr Ser Tyr Asn Gly Asn Lys Ile Ile Thr Thr Ser Gly Gly Gly
            180                 185                 190

Met Leu Ile Gly Lys Asn Lys Glu Lys Ile Glu Lys Ala Arg Phe Tyr
        195                 200                 205

Ser Thr Gln Ala Arg Glu Asn Cys Leu His Tyr Glu His Leu Asp Tyr
    210                 215                 220

Gly Tyr Asn Tyr Arg Leu Ser Asn Val Leu Gly Ala Ile Gly Val Ala
225                 230                 235                 240

Gln Met Glu Val Leu Glu Gln Arg Val Leu Lys Lys Arg Glu Ile Tyr
                245                 250                 255

Glu Trp Tyr Lys Glu Phe Leu Gly Glu Cys Phe Ser Phe Leu Asp Glu
            260                 265                 270

Leu Glu Asn Ser Arg Ser Asn Arg Trp Leu Ser Thr Ala Leu Ile Asp
        275                 280                 285

Phe Asp Lys Asn Glu Leu Asn Ser Cys Gln Lys Asp Ile Asn Ile Ser
    290                 295                 300

Gln Lys Asn Ile Thr Leu His Pro Lys Ile Ser Lys Leu Ile Glu Asp
305                 310                 315                 320

Leu Lys Asn Glu Gln Ile Glu Thr Arg Pro Leu Trp Lys Ala Met His
                325                 330                 335

Ala Gln Glu Val Phe Lys Gly Ala Lys Ala Tyr Leu Asn Gly Asn Ser
            340                 345                 350

Glu Leu Phe Phe Gln Lys Gly Ile Cys Leu Pro Ser Gly Thr Ala Met
        355                 360                 365

Ser Lys Asp Asp Val Tyr Glu Ile Ser Lys Leu Ile Leu Lys Ser Ile
    370                 375                 380

Lys Ala
385

<210> SEQ ID NO 67
<211> LENGTH: 1770
<212> TYPE: DNA
<213> ORGANISM: Campylobacter jejuni

<400> SEQUENCE: 67
atgatttttt ataaaagcaa aagattagca ttttttttaa cttcagatat tgttttaatt      60
ttacttagcg tttatctggc ttttttcttg agatttagtg gagatattcc gagtattttt     120
tatcatggta tgatggtttc tgctattatt ttgcttgttt aaaactttc atttttgttt     180 gtttttagaa tttataaagt agcttggaga ttttttttctc tcaatgaagc aagaaagatt     240
tttatcgctt tgcttttagc tgagttttgt ttttttctta ttttttatttt tttagtgat     300 ttttttaatc cttttccaag aagtgctatt gtgatagatt ttgttctttc ttatatgttt     360
ataggtactt taagaattag caaaagaatg cttgtggatt ttaaaccttc tagaatgaaa     420
gaagaagaaa ctccttgtat tgtagtaggg gcaacttcta aggctttgca tttgttaaaa     480
ggtgcaaaag aaggttcttt agggcttttt cctgtaggcg tagttgatgc gagaaaagag     540
cttataggga cttattgtga taaatttatt gtagaagaaa aagaaaaaat aaaatcttat     600
gtagaacaag gggtaaaaac tgccattatt gctttaagac ttgaacaaga agagcttaaa     660 aaacttttg aagaacttgt agcttatggt atttgcgatg taaaaatatt ttcttttaca     720
agaaacgaag caagagatat cagtatagaa gacttgcttg ctagaaaacc aaaagattta     780
gatgatagtg ctgtggcggc tttttttaaa gataaggtag ttttggtaag tggagcaggt     840
```

```
ggaactatag gcagtgaact ttgtaagcaa tgtattaaat ttggtgctaa gcatcttatc    900
atggttgatc atagtgagta taatctttat aagatcaatg atgatttaaa tttatataaa    960
gaaaaaatta ctcctatttt actgagtatt ttagataagc aaagtttaga tgaggtatta   1020
aaaacttata aacccgagct tattttacat gcagccgctt ataaacatgt gcctctttgc   1080
gaacaaaatc cacattcagc agtaatcaat aatattttag gaactaaaat tttatgcgac   1140
agtgctaaag aaaacaaagt agctaaattt gtgatgataa gtacagataa agcagtacga   1200
ccaacaaata ttatgggttg cactaagaga gtttgcgagc tttatacttt aagtatgagt   1260
gatgaaaatt ttgaagttgc ttgtgtgcgt tttggtaatg tttttaggttc tagtggtagt   1320 gtgataccga aatttaaagc acaaattgcc aataatgagc ctttaacttt aacgcaccct   1380
gatatagtgc gttattttat gcttgtggct gaggcagtgc aacttgtttt acaagctgga   1440
gctatcgcaa aaggggaga acttttttgtt ttggatatgg gtaagcctgt gaaaatcata   1500
gatttagcta aaaaaatgct tttactttct aatcgcaatg atttagaaat taaaatcaca   1560
ggcttaagaa aaggtgagaa gctttatgaa gagcttttga ttgatgaaaa tgatgctaaa   1620
acacaatatg agagtatttt tgtagcaaag aatgagaagg ttgatcttga ttggcttaat   1680
aaagagatag aaaatttaca aatatgtgaa gatatttcag aggctttatt aaagattgta   1740
cctgaattta aacacaataa agaaggtgta                                    1770
```

<210> SEQ ID NO 68
<211> LENGTH: 590
<212> TYPE: PRT
<213> ORGANISM: Campylobacter jejuni

<400> SEQUENCE: 68

```
Met Ile Phe Tyr Lys Ser Lys Arg Leu Ala Phe Phe Leu Thr Ser Asp
1               5                   10                  15

Ile Val Leu Ile Leu Leu Ser Val Tyr Leu Ala Phe Ser Leu Arg Phe
            20                  25                  30

Ser Gly Asp Ile Pro Ser Ile Phe Tyr His Gly Met Met Val Ser Ala
        35                  40                  45

Ile Ile Leu Leu Val Leu Lys Leu Ser Phe Leu Phe Val Phe Arg Ile
    50                  55                  60

Tyr Lys Val Ala Trp Arg Phe Phe Ser Leu Asn Glu Ala Arg Lys Ile
65                  70                  75                  80

Phe Ile Ala Leu Leu Leu Ala Glu Phe Cys Phe Phe Leu Ile Phe Tyr
                85                  90                  95

Phe Phe Ser Asp Phe Phe Asn Pro Phe Pro Arg Ser Ala Ile Val Ile
            100                 105                 110

Asp Phe Val Leu Ser Tyr Met Phe Ile Gly Thr Leu Arg Ile Ser Lys
        115                 120                 125

Arg Met Leu Val Asp Phe Lys Pro Ser Arg Met Lys Glu Glu Glu Thr
    130                 135                 140

Pro Cys Ile Val Val Gly Ala Thr Ser Lys Ala Leu His Leu Leu Lys
145                 150                 155                 160

Gly Ala Lys Glu Gly Ser Leu Gly Leu Phe Pro Val Gly Val Val Asp
                165                 170                 175

Ala Arg Lys Glu Leu Ile Gly Thr Tyr Cys Asp Lys Phe Ile Val Glu
            180                 185                 190

Glu Lys Glu Lys Ile Lys Ser Tyr Val Glu Gln Gly Val Lys Thr Ala
        195                 200                 205
```

Ile Ile Ala Leu Arg Leu Glu Gln Glu Glu Leu Lys Lys Leu Phe Glu
    210                 215                 220

Glu Leu Val Ala Tyr Gly Ile Cys Asp Val Lys Ile Phe Ser Phe Thr
225                 230                 235                 240

Arg Asn Glu Ala Arg Asp Ile Ser Ile Glu Asp Leu Leu Ala Arg Lys
                245                 250                 255

Pro Lys Asp Leu Asp Asp Ser Ala Val Ala Ala Phe Leu Lys Asp Lys
            260                 265                 270

Val Val Leu Val Ser Gly Ala Gly Gly Thr Ile Gly Ser Glu Leu Cys
        275                 280                 285

Lys Gln Cys Ile Lys Phe Gly Ala Lys His Leu Ile Met Val Asp His
290                 295                 300

Ser Glu Tyr Asn Leu Tyr Lys Ile Asn Asp Asp Leu Asn Leu Tyr Lys
305                 310                 315                 320

Glu Lys Ile Thr Pro Ile Leu Leu Ser Ile Leu Asp Lys Gln Ser Leu
                325                 330                 335

Asp Glu Val Leu Lys Thr Tyr Lys Pro Glu Leu Ile Leu His Ala Ala
            340                 345                 350

Ala Tyr Lys His Val Pro Leu Cys Glu Gln Asn Pro His Ser Ala Val
        355                 360                 365

Ile Asn Asn Ile Leu Gly Thr Lys Ile Leu Cys Asp Ser Ala Lys Glu
370                 375                 380

Asn Lys Val Ala Lys Phe Val Met Ile Ser Thr Asp Lys Ala Val Arg
385                 390                 395                 400

Pro Thr Asn Ile Met Gly Cys Thr Lys Arg Val Cys Glu Leu Tyr Thr
                405                 410                 415

Leu Ser Met Ser Asp Glu Asn Phe Glu Val Ala Cys Val Arg Phe Gly
            420                 425                 430

Asn Val Leu Gly Ser Ser Gly Ser Val Ile Pro Lys Phe Lys Ala Gln
        435                 440                 445

Ile Ala Asn Asn Glu Pro Leu Thr Leu Thr His Pro Asp Ile Val Arg
450                 455                 460

Tyr Phe Met Leu Val Ala Glu Ala Val Gln Leu Val Leu Gln Ala Gly
465                 470                 475                 480

Ala Ile Ala Lys Gly Gly Glu Leu Phe Val Leu Asp Met Gly Lys Pro
                485                 490                 495

Val Lys Ile Ile Asp Leu Ala Lys Lys Met Leu Leu Leu Ser Asn Arg
            500                 505                 510

Asn Asp Leu Glu Ile Lys Ile Thr Gly Leu Arg Lys Gly Glu Lys Leu
        515                 520                 525

Tyr Glu Glu Leu Leu Ile Asp Glu Asn Asp Ala Lys Thr Gln Tyr Glu
530                 535                 540

Ser Ile Phe Val Ala Lys Asn Glu Lys Val Asp Leu Asp Trp Leu Asn
545                 550                 555                 560

Lys Glu Ile Glu Asn Leu Gln Ile Cys Glu Asp Ile Ser Glu Ala Leu
                565                 570                 575

Leu Lys Ile Val Pro Glu Phe Lys His Asn Lys Glu Gly Val
            580                 585                 590

<210> SEQ ID NO 69
<211> LENGTH: 894
<212> TYPE: DNA
<213> ORGANISM: Campylobacter jejuni

<400> SEQUENCE: 69

```
atgtatataa aagatataca aagatttgaa gataatcgct atcgtgctag agcttatatg    60
agttatattt taacaagaaa tctgcccaat aaacttcctg atattcacct tgaaacgatt   120
aaaacagctt tggataaaat agctcatgaa gttgttgttt ttgatgcttt gtatatttta   180
gatatttcag gcatgcaaat agaaaatgcg atttccttaa ataaagctca tgaaataggg   240
cagggtgagg atagaagtac tcgttcttat ttttatagag ctgtaaaatt aagacgatgt   300
gttttgagcg atccttatcc ttcggtttta aataatgagc tttgcgtgac agcttctatg   360
ccaatttacg atgataaaaa taacttgctt tttgttgttt gtattgatat caagcttgaa   420
gatattttaa agattattca agcaggaaaa tttgaatttg tttttactca gtttagtcgt   480
ttggtatatt tttgcttcgc actggtttta tttgtgatta cttgtttttt atttcaaaaa   540
ggttttttta gtcttttga taatcaagct ataggtatag aacatatgtt tgaaagtacc   600
atcgctataa ctttggcttt agctattttt gatttggcaa aactttgat cgaacaagaa   660
gtattaggaa ggacgaaaaa agaagaaggt ggaattcaaa aactatggt gagattttg   720
ggttctatta tcattgcttt agctatagaa gctttgatgt tggtatttaa acttgctatt   780
ggtgatcttt ctcagatgat ttatgcgatt tatcttatcg gtggagtgag cttgcttctt   840
ttaggtttaa gtgtatattt atttacggtt aagtataaaa ataataatat ttga         894
```

<210> SEQ ID NO 70
<211> LENGTH: 297
<212> TYPE: PRT
<213> ORGANISM: Campylobacter jejuni

<400> SEQUENCE: 70

```
Met Tyr Ile Lys Asp Ile Gln Arg Phe Glu Asp Asn Arg Tyr Arg Ala
1               5                   10                  15

Arg Ala Tyr Met Ser Tyr Ile Leu Thr Arg Asn Leu Pro Asn Lys Leu
            20                  25                  30

Pro Asp Ile His Leu Glu Thr Ile Lys Thr Ala Leu Asp Lys Ile Ala
        35                  40                  45

His Glu Val Val Val Phe Asp Ala Leu Tyr Ile Leu Asp Ile Ser Gly
    50                  55                  60

Met Gln Ile Glu Asn Ala Ile Ser Leu Asn Lys Ala His Glu Ile Gly
65                  70                  75                  80

Gln Gly Glu Asp Arg Ser Thr Arg Ser Tyr Phe Tyr Arg Ala Val Lys
                85                  90                  95

Leu Arg Arg Cys Val Leu Ser Asp Pro Tyr Pro Ser Val Leu Asn Asn
            100                 105                 110

Glu Leu Cys Val Thr Ala Ser Met Pro Ile Tyr Asp Asp Lys Asn Asn
        115                 120                 125

Leu Leu Phe Val Val Cys Ile Asp Ile Lys Leu Glu Asp Ile Leu Lys
    130                 135                 140

Ile Ile Gln Ala Gly Lys Phe Glu Phe Val Phe Thr Gln Phe Ser Arg
145                 150                 155                 160

Leu Val Tyr Phe Cys Phe Ala Leu Val Leu Phe Val Ile Thr Cys Phe
                165                 170                 175

Leu Phe Gln Lys Gly Phe Phe Ser Leu Phe Asp Asn Gln Ala Ile Gly
            180                 185                 190

Ile Glu His Met Phe Glu Ser Thr Ile Ala Ile Thr Leu Ala Leu Ala
        195                 200                 205
```

```
Ile Phe Asp Leu Ala Lys Thr Leu Ile Glu Gln Glu Val Leu Gly Arg
    210                 215                 220
Thr Lys Lys Glu Glu Gly Gly Ile Gln Lys Thr Met Val Arg Phe Leu
225                 230                 235                 240
Gly Ser Ile Ile Ile Ala Leu Ala Ile Glu Ala Leu Met Leu Val Phe
                245                 250                 255
Lys Leu Ala Ile Gly Asp Leu Ser Gln Met Ile Tyr Ala Ile Tyr Leu
                260                 265                 270
Ile Gly Gly Val Ser Leu Leu Leu Gly Leu Ser Val Tyr Leu Phe
            275                 280                 285
Thr Val Lys Tyr Lys Asn Asn Asn Ile
    290                 295
```

<210> SEQ ID NO 71
<211> LENGTH: 1107
<212> TYPE: DNA
<213> ORGANISM: Campylobacter jejuni

<400> SEQUENCE: 71

```
atgcagcgat ttaaaaaatg gtttttgtct atcataaaaa atttcaagca acatgaaaaa      60
attaagatag atcttaataa tacaaagata gatcttaata tacaaagat agatcttaat     120
aatacaaaga tagatcttaa taatacaaag atagatctta ataatacaaa gatagatctt    180
aataatacaa agatagatct taataataca agatagatc ttaataatac aaagatagat    240
cttaataata caaagataga attatcgcaa ttaaaaaaag agcactataa agtattagat    300
tttcatttaa gaaaaattac acctcaagct tttttagaga ttgttgaaat tcatttagcc    360
gaatcatgta atttaaattg ttttggttgt aatcattttt cacaaatagc tgaaaaagaa    420
tttccagata tagaaatttt taaaaaagat atgcaaagac tttcagaaat atctaaaggt    480
attgtcggaa cttttagatt gatgggtggc gaacctcttt taaatcccaa ttgtatacag    540
ttttttgaca ttacaagata ttttttttcca aaaagtgcca tttggttggt aactaatggt    600
atttttacttg ataagcaaaa tgaggatttt tggaattcat gccaaaggaa taaaatgcaa    660
attcgtccaa caaagtatcc tataaaaatt aattgggatt tgattaaaga taagtgtgat    720
caatatgata tccccttgat atttttttaac aatggagagt tggaaaaaac ttcttggaaa    780
ttttctctag atccttctgg aaattgtgat aattaccata gttttacaaa ttgtagtatg    840
gcaaatcact gtgttcagtt taaagatgga aagctattta cttgtacctt tcctgcacat    900
gtacagcatt ttaataaaaa gtatggaaat cattttgaag tttgcgaatt tgactttatt    960
gatatttata agccaaggga ttatcaagaa atttatttt ttctttctaa gcctattcct   1020
ttttgtagat attgcaaggt atcacaatgg gcagaaattg aaaatggcg ttctagcaat   1080
aaaacaaaac atgaatattt aatttga                                        1107
```

<210> SEQ ID NO 72
<211> LENGTH: 1107
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
atgcagcgtt tcaaaaaatg gttcctgtct atcatcaaaa acttcaaaca gcacgaaaaa      60
atcaaaatcg acctgaacaa caccaaaatc gacctgaaca caccaaaat cgacctgaac    120
```

| | |
|---|---|
| aacaccaaaa tcgacctgaa caacaccaaa atcgacctga caacaccaa aatcgacctg | 180 |
| aacaacacca aaatcgacct gaacaacacc aaaatcgacc tgaacaacac caaaatcgac | 240 |
| ctgaacaaca ccaaaatcga actgtctcag ctgaaaaaag aacactacaa agttctggac | 300 |
| ttccacctgc gtaaaatcac cccgcaggcg ttcctggaaa tcgttgaaat ccacctggcg | 360 |
| gaatcttgca acctgaactg cttcggttgc aaccacttct ctcagatcgc ggaaaaagaa | 420 |
| ttcccggaca tcgaaatctt caaaaaagac atgcagcgtc tgtctgaaat ctctaaaggt | 480 |
| atcgttggta ccttccgtct gatgggtggt gaaccgctgc tgaacccgaa ctgcatccag | 540 |
| ttcttcgaca tcacccgtta cttcttcccg aaatctgcga tctggctggt taccaacggt | 600 |
| atcctgctgg acaaacagaa cgaagacttc tggaactctt gccagcgtaa caaaatgcag | 660 |
| atccgtccga ccaaataccc gatcaaaatc aactgggacc tgatcaaaga caaatgcgac | 720 |
| cagtacgaca tcccgctgat cttcttcaac aacggtgaac tggaaaaaac ctcttggaaa | 780 |
| ttctctctgg acccgtctgg taactgcgac aactaccact cttttcaccaa ctgctctatg | 840 |
| gcgaaccact gcgttcagtt caaagacggt aaactgttca cctgcacctt cccggcgcac | 900 |
| gttcagcact caacaaaaaa atacggtaac cacttcgaag tttgcgaatt cgacttcatc | 960 |
| gacatctaca aagcgaaaga ctaccaggaa atcctgttct tcctgtctaa accgatcccg | 1020 |
| ttctgccgat actgcaaagt ttctcagtgg gcggaaatcg gtaaatggcg ttcttctaac | 1080 |
| aaaaccaaac acgaataccc tgatctga | 1107 |

<210> SEQ ID NO 73
<211> LENGTH: 1107
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73

| | |
|---|---|
| atgcagcgtt tcaaaaaatg gttcctgtcc atcatcaaaa acttcaaaca gcacgaaaaa | 60 |
| atcaaaatcg acctgaacaa caccaaaatc gacctgaaca caccaaaat cgacctgaac | 120 |
| aacaccaaaa tcgacctgaa caacaccaaa atcgacctga caacaccaa aatcgacctg | 180 |
| aacaacacca aaatcgacct gaacaacacc aaaatcgacc tgaacaacac caaaatcgac | 240 |
| ctgaacaaca ccaaaatcga actgtcccag ctgaaaaaag aacactacaa agtgctggac | 300 |
| ttccacctgc gtaaaatcac cccgcaggcg ttcctggaaa tcgtggaaat ccacctggcg | 360 |
| gaatcctgca acctgaactg cttcggctgc aaccacttct cccagatcgc ggaaaaagaa | 420 |
| ttcccggaca tcgaaatctt caaaaaagac atgcagcgtc tgtccgaaat ctctaaaggc | 480 |
| atcgtgggca cttccgtct gatgggcggc gaaccgctgc tgaacccgaa ctgcatccag | 540 |
| ttcttcgaca tcacccgtta cttcttcccg aaatccgcga tctggctggt gaccaacggc | 600 |
| atcctgctgg acaaacagaa cgaagacttc tggaactcct gccagcgtaa caaaatgcag | 660 |
| atccgtccga ccaaataccc gatcaaaatc aactgggacc tgatcaaaga caaatgcgac | 720 |
| cagtacgaca tcccgctgat cttcttcaac aacggcgaac tggaaaaaac ctcctggaaa | 780 |
| ttctcctgg acccgtccgg caactgcgac aactaccact ccttcaccaa ctgctccatg | 840 |
| gcgaaccact gcgtgcagtt caaagacggc aaactgttca cctgcacctt cccggcgcac | 900 |
| gtgcagcact caacaaaaaa atacggcaac cacttcgaag tgtgcgaatt cgacttcatc | 960 |
| gacatctaca aagcgaaaga ctaccaggaa atcctgttct tcctgtccaa accgatcccg | 1020 |

```
ttctgccgat actgcaaagt gtcccagtgg gcggaaatcg gcaaatggcg ttcctccaac    1080
aaaaccaaac acgaatacct gatctga                                       1107
```

<210> SEQ ID NO 74
<211> LENGTH: 368
<212> TYPE: PRT
<213> ORGANISM: Campylobacter jejuni

<400> SEQUENCE: 74

```
Met Gln Arg Phe Lys Lys Trp Phe Leu Ser Ile Ile Lys Asn Phe Lys
1               5                   10                  15

Gln His Glu Lys Ile Lys Ile Asp Leu Asn Asn Thr Lys Ile Asp Leu
            20                  25                  30

Asn Asn Thr Lys Ile Asp Leu Asn Asn Thr Lys Ile Asp Leu Asn Asn
        35                  40                  45

Thr Lys Ile Asp Leu Asn Asn Thr Lys Ile Asp Leu Asn Asn Thr Lys
    50                  55                  60

Ile Asp Leu Asn Asn Thr Lys Ile Asp Leu Asn Asn Thr Lys Ile Asp
65                  70                  75                  80

Leu Asn Asn Thr Lys Ile Glu Leu Ser Gln Leu Lys Lys Glu His Tyr
                85                  90                  95

Lys Val Leu Asp Phe His Leu Arg Lys Ile Thr Pro Gln Ala Phe Leu
            100                 105                 110

Glu Ile Val Glu Ile His Leu Ala Glu Ser Cys Asn Leu Asn Cys Phe
        115                 120                 125

Gly Cys Asn His Phe Ser Gln Ile Ala Glu Lys Glu Phe Pro Asp Ile
    130                 135                 140

Glu Ile Phe Lys Lys Asp Met Gln Arg Leu Ser Glu Ile Ser Lys Gly
145                 150                 155                 160

Ile Val Gly Thr Phe Arg Leu Met Gly Gly Glu Pro Leu Leu Asn Pro
                165                 170                 175

Asn Cys Ile Gln Phe Phe Asp Ile Thr Arg Tyr Phe Phe Pro Lys Ser
            180                 185                 190

Ala Ile Trp Leu Val Thr Asn Gly Ile Leu Leu Asp Lys Gln Asn Glu
        195                 200                 205

Asp Phe Trp Asn Ser Cys Gln Arg Asn Lys Met Gln Ile Arg Pro Thr
    210                 215                 220

Lys Tyr Pro Ile Lys Ile Asn Trp Asp Leu Ile Lys Asp Lys Cys Asp
225                 230                 235                 240

Gln Tyr Asp Ile Pro Leu Ile Phe Phe Asn Asn Gly Glu Leu Glu Lys
                245                 250                 255

Thr Ser Trp Lys Phe Ser Leu Asp Pro Ser Gly Asn Cys Asp Asn Tyr
            260                 265                 270

His Ser Phe Thr Asn Cys Ser Met Ala Asn His Cys Val Gln Phe Lys
        275                 280                 285

Asp Gly Lys Leu Phe Thr Cys Thr Phe Pro Ala His Val Gln His Phe
    290                 295                 300

Asn Lys Lys Tyr Gly Asn His Phe Glu Val Cys Glu Phe Asp Phe Ile
305                 310                 315                 320

Asp Ile Tyr Lys Ala Lys Asp Tyr Gln Glu Ile Leu Phe Phe Leu Ser
                325                 330                 335

Lys Pro Ile Pro Phe Cys Arg Tyr Cys Lys Val Ser Gln Trp Ala Glu
            340                 345                 350

Ile Gly Lys Trp Arg Ser Ser Asn Lys Thr Lys His Glu Tyr Leu Ile
```

<210> SEQ ID NO 75
<211> LENGTH: 1149
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75

```
atgaaaaaga cagctatcgc gattgcagtg gcactggctg gtttcgctac cgtagcgcag      60
gccgctccga agataacac ctggtacgct ggtgctaaac tgggctggtc tcagtaccat      120
gacaccggct tcattcacaa tgatggcccg actcatgaaa accaactggg cgcaggtgct      180
tttggtggtt accaggttaa cccgtatgtc gacatcaaaa tcgacctgaa caacaccaaa      240
atcgacctga caacaccaa atcgacctg aacaacacca aaatcgacct gaacaacacc      300
aaaatcgacc tgaacaacac caaaatcgac ctgaacaaca ccaaaatcga cctgaacaac      360
accaaaatcg acctgaacaa caccaaaatc gacctgaaca caccaaaat cctgcagatc      420
actgacgatc tggacgttta cccgtctg ggtggtatgg tatggcgtgc agacaccaag      480
tctaacgtcc ctggcggccc gtctactaaa gaccacgaca ccggcgtttc cccggtattc      540
gcgggcggta tcgagtatgc tatcaccct gaaatcgcaa cccgtctgga ataccagtgg      600
actaacaaca tcggtgatgc caacaccatc ggcacccgtc cggacaacgg cctgctgagc      660
gtaggtgttt cctaccgttt cggccagcaa gaagctgctc cggtagtagc tccggcacca      720
gctccggctc cggaagtaca gaccaagcac ttcactctga gtctgacgt actgttcaac      780
ttcaacaaat ctaccctgaa gccggaaggc cagcaggctc tggatcagct gtacagccag      840
ctgagcaacc tggatccgaa agacggttcc gttgtcgttc tgggcttcac tgaccgtatc      900
ggttctgacg cttacaacca gggtctgtcc gagaaacgtg ctcagtctgt tgttgattac      960
ctgatctcca aaggtattcc gtctgacaaa atctccgcac gtggtatggg cgaatctaac     1020
ccggttaccg caacacctg tgacaacgtg aaacctcgcg ctgccctgat cgattgcctg     1080
gctccggatc gtcgcgtaga gatcgaagtt aaaggcgtta agacgtggt aactcagccg     1140
caggcttaa                                                            1149
```

<210> SEQ ID NO 76
<211> LENGTH: 382
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

```
Met Lys Lys Thr Ala Ile Ala Ile Ala Val Ala Leu Ala Gly Phe Ala
1               5                   10                  15

Thr Val Ala Gln Ala Ala Pro Lys Asp Asn Thr Trp Tyr Ala Gly Ala
                20                  25                  30

Lys Leu Gly Trp Ser Gln Tyr His Asp Thr Gly Phe Ile His Asn Asp
            35                  40                  45

Gly Pro Thr His Glu Asn Gln Leu Gly Ala Gly Ala Phe Gly Gly Tyr
        50                  55                  60

Gln Val Asn Pro Tyr Val Asp Ile Lys Ile Asp Leu Asn Asn Thr Lys
65                  70                  75                  80
```

Ile Asp Leu Asn Asn Thr Lys Ile Asp Leu Asn Asn Thr Lys Ile Asp
                85                  90                  95
Leu Asn Asn Thr Lys Ile Asp Leu Asn Asn Thr Lys Ile Asp Leu Asn
                100                 105                 110
Asn Thr Lys Ile Asp Leu Asn Thr Lys Ile Asp Leu Asn Asn Thr
            115                 120                 125
Lys Ile Asp Leu Asn Asn Thr Lys Ile Leu Gln Ile Thr Asp Asp Leu
        130                 135                 140
Asp Val Tyr Thr Arg Leu Gly Gly Met Val Trp Arg Ala Asp Thr Lys
145                 150                 155                 160
Ser Asn Val Pro Gly Gly Pro Ser Thr Lys Asp His Asp Thr Gly Val
                165                 170                 175
Ser Pro Val Phe Ala Gly Gly Ile Glu Tyr Ala Ile Thr Pro Glu Ile
                180                 185                 190
Ala Thr Arg Leu Glu Tyr Gln Trp Thr Asn Asn Ile Gly Asp Ala Asn
                195                 200                 205
Thr Ile Gly Thr Arg Pro Asp Asn Gly Leu Leu Ser Val Gly Val Ser
            210                 215                 220
Tyr Arg Phe Gly Gln Gln Glu Ala Ala Pro Val Val Ala Pro Ala
225                 230                 235                 240
Ala Pro Ala Pro Glu Val Gln Thr Lys His Phe Thr Leu Lys Ser Asp
                245                 250                 255
Val Leu Phe Asn Phe Asn Lys Ser Thr Leu Lys Pro Glu Gly Gln Gln
                260                 265                 270
Ala Leu Asp Gln Leu Tyr Ser Gln Leu Ser Asn Leu Asp Pro Lys Asp
                275                 280                 285
Gly Ser Val Val Val Leu Gly Phe Thr Asp Arg Ile Gly Ser Asp Ala
            290                 295                 300
Tyr Asn Gln Gly Leu Ser Glu Lys Arg Ala Gln Ser Val Val Asp Tyr
305                 310                 315                 320
Leu Ile Ser Lys Gly Ile Pro Ser Asp Lys Ile Ser Ala Arg Gly Met
                325                 330                 335
Gly Glu Ser Asn Pro Val Thr Gly Asn Thr Cys Asp Asn Val Lys Pro
                340                 345                 350
Arg Ala Ala Leu Ile Asp Cys Leu Ala Pro Asp Arg Arg Val Glu Ile
            355                 360                 365
Glu Val Lys Gly Val Lys Asp Val Val Thr Gln Pro Gln Ala
        370                 375                 380

<210> SEQ ID NO 77
<211> LENGTH: 1149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
atgaaaaaga cagctatcgc gattgcagtg gcactggctg gtttcgctac cgtagcgcag     60
gccgctccga agataacac ctggtacgct ggtgctaaac tgggctggtc tcagtaccat    120
gacaccggct tcattcacaa tgatggcccg actcatgaaa accaactggg cgcaggtgct    180
tttggtggtt accaggttaa cccgtatgtc gacatcaaaa tcgacctgaa caacaccaaa    240
atcgacctga caacaccaa atcgacctg aacaacacca aatcgacct gaacaacacc    300 aaaatcgacc tgaacaacac caaaatcgac ctgaacaaca ccaaaatcga cctgaacaac    360

```
accaaaatcg acctgaacaa caccaaaatc gacctgaaca acaccaaaat cctgcagatc    420
actgacgatc tggacgttta tacccgtctg ggtggtatgg tatggcgtgc agacaccaag    480
tctaacgtcc ctggcggccc gtctactaaa gaccacgaca ccggcgtttc cccggtattc    540
gcgggcggta tcgagtatgc tatcacccct gaaatcgcaa cccgtctgga ataccagtgg    600
actaacaaca tcggtgatgc caacaccatc ggcacccgtc cggacaacgg cctgctgagc    660
gtaggtgttt cctaccgttt cggccagcaa gaagctgctc cggtagtagc tccggcacca    720
gctccggctc cggaagtaca gaccaagcac ttcactctga agtctgacgt actgttcaac    780
ttcaacaaat ctaccctgaa gccggaaggc cagcaggctc tggatcagct gtacagccag    840
ctgagcaacc tggatccgaa agacggttcc gttgtcgttc tgggcttcac tgaccgtatc    900
ggttctgacg cttacaacca gggtctgtcc gagaaacgtg ctcagtctgt tgttgattac    960
ctgatctcca aaggtattcc gtctgacaaa atctccgcac gtggtatggg cgaatctaac   1020
ccggttaccg gcaacacctg tgacaacgtg aaacctcgcg ctgccctgat cgattgcctg   1080
gctccggatc gtcgcgtaga gatcgaagtt aaaggcgtta agacgtggt aactcagccg    1140 caggcttaa                                                           1149

<210> SEQ ID NO 78
<211> LENGTH: 1083
<212> TYPE: DNA
<213> ORGANISM: Escherichia coli

<400> SEQUENCE: 78
gtgaaaccag taacgttata cgatgtcgca gagtatgccg gtgtctctta tcagaccgtt     60
tcccgcgtgg tgaaccaggc cagccacgtt tctgcgaaaa cgcgggaaaa agtggaagcg    120
gcgatggcgg agctgaatta cattcccaac cgcgtggcac aacaactggc gggcaaacag    180
tcgttgctga ttggcgttgc cacctccagt ctggccctgc acgcgccgtc gcaaattgtc    240
gcggcgatta atctcgcgc cgatcaactg ggtgccagcg tggtggtgtc gatggtagaa    300
cgaagcggcg tcgaagcctg taaagcggcg gtgcacaatc ttctcgcgca acgcgtcagt    360
gggctgatca ttaactatcc gctggatgac caggatgcca ttgctgtgga agctgcctgc    420
actaatgttc cggcgttatt tcttgatgtc tctgaccaga cacccatcaa cagtattatt    480
ttctcccatg aagacggtac gcgactgggc gtggagcatc tggtcgcatt gggtcaccag    540
caaatcgcgc tgttagcggg cccattaagt tctgtctcgg cgcgtctgcg tctggctggc    600
tggcataaat atctcactcg caatcaaatt cagccgatag cggaacggga aggcgactgg    660
agtgccatgt ccggttttca acaaaccatg caaatgctga atgagggcat cgttcccact    720
gcgatgctgt tgccaacga tcagatggcg ctggcgcaa tgcgcgccat taccgagtcc    780
gggctgcgcg ttggtgcgga tatctcggta gtgggatacg acgataccga agacagctca    840
tgttatatcc cgccgttaac caccatcaaa caggattttc gcctgctggg gcaaaccagc    900
gtggaccgct tgctgcaact ctctcagggc caggcggtga agggcaatca gctgttgccc    960
gtctcactgg tgaaagaaa aaccacccctg gcgcccaata cgcaaaccgc ctctccccgc   1020
gcgttggccg attcattaat gcagctggca cgacaggttt cccgactgga aagcgggcag   1080
tga                                                                1083

<210> SEQ ID NO 79
<211> LENGTH: 360
<212> TYPE: PRT
```

<213> ORGANISM: Escherichia coli

<400> SEQUENCE: 79

```
Met Lys Pro Val Thr Leu Tyr Asp Val Ala Glu Tyr Ala Gly Val Ser
1               5                   10                  15
Tyr Gln Thr Val Ser Arg Val Val Asn Gln Ala Ser His Val Ser Ala
            20                  25                  30
Lys Thr Arg Glu Lys Val Glu Ala Ala Met Ala Glu Leu Asn Tyr Ile
        35                  40                  45
Pro Asn Arg Val Ala Gln Gln Leu Ala Gly Lys Gln Ser Leu Leu Ile
    50                  55                  60
Gly Val Ala Thr Ser Ser Leu Ala Leu His Ala Pro Ser Gln Ile Val
65                  70                  75                  80
Ala Ala Ile Lys Ser Arg Ala Asp Gln Leu Gly Ala Ser Val Val Val
                85                  90                  95
Ser Met Val Glu Arg Ser Gly Val Glu Ala Cys Lys Ala Ala Val His
            100                 105                 110
Asn Leu Leu Ala Gln Arg Val Ser Gly Leu Ile Ile Asn Tyr Pro Leu
        115                 120                 125
Asp Asp Gln Asp Ala Ile Ala Val Glu Ala Ala Cys Thr Asn Val Pro
    130                 135                 140
Ala Leu Phe Leu Asp Val Ser Asp Gln Thr Pro Ile Asn Ser Ile Ile
145                 150                 155                 160
Phe Ser His Glu Asp Gly Thr Arg Leu Gly Val Glu His Leu Val Ala
                165                 170                 175
Leu Gly His Gln Gln Ile Ala Leu Leu Ala Gly Pro Leu Ser Ser Val
            180                 185                 190
Ser Ala Arg Leu Arg Leu Ala Gly Trp His Lys Tyr Leu Thr Arg Asn
        195                 200                 205
Gln Ile Gln Pro Ile Ala Glu Arg Gly Asp Trp Ser Ala Met Ser
    210                 215                 220
Gly Phe Gln Gln Thr Met Gln Met Leu Asn Glu Gly Ile Val Pro Thr
225                 230                 235                 240
Ala Met Leu Val Ala Asn Asp Gln Met Ala Leu Gly Ala Met Arg Ala
                245                 250                 255
Ile Thr Glu Ser Gly Leu Arg Val Gly Ala Asp Ile Ser Val Val Gly
            260                 265                 270
Tyr Asp Asp Thr Glu Asp Ser Ser Cys Tyr Ile Pro Pro Leu Thr Thr
        275                 280                 285
Ile Lys Gln Asp Phe Arg Leu Leu Gly Gln Thr Ser Val Asp Arg Leu
    290                 295                 300
Leu Gln Leu Ser Gln Gly Gln Ala Val Lys Gly Asn Gln Leu Leu Pro
305                 310                 315                 320
Val Ser Leu Val Lys Arg Lys Thr Thr Leu Ala Pro Asn Thr Gln Thr
                325                 330                 335
Ala Ser Pro Arg Ala Leu Ala Asp Ser Leu Met Gln Leu Ala Arg Gln
            340                 345                 350
Val Ser Arg Leu Glu Ser Gly Gln
        355                 360
```

<210> SEQ ID NO 80
<211> LENGTH: 6
<212> TYPE: DNA
<213> ORGANISM: Unknown
<220> FEATURE:

-continued

```
<223> OTHER INFORMATION: Description of Unknown:
      Shine-Dalgarno sequence

<400> SEQUENCE: 80 aggagg                                                                  6

<210> SEQ ID NO 81
<211> LENGTH: 5
<212> TYPE: PRT
<213> ORGANISM: Campylobacter jejuni

<400> SEQUENCE: 81

Asp Leu Asn Asn Thr
1               5

<210> SEQ ID NO 82
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tataatattt ttggcagttt gttttaaagg atgtttta                              38
```

FOOD SAFETY VACCINE TO CONTROL *SALMONELLA ENTERICA* AND REDUCE CAMPYLOBACTER IN POULTRY

RELATED APPLICATION

This application is a 35 U.S.C. § 371 national stage filing of International Application No. PCT/US2018/015438, filed on Jan. 26, 2018, which in turn claims priority to U.S. Provisional Application No. 62/451,146, filed on Jan. 27, 2017. The entire contents of each of the foregoing applications is expressly incorporated herein by reference.

REFERENCE TO SEQUENCE LISTING

This application contains a Sequence Listing in computer readable form, which has been submitted electronically via EFS-web in ASCII format. Said ASCII copy, created on Jan. 21, 2021, is named 130667-00202_Seq_Listing and is 170,765 bytes in size. The computer readable form of the sequence listing is part of the specification or is otherwise incorporated herein by reference.

GOVERNMENTAL RIGHTS

This invention was made with government support under Grant No. 12229724 awarded by the National Institute of Food and Agriculture of the United States Department of Agriculture. The government has certain rights in the invention.

BACKGROUND

Foodborne human pathogens are a major public health problem. In particular, *Campylobacter* and *Salmonella* are leading causes of bacterial foodborne disease worldwide. *Campylobacter* gastroenteritis is associated with poor handling of raw chicken or consumption of undercooked chicken. (1)(2) Domestic poultry supply, including chickens, turkeys, ducks, and geese, is frequently infected with *C. jejuni* and *C. coli*. (3) *Salmonella* human infections are associated, in part, with the ingestion of foods contaminated by animal feces or cross-contaminated by other sources, including poultry. (4)(5) The increasing consumption of poultry and poultry products has rendered foodborne diseases associated with poultry a significant public health concern.

Strategies for controlling *Campylobacter* and *Salmonella* in poultry include the administration of antibiotics. However, the overuse of antibiotics and the risk of developing antibiotic-resistant bacterial strains has decreased interest in the use of antibiotics for these purposes. Thus, poultry vaccination has emerged as an important strategy to mitigate the prevalence of at least these two foodborne pathogens in poultry supplies.

Recombinant attenuated *Salmonella* vaccines (RASVs) have been developed as vaccines and antigen delivery systems to stimulate protective immune responses against a multitude of antigens. Improved RASVs that are engineered to include inducible promoter-regulated pathogenic attributes have been recently developed. Improvements in this technology has included the development of Regulated Delayed Attenuated RASVs (RDA RASVs) which are grown in vitro in the presence of an inducer (e.g., a sugar) to induce the expression of genes associated with pathogenesis. Upon administration to a subject, the RDA RASVs replicate with full virulence and colonize lymphoid tissues to induce potent immune responses. However, as the levels of inducer decreases within the subject and after multiple rounds of replication, the RDA RASVs become attenuated, thereby preventing further proliferation of the bacteria in vivo.

The use of RASVs for the prophylaxis and treatment of foodborne pathogens in poultry is particularly promising. However, new means to enhance the immunogenicity and safety of the vaccines in vivo are necessary. RASVs and pharmaceutical compositions capable of inducing potent immune responses to multiple foodborne pathogens in poultry are particularly desirable.

SUMMARY

The instant disclosure provides strains of recombinant bacteria, including *Salmonella*, with enhanced immunogenic properties and desirable safety features. The recombinant bacteria can be safely used to effectively deliver antigenic compounds to a subject (e.g., poultry) in order to mount potent immunogenic responses against pathogens such as *Campylobacter* and *Salmonella*. These strains deliver multiple conserved protective *Salmonella* surface/secreted antigens and/or *Campylobacter* N-glycan modified surface/secreted antigens to induce protective immunity.

In some embodiments, disclosed herein is a recombinant derivative of a pathogenic bacterium, comprising regulated-delayed attenuation, a regulated-delayed synthesis of an antigen of interest, a regulated-delayed lysis in vivo phenotype, and synthesizing and delivering one or more protein antigens of *C. jejuni*.

In some embodiments, the recombinant bacteria described herein are capable of synthesizing and attaching a *Campylobacter* N-glycan to an antigen of interest in order to enhance the immunogenicity of the antigen in vivo. The recombinant bacteria may depend on two or three sugars to regulate the virulence phenotype of the bacteria by controlling the expression of multiple virulence genes and, optionally, the antigen of interest, as well as a regulated delayed lysis phenotype, allowing for biological containment and the enhancement of immunogenic properties. The dependence on multiple sugars enhances the safety of the recombinant bacteria, given the improbability that the organisms will encounter all sugars in a naturally-occurring environment. See PCT/US18/14860, filed on Jan. 23, 2018, the entire contents of which are expressly incorporated herein by reference.

Specifically, the bacteria disclosed herein are based upon a recombinant attenuated *Salmonella* vaccine (RASV) derived from the highly avian virulent *S. typhimurium* UK-1 strain and can be used to synthesize and deliver multiple *Campylobacter jejuni* conserved protective protein antigens. Vaccination with these RASVs have been found to induce immunity against multiple *Salmonella* serotypes and *C. jejuni* infecting poultry. The instant disclosure further provides an innovative new RASV design strategy to generate these food safety vaccines that induce superior levels of protective immunity to several poultry pathogens. These RASV vectors were programed to undergo regulated delayed lysis in various cell compartments within the immunized animal to induce superior mucosal and systemic antibody and cellular immunities. In addition, these live RASVs display complete biological containment with no persistence in vivo and no survival if excreted. Widespread use of these RASVs is predicted to substantially reduce *Salmonella* and *C. jejuni* infections and ultimately eliminate *C. jejuni* colonization of chickens to reduce transmission of these pathogens through the food chain to humans. Furthermore, the use of these much improved vector systems will also decrease use of antibiotics during poultry husbandry and thus reduce the selective pressure for drug-resistant bacterial species that can also be transmitted through the food chain to humans.

Figure 2B:
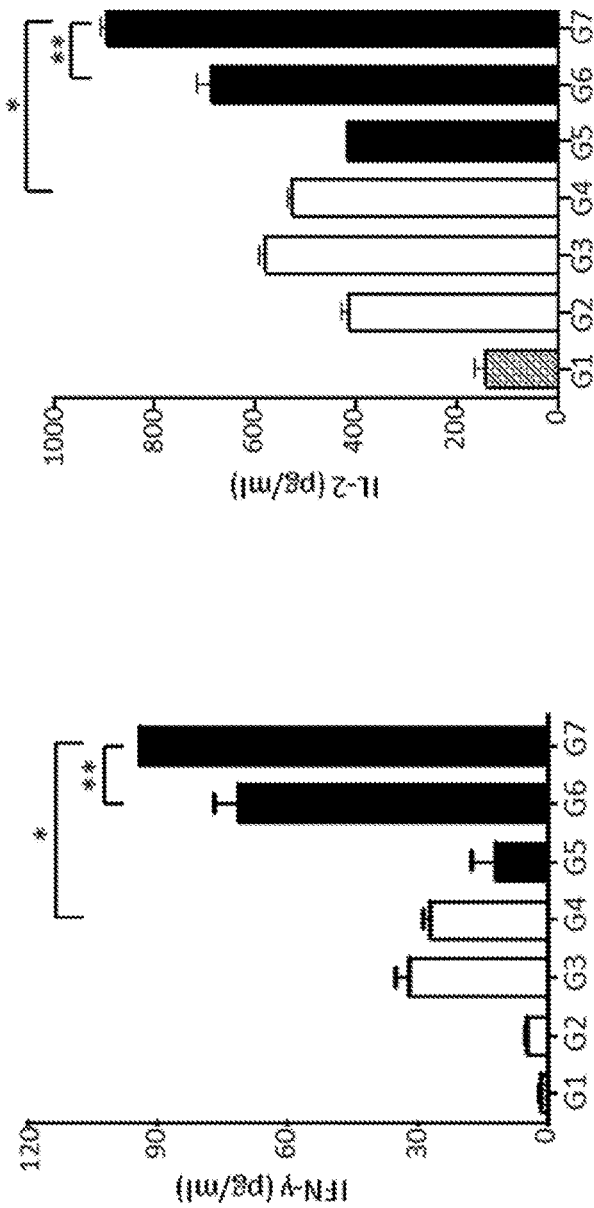

The instant disclosure further provides a validated and highly immunogenic *S. typhimurium* UK-1 RASV that displays regulated delayed attenuation, regulated delayed synthesis of recombinant antigens and regulated delayed lysis phenotypes. Derivatives were constructed that are enabled to synthesize and deliver multiple *C. jejuni* protein antigens. Thus, because of the RASV's inability to synthesize the serotype-specific LPS 0-antigen in vivo to expose the LPS core that is the same in all, *Salmonella* serotypes induce cross protective immunity to most *Salmonella* serotypes while also delivering multiple *C. jejuni* protein antigens to induce superior protective immunity against *C. jejuni*.

The RASVs constructed were designed to display at the time of course spray or oral delivery to poultry the same attributes as the wild-type virulent UK-1 parent strain to contend with host defense strategies, and successfully invade through mucosal surfaces to efficiently colonize internal effector lymphoid tissues before displaying the attenuation phenotype, and thus the inability to induce any disease symptoms or impair or reduce growth. The RASVs reaching these internal tissues were found to gradually commence to serve as factories to synthesize protective *C. jejuni* antigens to be delivered by secretion and ultimately by lysis of the RASV. Since lysis is enabled to occur in diverse extracellular and intracellular compartments, desired mucosal, systematic antibody and cellular immune responses were induced. These innovative strategies provide a classical means of attenuation used previously that reduced immunogenicity because of impaired colonizing abilities of attenuated strains. In addition, these RASVs with the regulated delayed lysis phenotype display completed biological containment with no persistence of vaccine cells in vivo and no survivors if excreted.

In one aspect, disclosed herein is a recombinant derivative of a pathogenic bacterium comprising a regulated-delayed attenuation phenotype; a regulated-delayed expression of an antigen of interest; a regulated-delayed lysis in vivo phenotype; and which is capable of synthesizing and delivering one or more protein antigens of *C. jejuni*. In one embodiment, the bacterium further comprises mutations that cause display of the universal LPS core polysaccharide in vivo.

In one aspect, disclosed herein is a recombinant derivative of a pathogenic bacterium comprising a regulated-delayed attenuation phenotype; a regulated-delayed expression of an antigen of interest; a regulated-delayed lysis in vivo phenotype; and which is capable of synthesizing and delivering one or more protein antigens that display the *Campylobacter jejuni* N-glycan.

In one aspect, disclosed herein is a recombinant derivative of a pathogenic bacterium comprising a regulated-delayed attenuation phenotype; a regulated-delayed expression of an antigen of interest; a regulated-delayed lysis in vivo phenotype; and which is capable of synthesizing and delivering one or more protein antigens of *C. jejuni* and also displays the *Campylobacter jejuni* N-glycan.

In one embodiment, the bacterium comprises one or more *Campylobacter* pgl operon genes. In one embodiment, the one or more *Campylobacter* pgl operon genes are codon-optimized for expression in the bacterium.

In one embodiment, the bacterium is a Gram-negative bacterium. In one embodiment, the bacterium belongs to the family Enterobacteriaceae.

In one embodiment, the antigen of interest is a *Campylobacter* antigen. In one embodiment, the *Campylobacter* antigen is an antigen selected from Table 4, or an antigen having homology or identity thereto, as described herein. In one embodiment, the antigen of interest is selected from the group consisting of Peb1, CjaA, Dps, TlyA, Omp18, Cj0998c, Cj0034c, Cj0168c, Cj0248, Peb3, CmeC, Cj0404, Cj0420, Cj0427, Cj0428, PorA, FlaA, CadF, and Cj1656c.

In one embodiment, the *C. jejuni* N-glycan is attached to the antigen of interest.

In one embodiment, the bacterium comprises insertion of all or part of the cj1433c gene into a deletion of the ompA gene to generate a fusion of the Cj1433c protein.

In one embodiment, the regulated-delayed attenuation is conferred by the gene fur or mntR.

In one embodiment, the regulated-delayed lysis in vivo phenotype is conferred by $\Delta P_{murA}$::TT araC $P_{BAD}$ murA, ΔasdA::TT araC $P_{BAD}$ c2, or Δ(wza-wcaM) deletions or deletion/insertion mutations.

In one embodiment, the bacterium further comprises a mutation in the sifA gene.

In one embodiment, the bacterium further comprises a mutation in the relA gene.

In one aspect, disclosed herein is a pharmaceutical composition comprising the recombinant bacterium, and a pharmaceutically acceptable carrier. In one embodiment, the pharmaceutical composition further comprises a second recombinant derivative of a pathogenic bacterium, wherein said bacterium comprises a nucleic acid encoding a second antigen of interest. In one embodiment, the second antigen of interest is a *Salmonella* antigen.

In one aspect, disclosed herein is a method for inducing protective immunity in an avian, the method comprising administering to the avian an effective amount of a pharmaceutical composition disclosed herein.

Other aspects and iterations of the invention are described more thoroughly below.

BRIEF DESCRIPTION OF THE FIGURES

FIGS. 1A and 1B depict proliferation assays of antigen-specific lymphocytes. In FIG. 1A, representative samples of splenic lymphocytes isolated from chickens immunized with the non-lysis vector control RASV χ11840(pYA3342) (G2), non-lysis RASV χ11442(pYA5301) (G3), non-lysis ΔsifA RASV χ11840(pYA5301) (G4), lysis vector control RASV χ11791(pYA3681) (G5), lysis RASV χ11730(pYA5293) (G6), and lysis ΔsifA RASV χ11791(pYA5293) (G7), were labeled with CSFE and stimulated with the *Eimeria* SO7 antigen. The proliferative lymphocyte population was defined by CFSE dilution. FIG. 1B presents a graphic analysis of cell proliferation in each group described in FIG. 1A. Bar, mean, and SD are the sum of 3 independent experiments each using three chickens per group. Asterisks represent significant differences between the groups as indicated ($p<0.05$). Also correlated with increased INF-γ and IL-2 production and increased CD4 and CD8 responses.

FIGS. 1C and 1D depict the induction of intestinal immunoglobulin A (IgA) against *E. tenella* SO7 in immunized chickens, either on day 35 post-immunization (FIG. 1C) or on day 42 post-immunization (FIG. 1D).

FIG. 2A depicts SO7-specific CD4 and CD8 proliferation analysis in non-lysis versus lysis RASVs without and with escape from SCV due to the ΔsifA mutation.

FIG. 2B depicts lymphocyte activation and cytokine secretion after in vitro homologous recall of splenic lymphocytes from chicks vaccinated with RASV vaccine strains.

FIGS. 3A and 3B depict lysis vector maps. FIG. 3A—Lysis vector pYA4763, pBR ori. FIG. 3B—Lysis vector pG8R17 with improved bla SS, pBR ori.

FIGS. 4A and 4B depict antigen productions in RASV strain χ12341.

FIG. 5 depicts western blot analyses of *C. jejuni* antigens in χ12452 *S. typhimurium* strain grown in L broth with 0.1% each of arabinose, rhamnose, and mannose with/without induction by 1 mM IPTG Monoclonal anti-poly-histidine antibody produced in mice was used for detection of antigens synthesized.

FIG. 6 depicts the genetic map of the *C. jejuni* pgl operon.

FIG. 7 depicts expression of the pgl operon with/without deletion of the pglB gene, with the addition of synthesized *C. jejuni* N-glycan to the LPS core in a *S. typhimurium* with a deletion of the wbaP gene.

FIGS. 8A and 8B depict the structural aspects of the modified *S. typhimurium* OmpA protein with the insertion of the Cj1433c gene encoded sequences, specifying the nine repeats to which the *C. jejuni* conserved N-glycan is attached as a consequence of the *C. jejuni* pgl operon and the activity of the *Salmonella* WaaL enzyme.

DETAILED DESCRIPTION

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

As used herein, the term "recombinant bacterium" refers to a bacterial cell that has been genetically modified from its native state. For instance, a recombinant bacterium may comprise one or more nucleotide insertions, nucleotide deletions, nucleotide rearrangements, and nucleotide modifications. These genetic modifications may be introduced into the chromosome of the bacterium, or alternatively be present on an extrachromosomal nucleic acid (e.g., a plasmid). Recombinant bacteria of the disclosure may comprise a nucleic acid located on a plasmid. Alternatively, the recombinant bacteria may comprise a nucleic acid located in the bacterial chromosome (e.g., stably incorporated therein). In some embodiments, the recombinant bacterium is avirulent. In some embodiments the recombinant bacterium exhibits reduced virulence. In some embodiments, the recombinant bacterium is non-virulent. In some embodiments, the recombinant bacterium is attenuated. In another embodiment, the recombinant bacterium is a recombinant derivative of a pathogenic bacterium.

As used herein, the term "gene" refers to a nucleic acid fragment that encodes a protein or a fragment thereof, or a functional or structural RNA molecule, and may optionally include a regulatory sequence preceding (5' non-coding sequences) and following (3' non-coding sequences) the coding sequence of the nucleic acid. In some embodiments, a "gene" does not include regulatory sequences preceding and following the coding sequence.

In one embodiment, the gene is a heterologous gene. In another embodiment, the nucleic acid is a heterologous nucleic acid. As used herein, the terms "heterologous gene" or "heterologous nucleic acid" refer to a gene or a nucleic acid sequence present in a recombinant cell, e.g., bacterium, that is not normally found in the wild-type cell, e.g., bacterium, in nature. In some embodiments, the heterologous gene or heterologous nucleic acid is exogenously introduced into a given cell. In some embodiments, a heterologous gene may include a gene, or fragment thereof, introduced into a non-native host cell. In some embodiments, the term "heterologous gene" includes a second copy of a native gene, or fragment thereof, that has been introduced into the host cell in addition to the corresponding native gene. A heterologous nucleic acid may also include, in some embodiments, a gene sequence that is naturally-found in a given cell but which has been modified, e.g., by regulation by a different promoter sequence, to expresses an unnatural amount of the nucleic acid and/or the polypeptide which it encodes; and/or two or more nucleic acid sequences that are not found in the same relationship to each other in nature.

As used herein, the term "endogenous gene" refers to a native gene that is present in its natural location in the genome of an organism (e.g., a bacterial chromosome).

A "promoter" as used herein, refers to a nucleic acid sequence that is capable of controlling the expression of a coding sequence or gene. A promoter may comprise one or more specific transcriptional regulatory sequences to further enhance expression and/or to alter the spatial expression and/or temporal expression of a nucleic acid. For example, a promoter may include one or more nucleic acids that are specifically recognized by a transcriptional activator protein (e.g., an enhancer element), a transcriptional repressor protein, a polymerase, and the like. The term "operably linked," as used herein, means that expression of a nucleic acid sequence is under the control of a promoter with which it is spatially connected. A promoter may be positioned 5' (upstream) of the nucleic acid sequence under its control. The distance between the promoter and a nucleic acid sequence to be expressed may be approximately the same as the distance between that promoter and the native nucleic acid sequence it controls. As is known in the art, variation in this distance may be accommodated without loss of promoter function. The nucleic acid sequences of the promoters described herein are known in the art, and methods of operably-linking these promoters to a gene (e.g., a gene encoding a repressor) are known in the art.

In some embodiments, the promoter for use as described herein may be regulated directly or indirectly by a sugar. For example, in some embodiments, the promoter is responsive to the level of arabinose, otherwise referred to herein as an "arabinose-regulatable promoter". Generally speaking, arabinose may be present during the in vitro growth of a bacterium, while typically absent from host tissue. In one embodiment, the promoter is derived from an araC-$P_{araBAD}$ system from *Escherichia coli*. The araC $P_{araBAD}$ system is a tightly regulated expression system, which has been shown to work as a strong promoter induced by the addition of low levels of arabinose. The araC-araBAD promoter is a bidirectional promoter controlling expression of the araBAD nucleic acid sequences in one direction, and the araC nucleic acid sequence in the other direction.

For convenience, the portion of the araC-araBAD promoter that mediates expression of the araBAD nucleic acid sequences, and which is controlled by the araC nucleic acid sequence product, is referred to herein as $P_{araBAD}$. For use as described herein, a cassette with the araC nucleic acid sequence and the araC-araBAD promoter may be used. This cassette is referred to herein as araC $P_{araBAD}$. The AraC protein is both a positive and negative regulator of $P_{araBAD}$.

In the presence of arabinose, the AraC protein is a positive regulatory element that allows expression from $P_{araBAD}$. In the absence of arabinose, the AraC protein represses expression from $P_{BAD}$. Other enteric bacteria contain arabinose regulatory systems homologous to the araC-araBAD system from *E. coli*, including, for example, *S. typhimurium*. For example, the *E. coli* AraC protein only activates *E. coli* $P_{araBAD}$ (in the presence of arabinose) and not *S. typhimurium* $P_{araBAD}$. Thus, an arabinose-regulated promoter may be used in a recombinant bacterium that possesses a similar arabinose operon, without substantial interference between the two, if the promoter and the operon are derived from two different species of bacteria. Generally speaking, the concentration of arabinose necessary to induce expression is typically less than about 2% (w/w) in a culture media. In some embodiments, the concentration is less than about 1.5%, 1%, 0.5%, 0.2%, 0.1%, or 0.05% (w/w) in a culture media. In other embodiments, the concentration is 0.05% or below, e.g. about 0.04%, 0.03%, 0.02%, or 0.01% (w/w). In an exemplary embodiment, the concentration is about 0.05% (w/w) in a culture media.

In other embodiments, the promoter may be responsive to the level of maltose in the environment, otherwise referred to herein as a "maltose-regulatable promoter". In some embodiments, the recombinant bacteria described herein are cultured in a medium comprising maltose. The malT gene encodes MalT, a positive regulator of four maltose-responsive promoters ($P_{PQ}$, $P_{EFG}$, $P_{KBM}$, and $P_S$). The combination of malT and a mal promoter creates a tightly regulated expression system that has been shown to work as a strong promoter induced in the presence of maltose. Unlike the araC-$P_{araBAD}$ system, malT expression is regulated by a promoter (i.e., $P_T$) that is functionally unrelated to the other mal promoters. $P_T$ is not regulated by MalT. The malEFG-malKBM promoter is a bidirectional promoter that controls expression of the malKBM nucleic acid sequences in one direction, and the malEFG nucleic acid sequences in the other direction. For convenience, the portion of the malEFG-malKBM promoter that mediates expression of the malKBM nucleic acid sequence, and which is controlled by MalT, is referred to herein as $P_{malKBM}$, and the portion of the malEFG-malKBM promoter that mediates expression of the malEFG nucleic acid sequence, and which is controlled by MalT, is referred to herein as $P_{EFG}$. Full induction of $P_{KBM}$ requires the presence of the MalT binding sites of $P_{malEFG}$. For use in the vectors and systems described herein, a gene cassette comprising a nucleic acid sequence encoding MalT and a mal promoter may be used. This gene cassette is referred to herein as malT-$P_{mal}$. In the presence of maltose, the MalT is a positive regulatory element that allows for expression mediated by $P_{mal}$. Generally speaking, the concentration of maltose necessary to induce expression is typically less than about 1% (w/w) in a culture media. In some embodiments, the concentration is less than about 1.0%, 0.9%, 0.8%, 0.7%, 0.6%, 0.5%, 0.4%, 0.3% 0.2%, 0.1%, or 0.05% (w/w) in a culture media. In other embodiments, the concentration is 0.05% or below, e.g. about 0.04%, 0.03%, 0.02%, or 0.01% (w/w). In an exemplary embodiment, the concentration is about 0.2% to about 0.4% (w/w) in a culture media.

In still other embodiments, the promoter used herein is responsive to the level of rhamnose in the environment, otherwise referred to herein as a "rhamnose-regulatable promoter". Analogous to the araC-$P_{araBAD}$ system described above, the rhaRS-$P_{rhaB}$ activator-promoter system is tightly regulated by rhamnose. Expression from the rhamnose promoter ($P_{rha}$) is induced to high levels in the presence of rhamnose. In some embodiments, the bacteria are cultured in the presence of rhamnose. Rhamnose is commonly found in bacteria but rarely found in human subjects. The rhaBAD operon is controlled by the $P_{rhaBAD}$ promoter. This promoter is regulated by two activators, RhaS and RhaR, and the corresponding nucleic acid sequences belong to one transcription unit that is located in the opposite direction of the rhaBAD nucleic acid sequences. In the presence of L-rhamnose, RhaR binds to the $P_{rhaRS}$ promoter and activates the production of RhaR and RhaS. RhaS together with L-rhamnose, in turn, bind to the $P_{rhaBAD}$ and the $P_{rhaT}$ promoters and activates the transcription of the structural nucleic acid sequences. Full induction of the arabinose, maltose and rhamonse regulated promoters described herein requires binding of the Crp-cAMP complex, which is a key regulator of catabolite repression.

Although both L-arabinose and L-rhamnose act directly as inducers of the expression of regulons that mediate their catabolism, important differences exist in regard to the regulatory mechanisms. L-Arabinose acts as an inducer with the activator AraC in the positive control of the arabinose regulon. However, the L-rhamnose regulon is subject to a regulatory cascade, and is therefore subject to even tighter control than the araC-$P_{araBAD}$ system. L-Rhamnose acts as an inducer with the activator RhaR for synthesis of RhaS, which in turn acts as an activator in the positive control of the rhamnose regulon. In the present disclosure, rhamnose may be used to interact with the RhaR protein and then the RhaS protein may activate transcription of a nucleic acid sequence operably-linked to the $P_{rhaBAD}$ promoter.

In still other embodiments, the promoter may be responsive to the level of xylose in the environment, referred to herein as a "xylose-regulatable promoter". Generally, xylose concentrations of between 0.0002% to 0.63% (w/w) in the environment activate the expression of a xylose inducible promoter described herein. (6) The xy/R-$P_{xy1A}$ system is another well-established inducible activator-promoter system. Xylose induces xylose-specific operons (e.g., xylE, xylFGHR, and xylAB) which are regulated by XylR and the cyclic AMP-Crp system. The XylR protein serves as a positive regulator by binding to two distinct regions of the xyl nucleic acid sequence promoters. As with the araC-$P_{araBAD}$ system described above, the xylR-$P_{xylAB}$ and/or xylR-$P_{xylFGH}$ regulatory systems may be used. In these embodiments, xylR-$P_{xylAB}$ xylose interacting with the XylR protein activates transcription of nucleic acid sequences operably-linked to either of the two $P_{xy1}$ promoters.

As used herein, the term "exogenous" refers to a substance (e.g., a nucleic acid or polypeptide) present in a cell other than its native source. The term exogenous can refer to a nucleic acid or a protein that has been introduced by a process involving the hand of man into a biological system such as a cell or organism in which it is not normally found or in which it is found in undetectable amounts. A substance can be considered exogenous if it is introduced into a cell or an ancestor of the cell that inherits the substance. In contrast, the term "endogenous" refers to a substance that is native to the biological system or cell.

As used herein, the term "invasive" when used in reference to a bacterium refers to a bacterium that is able to be absorbed by an eukaryotic cell, or a bacterium that actively penetrates an eukaryotic cell. In some embodiments, an invasive bacterium penetrates an eukaryotic cell and reaches the eukaryotic cell cytoplasm by lysis of a vacuolar membrane.

As used herein, the term "pathogenic" when used in reference to a bacterium refers to a bacterium capable of infecting and causing disease in a host, as well as producing infection-related symptoms in the infected host. A bacterial species that is a pathogen and is pathogenic can be rendered attenuated or avirulent such that it no longer produces infection-related symptoms in the infected host. Such bacteria are referred to as "attenuated derivatives of pathogenic bacteria."

A "pharmaceutical composition," as used herein, refers to a composition comprising an active ingredient (e.g., a recombinant bacterium described herein) with other components such as a physiologically suitable carrier and/or excipient.

As used herein, the term "pharmaceutically acceptable carrier" or a "pharmaceutically acceptable excipient" refers to a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline (e.g., phosphate-buffered saline (PBS)); (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable excipient" or the like are used interchangeably herein.

A "plasmid" or "vector" includes a nucleic acid construct designed for delivery to a host cell or transfer between different host cell. The nucleic acid incorporated into the plasmid can be operatively linked to an expression control sequence when the expression control sequence controls and regulates the transcription and translation of that polynucleotide sequence.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. The terms "protein" and "polypeptide" as used herein refer to both large polypeptides and small peptides. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

A "nucleic acid" or "nucleic acid sequence" may be any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA, rRNA, and tRNA.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (7); Bauer et al. (8); Craik (9); Smith et al. (10); and U.S. Pat. No. 4,518,584 (11) and U.S. Pat. No. 4,737,462 (12), which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

The term "statistically significant" or "significantly" refers to statistical significance and generally means a two standard deviation (2SD) or greater difference.

As used herein, the term "host cell" refers to a cell in an organism to which the recombinant bacterium is being administered in order to, for example, induce an immune response. In one embodiment, a host is a bird, equine, or human and a host cell refers, respectively, to a bird cell, an equine cell, or a human cell.

Other than in the operating examples, or where otherwise indicated, all numbers expressing quantities of ingredients or reaction conditions used herein should be understood as modified in all instances by the term "about." The term "about" when used in connection with percentages can mean ±1%.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

I. Recombinant Bacteria

The present disclosure provides, in some embodiments, a recombinant bacterium capable of regulated expression of at least one nucleic acid sequence encoding an antigen of interest (e.g., a *Campylobacter* antigen). The recombinant bacterium described herein is particularly effective in eliciting an immune response (e.g., protective immunity) against the antigen of interest because the bacterium comprise multiple recombinant regulatory systems that permit the bacterium to replicate upon administration and to colonize lymphoid tissues in a subject in order to elicit potent immune responses. However, after multiple replication cycles in vivo, the bacterium ultimately exhibits an attenuated phenotype which allows for safe administration to a subject, for example as a vaccine composition. The recombinant regulatory systems of the bacteria described herein depend, in part, on multiple genetic regulatory elements that are responsive to one or more sugars (e.g., arabinose, rhamnose, mannose, maltose, xylose, and galactose) that not available to the bacterium in vivo. Thus, using the phenotype of the recombinant bacteria described herein can be altered upon administration to a subject. In some embodiments, the phenotype of the recombinant bacteria described herein is regulated-delayed expression of an antigen of interest, and the gene conferring the phenotype encodes an antigen of interest. In some embodiments, the subject is administered one or more sugars before, after or concurrently with the administration of a recombinant bacterium described herein in order to activate and/or repress a sugar-responsive regulatory system of the bacteria. In some embodiments, the recombinant bacterium described herein comprises at least three regulatory systems, each dependent on a different sugar, which facilitates initial invasion of a host cell in the subject, delayed attenuation, and improved immunogenicity.

In some embodiments, the recombinant bacterium described herein can be regulated for delayed attenuation in vivo. In some embodiments, the recombinant bacterium described herein is capable of regulated delayed expression of a nucleic acid encoding an antigen of interest. In some embodiments, the recombinant bacterium described herein exhibits regulated production of Generalized Modules for Membrane Antigens (GMMA) in vivo, which may lead to enhanced production of conserved outer membrane proteins present in the bacterium, and ultimately improved immunogenicity. In some embodiments, the recombinant bacterium described herein is capable of both regulated expression of at least one nucleic acid encoding at least one antigen of interest and regulated attenuation. In some embodiments, the recombinant bacterium described herein is capable of both regulated expression of at least one nucleic acid encoding at least one antigen of interest and regulated production of GMMA in vivo. In some embodiments, the recombinant bacterium described herein is capable of both regulated production of GMMA in vivo, and regulated attenuation. In some embodiments, the recombinant bacterium described herein is capable of regulated expression of at least one nucleic acid encoding at least one antigen of interest, regulated attenuation, and regulated production of GMMA in vivo. In some embodiments, each of these properties is directly or indirectly regulated by the abundance of at least one sugar (e.g., arabinose, rhamnose, mannose, xylose, maltose, and galactose).

In some embodiments, the bacterium described herein is a Gram negative bacterium. In some embodiments, the bacterium is a pathogenic bacterium. In some embodiments, the bacterium is an avirulent bacterium. In some embodiments, the bacterium belongs to the Enterobaceteriaceae. In some embodiments, the bacterium belongs to a genus selected from: *Alterococcus, Aquamonas, Aranicola, Arsenophonus, Brenneria, Budvicia, Buttiauxella, Candidatus Phlomobacter, Cedeceae, Citrobacter, Edwardsiella, Enterobacter, Erwinia, Escherichia, Ewingella, Hafnia, Klebsiella, Kluyvera, Leclercia, Leminorella, Moellerella, Morganella, Obesumbacterium, Pantoea, Pectobacterium, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhbdus, Yersinia, Yokenella*. In some embodiments, the bacterium is a pathogenic species of Enterobaceteriaceae. In some embodiments, the bacterium is selected from the group consisting of *Escherichia coli, Shigella, Edwardsiella, Salmonella, Citrobacter, Klebsiella, Enterobacter, Serratia, Proteus, Morganella, Providencia* and *Yersinia*. In some embodiments, the bacterium is of the genus *Salmonella*. In some embodiments, the bacterium is of the genus *Yersinia*. In some embodiments, the bacterium is of the genus *Edwardsiella*. In some embodiments, the bacterium is of a genus, species, or strain commonly used as a live or attenuated vaccine.

Some embodiments of the instant disclosure comprise a species or subspecies of the *Salmonella* genera (e.g., *S. enterica* or *S. bongori*). For instance, the recombinant bacterium may be a *Salmonella enterica* serovar, including, for example, Paratyphi A, *Enteritidis, typhi*, and *typhimurium*. In some embodiments, the recombinant bacterium is of the serovar *S. typhimurium, S. typhi, S. paratyphi, S. gallinarum, S. enteritidis, S. choleraesius, S. arizonae, S. newport, S. heidelberg, S. infantis, S. cholerasiuis*, or *S. dublin*.

A recombinant bacterium derived from *Salmonella* may be particularly suited to use as a vaccine. For example, oral infection of a host with a *Salmonella* strain typically leads to colonization of the gut-associated lymphoid tissue (GALT), which leads to the induction of a generalized mucosal immune response to the recombinant bacterium. Further penetration of the bacterium into the mesenteric lymph nodes, liver and spleen may augment the induction of systemic and cellular immune responses directed against the bacterium. Thus, the use of recombinant *Salmonella* for oral immunization stimulates all three branches of the immune system, which is particularly important for immunizing against infectious disease agents that colonize on and/or invade through mucosal surfaces. In some embodiments, the recombinant bacterium described herein is used to induce an immune response in poultry (e.g., as a vaccine). When used in poultry, the recombinant bacterium may be administered by course spray and thereby inoculate the conjunctiva-associated lymphoid tissue (CALT) via eye exposure, the nasal-associated lymphoid tissue (NALT) and bronchus-associated lymphoid tissue (BALT) via respiratory exposure and the GALT via oral exposure. In some embodiments, the recombinant bacterium described herein is administered to newly-hatched chicks.

A. Antigens

As used herein, "antigen" refers to a biomolecule capable of eliciting an immune response in a host. In some embodiments, an antigen may be a protein, or fragment of a protein. In some embodiments, the recombinant bacterium comprises a nucleic acid (e.g., a plasmid) encoding an antigen of interest, wherein the nucleic acid is expressed by the host cell (e.g., a DNA vaccine). In some embodiments, the recombinant bacterium comprises a nucleic acid encoding an antigen of interest. In some embodiments, the recombinant bacterium comprises at least one, at least two, at least three, at least four, at least five, at least six, at least seven, at least eight or more nucleic acids encoding an antigen of interest (e.g., one or more copies of a nucleic acid encoding a specific antigen, one or more nucleic acids encoding different antigens of interest, or combinations thereof). In an exemplary embodiment, the antigen elicits a protective immune response in a subject.

As used herein, "protective" means that the immune response contributes to the lessening of any symptoms associated with infection of a host with the pathogen the antigen was derived from or designed to elicit a response against. For example, a protective antigen from a pathogen, such as *Salmonella*, may induce an immune response that helps to ameliorate symptoms associated with *Salmonella* infection or reduce the morbidity and mortality associated with infection with the pathogen or may reduce the ability of *Salmonella* to infect and colonize the host. The use of the term "protective" in this disclosure does not necessarily require that the host is completely protected from the effects of the pathogen.

*C. jejuni* is a commensal for poultry and causes no disease symptoms. Thus, when "protective" immunity to *C. jejuni* is induced in poultry, this refers to the ability of the vaccine to reduce the levels of Cj colonization in the intestine and ceca. This is also true for *Salmonella*. Thus, although several stains of *Salmonella* can cause disease and mortality in newly hatched chicks, chicks become totally tolerant of *Salmonella* by one week of age, after which most strains of *Salmonella* persist in the GI tract as a commensal.

In some embodiments, the antigen of interest is an antigen derived from an infectious agent. In some embodiments, the antigen of interest is derived from an infectious agent selected from the group consisting of a virus, a bacteria, a protozoan, a prion, a fungi, and a helminth. In some embodiments, the antigen of interest is derived from a bacteria.

Alternatively, antigens may be derived from organisms newly identified or newly associated with a disease or pathogenic condition, or new or emerging pathogens of animals or humans, including those now known or identified in the future, may be expressed by a bacterium detailed herein. Furthermore, antigens are not limited to those from pathogenic organisms.

Immunogenicity of the bacterium may be augmented and/or modulated by constructing strains that also express sequences for cytokines, adjuvants, and other immunomodulators.

Some examples of microorganisms useful as a source for antigen are listed below. These may include microorganisms for the control of plague caused by *Yersinia pestis* and other *Yersinia* species such as *Y. pseudotuberculosis* and *Y. enterocolitica*, for the control of gonorrhea caused by *Neisseria gonorrhoea*, for the control of syphilis caused by *Treponema pallidum*, and for the control of venereal diseases as well as eye infections caused by *Chlamydia trachomatis*. Species of *Streptococcus* from both group A and group B, such as those species that cause sore throat or heart diseases, *Streptococcus equi*, which causes strangles in equines, *Streptococcus mutans*, which causes cavities, and *Streptococcus pneumoniae*, *Erysipelothrix rhusiopathiae*, *Neisseria meningitidis*, *Mycoplasma pneumoniae* and other *Mycoplasma*-species, *Hemophilus influenza*, *Bordetella pertussis*, *Mycobacterium tuberculosis*, *Mycobacterium leprae*, other *Bordetella* species, *Escherichia coli*, *Streptococcus equi*, *Streptococcus pneumoniae*, *Brucella abortus*, *Pasteurella hemolytica* and *P. multocida*, *Vibrio cholera*, *Shigella* species, *Borrellia* species, *Bartonella* species, *Heliobacter pylori*, *Campylobacter* species, *Pseudomonas* species, *Moraxella* species, *Brucella* species, *Francisella* species, *Aeromonas* species, *Actinobacillus* species, *Clostridium* species, *Rickettsia* species, *Bacillus* species, *Coxiella* species, *Ehrlichia* species, *Listeria* species, and *Legionella pneumophila* are additional examples of bacteria within the scope of this disclosure from which antigen nucleic acid sequences could be obtained.

In some embodiments, the antigen is a *Campylobacter* antigen (e.g., a *C. jejuni* antigen or a *C. coli* antigen). In some embodiments, the *Campylobacter* antigen is selected from the group consisting of Peb1 (encoded by the cj0921c gene), CjaA (encoded by the cj0982c gene), Dps (encoded by the cj1534c gene), TlyA (encoded by the cj0588 gene), Omp18 (encoded by the cj0113 gene), Cj0998c (encoded by the cj0998c gene), Cj0034c (encoded by the cj0034c gene), Cj0168c (encoded by the cj0168c gene), Cj0248 (encoded by the cj0248 gene), Peb3 (encoded by the cj0289 gene), CmeC (encoded by the cj0365 gene), Cj0404 (encoded by the cj0404 gene), Cj0420 (encoded by the cj0420 gene), Cj0427 (encoded by the cj0427 gene), Cj0428 (encoded by the cj0428 gene), PorA (encoded by the cj1259 gene), Fla (encoded by the cj1339c gene), CadF (encoded by the cj1478c gene), and Cj1656c (encoded by the cj1656c gene).

In some embodiments, the *Campylobacter* antigen comprises a canonical *Campylobacter* N-glycosylation amino acid sequence. In some embodiments, the canonical *Campylobacter* N-glycosylation amino acid sequence comprises the amino acid sequence Asp/Glu-Xaa-Asn-tyr-Ser/Thr (SEQ ID NO: 1). The presence of the canonical *Campylobacter* N-glycosylation amino acid sequence allows for the glycosylation of the antigen when produced by a recombinant bacterium comprising a pgl operon (e.g., a *Campylobacter* pgl operon) or one or more pgl operon genes (e.g., wlaA, gne, pglK, pglH, pglI, pglJ, pglB, pglA, pglC, pglD, wlaJ, pglE, pglF, and pglG). In one embodiment, the PglB enzyme can add the N-glycan to a slightly different aa sequence, DGGK (SEQ ID NO:2), different from the N-glycosylation sequence used in eukaryotes (Barre et al., 2017. Glycobiology 27:978-989).

In some embodiments, the antigen of interest comprises a native canonical *Campylobacter* N-glycosylation amino acid sequence. In some embodiments, the antigen of interest is engineered to comprise at least one non-native canonical *Campylobacter* N-glycosylation amino acid sequence Asp/Glu-Xaa-Asn-tyr-Ser/Thr (SEQ ID NO: 1), such that the antigen is N-glycosylated when produced by a recombinant bacterium comprising a pgl operon (e.g., a *Campylobacter* pgl operon) or one or more pgl operon genes.

In certain embodiments, an antigen may comprise a B-cell epitope or a T-cell epitope. Alternatively, an antigen to which an immune response is desired may be expressed as a fusion to a carrier protein that contains a strong promiscuous T-cell epitope and/or serves as an adjuvant and/or facilitates presentation of the antigen to enhance, in all cases, the immune response to the antigen or its component part. This can be accomplished by methods known in the art. Fusion to tetanus toxin fragment C, CT-B, LT-B and hepatitis virus B core are particularly useful for these purposes, although other epitope presentation systems are well known in the art.

In further embodiments, a nucleic acid sequence encoding an antigen may comprise a secretion signal.

As stated above, the level of synthesis of an antigen of interest may be optimized by modifying the nucleic acid sequence encoding the repressor and/or promoter. As used herein, "modify" refers to an alteration of the nucleic acid sequence of the repressor and/or promoter that results in a change in the level of transcription of the nucleic acid sequence encoding the repressor, or that results in a change in the level of synthesis of the repressor. For instance, in one embodiment, modify may refer to altering the start codon of the nucleic acid sequence encoding the repressor. Generally speaking, a GTG or TTG start codon, as opposed to an ATG start codon, may decrease translation efficiency ten-fold. In another embodiment, modify may refer to altering the Shine-Dalgarno (SD) sequence of the nucleic acid sequence encoding the repressor. The SD sequence is a ribosomal binding site generally located 6-7 nucleotides upstream of the start codon. The SD consensus sequence is AGGAGG (SEQ ID NO:80), and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence encoding the repressor to alter the level of translation of the mRNA encoding the repressor. For instance, non-A rich codons initially after the start codon of the nucleic acid sequence encoding the repressor may not maximize translation of the mRNA encoding the repressor. Similarly, the codons of the nucleic acid sequence encoding any of the proteins described herein may be codon-optimized, i.e., altered so as to mimic the codons from highly synthesized proteins of a particular organism. In a further embodiment, modify may refer to altering the GC content of the nucleic acid sequence encoding the repressor to change the level of translation of the mRNA encoding the repressor. Methods of modifying a nucleic acid sequence are known in the art.

In some embodiments, more than one modification or type of modification may be performed to optimize the expression level of a nucleic acid described herein (e.g., a nucleic acid encoding a repressor or antigen of interest). For instance, at least one, two, three, four, five, six, seven, eight, or nine modifications, or types of modifications, may be performed to optimize the expression level of a nucleic acid described herein. By way of non-limiting example, when the repressor is LacI, then the nucleic acid sequence of LacI and the promoter may be altered so as to increase the level of LacI synthesis. In one embodiment, the start codon of the LacI repressor may be altered from GTG to ATG. In another embodiment, the SD sequence may be altered from AGGG to AGGA. In yet another embodiment, the codons of lacI may be optimized according to the codon usage for highly synthesized proteins of *Salmonella*. In a further embodiment, the start codon of lacI may be altered, the SD sequence may be altered, and the codons of lacI may be optimized.

In some embodiments, the recombinant bacterium comprises a nucleic acid that is located in a plasmid or vector. As used herein, "vector" refers to an autonomously replicating nucleic acid unit. The present disclosure can be practiced with any known type of vector, including viral, cosmid, phasmid, and plasmid vectors. The most preferred type of vector is a plasmid vector. In some embodiments, the plasmid or vector is a high copy plasmid. In some embodiments, the plasmid or vector is a low copy plasmid or vector.

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In some embodiments, the plasmid comprises a nucleic acid sequence encoding an aspartate-semialdehyde dehydrogenase gene (e.g., asdA). These plasmids may be advantageously used to complement a bacterium that comprises an aspartate-semialdehyde dehydrogenase gene (e.g., asdA). In some embodiments, the plasmid is selected from the group consisting of pYA3342, pYA3337, and pYA3332.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

In still other cases, a high copy number vector might be optimal for the induction of maximal antibody responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR ori or the pUC ori.

Additionally, vector copy number may be increased by selecting for mutations that increase plasmid copy number. These mutations may occur in the bacterial chromosome but are more likely to occur in the plasmid vector.

Preferably, vectors used herein do not comprise antibiotic resistance markers to select for maintenance of the vector.

In some embodiments, the nucleic acid sequences described herein are operably-linked to a promoter. Promoters for use in the embodiments described herein are known in the art. One of skill in the art would recognize that the selection of a repressor dictates, in part, the selection of the promoter to be used to regulate the expression of a nucleic acid described herein. For instance, if the repressor is LacI, then the promoter may be selected from the group consisting of LacI responsive promoters, such as $P_{trc}$, $P_{lac}$, $P_{T7lac}$ and $P_{tac}$. If the repressor is C2, then the promoter may be selected from the group consisting of C2 responsive promoters, such as P22 promoters $P_L$ and $P_R$. If the repressor is C1, then the promoter may be selected from the group consisting of C1 responsive promoters, such as λ promoters $P_L$ and $P_R$.

In each embodiment herein, the promoter regulates expression of a nucleic acid sequence. In some embodiments, the promoter comprises a regulatory sequence controlled by a repressor, such that expression of the nucleic acid sequence is repressed when the repressor is synthesized (e.g., during in vitro growth of the bacterium), but expression of the nucleic acid sequence encoding an antigen is high when the repressor is not synthesized (e.g., in vivo). Generally speaking, the concentration of the repressor will decrease with every cell division after expression of the gene encoding the repressor ceases. In some embodiments, the concentration of the repressor decreases such that high levels of expression of the nucleic acid sequence that is being regulated is achieved after about 2, 3, 4, 5, 6, 7, 8, 9, 10, 11, or 12 divisions of the bacterium. In an exemplary embodiment, the concentration of the repressor decreases enough to allow high-level expression of the nucleic acid sequence encoding an antigen after about 5 divisions of the bacterium in vivo.

In certain embodiments, the promoter may comprise other regulatory elements. For instance, the promoter may comprise lacO if the repressor is LacI. This is the case with the lipoprotein promoter P$_{lpplacO}$ that is regulated by LacI since it possesses the LacI binding domain lacO. In one embodiment, the repressor is a LacI repressor and the promoter is P$_{trc}$.

In some embodiments, the expression of the nucleic acid sequence regulated by a repressor is repressed in vivo. Expression may be "repressed" or "partially repressed" when it is about 50%, 45%, 40%, 35%, 30%, 25%, 20%, 15%, 10%, 5%, 1%, or even less than 1% of the expression under non-repressed conditions. Thus although the level of expression under conditions of "complete repression" might be exceeding low, it is likely to be detectable using very sensitive methods since repression can never by absolute.

Conversely, the expression of the nucleic acid sequence encoding the antigen should be high when the expression of the repressor is repressed. For instance, if the repressor is not expressed during growth of the recombinant bacterium in a host, the expression of the nucleic acid under the control of the repressor will be high. As used herein, "high level" expression refers to expression that is strong enough to elicit an immune response to the antigen. Consequently, the copy number correlating with high level expression can and will vary depending on the antigen and the type of immune response desired. Methods of determining whether an antigen elicits an immune response such as by measuring antibody levels or antigen-dependent T cell populations or antigen-dependent cytokine levels are known in the art, and methods of measuring levels of expression of antigen encoding sequences by measuring levels of mRNA transcribed or by quantitating the expression level of a protein are also known in the art.

In each of the above embodiments, a recombinant bacterium capable of regulated expression may also be attenuated. "Attenuated" refers to the state of the bacterium wherein the bacterium has been weakened from its wild-type fitness by some form of recombinant or physical manipulation. This includes altering the genotype of the bacterium to reduce its ability to cause disease. However, the bacterium's ability to colonize the gut (in the case of *Salmonella*) and induce immune responses is, preferably, not substantially compromised.

In an exemplary embodiment, a recombinant bacterium may be attenuated as described above. In which case, both regulated attenuation and regulated expression of an antigen encoding sequence may be dependent upon a sugar regulatable system. Consequently, the concentration of sugar (e.g., arabinose) needed for optimal expression of the regulated antigen encoding sequence may not be the same as the concentration for optimal expression of attenuation. In an exemplary embodiment, the concentration of arabinose for the optimization of both regulated attenuation and regulated expression of sequences encoding antigen will be substantially the same.

Accordingly, the promoter and/or the nucleic acid sequence encoding an attenuation protein may be modified to optimize the system. Methods of modification are detailed above. Briefly, for example, the SD ribosome binding sequence may be altered, and/or the start codon may be altered from ATG to GTG for the nucleic acid sequences fur and phoPQ, so that the production levels of Fur and PhoPQ are optimal for both the regulated attenuation phenotype and the regulated expression when growing strains with a given concentration of arabinose. One of skill in the art will appreciate that other nucleic acid sequences, in addition to fur and phoPQ, may also be altered as described herein in combination with other well-known protocols. In addition, these attenuating nucleic acid sequences may be regulated by other systems using well-established protocols known to one of skill in the art. For example, they may be regulated using with promoters dependent on addition of maltose, rhamnose, or xylose rather than arabinose.

cj0034c—In some embodiments, the recombinant bacterium comprises a nucleic acid comprising a cj0034c gene (e.g., a *C. jejuni* cj0034c gene).

In some embodiments, the nucleic acid comprising a cj0034c gene is located on a plasmid in the bacterium. In some embodiments, the nucleic acid comprising a cj0034c gene is located on a chromosome of the bacterium.

The nucleic acid sequence of an exemplary *C. jejuni* cj0034c gene is provided below:

```
                                                    (SEQ ID NO: 3)
ATGAAAACAAATAATATCTTTATGGCTTTAGCCATAGTTTTGGCAAGTTT

GATTCTAGCTTTTGGATTTAACAAGGCTTTAAGTGATTTTAAAACACTTG

AAAGAAGTGTAAGTGTAAAGGGTTTAAGTCAAAAAGAAGTCGAAGCGGAT

ACTTTGATACTTCCTATAAAATTCACAAGATCAAACAACAATCTTACAAA

TTTATACGAAGAACTAGAACAAGATAAAGAAAATATCATCAAATTTTTAG

AAAAACAAGGCATAAAAGAAGATGAGATCAGCTACAACTCGCCAAATATC

ATAGATCGTTTAAGCGATCCTTATAGCAACGACACTCAAGCTGCATACCG

ATACATAGGCACTGCGAATTTACTCATCTATACTCAAAATGTAAAGCTTG

GAAAAAGCATACTAGAAAACATTTCAAGTCTTGCAAAATTTGGTATAGTA

ACAAAAATCGATGATTATGATATAGAATACCTTTACACCAAGCTAAATGA

TATAAAACCACAAATGATAGAAGAAGCAACGCTCAATGCTAGAAATGCAG

CGATAAAATTCGCACAAGACTCAAACAGCCATCTAGGCAAGATAAAAAAG

GCTTCTCAAGGACAATTTAGCATTAGCAACAGAGATAAAAACACCCCTTA

TATCAAAACCATAAGAGTGGTTTCTACTATAGAATACTACTTAAAAGACT

GA
```

The amino acid sequence of the Cj0034c protein encoded by the nucleic acid of SEQ ID NO: 3 is provided below:

(SEQ ID NO: 4)
MKTNNIFMALAIVLASLILAFGFNKALSDFKTLERSVSVKGLSQKEVEAD

TLILPIKFTRSNNNLTNLYEELEQDKENIIKFLEKQGIKEDEISYNSPNI

IDRLSDPYSNDTQAAYRYIGTANLLIYTQNVKLGKSILENISSLAKFGIV

TKIDDYDIEYLYTKLNDIKPQMIEEATLNARNAAIKFAQDSNSHLGKIKK

ASQGQFSISNRDKNTPYIKTIRVVSTIEYYLKD

In some embodiments, the nucleic acid comprises a *C. jejuni* cj0034c gene (provided as SEQ ID NO: 3). In some embodiments, the nucleic acid comprises a cj0034c gene, wherein the cj0034c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 3. In some embodiments, the nucleic acid comprises a cj0034c gene, wherein the cj0034c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 3.

In some embodiments, the nucleic acid comprises a nucleic acid sequence encoding a Cj0034c protein, wherein said Cj0034c protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 4. In some embodiments, the nucleic acid comprises a nucleic acid sequence encoding a Cj0034c protein, wherein said Cj0034c protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 4.

cj0113—In some embodiments, the recombinant bacterium comprises a nucleic acid comprising a cj0113 gene (e.g., a *C. jejuni* cj0113 gene).

In some embodiments, the nucleic acid comprising a cj0113 gene is located on a plasmid in the bacterium. In some embodiments, the nucleic acid comprising a cj0113 gene is located on a chromosome of the bacterium.

The nucleic acid sequence of an exemplary *C. jejuni* cj0113 gene is provided below:

(SEQ ID NO: 5)
ATGAAAAAAGTTTTATTGAGTTCATTGGTTGCGGTGTCTTTGTTAAGCAC

AGGTTTGTTTGCTAAAGAATATACTTTAGATAAAGCACATACAGATGTAG

GTTTTAAAATCAAACATTTACAAATTAGCAATGTAAAAGGAAATTTCAAA

GATTATTCTGCGGTGATTGATTTTGATCCTGCGAGTGCTGAATTTAAAAA

GCTTGATGTAACTATAAAAATCGCATCTGTAAATACAGAAAATCAAACAA

GAGATAATCACTTACAACAAGATGATTTTTTCAAAGCAAAAAAATATCCT

GATATGACTTTTACAATGAAAAAATATGAAAAAATCGATAATGAAAAAGG

CAAAATGACAGGAACTTTAACTATAGCTGGAGTTTCTAAAGATATCGTTT

TAGATGCTGAAATCGGCGGTGTAGCTAAAGGCAAAGATGGAAAAGAAAAA

ATAGGATTTTCTTTAAATGGAAAAATCAAACGCTCTGATTTTAAATTTGC

AACAAGTACTTCAACTATTACTTTAAGTGATGATATTAATTTAAATATCG

AAGTTGAAGCGAACGAAAAATAA

The amino acid sequence of the Omp18 protein encoded by the nucleic acid of SEQ ID NO: 5 is provided below:

(SEQ ID NO: 6)
MKKVLLSSLVAVSLLSTGLFAKEYTLDKAHTDVGFKIKHLQISNVKGNFK

DYSAVIDFDPASAEFKKLDVTIKIASVNTENQTRDNHLQQDDFFKAKKYP

DMTFTMKKYEKIDNEKGKMTGTLTIAGVSKDIVLDAEIGGVAKGKDGKEK

IGFSLNGKIKRSDFKFATSTSTITLSDDINLNIEVEANEK

In some embodiments, the nucleic acid comprises a *C. jejuni* cj0113 gene (provided as SEQ ID NO: 5). In some embodiments, the nucleic acid comprises a cj0113 gene, wherein the cj0113 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 5. In some embodiments, the nucleic acid comprises a cj0113 gene, wherein the cj0113 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 5.

In some embodiments, the nucleic acid comprises a nucleic acid sequence encoding a Omp18 protein, wherein said Omp18 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 6. In some embodiments, the nucleic acid comprises a nucleic acid sequence encoding a Omp18 protein, wherein said Omp18 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 6.

cj0168c—In some embodiments, the recombinant bacterium comprises a nucleic acid comprising a cj0168c gene (e.g., a *C. jejuni* cj0168c gene).

In some embodiments, the nucleic acid comprising a cj0168c gene is located on a plasmid in the bacterium. In some embodiments, the nucleic acid comprising a cj0168c gene is located on a chromosome of the bacterium.

The nucleic acid sequence of an exemplary *C. jejuni* cj0168c gene is provided below:

(SEQ ID NO: 7)
ATGAAAAAAGTTGTACTAATCTCAGCATTACTAGGTGCTTTCGCAGCTAA

TGTTTTTGCAGCTAATACTCCAAGCGATGTAAATCAAACACATACAAAAG

CTAAAGCTGATAAAAAACATGAAGCTAAAACTCACAAAAAAACAAAAGAG

CAAACACCAGCTCAATAA

The amino acid sequence of the Cj0168c protein encoded by the nucleic acid of SEQ ID NO: 7 is provided below:

(SEQ ID NO: 8)
MKKVVLISALLGAFAANVFAANTPSDVNQTHTKAKADKKHEAKTHKKTKE

QTPAQ

In some embodiments, the nucleic acid comprises a *C. jejuni* cj0168c gene (provided as SEQ ID NO: 7). In some embodiments, the nucleic acid comprises a cj0168c gene, wherein the cj0168c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 7. In some embodiments, the nucleic acid comprises a cj0168c gene, wherein the cj0168c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 7.

In some embodiments, the nucleic acid comprises a nucleic acid sequence encoding a Cj0168c protein, wherein said Cj0168c protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 8. In some embodiments, the nucleic acid comprises a nucleic acid sequence encoding a Cj0168c protein, wherein said Cj0168c protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 8.

cj0248—In some embodiments, the recombinant bacterium comprises a nucleic acid comprising a cj0248 gene (e.g., a *C. jejuni* cj0248 gene).

In some embodiments, the nucleic acid comprising a cj0248 gene is located on a plasmid in the bacterium. In some embodiments, the nucleic acid comprising a cj0248 gene is located on a chromosome of the bacterium.

The nucleic acid sequence of an exemplary *C. jejuni* cj0248 gene is provided below:

(SEQ ID NO: 9)
ATGATTGGAGATATGAATGAGCTTTTATTAAAAAGCGTTGAAGTATTGCC

ACCTTTACCTGATACTGTAAGTAAGTTAAGAAAATATGTGAGCGAGGCTA

ATTCAAATATAGAAACTATGAAAGTTGCTGAAATCATTTCAAGCGATCCG

TTGATGACGGCTAAGCTTTTGCAATTAGCAAATTCTCCTTATTATGGTTT

TACAAGAGAAATTACAACCATAAATCAAGTGATTACTTTATTAGGCGTTG

GTAATATCATCAATATAGTTATGGCTGACTCCATTAGAGATAATTTTAAA

ATAGACGTTTCACCTTATGGTTTAAATACTCAAAATTTTTTAAAAACGTG

CAATGAAGAGGCAACTTTTATCGCAAATTGGCTTAATGATGAAGATAAAA

AACTTTCTCATCTTTTAGTTCCTTGTGCAATGCTTTTAAGGCTTGGTATT

GTTATTTTTTCAAATTTTCTTATACAAAATCATAAGGATAAGGATTTTTT

AGCTTTTTTAAATAAAAATGAAAATCTTGCTTTAGCGGAGAATGAATTTT

TAGGCGTAGATCATATTTCTTTCTTGGGATTTTTGTTACATCGTTGGAAT

TTTGATGATGTTTTGATTGAAAGTATATGTTTTGTTCGCACTCCTCATGC

TGCTCGCGAAAAAGTGAAAAAATCCGCTTATGCTTTAGCAATAACAGATC

ATCTTTTTGCTCCGCATGATGGTTCTTCTCCATTTAACGCAAAAGCTGCA

GTTGCTTTACTTAAAGAGGCAAAAACTCAAGGAATTAATTTTGATTTAAA

CAATCTTTTATCTAAGCTTCCTAACAAAGCTAAGGAAAATTTAAACAAAG

AAGATTAA

The amino acid sequence of the Cj0248 protein encoded by the nucleic acid of SEQ ID NO: 9 is provided below:

(SEQ ID NO: 10)
MIGDMNELLLKSVEVLPPLPDTVSKLRKYVSEANSNIETMKVAEIISSDP

LMTAKLLQLANSPYYGFTREITTINQVITLLGVGNIINIVMADSIRDNFK

IDVSPYGLNTQNFLKTCNEEATFIANWLNDEDKKLSHLLVPCAMLLRLGI

VIFSNFLIQNHKDKDFLAFLNKNENLALAENEFLGVDHISFLGFLLHRWN

FDDVLIESICFVRTPHAAREKVKKSAYALAITDHLFAPHDGSSPFNAKAA

VALLKEAKTQGINFDLNNLLSKLPNKAKENLNKED

In some embodiments, the nucleic acid comprises a *C. jejuni* cj0248 gene (provided as SEQ ID NO: 9). In some embodiments, the nucleic acid comprises a cj0248 gene, wherein the cj0248 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 9. In some embodiments, the nucleic acid comprises a cj0248 gene, wherein the cj0248 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 9.

In some embodiments, the nucleic acid comprises a nucleic acid sequence encoding a Cj0248 protein, wherein said Cj0248 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 10. In some embodiments, the nucleic acid comprises a nucleic acid sequence encoding a Cj0248 protein, wherein said Cj0248 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 10.

cj0289c—In some embodiments, the recombinant bacterium comprises a nucleic acid comprising a cj0289c gene (e.g., a *C. jejuni* cj0289c gene).

In some embodiments, the nucleic acid comprising a cj0289c gene is located on a plasmid in the bacterium. In some embodiments, the nucleic acid comprising a cj0289c gene is located on a chromosome of the bacterium.

The nucleic acid sequence of an exemplary *C. jejuni* cj0289c gene is provided below:

```
                                            (SEQ ID NO: 11)
ATGAAAAAAATTATTACTTTATTTGGTGCATGTGCCTTAGCTTTTAGTAT

GGCAAATGCAGACGTGAACCTGTACGGCCCGGGCGGCCCGCACACGGCCC

TGAAAGACATCGCAAACAAATATAGCGAAAAAACCGGCGTGAAAGTGAAC

GTGAACTTTGGCCCGCAGGCGACCTGGTTTGAAAAAGCGAAAAAAGACGC

GGACATCCTGTTTGGCGCGTCAGACCAGTCCGCTCTGGCTATCGCGAGCG

ACTTTGGCAAAGACTTTAACGTGAGCAAAATCAAACCGCTGTATTTTCGT

GAAGCCATCATCCTGACCCAGAAAGGCAACCCGCTGAAAATCAAAGGCCT

GAAAGACCTGGCGAACAAAAAAGTGCGTATCGTGGTGCCGGAAGGCGCGG

GCAAAAGCAACACCTCTGGCACCGGCGTGTGGGAAGACATGATCGGCCGT

ACCCAGGACATCAAAACCATCCAGAACTTTCGTAACAACATCGTGGCCTT

TGTGCCGAACAGCGGTAGCGCGCGTAAACTGTTCGCGCAGGACCAGGCCG

ACGCTTGGATCACTTGGATCGACTGGTCAAAAAGCAACCCGGACATCGGC

ACTGCCGTGGCTATCGAAAAAGACCTGGTGGTGTATCGTACTTTTAACGT

GATCGCGAAAGAAGGCGCGAGCAAAGAAACACAGGACTTTATCGCTTATC

TGAGTTCTAAAGAAGCGAAAGAAATCTTTAAAAAATACGGCTGGCGTGAA

TAA
```

The amino acid sequence of the Peb3 protein encoded by the nucleic acid of SEQ ID NO: 11 is provided below:

```
                                            (SEQ ID NO: 12)
MKKIITLFGACALAFSMANADVNLYGPGGPHTALKDIANKYSEKTGVKVN

VNFGPQATWFEKAKKDADILFGASDQSALAIASDFGKDFNVSKIKPLYFR

EAIILTQKGNPLKIKGLKDLANKKVRIVVPEGAGKSNTSGTGVWEDMIGR

TQDIKTIQNFRNNIVAFVPNSGSARKLFAQDQADAWITWIDWSKSNPDIG

TAVAIEKDLVVYRTFNVIAKEGASKETQDFIAYLSSKEAKEIFKKYGWRE
```

In some embodiments, the nucleic acid comprises a *C. jejuni* cj0289c gene (provided as SEQ ID NO: 11). In some embodiments, the nucleic acid comprises a cj0289c gene, wherein the cj0289c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 11. In some embodiments, the nucleic acid comprises a cj0289c gene, wherein the cj0289c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 11.

In some embodiments, the nucleic acid comprises a nucleic acid sequence encoding a Peb3 protein, wherein said Peb3 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 12. In some embodiments, the nucleic acid comprises a nucleic acid sequence encoding a Peb3 protein, wherein said Peb3 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 12.

cj0365c—In some embodiments, the recombinant bacterium comprises a nucleic acid comprising a cj0365c gene (e.g., a *C. jejuni* cj0365c gene).

In some embodiments, the nucleic acid comprising a cj0365c gene is located on a plasmid in the bacterium. In some embodiments, the nucleic acid comprising a cj0365c gene is located on a chromosome of the bacterium.

The nucleic acid sequence of an exemplary *C. jejuni* cj0365c gene is provided below:

```
                                            (SEQ ID NO: 13)
ATGAATAAAATAATTTCAATTAGTGCTATAGCAAGTTTTACTCTTTTGAT

TTCAGCTTGCTCTTTAAGTCCAAATTTAAATATTCCCGAAGCAAACTATA

GCATTGATAATAAGCTTGGAGCCTTATCTTGGGAAAAAGAAAACAATAGC

TCTATCACAAAAAATTGGTGGAAAGACTTTGATGATGAAAATTTAAATAA

AGTGGTTGATTTAGCACTTAAAAATAATAATGATTTAAAACTTGCTTTCA

TACACATGGAACAAGCTGCTGCTCAATTAGGTATAGATTTTAGCAGTTTG

TTGCCAAAATTTGATGGTAGCGCAAGCGGAAGTCGTGCAAAAACAGCTAT

AAATGCTCCAAGCAATCGAACTGGGGAAGTAAGTTACGGTAATGATTTTA

AAATGGGACTTAATTTAAGCTATGAAATCGATCTTTGGGGAAAATATCGC

GATACATATCGCGCCTCAAAATCAGGCTTTAAAGCAAGTGAGTATGATTA

TGAAGCTGCAAGACTTTCTGTTATTTCAAATACAGTTCAAACTTATTTTA

ATCTTGTAAATGCTTATGAAAATGAAATGCTCTTAAAGAAGCCTATAAA
```

```
TCTGCAAAAGAAATTTATAGGATTAATGATGAAAAATTTCAAGTTGGTGC

TGTAGGTGAATATGAACTTGCTCAAGCAAGAGCCAACTTAGAAAGTATGG

CTTTGCAATATAATGAAGCAAAGTTAAATAAAGAAAATTACCTTAAAGCT

TTAAAAATTTTAACTTCAAATGATTTAAATGACATACTTTACAAAAATCA

AAGCTATCAAGTTTTTAATCTTAAAGAATTTGACATTCCAACTGGAATTT

CAAGTACCATCTTGCTTCAACGTCCAGATATTGGCTCTTCTTTAGAAAAA

TTAACTCAGCAAAATTATCTTGTTGGAGTAGCTCGCACGGCTTTCTTACC

TAGCCTTTCTTTAACAGGATTATTGGGATTTGAAAGCGGGGATTTAGATA

CCTTGGTTAAAGGAGGTTCTAAGACTTGGAATATAGGTGGAAACTTTACT

CTGCCTATTTTTCATTGGGGTGAAATTTACCAAAATGTAAATTTAGCCAA

GCTTAATAAAGATGAAGCTTTTGTAAATTATCAAAATACTTTGATTACTG

CTTTTGGAGAAATTCGCTATGCTTTAGTAGCTAGAAAAACTATACGCTTA

CAATACGATAATGCACAAGCAAGCGAACAATCTTACAAAAGAATCTATGA

AATTGCTAAAGAACGCTATGATATAGGAGAAATGTCTTTGCAAGATTATT

TAGAGGCACGTCAAAATTGGCTTAATGCTGCGGTTGCTTTTAATAATATT

AAATATTCTTATGCCAATTCCATAGTAGATGTAATCAAAGCATTTGGTGG

AGGATTTGAGCAAAGTGAAGATACGAGTAAAAATATAAAAGAAGAATCAA

AAAATTTAGATATGTCTTTTAGAGAATAG
```

The amino acid sequence of the CmeC protein encoded by the nucleic acid of SEQ ID NO: 13 is provided below:

```
                                            (SEQ ID NO: 14)
MNKIISISAIASFTLLISACSLSPNLNIPEANYSIDNKLGALSWEKENNS

SITKNWWKDFDDENLNKVVDLALKNNNDLKLAFIHMEQAAAQLGIDFSSL

LPKFDGSASGSRAKTAINAPSNRTGEVSYGNDFKMGLNLSYEIDLWGKYR

DTYRASKSGFKASEYDYEAARLSVISNTVQTYFNLVNAYENENALKEAYK

SAKEIYRINDEKFQVGAVGEYELAQARANLESMALQYNEAKLNKENYLKA

LKILTSNDLNDILYKNQSYQVFNLKEFDIPTGISSTILLQRPDIGSSLEK

LTQQNYLVGVARTAFLPSLSLTGLLGFESGDLDTLVKGGSKTWNIGGNFT

LPIFHWGEIYQNVNLAKLNKDEAFVNYQNTLITAFGEIRYALVARKTIRL

QYDNAQASEQSYKRIYEIAKERYDIGEMSLQDYLEARQNWLNAAVAFNNI

KYSYANSIVDVIKAFGGGFEQSEDTSKNIKEESKNLDMSFRE
```

In some embodiments, the nucleic acid comprises a *C. jejuni* cj0365c gene (provided as SEQ ID NO: 13). In some embodiments, the nucleic acid comprises a cj0365c gene, wherein the cj0365c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 13. In some embodiments, the nucleic acid comprises a cj0365c gene, wherein the cj0365c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 13.

In some embodiments, the nucleic acid comprises a nucleic acid sequence encoding a CmeC protein, wherein said CmeC protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 14. In some embodiments, the nucleic acid comprises a nucleic acid sequence encoding a CmeC protein, wherein said CmeC protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 14.

cj0404—In some embodiments, the recombinant bacterium comprises a nucleic acid comprising a cj0404 gene (e.g., a *C. jejuni* cj0404 gene).

In some embodiments, the nucleic acid comprising a cj0404 gene is located on a plasmid in the bacterium. In some embodiments, the nucleic acid comprising a cj0404 gene is located on a chromosome of the bacterium.

The nucleic acid sequence of an exemplary *C. jejuni* cj0404 gene is provided below:

```
                                            (SEQ ID NO: 15)
ATGGAAAATCAAAAAAATGAATTTGATGATATTATTTTAGAAAAAAGTAA

TAAAAGTGAAAAAGTAAAAAAAATTCTTTTACGAGTTATTGCTTTAGTTA

TTTTGTTTTTAGCTATCATGATAGTTATGAAGCTTATTAATGGTAGTGGT

GATGAAAATACGCAAAATCAAAGTGTATTGCCAAGTGAACCTATAGCAAC

TCAAGACAATAACAATGATACTTCTTTTGAAAGTATGCCAATTACAGATA

ATACTTCAGCAGAAGATCAATTTGAGGCATTAAGAAAACAATTTCAAGAT

GAACAAAATACAACTCAAAATACAACAACCTCTAGTTCAAATAACAATGA

TACTACAAATTTTGCTATGCCTGATCAAGAAGTTCCAGCAGAACCAACAG

CAACTACTTCAGCAAATACCACTCCACAAGCAAGTACTCCTAAACAAGAA

GTAACACAAACTGCAAAATCTAAAGAAGAAGCAAAAAAACAAACAGCTGT

AAAAAAAGAAAAAGAAAGTGCAAAACAAACCCCTAAAAAAGAACAAAATG

CAAATGATTTATTTAAAAATGTTGATGCTAAACCTGTACATCCAAGTGGT

TTAGCATCGGGTATTTATGTGCAAATTTTCTCAGTAAGTAATTTGGATCA

AAAATCAAAAGAACTTGCTTCTGTAAAGCAAAAAGGTTATGATTATAAAC

TTTATAAAACTACAGTTGGAAGTAAAGAAATTACCAAGGTTTTAATAGGA

CCATTTGAAAAGGCAGATATTGCAGCAGAACTTGCTAAAATCCGTAAGGA

TATTGCAAAAGATGCTTTTTCTTTTACTTTAAAATGA
```

The amino acid sequence of the Cj0404 protein encoded by the nucleic acid of SEQ ID NO: 15 is provided below:

(SEQ ID NO: 16)
MENQKNEFDDIILEKSNKSEKVKKILLRVIALVILFLAIMIVMKLINGSG

DENTQNQSVLPSEPIATQDNNNDTSFESMPITDNTSAEDQFEALRKQFQD

EQNTTQNTTTSSSNNNDTTNFAMPDQEVPAEPTATTSANTTPQASTPKQE

VTQTAKSKEEAKKQTAVKKEKESAKQTPKKEQNANDLFKNVDAKPVHPSG

LASGIYVQIFSVSNLDQKSKELASVKQKGYDYKLYKTTVGSKEITKVLIG

PFEKADIAAELAKIRKDIAKDAFSFTLK

In some embodiments, the nucleic acid comprises a *C. jejuni* cj0404 gene (provided as SEQ ID NO: 15). In some embodiments, the nucleic acid comprises a cj0404 gene, wherein the cj0404 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 15. In some embodiments, the nucleic acid comprises a cj0404 gene, wherein the cj0404 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 15.

In some embodiments, the nucleic acid comprises a nucleic acid sequence encoding a Cj0404 protein, wherein said Cj0404 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 16. In some embodiments, the nucleic acid comprises a nucleic acid sequence encoding a Cj0404 protein, wherein said Cj0404 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 16.

cj0420—In some embodiments, the recombinant bacterium comprises a nucleic acid comprising a cj0420 gene (e.g., a *C. jejuni* cj0420 gene).

In some embodiments, the nucleic acid comprising a cj0420 gene is located on a plasmid in the bacterium. In some embodiments, the nucleic acid comprising a cj0420 gene is located on a chromosome of the bacterium.

The nucleic acid sequence of an exemplary *C. jejuni* cj0420 gene is provided below:

(SEQ ID NO: 17)
ATGAAAAAAGTTTTATTGAGTTCATTGGTTGCGGTGTCTTTGTTAAGCAC

AGGTTTGTTTGCTAAAGAATATACTTTAGATAAAGCACATACAGATGTAG

GTTTTAAAATCAAACATTTACAAATTAGCAATGTAAAAGGAAATTTCAAA

GATTATTCTGCGGTGATTGATTTTGATCCTGCGAGTGCTGAATTTAAAAA

GCTTGATGTAACTATAAAAATCGCATCTGTAAATACAGAAAATCAAACAA

GAGATAATCACTTACAACAAGATGATTTTTTCAAAGCAAAAAAATATCCT

GATATGACTTTTACAATGAAAAAATATGAAAAAATCGATAATGAAAAAGG

CAAAATGACAGGAACTTTAACTATAGCTGGAGTTTCTAAAGATATCGTTT

TAGATGCTGAAATCGGCGGTGTAGCTAAAGGCAAAGATGGAAAAGAAAAA

ATAGGATTTTCTTTAAATGGAAAAATCAAACGCTCTGATTTTAAATTTGC

AACAAGTACTTCAACTATTACTTTAAGTGATGATATTAATTTAAATATCG

AAGTTGAAGCAACGAAAAATAA

The amino acid sequence of the Cj0420 protein encoded by the nucleic acid of SEQ ID NO: 17 is provided below:

(SEQ ID NO: 18)
MKKVLLSSLVAVSLLSTGLFAKEYTLDKAHTDVGFKIKHLQISNVKGNFK

DYSAVIDFDPASAEFKKLDVTIKIASVNTENQTRDNHLQQDDFFKAKKYP

DMTFTMKKYEKIDNEKGKMTGTLTIAGVSKDIVLDAEIGGVAKGKDGKEK

IGFSLNGKIKRSDFKFATSTSTITLSDDINLNIEVEANEK

In some embodiments, the nucleic acid comprises a *C. jejuni* cj0420 gene (provided as SEQ ID NO: 17). In some embodiments, the nucleic acid comprises a cj0420 gene, wherein the cj0420 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 17. In some embodiments, the nucleic acid comprises a cj0420 gene, wherein the cj0420 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 17.

In some embodiments, the nucleic acid comprises a nucleic acid sequence encoding a Cj0420 protein, wherein said Cj0420 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 18. In some embodiments, the nucleic acid comprises a nucleic acid sequence encoding a Cj0420 protein, wherein said Cj0420 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 18.

cj0427—In some embodiments, the recombinant bacterium comprises a nucleic acid comprising a cj0427 gene (e.g., a *C. jejuni* cj0427 gene).

In some embodiments, the nucleic acid comprising a cj0427 gene is located on a plasmid in the bacterium. In some embodiments, the nucleic acid comprising a cj0427 gene is located on a chromosome of the bacterium.

The nucleic acid sequence of an exemplary *C. jejuni* cj0427 gene is provided below:

(SEQ ID NO: 19)
ATGATGGCTAAATTTAGAATTCAATACAGCGCAGGTTTTGGGCACTATAC

GCAAAATCACAAGGGTTTTGGACCTACGATTTATATAGAAGAGGTCGTAG

AGTTTGATAATGGCAAGGATTATTTTGACTATATAGATTTTTATAAAACT

TATTCAAAGAGCGATGATACTTATTTTCATATCAGTTTTTTAGAAGATAG

ACCTCTAAGCGATAAAGAAATCACCATTCGCAATGAATACCGCAAAATGC

GTGATGAAAACTGTAAAAAAGCCAAGGAGGAATTTATAGCCAACAATGAG

CTTGATGTGGAGCATTTGCCTACTCACCATGATTAA

The amino acid sequence of the Cj0427 protein encoded by the nucleic acid of SEQ ID NO: 19 is provided below:

(SEQ ID NO: 20)
MMAKFRIQYSAGFGHYTQNHKGFGPTIYIEEVVEFDNGKDYFDYIDFYKT

YSKSDDTYFHISFLEDRPLSDKEITIRNEYRKMRDENCKKAKEEFIANNE

LDVEHLPTHHD

In some embodiments, the nucleic acid comprises a *C. jejuni* cj0427 gene (provided as SEQ ID NO: 19). In some embodiments, the nucleic acid comprises a cj0427 gene, wherein the cj0427 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 19. In some embodiments, the nucleic acid comprises a cj0427 gene, wherein the cj0427 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 19.

In some embodiments, the nucleic acid comprises a nucleic acid sequence encoding a Cj0427 protein, wherein said Cj0427 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 20. In some embodiments, the nucleic acid comprises a nucleic acid sequence encoding a Cj0427 protein, wherein said Cj0427 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 20.

cj0428—In some embodiments, the recombinant bacterium comprises a nucleic acid comprising a cj0428 gene (e.g., a *C. jejuni* cj0428 gene).

In some embodiments, the nucleic acid comprising a cj0428 gene is located on a plasmid in the bacterium. In some embodiments, the nucleic acid comprising a cj0428 gene is located on a chromosome of the bacterium.

The nucleic acid sequence of an exemplary *C. jejuni* cj0428 gene is provided below:

(SEQ ID NO: 21)
ATGCAGGTAAATTATAGAACGATTAGCTCGTATGAATACGATGCTATTAG

TGGTCAGTATAAACAGGTGGATAAACAGATTGAAGATTATTCTTCATCTG

GAGATTCTGATTTTATGGATATGTTAAATAAGGCGGATGAGAAGTCAAGC

GGAGATGCTTTAAATTCTAGCAGTAGTTTTCAAAGCAATGCGCAAAACTC

AAATTCAAATTTAAGTAATTATGCTCAAATGTCAAATGTTTACGCTTATC

GTTTTAGACAAAATGAAGGCGAGCTGTCTATGAGAGCTCAAAGTGCTAGC

GTTCATAATGATCTTACACAACAAGGTGCAAATGAACAAAGTAAGAATAA

TACTTTGTTAAATGATTTATTGAACGCAATTTAA

The amino acid sequence of the Cj0428 protein encoded by the nucleic acid of SEQ ID NO: 21 is provided below:

(SEQ ID NO: 22)
MQVNYRTISSYEYDAISGQYKQVDKQIEDYSSSGDSDFMDMLNKADEKSS

GDALNSSSSFQSNAQNSNSNLSNYAQMSNVYAYRFRQNEGELSMRAQSAS

VHNDLTQQGANEQSKNNTLLNDLLNAI

In some embodiments, the nucleic acid comprises a *C. jejuni* cj0428 gene (provided as SEQ ID NO: 21). In some embodiments, the nucleic acid comprises a cj0428 gene, wherein the cj0428 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 21. In some embodiments, the nucleic acid comprises a cj0428 gene, wherein the cj0428 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 21.

In some embodiments, the nucleic acid comprises a nucleic acid sequence encoding a Cj0428 protein, wherein said Cj0428 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 22. In some embodiments, the nucleic acid comprises a nucleic acid sequence encoding a Cj0428 protein, wherein said Cj0428 protein comprises an amino acid sequence that is at least 75%, at least 80%, at least 81%, at least 82%, at least 83%, at least 84%, at least 85%, at least 86%, at least 87%, cj0588—In some embodiments, the recombinant bacterium comprises a nucleic acid comprising a cj0588 gene (e.g., a *C. jejuni* cj0588 gene).

In some embodiments, the nucleic acid comprising a cj0588 gene is located on a plasmid in the bacterium. In some embodiments, the nucleic acid comprising a cj0588 gene is located on a chromosome of the bacterium.

The nucleic acid sequence of an exemplary *C. jejuni* cj0588 gene is provided below:

```
                                        (SEQ ID NO: 23)
ATGCGTTTCGACTTCTTCGTGTCCAAACGTCTGAACATCAGCCGTAACAA

AGCGCTGGAGCTGATCGAAAACGAAGAGATCCTGCTGAACGGCAAAAGCT

TCAAAGCGTCCTTCGACGTGAAAAACTTCCTGGAAAACCTGAAAAAAACC

CAGGACCTGAACCCGGAAGACATCCTGCTGGCGAACGAGCTGAAACTGGA

CCTGCTGAGCGAAATCTACGTGTCCCGTGCGGCGCTGAAACTGAAAAAAT

TCCTGGAAGAAAACGACATCGAAATCAAACACAAAAACTGTCTGGACATC

GGCTCCAGCACCGGCGGCTTCGTGCAGATCCTGCTGGAAAACCAGGCGCT

GAAAATCACCGCGCTGGACGTGGGCAGCAACCAGCTGCACCCGAGCCTGC

GTGTGAACGAAAAAATCATCCTGCACGAAAACACCGACCTGCGTGCGTTC

AAAAGCGAAGAAAAATTCGAACTGGTGACCTGCGACGTGAGCTTCATCTC

CCTGATCAACCTGCTGTACTACATCGACAACCTGGCGCTGAAAGAAATCA

TCCTGCTGTTCAAACCGCAGTTCGAAGTGGGCAAAAACATCAAACGTGAC

AAAAAAGGCGTGCTGAAAGACGACAAAGCGATCCTGAAAGCGCGTATGGA

CTTCGAAAAAGCGTGCGCGAAACT
```

The amino acid sequence of the TlyA protein encoded by the nucleic acid of SEQ ID NO: 23 is provided below:

```
                                        (SEQ ID NO: 24)
MRFDFFVSKRLNISRNKALELIENEEILLNGKSFKASFDVKNFLENLKKT

QDLNPEDILLANELKLDLLSEIYVSRAALKLKKFLEENDIEIKHKNCLDI

GSSTGGFVQILLENQALKITALDVGSNQLHPSLRVNEKIILHENTDLRAF

KSEEKFELVTCDVSFISLINLLYYIDNLALKEIILLFKPQFEVGKNIKRD

KKGVLKDDKAILKARMDFEKACAKLGWLLKNTQKSSIKGKEGNVEYFYYY

IKN
```

In some embodiments, the nucleic acid comprises a *C. jejuni* cj0588 gene (provided as SEQ ID NO: 23). In some embodiments, the nucleic acid comprises a cj0588 gene, wherein the cj0588 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 23. In some embodiments, the nucleic acid comprises a cj0588 gene, wherein the cj0588 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 23.

In some embodiments, the nucleic acid comprises a nucleic acid sequence encoding a TlyA protein, wherein said TlyA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:24. In some embodiments, the nucleic acid comprises a nucleic acid sequence encoding a TlyA protein, wherein said TlyA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 24.

cj0921c—In some embodiments, the recombinant bacterium comprises a nucleic acid comprising a cj0921c gene (e.g., a *C. jejuni* cj0921c gene).

In some embodiments, the nucleic acid comprising a cj0921c gene is located on a plasmid in the bacterium. In some embodiments, the nucleic acid comprising a cj0921c gene is located on a chromosome of the bacterium.

The nucleic acid sequence of an exemplary *C. jejuni* cj0921c gene is provided below:

```
                                        (SEQ ID NO: 25)
ATGGTTTTTAGAAAATCTTTGTTAAAGTTGGCAGTTTTTGCTCTAGGTGC

TTGTGTTGCATTTAGCAATGCTAATGCAGCAGAAGGCAAACTGGAGTCCA

TCAAATCCAAAGGCCAGCTGATCGTGGGCGTGAAAAACGACGTGCCGCAC

TACGCTCTGCTGGACCAGGCAACCGGCGAAATCAAAGGCTTCGAAGTGGA

CGTGGCCAAACTGCTGGCTAAAAGCATCCTGGGGGACGACAAAAAAATCA

AACTGGTGGCAGTGAACGCCAAAACCCGTGGCCCGCTGCTGGACAACGGC

AGCGTGGACGCGGTGATCGCAACCTTCACCATCACCCCGGAGCGCAAACG

TATCTATAACTTCTCCGAGCCGTATTATCAGGACGCTATCGGCCTGCTGG

TTCTGAAAGAAAAAAAATATAAATCTCTGGCTGACATGAAAGGTGCAAAC

ATCGGCGTGGCTCAAGCTGCAACTACAAAAAAAGCTATCGGCGAAGCTGC

TAAAAAAATCGGCATCGACGTGAAATTCAGCGAATTCCCGGACTATCCGA

GCATCAAAGCTGCTCTGGACGCTAAACGTGTGGACGCGTTCTCTGTGGAC

AAATCCATCCTGCTGGGCTATGTGGACGACAAAAGCGAAATCCTGCCGGA

CAGCTTCGAACCGCAGAGCTATGGCATCGTGACCAAAAAAGACGACCCGG

CTTTCGCAAAATATGTGGACGACTTCGTGAAAGAACACAAAAACGAAATC

GACGCTCTGGCGAAAAAATGGGGCCTGTAA
```

The amino acid sequence of the Peb1 protein encoded by the nucleic acid of SEQ ID NO: 25 is provided below:

(SEQ ID NO: 26)
MVFRKSLLKLAVFALGACVAFSNANAAEGKLESIKSKGQLIVGVKNDVPH

YALLDQATGEIKGFEVDVAKLLAKSILGDDKKIKLVAVNAKTRGPLLDNG

SVDAVIATFTITPERKRIYNFSEPYYQDAIGLLVLKEKKYKSLADMKGAN

IGVAQAATTKKAIGEAAKKIGIDVKFSEFPDYPSIKAALDAKRVDAFSVD

KSILLGYVDDKSEILPDSFEPQSYGIVTKKDDPAFAKYVDDFVKEHKNEI

DALAKKWGL

In some embodiments, the nucleic acid comprises a *C. jejuni* cj0921c gene (provided as SEQ ID NO: 25). In some embodiments, the nucleic acid comprises a cj0921c gene, wherein the cj0921c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 25. In some embodiments, the nucleic acid comprises a cj0921c gene, wherein the cj0921c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 25.

In some embodiments, the nucleic acid comprises a nucleic acid sequence encoding a Peb1 protein, wherein said Peb1 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 26. In some embodiments, the nucleic acid comprises a nucleic acid sequence encoding a Peb1 protein, wherein said Peb1 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 26.

cj0982c—In some embodiments, the recombinant bacterium comprises a nucleic acid comprising a cj0982c gene (e.g., a *C. jejuni* cj0982c gene).

In some embodiments, the nucleic acid comprising a cj0982c gene is located on a plasmid in the bacterium. In some embodiments, the nucleic acid comprising a cj0982c gene is located on a chromosome of the bacterium.

The nucleic acid sequence of an exemplary *C. jejuni* cj0982c gene is provided below:

(SEQ ID NO: 27)
ATGAAAAAAATACTTCTAAGTGTTTTAACGGCCTTTGTTGCAGTAGTATT

GGCTGCGGCGGCAACTCCGACTCCAAAACCCTGAACTCCCTGGACAAAAT

CAAACAGAACGGCGTGGTGCGTATCGGCGTGTTTGGCGACAAACCGCCGT

TTGGCTATGTGGACGAAAAAGGCAACAACCAGGGCTATGACATCGCTCTG

GCTAAACGTATCGCGAAAGAACTGTTTGGCGACGAAAACAAAGTGCAGTT

TGTGCTGGTGGAAGCTGCGAACCGTGTGGAGTTTCTGAAATCCAACAAAG

TGGACATCATCCTGGCTAACTTTACCCAGACCCCGCAGCGTGCGGAGCAG

GTGGACTTTTGCTCCCCGTATATGAAAGTGGCTCTGGGCGTGGCTGTGCC

GAAAGACAGCAACATCACCAGCGTGGAAGACCTGAAAGACAAAACCCTGC

TGCTGAACAAAGGCACCACCGCGGACGCTTATTTTACCCAGAACTATCCG

AACATCAAAACCCTGAAATATGACCAGAACACCGAAACCTTTGCGGCTCT

GATGGACAAACGTGGCGACGCTCTGAGCCACGACAACACCCTGCTGTTTG

CTTGGGTGAAAGACCACCCGGACTTTAAAATGGGCATCAAAGAGCTGGGC

AACAAAGACGTGATCGCGCCGGCGGTGAAAAAAGGCGACAAAGAACTGAA

AGAATTTATCGACAACCTGATCATCAAACTGGGCCAGGAGCAGTTTTTTC

ACAAAGCTTATGACGAAACCCTGAAAGCTCACTTTGGCGACGACGTGAAA

GCGGACGACGTGGTGATCGAAGGCGGCAAAATCTAA

The amino acid sequence of the CjaA protein encoded by the nucleic acid of SEQ ID NO: 27 is provided below:

(SEQ ID NO: 28)
MKKILLSVLTAFVAVVLAACGGNSDSKTLNSLDKIKQNGVVRIGVFGDKP

PFGYVDEKGNNQGYDIALAKRIAKELFGDENKVQFVLVEAANRVEFLKSN

KVDIILANFTQTPQRAEQVDFCSPYMKVALGVAVPKDSNITSVEDLKDKT

LLLNKGTTADAYFTQNYPNIKTLKYDQNTETFAALMDKRGDALSHDNTLL

FAWVKDHPDFKMGIKELGNKDVIAPAVKKGDKELKEFIDNLIIKLGQEQF

FHKAYDETLKAHFGDDVKADDVVIEGGKI

In some embodiments, the nucleic acid comprises a *C. jejuni* cj0982c gene (provided as SEQ ID NO: 27). In some embodiments, the nucleic acid comprises a cj0982c gene, wherein the cj0982c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 27. In some embodiments, the nucleic acid comprises a cj0982c gene, wherein the cj0982c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 27.

In some embodiments, the nucleic acid comprises a nucleic acid sequence encoding a CjaA protein, wherein said CjaA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 28. In some embodiments, the nucleic acid comprises a nucleic acid sequence encoding a CjaA protein, wherein said CjaA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 28.

cj0998c—In some embodiments, the recombinant bacterium comprises a nucleic acid comprising a cj0998c gene (e.g., a *C. jejuni* cj0998c gene).

In some embodiments, the nucleic acid comprising a cj0998c gene is located on a plasmid in the bacterium. In some embodiments, the nucleic acid comprising a cj0998c gene is located on a chromosome of the bacterium.

The nucleic acid sequence of an exemplary *C. jejuni* cj0998c gene is provided below:

```
                                          (SEQ ID NO: 29)
ATGAAAAAAATTCTTGTAAGTGTTTTAAGTTCTTGCTTGTTAGCTTCGGC

TTTAAGTGCGGTGTCCTTCAAAGAAGACAGCCTGAAAATCTCCTTCGAAG

GCTACAAAACCAAAGACATGATCGGCACCAAAGGCGAATTCAAAAACGTG

GAATACAAATTCTCCAAAAACATCAAAGACCTGGCGAGCTACCTGAAAGG

CGCGAAAGCGACCATCAAACCGAGCAACGCGTTCATGGGCGAAGGCAACG

ACATCATCACCAACAACATCACCAAAGTGTTCTTCCCGGCGCTGCTGGGC

GACACGGACATCAAAGTGGTGTTTCAGGACGTGATCGCGGGCGAAAACAA

AGGCGTGATCTCCGCGAAAATCACCATGGACAAAAAAAGCACCATCGTGC

CGCTGACCTATACCATCAAAGACAACAAATTTGAAGCGAAAGGCCAGCTG

GACCTGCACACCTTTAAAAACGGCTCCAAAGCGCTGAAAGCGCTGAGCGA

CGTGGCTGCAGGCCACGGCGGCATCTCCTGGCCGCTGGTGGACATCAGCT

TTAACGCGGACCTGGCGGAATAA
```

The amino acid sequence of the Cj0998c protein encoded by the nucleic acid of SEQ ID NO: 29 is provided below:

```
                                          (SEQ ID NO: 30)
MKKILVSVLSSCLLASALSAVSFKEDSLKISFEGYKTKDMIGTKGEFKNV

EYKFSKNIKD

LASYLKGAKATIKPSNAFMGEGNDIITNNITKVFFPALLGDTDIKVVFQD

VIAGENKGVI

SAKITMDKKSTIVPLTYTIKDNKFEAKGQLDLHTFKNGSKALKALSDVAA

GHGGISWPLVDISFNADLAE
```

In some embodiments, the nucleic acid comprises a *C. jejuni* cj0998c gene (provided as SEQ ID NO: 29). In some embodiments, the nucleic acid comprises a cj0998c gene, wherein the cj0998c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 29. In some embodiments, the nucleic acid comprises a cj0998c gene, wherein the cj0998c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 29.

In some embodiments, the nucleic acid comprises a nucleic acid sequence encoding a Cj0998c protein, wherein said Cj0998c protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 30. In some embodiments, the nucleic acid comprises a nucleic acid sequence encoding a Cj0998c protein, wherein said Cj0998c protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 30.

cj1259—In some embodiments, the recombinant bacterium comprises a nucleic acid comprising a cj1259 gene (e.g., a *C. jejuni* cj1259 gene).

In some embodiments, the nucleic acid comprising a cj1259 gene is located on a plasmid in the bacterium. In some embodiments, the nucleic acid comprising a cj1259 gene is located on a chromosome of the bacterium.

The nucleic acid sequence of an exemplary *C. jejuni* cj1259 gene is provided below:

```
                                          (SEQ ID NO: 31)
ATGAAACTAGTTAAACTTAGTTTAGTTGCAGCTCTTGCTGCAGGTGCTTT

TTCAGCAGCTAACGCTACCCCGCTGGAAGAAGCGATCAAAGACGTGGACG

TGTCCGGCGTGCTGCGTTACCGTTACGACACCGGCAACTTTGACAAAAAC

TTCGTGAACAACTCCAACCTGAACAACAGCAAACAGGACCACAAATATCG

TGCACAGGTGAACTTCAGTGCTGCTATCGCTGACAACTTCAAAGCTTTTG

TGCAGTTTGACTATAACGCTGCTGACGGTGGCTATGGCGCTAACGGCATC

AAAAACGACCAGAAAGGCCTGTTTGTGCGTCAGCTGTACCTGACTTATAC

CAACGAAGACGTGGCTACCAGTGTGATCGCTGGTAAACAGCAGCTGAACC

TGATCTGGACGGACAACGCTATCGACGGTCTGGTGGGCACCGGTGTGAAA

GTGGTGAACAACAGCATCGACGGTCTGACTCTGGCTGCTTTTGCTGTGGA

CAGCTTCATGGCTGCGGAGCAGGGTGCGGACCTGCTGGAACACAGTAACA

TCTCCACCACCTCCAACCAGGCTCCGTTTAAAGTGGACTCCGTGGGCAAC

CTGTACGGTGCTGCTGCTGTGGGTTCTTATGACCTGGCTGGTGGCCAGTT

CAACCCGCAGCTGTGGCTGGCTTATTGGGACCAGGTGGCATTCTTCTATG

CTGTGGACGCAGCTTATAGCACAACTATCTTTGACGGCATCAACTGGACA

CTGGAAGGCGCTTACCTGGGAAACAGCCTGGACAGCGAACTGGACGACAA

AACACACGCTAACGGCAACCTGTTTGCTCTGAAAGGCAGCATCGAAGTGA

ACGGCTGGGACGCTAGCCTGGGTGGTCTGTACTACGGCGACAAAGAAAAA

GCTTCTACAGTGGTGATCGAAGACCAGGGTAACCTGGGTTCTCTGCTGGC

AGGTGAGGAAATCTTCTATACTACTGGCTCACGCCTGAACGGTGACACTG
```

-continued
```
GTCGTAACATCTTCGGTTATGTGACTGGTGGATATACTTTCAACGAAACA

GTGCGCGTGGGTGCTGACTTCGTGTATGGTGGAACAAAAACAGAAGCTGC

TAACCACCTGGGTGGTGGTAAAAAACTGGAAGCTGTGGCACGCGTGGACT

ACAAATACTCTCCGAAACTGAACTTCTCAGCATTCTATTCTTATGTGAAC

CTGGACCAGGGTGTGAACACTAACGAAAGTGCTGACCACAGCACTGTGCG

TCTGCAGGCTCTGTACAAATTCTAA
```

The amino acid sequence of the PorA protein encoded by the nucleic acid of SEQ ID NO: 31 is provided below:

```
                                            (SEQ ID NO: 32)
MKLVKLSLVAALAAGAFSAANATPLEEAIKDVDVSGVLRYRYDTGNFDKN

FVNNSNLNNSKQDHKYRAQVNFSAAIADNFKAFVQFDYNAADGGYGANGI

KNDQKGLFVRQLYLTYTNEDVATSVIAGKQQLNLIWTDNAIDGLVGTGVK

VVNNSIDGLTLAAFAVDSFMAAEQGADLLEHSNISTTSNQAPFKVDSVGN

LYGAAAVGSYDLAGGQFNPQLWLAYWDQVAFFYAVDAAYSTTIFDGINWT

LEGAYLGNSLDSELDDKTHANGNLFALKGSIEVNGWDASLGGLYYGDKEK

ASTVVIEDQGNLGSLLAGEEIFYTTGSRLNGDTGRNIFGYVTGGYTFNET

VRVGADFVYGGTKTEAANHLGGGKKLEAVARVDYKYSPKLNFSAFYSYVN

LDQGVNTNESADHSTVRLQALYKF
```

In some embodiments, the nucleic acid comprises a *C. jejuni* cj1259 gene (provided as SEQ ID NO: 31). In some embodiments, the nucleic acid comprises a cj1259 gene, wherein the cj1259 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 31. In some embodiments, the nucleic acid comprises a cj1259 gene, wherein the cj1259 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 31.

In some embodiments, the nucleic acid comprises a nucleic acid sequence encoding a PorA protein, wherein said PorA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 32. In some embodiments, the nucleic acid comprises a nucleic acid sequence encoding a PorA protein, wherein said PorA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 32.

cj1339c—In some embodiments, the recombinant bacterium comprises a nucleic acid comprising a cj1339c gene (e.g., a *C. jejuni* cj1339c gene).

In some embodiments, the nucleic acid comprising a cj1339c gene is located on a plasmid in the bacterium. In some embodiments, the nucleic acid comprising a cj1339c gene is located on a chromosome of the bacterium.

The nucleic acid sequence of an exemplary *C. jejuni* cj1339c gene is provided below:

```
                                            (SEQ ID NO: 33)
ATGGGTTTTCGTATCAACACCAACGTGGCGGCTCTGAACGCAAAAGCAAA

CGCGGATCTGAACAGCAAAAGCCTGGATGCTTCTCTGAGCCGTCTGAGCT

CCGGCCTGCGTATCAACTCCGCAGCAGATGATGCTTCCGGGATGGCGATC

GCAGATAGCCTGCGTTCTCAGGCTAACACTCTGGGCCAGGCTATCTCTAA

CGGCAACGATGCTCTGGGCATCCTGCAGACTGCTGATAAAGCTATGGACG

AGCAGCTGAAAATCCTGGATACCATCAAAACTAAAGCAACCCAGGCGGCT

CAGGATGGCCAGAGCCTGAAAACCCGTACCATGCTGCAGGCAGATATCAA

CCGTCTGATGGAAGAACTGGACAACATCGCAAACACTACTTCCTTTAACG

GTAAACAGCTGCTGAGCGGCAACTTTATCAACCAGGAATTTCAGATCGGC

GCAAGCTCCAACCAGACTGTGAAAGCTACTATCGGCGCAACTCAGTCTTC

TAAAATCGGTCTGACCCGCTTTGAAACCGGCGGCCGTATCTCCACTAGCG

GCGAAGTGCAGTTTACTCTGAAAAACTACAACGGTATCGATGATTTTCAG

TTTCAGAAAGTGGTGATCTCCACTTCCGTGGGCACCGGCCTGGGCGCTCT

GGCAGATGAGATCAACAAAAACGCTGATAAAACCGGTGTGCGTGCTACTT

TTACAGTGGAAACTCGTGGTATCGCTGCAGTGCGTGCAGGCGCTACTTCA

GATACTTTTGCTATCAACGGGGTGAAAATCGGCAAAGTGGATTACAAAGA

TGGCGATGCTAACGGCGCCCTGGTGGCTGCAATCAACTCGGTGAAAGATA

CCACCGGCGTGGAAGCTTCGATCGATGCTAACGGCCAGCTGCTGCTGACT

TCCCGTGAAGGCCGTGGCATCAAAATCGATGGTAACATCGGTGGCGGTGC

CTTTATCAACGCTGATATGAAAGAAAACTATGGCCGCCTGTCTCTGGTGA

AAAACGATGGTAAAGATATCCTGATCAGCGGTAGCAACCTGTCTTCTGCA

GGTTTTGGTGCAACCCAGTTTATCTCTCAGGCTTCTGTGTCTCTGCGTGA

GTCCAAAGGCCAGATCGATGCTAACATCGCTGATGCTATGGGCTTTGGCT

CTGCAAACAAAGGCGTGGTGCTGGGTGGTTATTCTTCTGTGAGCGCCTAT

ATGAGCAGCGCAGGCAGCGGCTTTTCTTCCGGTTCCGGTTATTCTGTGGG

TAGCGGCAAAAACTATTCCACCGGTTTTGCAAACGCTATCGCTATCTCCG

CTGCTTCGCAGCTGTCTACGGTGTATAACGTGTCTGCAGGCTCAGGTTTT

TCAAGCGGTTCCACCCTGTCTCAGTTTGCCACTATGAAACCACTGCTTT

TGGCGTGAAAGATGAAACCGCAGGTGTGACCACCCTGAAAGGCGCTATGG

CTGTGATGGATATCGCTGAAACCGCTATCACCAACCTGGATCAGATCCGT

GCCGACATCGGCTCGGTGCAGAACCAGGTGACATCCACTATCAACAACAT

CACCGTGACTCAGGTGAACGTGAAAGCAGCAGAATCGCAGATCCGTGATG
```

-continued

TGGACTTTGCAGCCGAGAGCGCAAACTACTCTAAAGCAAACATCCTGGCT

CAGAGCGGCTCTTATGCCATGGCACAGGCTAACTCTGTGCAGCAGAACGT

GCTGCGTCTGCTGCAGTA

The amino acid sequence of the FlaA protein encoded by the nucleic acid of SEQ ID NO: 33 is provided below:

(SEQ ID NO: 34)
MGFRINTNVAALNAKANADLNSKSLDASLSRLSSGLRINSAADDASGMAI

ADSLRSQANTLGQAISNGNDALGILQTADKAMDEQLKILDTIKTKATQAA

QDGQSLKTRTMLQADINRLMEELDNIANTTSFNGKQLLSGNFINQEFQIG

ASSNQTVKATIGATQSSKIGLTRFETGGRISTSGEVQFTLKNYNGIDDFQ

FQKVVISTSVGTGLGALADEINKNADKTGVRATFTVETRGIAAVRAGATS

DTFAINGVKIGKVDYKDGDANGALVAAINSVKDTTGVEASIDANGQLLLT

SREGRGIKIDGNIGGGAFINADMKENYGRLSLVKNDGKDILISGSNLSSA

GFGATQFISQASVSLRESKGQIDANIADAMGFGSANKGVVLGGYSSVSAY

MSSAGSGFSSGSGYSVGSGKNYSTGFANAIAISAASQLSTVYNVSAGSGF

SSGSTLSQFATMKTTAFGVKDETAGVTTLKGAMAVMDIAETAITNLDQIR

ADIGSVQNQVTSTINNITVTQVNVKAAESQIRDVDFAAESANYSKANILA

QSGSYAMAQASVQQNVLRLLQ

In some embodiments, the nucleic acid comprises a *C. jejuni* cj1339c gene (provided as SEQ ID NO: 33). In some embodiments, the nucleic acid comprises a cj1339c gene, wherein the cj1339c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 33. In some embodiments, the nucleic acid comprises a cj1339c gene, wherein the cj1339c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 33.

In some embodiments, the nucleic acid comprises a nucleic acid sequence encoding a FlaA protein, wherein said FlaA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 34. In some embodiments, the nucleic acid comprises a nucleic acid sequence encoding a FlaA protein, wherein said FlaA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 34.

cj1478c—In some embodiments, the recombinant bacterium comprises a nucleic acid comprising a cj1478c gene (e.g., a *C. jejuni* cj1478c gene).

In some embodiments, the nucleic acid comprising a cj1478c gene is located on a plasmid in the bacterium. In some embodiments, the nucleic acid comprising a cj1478c gene is located on a chromosome of the bacterium.

The nucleic acid sequence of an exemplary *C. jejuni* cj1478c gene is provided below:

(SEQ ID NO: 35)
ATGAAAAAAATCTTCCTGTGTCTGGGCCTGGCGAGCGTGCTGTTTGGCGC

TGACAACAACGTGAAATTTGAAATCACCCCGACCCTGAACTATAACTACT

TTGAAGGCAACCTGGACATGGACAACCGTTATGCGCCGGGGATCCGTCTG

GGCTATCACTTTGACGACTTTTGGCTGGACCAGCTGGAATTTGGGCTGGA

GCACTATTCTGACGTGAAATATACCAACACCAACAAAACCACCGACATCA

CCCGTACCTATCTGAGCGCTATCAAAGGCATCGACGTGGGTGAGAAATTT

TATTTCTATGGCCTGGCAGGCGGCGGCTATGAGGACTTTTCCAACGCTGC

GTATGACAACAAAAGCGGCGGCTTTGGCCACTATGGCGCGGGCGTGAAAT

TCCGTCTGAGCGACTCTCTGGCTCTGCGTCTGGAAACCCGTGACCAGATC

AACTTCAACCACGCAAACCACAACTGGGTGTCCACTCTGGGCATCAGCTT

TGGCTTTGGCGGCAAAAAAGAAAAAGCTGTGGAAGAAGTGGCTGACACCC

GTGCAACTCCGCAGGCCAAATGTCCGGTGGAACCGCGTGAAGGCGCTCTG

CTGGACGAAAACGGCTGCGAAAAAACCATCTCTCTGGAAGGCCACTTTGG

CTTTGACAAAACCACCATCAACCCGACTTTTCAGGAAAAAATCAAAGAAA

TCGCAAAAGTGCTGGACGAAAACGAACGTTATGACACTATCCTGGAAGGC

CACACCGACAACATCGGCTCCCGTGCTTATAACCAGAAACTGTCCGAACG

TCGTGCTAAAAGCGTGGCTAACGAACTGGAAAAATATGGCGTGGAAAAAA

GCCGCATCAAAACAGTGGGCTATGGCCAGGACAACCCGCGCTCCAGCAAC

GACACCAAAGAAGGCCGCGCGGACAACCGTCGCGTGGACGCTAAATTTAT

CCTGCGCTAA

The amino acid sequence of the CadF protein encoded by the nucleic acid of SEQ ID NO: 35 is provided below:

(SEQ ID NO: 36)
MKKIFLCLGLASVLFGADNNVKFEITPTLNYNYFEGNLDMDNRYAPGIRL

GYHFDDFWLDQLEFGLEHYSDVKYTNTNKTTDITRTYLSAIKGIDVGEKF

YFYGLAGGGYEDFSNAAYDNKSGGFGHYGAGVKFRLSDSLALRLETRDQI

NFNHANHNWVSTLGISFGFGGKKEKAVEEVADTRATPQAKCPVEPREGAL

LDENGCEKTISLEGHFGFDKTTINPTFQEKIKEIAKVLDENERYDTILEG

HTDNIGSRAYNQKLSERRAKSVANELEKYGVEKSRIKTVGYGQDNPRSSN

DTKEGRADNRRVDAKFILR

In some embodiments, the nucleic acid comprises a *C. jejuni* cj1478c gene (provided as SEQ ID NO: 35). In some embodiments, the nucleic acid comprises a cj1478c gene, wherein the cj1478c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 35. In some embodiments, the nucleic acid comprises a cj1478c gene, wherein the cj1478c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 35.

In some embodiments, the nucleic acid comprises a nucleic acid sequence encoding a CadF protein, wherein said CadF protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 36. In some embodiments, the nucleic acid comprises a nucleic acid sequence encoding a CadF protein, wherein said CadF protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 36.

cj1534c—In some embodiments, the recombinant bacterium comprises a nucleic acid comprising a cj1534c gene (e.g., a *C. jejuni* cj1534c gene).

In some embodiments, the nucleic acid comprising a cj1534c gene is located on a plasmid in the bacterium. In some embodiments, the nucleic acid comprising a cj1534c gene is located on a chromosome of the bacterium.

The nucleic acid sequence of an exemplary *C. jejuni* cj1534c gene is provided below:

```
                                    (SEQ ID NO: 37)
ATGTCCGTGACCAAACAGCTGCTGCAGATGCAGGCGGACGCGCACCACCT

GTGGGTGAAATTCCACAACTACCACTGGAACGTGAAAGGCCTGCAGTTCT

TCTCCATCCACGAGTACACCGAAAAAGCGTACGAAGAAATGGCAGAACTG

TTCGACAGCTGTGCGGAACGTGTGCTGCAGCTGGGCGAAAAAGCGATCAC

CTGCCAGAAAGTGCTGATGGAAAACGCGAAAAGCCCGAAAGTGGCGAAAG

ACTGCTTCACCCCGCTGGAAGTGATCGAACTGATCAAACAGGACTACGAA

TACCTGCTGGCGGAATTCAAAAAACTGAACGAAGCGGCAGAAAAAGAAAG

CGACACCACCACCGCTGCTTTCGCGCAGGAAAACATCGCGAAATATGAAA

AAAGTCTGTGGATGATCGGCGCTACCCTGCAGGGCGCTTGCAAAATGTAA
```

The amino acid sequence of the Dps protein encoded by the nucleic acid of SEQ ID NO: 37 is provided below:

```
                                    (SEQ ID NO: 38)
MSVTKQLLQMQADAHHLWVKFHNYHWNVKGLQFFSIHEYTEKAYEEMAEL

FDSCAERVLQLGEKAITCQKVLMENAKSPKVAKDCFTPLEVIELIKQDYE

YLLAEFKKLNEAAEKESDTTTAAFAQENIAKYEKSLWMIGATLQGACKM
```

In some embodiments, the nucleic acid comprises a *C. jejuni* cj1534c gene (provided as SEQ ID NO: 37). In some embodiments, the nucleic acid comprises a cj1534c gene, wherein the cj1534c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 37. In some embodiments, the nucleic acid comprises a cj1534c gene, wherein the cj1534c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 37.

In some embodiments, the nucleic acid comprises a nucleic acid sequence encoding a Dps protein, wherein said Dps protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 38. In some embodiments, the nucleic acid comprises a nucleic acid sequence encoding a Dps protein, wherein said Dps protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 38.

cj1656c—In some embodiments, the recombinant bacterium comprises a nucleic acid comprising a cj1656c gene (e.g., a *C. jejuni* cj1656c gene).

In some embodiments, the nucleic acid comprising a cj1534c gene is located on a plasmid in the bacterium. In some embodiments, the nucleic acid comprising a cj1534c gene is located on a chromosome of the bacterium.

The nucleic acid sequence of an exemplary *C. jejuni* cj1656c gene is provided below:

```
ATGGTTTCAGATGTTTCTATGGGTAATGTTAATTTAATGACTGCTGTTAA

TACTTCAGTTTTGAAAAAATCTATGGACACAAACGAGGCATTGATGAATG

AACTCATCGAAGGTATGGAAGGTGTCTCTCAAGCCTCCGCTCCACAAGCT

TCTAGCTCTAGTGGTTTGGATATTTACGCTTAA
```

(SEQ ID NO: 39)

The amino acid sequence of the Cj1656c protein encoded by the nucleic acid of SEQ ID NO: 39 is provided below:

```
                                    (SEQ ID NO: 40)
MVSDVSMGNVNLMTAVNTSVLKKSMDTNEALMNELIEGMEGVSQASAPQA

SSSSGLDIYA
```

In some embodiments, the nucleic acid comprises a *C. jejuni* cj1656c gene (provided as SEQ ID NO: 39). In some embodiments, the nucleic acid comprises a cj1656c gene, wherein the cj1656c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 39. In some embodiments, the nucleic acid comprises a cj1656c gene, wherein the cj1656c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO:39.

In some embodiments, the nucleic acid comprises a nucleic acid sequence encoding a Cj1656c protein, wherein said Cj1656cs protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 40. In some embodiments, the nucleic acid comprises a nucleic acid sequence encoding a Cj1656c protein, wherein said Cj1656c protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 40.

B. *Campylobacter* Glycosylation Proteins

In some embodiments, the recombinant bacterium has been genetically engineered to produce the *Campylobacter jejuni* N-glycan in its surface. The *C. jejuni* N-glycan is a heptasaccharide ((GalNAc-α1,4-GalNAc-α1,4-[Glc-β-1,3] GalNAc-α1,4-GalNAc-α1,4-GalNAc-α1,3-diNAcBac; diNAcBac is 2,4-diacetamido-2,4,6-trideoxy-D-glucopyranose, GalNAc is N-acetylgalactosamine and Glc is glucose), and is commonly found in all *C. jejuni* and *Campylobacter coli* isolates. In *Campylobacter*, the N-glycan is added to multiple periplasmic and membrane proteins, and is immunogenic in rabbits and humans (see, e.g., Nothaft et al. (2012) *Mol. Cell. Proteomics* 11: 1203-19 (13); and Szymanski et al. (2003) *J Biol Chem.* 278: 24509-20 (14)).

Figure 6:
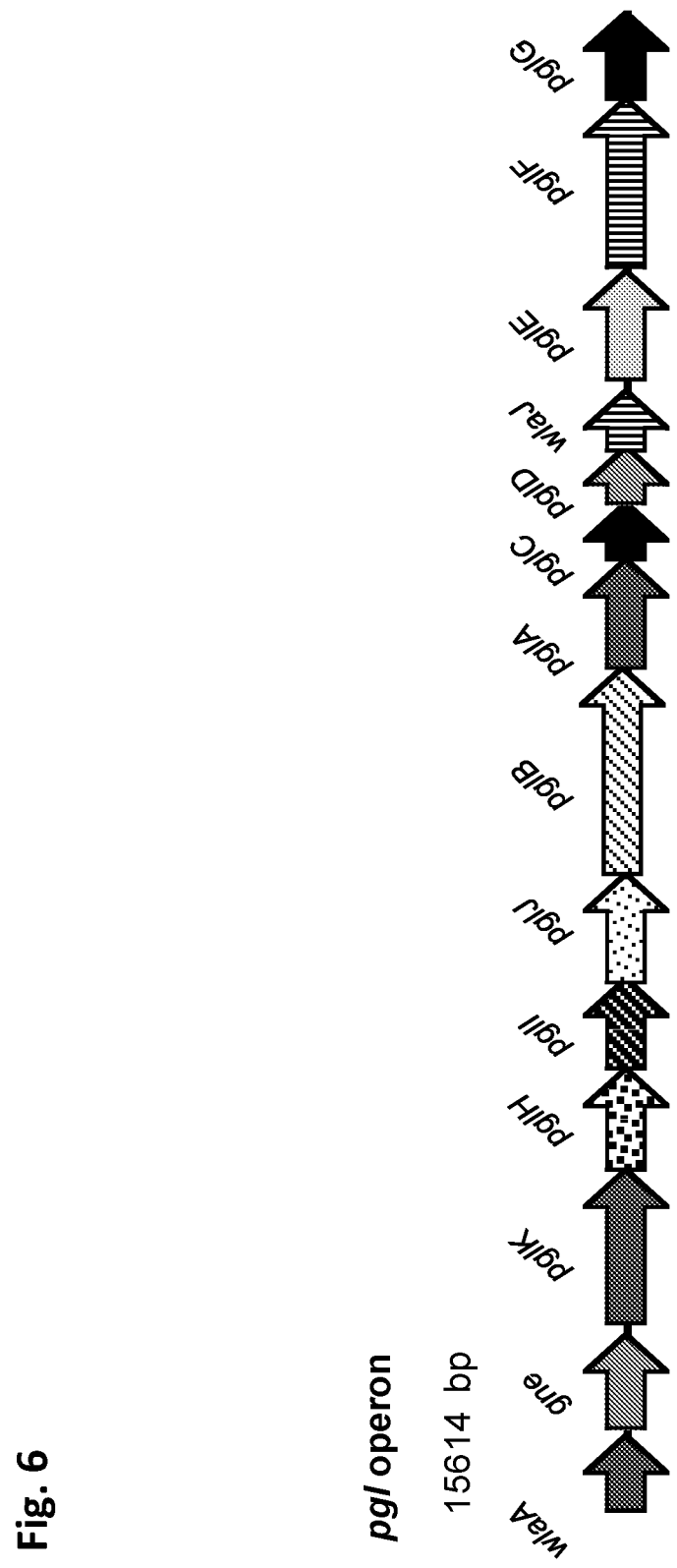
Figure 7:
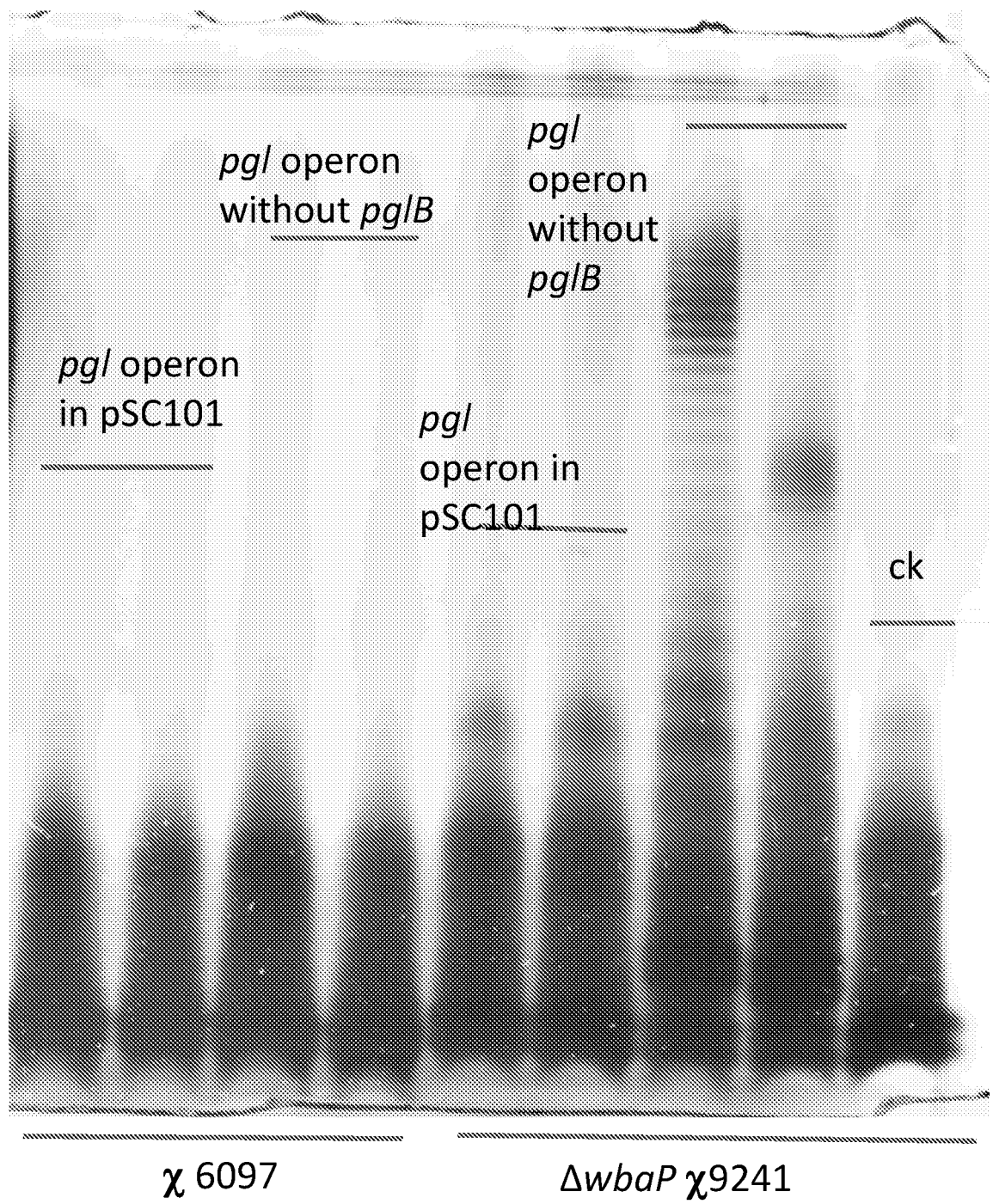

The *C. jejuni* N-glycan is conjugated onto the asparagine within the Glu/Asp Xaa1 Asn-Xaa2-Ser/Thr (SEQ ID NO: 41) glycosylation consensus motif. In *C. jejuni*, the genes encoding proteins that mediate N-linked glycosylation are present in a 17-kb locus named the pgl operon which contains 14 open reading frames (ORFs) (see Wacker et al. (2002) *Science* 298: 1790-3(15)). The 14 ORFs encode several glycotransferases and sugar biosynthetic enzymes which in concert generate a lipid-linked heptasaccharide precursor. The heptasaccharide is transferred onto the target asparagine by PglB in the bacterial periplasm. The *C. jejuni* pgl operon comprises the following genes: wlaA, gne, pglK, pglH, pglI, pglJ, pglB, pglA, pglC, pglD, wlaJ, pglE, pglF, and pglG (FIG. 6).

TABLE A pgl operon gene size and GC contents

| gene | aa | bp | GC % |
| --- | --- | --- | --- |
| wlaA | 264 | 795 | 29.6 |
| gne | 330 | 993 | 34.0 |
| pglK | 526 | 1581 | 29.0 |
| pglH | 354 | 1062 | 30.7 |
| pglI | 304 | 912 | 29.3 |
| pglJ | 362 | 1089 | 29.6 |
| pglB | 713 | 2142 | 29.2 |
| pglA | 376 | 1128 | 30.8 |
| pglC | 198 | 597 | 31.7 |
| pglD | 195 | 588 | 31.1 |
| wlaJ | 217 | 654 | 24.3 |
| pglE | 386 | 1161 | 31.0 |
| pglF | 590 | 1770 | 30.7 |
| pglG | 297 | 894 | 30.1 |

In some embodiments, the recombinant bacterium comprises a nucleic acid comprising a pgl operon (e.g., a *C. jejuni* pgl operon or a *C. coli* pgl operon). In some embodiments, the recombinant bacterium comprises at least one pgl operon gene selected from the group consisting of walA, gne, pglK, pglH, pglI, pglJ, pglB, pglA, pglC, pglD, wlaJ, pglE, pglF, and pglG. Expression of the nucleic acid comprising the pgl operon or of one or more of the pgl operon genes may confer the bacterium (e.g., a non-*Campylobacter* bacterium) the ability to synthesize and N-glycan and conjugate the N-glycan to proteins comprising the Glu/Asp Xaa1 Asn-Xaa2-Ser/Thr (SEQ ID NO: 41) glycosylation consensus motif.

In some embodiments, the nucleic acid comprising a pgl operon is located on a plasmid in the bacterium. In some embodiments, the nucleic acid comprising a pgl operon is located on a chromosome of the bacterium. In some embodiments, the nucleic acid comprising a pgl operon is located at the chromosomal locus corresponding to the locus of an endogenous cysG gene that has been deleted or altered in the bacterial chromosome. In some embodiments, the nucleic acid comprising a pgl operon is operably linked to a regulatable promoter (e.g., a LacI-regulatable promoter such as $P_{trc}$).

The nucleic acid sequence of an exemplary *C. jejuni* pgl operon is provided below:

```
                                          (SEQ ID NO: 42)
GGATTACAAATGGCAAAAAATGAAGGTTATATTTGTGTTTTTGATTGTGA

GAGTGTGCCAGATGTTGAGCTTATCCGCAAAACTTTGGGTTTTGAAGGAA

GTGATTTAGAGGTAAGTTTAAAAGCACTTCAGTGGCAAAAAGAACAAAGT

GGGAGTGAGTTTTTGCCTTTGCCTTATCATAAAATTATCAGTATTTGTGC

GGTTTTAAGTGATAATTTTGGAAAATTTATCAAAGTGAATAAAATTGATG

GACAAAATGAAAAAGAAATGATTGAGAATTTTTTCAATTTTATAGAAAAT

TATGAGCCAAAATTAGTCAGTTTTAATGGTAAAAATTTCGATATGCCTGT

TCTTGTTTTAAGGGCTTTAAAATACAATTTAAAAGCAGCAACTTATTTGG

ATACTCAAAGTGATAAATGGAATAATTATAAAACAAGATTTTCAGAATTA

AAACATTGTGATTTATTAGAATCCTTAGGATCTAACGGGCGTGGAATAAA

GCTTGATACACTTTGTTCTATGGTGGGTTTGCCAGGAAAATATGATGTGC

ATGGCGATGAGGTAATGAAACTTTTTTATGAAAATAAACTTGAAAAAATC
```

-continued

CACGAATATTGTGAAAGTGATGTTTTAAACACCTATATGCTTTTTTAAA
ATATGAACTTATTAAAGCTAATGTTGATGAAGAAGATTATGTTGGTTTTC
TTTCTTATATGAGAGATTTCTTGTGTGCAAAAAAATCAGATCGTTCTTAT
ACAGAAGTTTTTGCAAAAGCTTGTGAGAGTGAAATTTCAAAAGTTCGATC
TTAAGTATTTAAGAAAATATATTAAAATTTATTTTTGACATTTTTAAAAA
AAGGAATGATGATGAAAATTCTTATTAGCGGTGGTGCAGGTTATATAGGT
TCTCATACTTTAAGACAATTTTTAAAAACAGATCATGAAATTTGTGTTTT
AGATAATCTTTCTAAGGGTTCTAAAATCGCAATAGAAGATTTGCAAAAAA
CAAGAGCTTTTAAATTTTTCGAACAAGATTTAAGTGATTTTCAAGGCGTA
AAAGCATTGTTTGAGAGAGAAAATTTGACGCTATTGTGCATTTTGCAGC
AAGCATTGAAGTTTTTGAAAGTATGCAAAATCCTTTAAAATATTATATGA
ACAACACTGTTAATACGACAAATCTCATCGAAACTTGTTTGCAAACTGGA
GTGAATAAATTTATATTTTCTTCAACGGCGGCCACTTATGGCGAACCACA
AACTCCCGTTGTGAGCGAAACAAGTCCTTTAGCACCTATTAATCCTTATG
GGCGTAGTAAGCTTATGAGTGAAGAAGTTTTGCGTGATGCAAGTATGGCA
AATCCTGAATTTAAGCATTGTATTTTAAGATATTTTAATGTTGCAGGTGC
TTGTATGGATTATACTTTAGGACAACGCTATCCAAAAGCGACTTTGCTTA
TAAAAGTTGCAGCTGAATGTGCCGCAGGAAAACGTGATAAACTTTTCATA
TTTGGCGATGATTATGATACAAAAGATGGTACTTGCATAAGAGATTTAT
CCATGTAGATGATATTTCAAGTGCACATTTAGCGGCTTTGGATTATTTAA
AAGAGAATGAAAGCAATGTTTTTAATGTAGGTTATGGACATGGTTTTAGC
GTAAAAGAAGTGATTGAAGCGATGAAAAAAGTTAGCGGAGTGGATTTTAA
AGTAGAACTTGCCCCACGCCGTGCGGGTGATCCTAGTGTATTGATTTCTG
ATGCAAGTAAAATCAGAAATCTTACTTCTTGGCAGCCTAAATATGATGAT
TTAGAGCTTATTTGTAAATCTGCTTTTGATTGGGAAAACAGTGTTAAAA
AAACTTTTTTTATTTTAAGTAAGGAAGATAAAAATTTTTATTTTTCTT
GCTTGTTTTTTCAGTATTTATTTCTTTTATAGAAACTTTTGCAATTTCTT
TGGTAATGCCTTTTATCACTTTGGCTAGTGATTTTTCTTATTTTGATCGT
AATAAATATTTAATCAGCCTAAAAGAATATCTTAATATCCCTGTTTTTGA
AATCATTGTTTATTTTGGAGTGGGGCTTATTGTTTTTATGTGTTTAGAG
CTTTGTTAAATGCGTATTATTTTCATCTTTTGGCAAGATTTTCTAAAGGG
CGTTATCATGCGATCGCTTATAAGGTTTTTTCTAAATTTTTAAATATTAA
TTATGAAAAATTTACTCAAAAAAATCAATCTGAAATTTTAAAGTCCATTA
CAGGGGAAGTTTATAATCTAAGCACTATGATTTCATCATTTTTACTTTTG
ATGAGTGAAATTTTTGTAGTACTTTTGCTTTATGCTTTAATGCTTTTGAT
TAATTATAAAATCACTTTGTTTTTAAGTATTTTTATGGTGTTAAATGCCT
TTATTTTAGTGAAAATTTTAAGCCCTATCATTAAAAAAGCAGGAGTAAGA
CGCGAAGAAGCGATGAAAAATTTCTTTGAAATTTTAAATACAAATTTAAA
TAATTTCAAATTTATTAAGCTTAAAACCAAAGAAGATGGAGTATTAAGTC
TTTTTAAAGCGCAAAGTGAAGCTTTTTCTAAAGCAAATATTACCAACGAA
AGCGTAGCTGCGGTGCCTAGAATTTATCTTGAAGGAATAGGCTTTTGCGT

-continued

ACTTGTTTTTATCGTGGTATTTTTGGTTTTGAAAAATGAAAGTGATATTT
CAGGTATTTTATCCACGATTTCTATTTTTGTTTTAGCGCTTTATCGCTTA
ATGCCAAGTGCAAATCGTATTATTACAAGTTATCATGATTTGCTTTATTA
TCATTCTTCTTTGGATATTATTTATCAAAATTTAAGACAAGAAGAAGAAA
ATTTGGGCGAGGAAAAATTAAGCTTTAATCAAGAGCTTAAAATTTGCAAT
CTTAGCTTTGGTTATGAGGGAAAAAAATATTTATTTAAAAATCTTAACTT
AAATATTAAAAAAGGCGAAAAAATCGCTTTTATAGGGGAGAGTGGTTGTG
GAAAAAGTACCTTAGTAGATCTTATCATAGGACTTTTAAAACCAAAAGAA
GGGCAAATTTTAATTGATGAGCAAGAATTAAATGCAAATAATACAAAAAA
TTATCGCCAAAAAATAGGCTATATCCCGCAAAATATCTATCTTTTTAATG
ACAGTATAGCTAAAAATATCACTTTTGGAGATGCGGTTGATGAAGAAAAA
CTTAATAGGGTTATCAAACAAGCAAATTTAGAGCATTTTATAAAAAATTT
ACCTCAAGGAGTGCAAACAAAAGTGGGCGATGGGGGGAGTAATTTAAGCG
GGGGACAAAAACAACGCATAGCTATAGCAAGAGCTTTATATTTAGAGCCT
GAAATGTTAGTGCTTGATGAAGCAACTTCTGCGCTTGATACTCAAAGTGA
AGCAAAAATTATGGATGAAATTTATAAAATTTCTAAAGATAAAACCATGA
TTATTATCGCACATCGCCTTTCTACGATAACACAATGTGATAAGGTTTAT
CGTTTAGAACACGGTAAGCTTAAAGAGGAGAAATGATGAAAATAAGCTTT
ATTATCGCAACTTTAAATTCAGGAGGTGCTGAGCGTGCTTTAGTAACCTT
AGCTAATGCACTTTGCAAAGAGCATGAAGTAAGTATTATTAAATTTCATG
CAGGAGAATCTTTTTATAAGCTTGAAAATGAAGTTAAAGTTACAAGTTTG
GAACAATTTAGATTTGACACGCTTTATCATAAAATCGCAAGTCGTTTTAA
GAAATTTTTTGCTTTAAGAAAGGCTTTGAAAGAAAGTAAGTCTGATGTTT
TTATTTCTTTTTTGGATACGACTAATATTGCTTGTATTGCTGCGAAAATA
GGGCTTAAAACTCCACTCATTATAAGTGAGCATAGCAATGAAGCGTATTT
AAAACCTAAAATTTGGCGTTTTTTAAGAAGGGTAAGCTATCCTTTTTGTG
ATGCTTTAAGTGTGCTTGGAAGCAGTGATAAGGTGTATTATGAAAGATTT
GTAAAAAGGGTTAAGCTTTTATTAAACCCTTGTCATTTTAGCGATGAAAT
TTCTTTTGATTCTAGTTTTGAAAAGGAAAATTTGGTTCTTTTTATAGGGC
GTTTAGATCACAACAAAAACCCTGTAATGTTTTAAAAGCTATAGCGCAT
TTGGATAAAAATTTACAAGAAAATTATAAATTTGTTATAGCAGGAGATGG
ACAGTTAAGACAAGAACTTGAATATAAGGTAAAATCTTTAGGAATAAAAG
TTGATTTTTAGGACGCGTTGAAAATGTCAAGGCTCTTTATGAAAAAGCA
AAAGTGCTTTGCCTTTGTTCTTTTGTAGAGGGTTTGCCAACGGTTTTAAT
TGAAAGTTTGTATTTTGAGGTTTGTAGAATTTCAAGTTCTTATTATAATG
GTGCTAAGGATTTAATCAAAGATAATCATGATGGGCTTTTGGTAGGTTGT
GATGATGAAATAGCACTTGCTAAAAAACTTGAACTTGTTTTAAATGATGA
AATTTTAGAAAAGAACTTGTAAATAATGCCAAACAAAGGTGTAAAGACT
TTGAAATTTCTCATATCAAAGAAGAATGGCTTAAGCTTATAGCCGAGGTT
AAAAATGCCTAAACTTTCTGTTATAGTACCAACTTTTAATCGTCAAGTTT

-continued

```
TGTTAGAAAAGGCTATTAAAAGCATACAAAATCAAGATTTTAAAGATTTA
GAAATTATTGTAAGCGATGATAATTCTAGCGATGATACTAAAAGTGTGGT
GCAAAATTTACAAAAAGATGATGATCGCATTAAGTATTTTTTAAATCAAA
ATTACAAACAAGGTCCAAATGGCAATAAAAACAATGGCTTAGATCAAGCA
AGTGGCGAGTTTGTAACTTTTTTAGATGATGATGATGAGCTTTTATCCGG
GGCTTTAAGTACCTTGATGCAAAAAGCAAATGAGGGTTATGCTCATGTTT
TTGGAAATTGTTTGATAGAAAAGAAGGAAATTTAAGCAAGGAATTTAGC
GGCAAGGGCTTGGAAAAAGATAGTGAAATTTCTAAAAAAGATTTTTTAAT
GGCTAAATTTAGCGGAGAGTTTTTTTCTGTTTTTAAAAAATCCCTACTTG
AAAATAAGCGTTTTAATGAAGAATTTTATGGCAATGAAGCCACGCTTTGG
GTAAATTTATACAAAGAAAAAGTTTTTATATCCATAAGGCTTTTAGGAT
TTATAGAATTTTTAGGCAAGATAGCGTGACTTTAGGGGCGAGTAAAAATG
CTTATAGGGTGTATTTGGGATATTTAGAGCTTGCTAAAATTTTAGAAAAT
GAACTTAGAATGAGTAAGGATAAAGATTATAAAAAAACTTGTGCGAGTTA
TTATAAAATGGCAGCTTATTATGCAAAACTTGCAAAAAATTATAAAGCCC
TTTATAAATGTTTGTTTAAAAGCCTAAGTATAAAAATCAACGCTCCTGCT
TTGATATTACTCATTTTAAGTATAATTCCAAATAATATGATTGAAAAATT
ATCAAAAATTCGGGTGGCTTTATGCAAAAATTAGGCATTTTTATTTATTC
TTTAGGAAGTGGTGGTGCTGAAAGAGTTGTGGCGACTTTATTGCCTATTT
TAAGTTTGAAATTTGAAGTGCATTTGATCTTGATGAATGATAAAATTTCT
TATGAAATTCCAGAGTGTCAAATTCATTTTTTAGAATGTTCAAAACCTAG
TGAAAATCCTATTTTGAAATTTTTAAAACTACCTTTTTTGGCTTTAAAAT
ACAAAAAACTTTGCAGAAATTTAGGTATTGATACAGAATTTGTTTTTTA
AATCGACCTAATTATATAGCTTTAATGGCAAGAATGTTTGGAAACAAAAC
TCGCCTTGTGATCAATGAATGCACTACGCCAAGTGTGATGTATATGAAAA
ATAATTTTAATTCTTTGGTAAATAAATTTTTAATTTCTTTGCTTTACCCA
AAAGCTGATTTAATCTTGCCTAATTCTAAGGGAAATTTAGAAGATTTAGT
GCAAAATTTTAGTATAAGTCCAAAAAAATGTGAAATTTTATACAATGCCA
TCGATTTAGAAAACATAGGGCAAAAAGCCCTTGAAGACATAGCTTTAAAA
GATAAATTTATTTTAAGTGTAGGCAGGCTTGATAAAGGTAAAAATCATGC
TTTATTAATTCGTGCTTATGCGAGATTGAAAACAGATTTAAAGCTTGTGA
TTTTAGGTGAAGGTGTGCTTAAGGATGAGCTTTTAGCTTTGATTAAAGAA
TTAAATTTGGAAGAAAAGGTTTTGCTTTTAGGATTTGATAATAATCCTTA
TAAATACATGGCTAAATGCGAATTTTTTGCTTTTGCTTCTGTGTTTGAAG
GTTTTTCAAATGTTTTAATCGAAAGTTTGGCTTGTTCTTGTGCGGTGGTT
TGCACTGATCATAAAAGTGGTGCAAGAGAGCTTTTTGGCGATGATGAATT
TGGACTTTTAGTAGAAGTAGATAATGAAAACTCTATGTTTCAGGGTTTAA
AAACTATGCTTGAAGACGATAAATTAAGAAAAGCGTATAAAAACAAAGCT
AAAACTAGGGCTAAAGCCTTTGATAAAGTAAAAATTGCACGCGATGCTTT
GAAATATTTATTAGGATAAAAGATGTTGAAAAAGAGTATTTAAAAAACC
CTTATTTAGTTTTGTTTGCGATGATTGTATTAGCTTATGTTTTTAGTGTA
TTTTGCAGGTTTTATTGGGTTTGGTGGGCAAGTGAGTTAACGAGTATTT
TTTCAATAATCAATTAATGATCATTTCAAACGATGGCTATGCTTTTGCTG
AGGGCGCAAGAGATATGATAGCAGGTTTTCATCAGCCTAATGATTTGAGT
TATTATGGATCTTCTTTATCTACGCTTACTTATTGGCTTTATAAAATCAC
ACCTTTTTCTTTTGAAAGTATCATTTTATATATGAGTACTTTTTTATCTT
CTTTGGTGGTGATTCCTATTATTTTACTAGCTAATGAATACAAACGCCCT
TTAATGGGCTTTGTAGCTGCTCTTTTAGCAAGTGTAGCAAACAGTTATTA
TAATCGCACTATGAGTGGGTATTATGATACGGATATGCTGGTAATTGTTT
TACCTATGTTTATTTTATTTTTTATGGTAAGAATGATTTTAAAAAAAGAC
TTTTTTTCATTGATTGCCTTGCCATTATTTATAGGAATTTATCTTTGGTG
GTATCCTTCAAGTTATACTTTAAATGTAGCTTTAATTGGACTTTTTTAA
TTTATACACTTATTTTTCATAGAAAAGAAAAGATTTTTTATATAGCTGTG
ATTTTGTCTTCTCTTACTCTTTCAAATATAGCATGGTTTTATCAAAGTGC
CATTATAGTAATACTTTTTGCTTTATTTGCTTTAGAGCAAAAACGCTTAA
ATTTTATGATTATAGGAATTTTAGGTAGTGCAACTTTGATATTTTTGATT
TTAAGTGGTGGGGTTGATCCCATACTTTATCAGCTTAAATTTTATATTTT
TAGAAGCGATGAAAGTGCGAATTTAACACAGGGCTTTATGTATTTTAATG
TTAATCAAACCATACAAGAAGTTGAAAATGTAGATTTTAGCGAATTTATG
CGAAGAATTAGTGGTAGTGAAATTGTTTTCTTGTTTTCTTTGTTTGGTTT
TGTATGGCTTTTGAGAAAACATAAAAGTATGATTATGGCTTTACCTATAT
TGGTGCTTGGGTTTTTAGCCTTAAAAGGAGGACTTAGATTTACCATTTAT
TCTGTACCTGTAATGGCTTTAGGATTTGGTTTTTTATTGAGCGAGTTTAA
GGCTATATTGGTTAAAAAATATAGCCAATTAACTTCAATGTTTGTATTGT
TTTTGCAACTATTTTGACTTTGGCTCCAGTATTTATCCATATTTACAACT
ATAAAGCGCCAACAGTTTTTTTCTCAAAATGAAGCATCATTATTAAATCAA
TTAAAAAATATAGCCAATAGAGAAGATTATGTGGTAACTTGGTGGGATTA
TGGTTATCCTGTGCGTTATTATAGCGATGTGAAAACTTTAGTAGATGGTG
GAAAGCATTTAGGTAAGGATAATTTTTTCCCTTCTTTTTCTTTAAGTAAA
GATGAACAAGCTGCAGCTAATATGGCAAGACTTAGTGTAGAATATACAGA
AAAAAGCTTTTATGCTCCGCAAAATGATATTTTAAAATCAGACATTTTAC
AAGCCATGATGAAAGATTATAATCAAAGCAATGTGGATTTATTTCTAGCT
TCATTATCAAAACCTGATTTTAAAATCGATACACCAAAAACTCGTGATAT
TTATCTTTATATGCCCGCTAGAATGTCTTTGATTTTTTCTACGGTGGCTA
GTTTTTCTTTTATTAATTTAGATACAGGAGTTTTGGATAAACCTTTTACC
TTTAGCACAGCTTATCCACTTGATGTTAAAAATGGAGAAATTTATCTTAG
CAACGGAGTGGTTTTAAGCGATGATTTTAGAAGTTTAAAATAGGTGATA
ATGTGGTTTCTGTAAATAGTATCGTAGAGATTAATTCTATTAAACAAGGT
GAATACAAAATCACTCCAATCGATGATAAGGCTCAGTTTTATATTTTTTA
TTTAAAGGATAGTGCTATTCCTTACGCACAATTTATTTTAATGGATAAAA
CCATGTTTAATAGTGCTTATGTGCAAATGTTTTTTTTGGGAAATTATGAT
```

-continued

AAGAATTTATTTGACTTGGTGATTAATTCTAGAGATGCTAAAGTTTTTAA

ACTTAAAATTTAAGGGTTGAAAATGAGAATAGGATTTTTATCACATGCAG

GAGCGAGTATTTATCATTTTAGAATGCCTATTATAAAAGCGTTAAAAGAT

AGAAAAGACGAAGTTTTTGTTATAGTGCCGCAAGATGAATACACGCAAAA

ACTTAGAGATCTTGGCTTAAAAGTAATTGTTTATGAGTTTTCAAGAGCTA

GTTTAAATCCTTTTGTGGTTTTAAAGAATTTTTTTTATCTTGCTAAGGTT

TTGAAAAATTTAAATCTTGATTTTATTCAAAGTGCGGCACACAAAAGCAA

TACTTTTGGAATTTTAGCAGCAAAATGGGCAAAAATTCCTTATCGTTTTG

CCTTAGTAGAAGGCTTGGGATCTTTTTATATAGATCAAGGTTTTAAGGCA

AATTTAGTGCGTTTTGTTATTAATAGTCTTTATAAATTAAGTTTTAAATT

TGCACACCAATTTATTTTTGTCAATGAAAGTAATGCTGAGTTTATGCGGA

ATTTAGGACTTAAAGAAAATAAAATTTGCGTGATAAAATCTGTAGGGATC

AATTTAAAAAAATTTTTTCCTATTTATGTAGAATCGGAAAAAAAAGAGCT

TTTTTGGAAAAATTTAAACATAGATAAAAAACCCATTGTGCTTATGATAG

CAAGAGCTTTATGGCATAAGGGTGTAAAAGAATTTTATGAAAGTGCTACT

ATGCTAAAAGACAAAGCAAATTTTGTTTTAGTTGGTGGAAGAGATGAAAA

TCCTTCTTGTGCAAGTTTGGAGTTTTTAAACTCTGGCGCGGTGCATTATT

TGGGTGCTAGAAGTGATATAGTCGAGCTTTTGCAAAATTGTGATATTTTT

GTTTTGCCAAGCTATAAAGAAGGCTTTCCTGTAAGTGTTTTGGAGGCAAA

AGCTTGCGGTAAGGCTATAGTGGTGAGTGATTGTGAAGGTTGTGTGGAGG

CTATTTCTAATGCTTATGATGGACTTTGGGCAAAAACAAAAAATGCTAAA

GATTTAAGCGAAAAAATTTCACTTTTATTAGAAGATGAAAAATTAAGATT

AAAATTTAGCTAAAAATGCCGCCCAAGATGCTTTACAATACGATGAAAATA

TAATCGCACAGCGTTATTTAAAACTTTATGATAGGGTAATTAAGAATGTA

TGAAAAAGTTTTTAAAAGAATTTTTGATTTTATTTTAGCTTTAGTGCTTT

TAGTGCTTTTTTCTCCGGTGATTTTAATCACTGCTTTACTTTTAAAAATC

ACTCAAGGAAGTGTGATTTTTACCCAAAATCGTCCCGGGTTAGATGAAAA

AATTTTTAAAATTTATAAATTTAAAACCATGAGCGATGAAAGAGATGAAA

AGGGTGAGTTATTAAGCGATGAATTGCGTTTGAAAGCTTTTGGAAAAATC

GTTAGAAGCTTAAGTTTGGATGAGCTTTTGCAACTTTTTAATGTTTTAAA

AGGGGATATGAGTTTTGTTGGACCTAGACCTCTTTTGGTTGAGTATTTGC

CTCTTTACAATAAAGAGCAAAAATTGCGTCATAAAGTGCGTCCAGGTATA

ACAGGATGGGCGCAGGTAAATGGTAGAAATGCTATTTCTTGGCAGAAAAA

ATTCGAACTTGATGTGTATTATGTGAAAAATATTTCTTTTTTGCTTGATT

TAAAAATCATGTTTTTAACAGCTTTAAAGGTTTTAAAACGAAGTGGGGTA

AGCAAAGAAGGCCATGTTACAACAGAGAAATTTAATGGCAAGAACTGAAA

AAATTTATATTTATGGTGCTAGTGGTCATGGGCTTGTTTGTGAAGATGTG

GCTAAAAATATGGGTTATAAAGAATGTATTTTTTAGATGATTTTAAAGG

AATGAAATTTGAAAGTACCTTACCTAAAATATGATTTTTTTATAGCCATAG

GAAACAATGAAATTCGAAAAAGATTTATCAAAAAATTTCAGAAAATGGC

TTTAAAATTGTCAATCTTATCCATAAAAGCGCGCTTATAAGTCCTAGCGC

AATCGTGGAAGAAAATGCAGGAATTTTAATCATGCCTTATGTAGTGATTA

ACGCTAAAGCTAAAATAGAAAAAGGTGTGATTTTAAATACTTCAAGCGTA

ATTGAGCATGAATGTGTGATAGGGGAATTTTCTCATGTGAGTGTGGGAGC

TAAATGTGCGGGTAATGTAAAAATTGGTAAAAATTGTTTTTTAGGGATTA

ATTCTTGTGTTTTGCCTAATTTAAGTTTGGCAGATGATAGTATTTTAGGT

GGTGGAGCAACTTTAGTTAAAAATCAAGATGAAAAAGGTGTTTTTGTGGG

AGTACCTGCAAAAAGGATGTAAATTGCATTTTAATAACAATCTTGTTGTT

CACTATATAGTAAATCCTTCGCCTTTGGGGTGGATTGTCATTAATTTACT

AACCATATGTCTAATATGCTACATATTTCCTTTGAAAAATTCTTTAAAAC

ACAAAAAACTTTTTAGTCTTAAAGCAAATGTAAATTCTAAAAATAGTAGG

ATTATAAAATATACAGGTATTGCTGCTTTTTTGGGTGGATTAATAGGAAT

TTGGTATAATTTTGAAGGTTTTTATCAACTTCTTTTTTTCTTTGAATTAG

AAAATGAAAATTTAAAAACACTTTGGAGTTTGCAAGTATCAGTTTCTTCT

GTGATAACAGGTATGTTATTATTGTTGATATATGTTATAAATTTAGCAAT

GGTTTGTGAAAATGGAATTTATATAGTTAGTAAATTTAATCTTTTTTATA

TGTATTTTATAAAACGAGAAGATTTGGAAATTGTTAAAATAGAAAAAATG

AAATTTTTAAATCAAGTTGAAGTTTGTTTTGTTATCAAAACAAAAAATAA

AATACTCCTTAAATGCTTTGAAAGTATTTATAAAAAGAAGACTTAGAAA

AGCTTAAAAATTGGTATGAAAACAAGCTTTGACTATAAAAGAATTTAAA

TATTTGAATCTTTGTAAATTTTTTAGGTAAAATAGAGTCAATTTATAAA

AATTTTGTTTTACACAAAGGATAAATCATGAGATTTTTTCTTTCTCCTCC

GCATATGGGTGGTAATGAATTAAAATACATAGAAGAAGTTTTCAAAAGCA

ATTATATAGCACCTTTGGGTGAATTTGTAAATCGCTTTGAACAAAGTGTC

AAGGCTTACAGTAAAAGTGAAAATGCCTTAGCTTTAAATTCAGCCACAGC

GGCTTTGCATTTAGCTTTAAGGGTGGCAGGGGTAAAACAAGATGATATTG

TTTTGGCTTCTTCTTTTACTTTTATCGCTTCAGTAGCACCTATTTGTTAT

CTTAAAGCAAACCTGTATTTATAGATTGTGATGAAACTTATAATATCGA

TGTAGATTATTAAAGCTTGCTATTAAAGAATGTGAAAAAAAACCAAAAG

CATTGATTTTAACTCATCTTTATGGCAATGCGGCTAAAATGGATGAAATT

GTTGAAATTTGCAAAGAAAATGAAATTGTTTTAATCGAAGATGCTGCTGA

AGCTTTAGGAAGTTTTTATAAGAATAAAGCTTTAGGAACTTTTGGAGAAT

TTGGAGCTTATTCTTATAATGGCAATAAAATTATCACCACTTCAGGTGGA

GGTATGCTTATAGGAAAAATAAAGAAAGATTGAAAAGCAAGATTTTA

TAGCACTCAAGCTAGGGAAAATTGTTTGCATTATGAACATTTAGATTATG

GTTATAATTACCGCTTAAGCAATGTTTTAGGAGCTATTGGCGTAGCGCAA

ATGGAGGTTTTAGAACAAAGAGTGCTTAAAAAAAGAGAAATTTATGAGTG

GTATAAAGAATTTTTAGGAGAGTGTTTTAGCTTTTTAGATGAATTAGAAA

ATTCAAGAAGCAATCGCTGGTTAAGTACAGCTTTGATTGATTTTGATAAA

AATGAACTTAATTCTTGTCAAAAAGATATAAATATCAGTCAAAAAAATAT

TACTTTGCATCCAAAAATTTCAAAACTCATAGAAGATTTGAAAAATGAAC

-continued
```
AAATAGAAACAAGACCATTATGGAAAGCTATGCACGCTCAAGAAGTATTT

AAAGGAGCTAAGGCTTATCTTAATGGCAATAGTGAGTTATTTTTCCAAAA

AGGAATTTGTTTGCCAAGTGGCACGGCGATGAGTAAAGATGATGTTTATG

AAATTTCAAACTGATCTTAAAGAGCATAAAGGCTTAAAATGATTTTTTA

TAAAAGCAAAAGATTAGCATTTTTTTTAACTTCAGATATTGTTTTAATTT

TACTTAGCGTTTATCTGGCTTTTTCTTTGAGATTTAGTGGAGATATTCCG

AGTATTTTTATCATGGTATGATGGTTTCTGCTATTATTTTGCTTGTTTT

AAAACTTTCATTTTTGTTTGTTTTAGAATTTATAAAGTAGCTTGGAGAT

TTTTTTCTCTCAATGAAGCAAGAAAGATTTTTATCGCTTTGCTTTTAGCT

GAGTTTTGTTTTTTCTTATTTTTATTTTTTAGTGATTTTTTTAATCC

TTTTCCAAGAAGTGCTATTGTGATAGATTTTGTTCTTTCTTATATGTTTA

TAGGTACTTTAAGAATTAGCAAAAGAATGCTTGTGGATTTTAAACCTTCT

AGAATGAAAGAAGAAGAAACTCCTTGTATTGTAGTAGGGGCAACTTCTAA

GGCTTTGCATTTGTTAAAAGGTGCAAAAGAAGGTTCTTTAGGGCTTTTTC

CTGTAGGCGTAGTTGATGCGAGAAAAGAGCTTATAGGGACTTATTGTGAT

AAATTTATTGTAGAAGAAAAAGAAAAAATAAAATCTTATGTAGAACAAGG

GGTAAAAACTGCCATTATTGCTTTAAGACTTGAACAAGAAGAGCTTAAAA

AACTTTTTGAAGAACTTGTAGCTTATGGTATTTGCGATGTAAAAATATTT

TCTTTTACAAGAAACGAAGCAAGAGATATCAGTATAGAAGACTTGCTTGC

TAGAAAACCAAAAGATTTAGATGATAGTGCTGTGGCGGCTTTTTTAAAAG

ATAAGGTAGTTTTGGTAAGTGGAGCAGGTGGAACTATAGGCAGTGAACTT

TGTAAGCAATGTATTAAATTTGGTGCTAAGCATCTTATCATGGTTGATCA

TAGTGAGTATAATCTTTATAAGATCAATGATGATTTAAATTTATATAAAG

AAAAAATTACTCCTATTTTACTGAGTATTTTAGATAAGCAAAGTTTAGAT

GAGGTATTAAAAACTTATAAACCCGAGCTTATTTTACATGCAGCCGCTTA

TAAACATGTGCCTCTTTGCGAACAAAATCCACATTCAGCAGTAATCAATA

ATATTTTAGGAACTAAAATTTTATGCGACAGTGCTAAAGAAAACAAAGTA

GCTAAATTTGTGATGATAAGTACAGATAAAGCAGTACGACCAACAAATAT

TATGGGTTGCACTAAGAGAGTTTGCGAGCTTTATACTTTAAGTATGAGTG

ATGAAAATTTTGAAGTTGCTTGTGTGCGTTTTGGTAATGTTTTAGGTTCT

AGTGGTAGTGTGATACCGAAATTTAAAGCACAAATTGCCAATAATGAGCC

TTTAACTTTAACGCACCCTGATATAGTGCGTTATTTTATGCTTGTGGCTG

AGGCAGTGCAACTTGTTTTACAAGCTGGAGCTATCGCAAAAGGGGGAGAA

CTTTTTGTTTTGGATATGGGTAAGCCTGTGAAAATCATAGATTTAGCTAA

AAAAATGCTTTTACTTTCTAATCGCAATGATTTAGAAATTAAAATCACAG

GCTTAAGAAAAGGTGAGAAGCTTTATGAAGAGCTTTTGATTGATGAAAAT

GATGCTAAAACACAATATGAGAGTATTTTTGTAGCAAAGAATGAGAAGGT

TGACCTTGATTGGCTTAATAAAGAGATAGAAAATTTACAAATATGTGAAG

ATATTTCAGAGGCTTTATTAAAGATTGTACCTGAATTTAAACACAATAAA

GAAGGTGTATAATGTATATAAAAGATATACAAAGATTTGAAGATAATCGC

TATCGTGCTAGAGCTTATATGAGTTATATTTTAACAAGAAATCTGCCCAA
```
-continued
```
TAAACTTCCTGACATTCACCTTGAAACGATTAAAACAGCTTTGGATAAAA

TAGCTCATGAAGTTGTTGTTTTTGATGCTTTGTATATTTTAGATATTTCA

GGCATGCAAATAGAAAATGCGATTTCCTTAAATAAAGCTCATGAAATAGG

GCAGGGTGAGGATAGAAGTACTCGTTCTTATTTTTATAGAGCTGTAAAAT

TAAGACGATGTGTTTTGAGCGATCCTTATCCTTCGGTTTTAAATAATGAG

CTTTGCGTGACAGCTTCTATGCCAATTTACGATGATAAAAATAACTTGCT

TTTTGTTGTTTGTATTGATATCAAGCTTGAAGATATTTTAAAGATTATTC

AAGCAGGAAAATTTGAATTTGTTTTTACTCAGTTTAGTCGTTTGGTATAT

TTTTGCTTCGCACTGGTTTTATTTGTGATTACTTGTTTTTTATTTCAAAA

AGGTTTTTTAGTCTTTTTGATAATCAAGCTATAGGTATAGAACATATGT

TTGAAAGTACCATCGCTATAACTTTGGCTTTAGCTATTTTTGATTTGGCA

AAAACTTTGATCGAACAAGAAGTATTAGGAAGGACGAAAAAAGAAGAAGG

TGGAATTCAAAAAACTATGGTGAGATTTTTGGGTTCTATTATCATTGCTT

TAGCTATAGAAGCTTTGATGTTGGTATTTAAACTTGCTATTGGTGATCTT

TCTCAGATGATTTATGCGATTTATCTTATCGGTGGAGTGAGCTTGCTTCT

TTTAGGTTTAAGTGTATATTTATTTACGGTTAAGTATAAAAATAATAATA

TTTGAACTTAGT.
```

In some embodiments, the nucleic acid comprises a *C. jejuni* pgl operon (provided as SEQ ID NO: 42). In some embodiments, the nucleic acid comprises a *C. jejuni* pgl operon, wherein the *C. jejuni* pgl operon comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 42. In some embodiments, the nucleic acid comprises *C. jejuni* pgl operon, wherein *C. jejuni* pgl operon comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 42.

wlaA—In some embodiments, the recombinant bacterium comprises a nucleic acid comprising a wlaA gene (e.g., a *C. jejuni* wlaA gene).

In some embodiments, the nucleic acid comprising a wlaA gene is located on a plasmid in the bacterium. In some embodiments, the nucleic acid comprising a wlaA gene is located on a chromosome of the bacterium.

The nucleic acid sequence of an exemplary *C. jejuni* wlaA gene is provided below:

(SEQ ID NO: 43)
```
ATGGCAAAAAATGAAGGTTATATTTGTGTTTTTGATTGTGAGAGTGTGCC

AGATGTTGAGCTTATCCGCAAAACTTTGGGTTTTGAAGGAAGTGATTTAG

AGGTAAGTTTAAAAGCACTTCAGTGGCAAAAAGAACAAAGTGGGAGTGAG

TTTTTGCCTTTGCCTTATCATAAAATTATCAGTATTTGTGCGGTTTTAAG
```

-continued

TGATAATTTTGGAAAATTTATCAAAGTGAATAAAATTGATGGACAAAATG

AAAAAGAAATGATTGAGAATTTTTTCAATTTTATAGAAAATTATGAGCCA

AAATTAGTCAGTTTTAATGGTAAAAATTTCGATATGCCTGTTCTTGTTTT

AAGGGCTTTAAAATACAATTTAAAAGCAGCAACTTATTTGGATACTCAAA

GTGATAAATGGAATAATTATAAAACAAGATTTTCAGAATTAAAACATTGT

GATTTATTAGAATCCTTAGGATCTAACGGGCGTGGAATAAAGCTTGATAC

ACTTTGTTCTATGGTGGGTTTGCCAGGAAAATATGATGTGCATGGCGATG

AGGTAATGAAACTTTTTTATGAAAATAAACTTGAAAAAATCCACGAATAT

TGTGAAAGTGATGTTTTAAACACCTATATGCTTTTTTTAAAATATGAACT

TATTAAAGCTAATGTTGATGAAGAAGATTATGTTGGTTTTCTTTCTTATA

TGAGAGATTTCTTGTGTGCAAAAAAATCAGATCGTTCTTATACAGAAGTT

TTTGCAAAAGCTTGTGAGAGTGAAATTTCAAAAGTTCGATCTTAA

The amino acid sequence of the WlaA protein encoded by the nucleic acid of SEQ ID NO: 43 is provided below:

MAKNEGYICVFDCESVPDVELIRKTLGFEGSDLEVSLKALQWQKEQSGSE

FLPLPYHKIISICAVLSDNFGKFIKVNKIDGQNEKEMIENFFNFIENYEP

KLVSFNGKNFDMPVLVLRALKYNLKAATYLDTQSDKWNNYKTRFSELKHC

DLLESLGSNGRGIKLDTLCSMVGLPGKYDVHGDEVMKLFYENKLEKIHEY

CESDVLNTYMLFLKYELIKANVDEEDYVGFLSYMRDFLCAKKSDRSYTEV

FAKACESEISKVRS

In some embodiments, the nucleic acid comprises a *C. jejuni* wlaA gene (provided as SEQ ID NO: 43). In some embodiments, the nucleic acid comprises a wlaA gene, wherein the wlaA gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO:43. In some embodiments, the nucleic acid comprises a wlaAgene, wherein the wlaA gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 43.

In some embodiments, the nucleic acid comprises a nucleic acid sequence encoding a WlaA protein, wherein said WlaA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 44. In some embodiments, the nucleic acid comprises a nucleic acid sequence encoding a WlaA protein, wherein said WlaA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 44.

wlaJ—In some embodiments, the recombinant bacterium comprises a nucleic acid comprising a wlaJ gene (e.g., a *C. jejuni* wlaA gene).

In some embodiments, the nucleic acid comprising a wlaJ gene is located on a plasmid in the bacterium. In some embodiments, the nucleic acid comprising a wlaJ gene is located on a chromosome of the bacterium.

The nucleic acid sequence of an exemplary *C. jejuni* wlaJ gene is provided below:

(SEQ ID NO: 45)
ATGAAAAAGGTGTTTTTGTGGGAGTACCTGCAAAAAGGATGTAAATTGCA

TTTTAATAACAATCTTGTTGTTCACTATATAGTAAATCCTTCGCCTTTGG

GGTGGATTGTCATTAATTTACTAACCATATGTCTAATATGCTACATATTT

CCTTTGAAAAATTCTTTAAAACACAAAAAACTTTTTAGTCTTAAAGCAAA

TGTAAATTCTAAAAATAGTAGGATTATAAAATATACAGGTATTGCTGCTT

TTTTGGGTGGATTAATAGGAATTTGGTATAATTTTGAAGGTTTTTATCAA

CTTCTTTTTTTCTTTGAATTAGAAAATGAAAATTTAAAAACACTTTGGAG

TTTGCAAGTATCAGTTTCTTCTGTGATAACAGGTATGTTATTATTGTTGA

TATATGTTATAAATTTAGCAATGGTTTGTGAAAATGGAATTTATATAGTT

AGTAAATTTAATCTTTTTTATATGTATTTTATAAAACGAGAAGATTTGGA

AATTGTTAAAATAGAAAAAATGAAATTTTTAAATCAAGTTGAAGTTTGTT

TTGTTATCAAAACAAAAAATAAAATACTCCTTAAATGCTTTGAAAGTATT

TATAAAAAAGAAGACTTAGAAAAGCTTAAAAATTGGTATGAAAACAAGCT

TTGA.

The amino acid sequence of the WlaJ protein encoded by the nucleic acid of SEQ ID NO: 45 is provided below:

MKKVFLWEYLQKGCKLHFNNNLVVHYIVNPSPLGWIVINLLTICLICYIF

PLKNSLKHKKLFSLKANVNSKNSRIIKYTGIAAFLGGLIGIWYNFEGFYQ

LLFFFELENENLKTLWSLQVSVSSVITGMLLLLIYVINLAMVCENGIYIV

SKFNLFYMYFIKREDLEIVKIEKMKFLNQVEVCFVIKTKNKILLKCFESI

YKKEDLEKLKNWYENKL.

In some embodiments, the nucleic acid comprises a *C. jejuni* wlaJ gene (provided as SEQ ID NO: 45). In some embodiments, the nucleic acid comprises a wlaJ gene, wherein the wlaJ gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 45. In some embodiments, the nucleic acid comprises a wlaJ gene, wherein the wlaJ gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 45.

In some embodiments, the nucleic acid comprises a nucleic acid sequence encoding a WlaJ protein, wherein said WlaJ protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 46. In some embodiments, the nucleic acid comprises a nucleic acid sequence encoding a WlaJ protein, wherein said WlaJ protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 46.

gne—In some embodiments, the recombinant bacterium comprises a nucleic acid comprising a gne gene (e.g., a *C. jejuni* gne gene).

In some embodiments, the nucleic acid comprising a gne gene is located on a plasmid in the bacterium. In some embodiments, the nucleic acid comprising a gne gene is located on a chromosome of the bacterium.

The nucleic acid sequence of an exemplary *C. jejuni* gne gene is provided below:

```
                                          (SEQ ID NO: 47)
ATGATGATGAAAATTCTTATTAGCGGTGGTGCAGGTTATATAGGTTCTCA

TACTTTAAGACAATTTTTAAAAACAGATCATGAAATTTGTGTTTTAGATA

ATCTTTCTAAGGGTTCTAAAATCGCAATAGAAGATTTGCAAAAAACAAGA

GCTTTTAAATTTTTCGAACAAGATTTAAGTGATTTTCAAGGCGTAAAAGC

ATTGTTTGAGAGAGAAAAATTTGACGCTATTGTGCATTTTGCAGCAAGCA

TTGAAGTTTTTGAAAGTATGCAAAATCCTTTAAAATATTATATGAACAAC

ACTGTTAATACGACAAATCTCATCGAAACTTGTTTGCAAACTGGAGTGAA

TAAATTTATATTTTCTTCAACGGCGGCCACTTATGGCGAACCACAAACTC

CCGTTGTGAGCGAAACAAGTCCTTTAGCACCTATTAATCCTTATGGGCGT

AGTAAGCTTATGAGTGAAGAAGTTTTGCGTGATGCAAGTATGGCAAATCC

TGAATTTAAGCATTGTATTTTAAGATATTTTAATGTTGCAGGTGCTTGTA

TGGATTATACTTTAGGACAACGCTATCCAAAAGCGACTTTGCTTATAAAA

GTTGCAGCTGAATGTGCCGCAGGAAAACGTGATAAACTTTTCATATTTGG

CGATGATTATGATACAAAAGATGGTACTTGCATAAGAGATTTTATCCATG

TAGATGATATTTCAAGTGCACATTTAGCGGCTTTGGATTATTTAAAAGAG

AATGAAAGCAATGTTTTTAATGTAGGTTATGGACATGGTTTTAGCGTAAA

AGAAGTGATTGAAGCGATGAAAAAAGTTAGCGGAGTGGATTTTAAAGTAG

AACTTGCCCCACGCCGTGCGGGTGATCCTAGTGTATTGATTTCTGATGCA

AGTAAAAATCAGAAATCTTACTTCTTGGCAGCCTAAATATGATGATTTAGA

GCTTATTTGTAAATCTGCTTTTGATTGGGAAAAACAGTGTTAA
```

The amino acid sequence of the Gne protein encoded by the nucleic acid of SEQ ID NO: 47 is provided below:

```
                                          (SEQ ID NO: 48)
MMMKILISGGAGYIGSHTLRQFLKTDHEICVLDNLSKGSKIAIEDLQKTR

AFKFFEQDLSDFQGVKALFEREKFDAIVHFAASIEVFESMQNPLKYYMNN

TVNTTNLIETCLQTGVNKFIFSSTAATYGEPQTPVVSETSPLAPINPYGR

SKLMSEEVLRDASMANPEFKHCILRYFNVAGACMDYTLGQRYPKATLLIK

VAAECAAGKRDKLFIFGDDYDTKDGTCIRDFIHVDDISSAHLAALDYLKE

NESNVFNVGYGHGFSVKEVIEAMKKVSGVDFKVELAPRRAGDPSVLISDA

SKIRNLTSWQPKYDDLELICKSAFDWEKQC.
```

In some embodiments, the nucleic acid comprises a *C. jejuni* gne gene (provided as SEQ ID NO: 47). In some embodiments, the nucleic acid comprises a gne gene, wherein the gne gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 47. In some embodiments, the nucleic acid comprises a gne gene, wherein the gne gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 47.

In some embodiments, the nucleic acid comprises a nucleic acid sequence encoding a Gne protein, wherein said Gne protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 48. In some embodiments, the nucleic acid comprises a nucleic acid sequence encoding a Gne protein, wherein said Gne protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 48.

pglK—In some embodiments, the recombinant bacterium comprises a nucleic acid comprising a pglK gene (e.g., a *C. jejuni* pglK gene).

In some embodiments, the nucleic acid comprising a pglK gene is located on a plasmid in the bacterium. In some embodiments, the nucleic acid comprising a pglK gene is located on a chromosome of the bacterium.

The nucleic acid sequence of an exemplary *C. jejuni* pglK gene is provided below:

```
                                          (SEQ ID NO: 49)
ATGCCTTTTATCACTTTGGCTAGTGATTTTTCTTATTTTGATCGTAATAA

ATATTTAATCMAGCCTAAAAGAATATCTTAATATCCCTGTTTTTGAAATC

ATTGTTTATTTTGGAGTGGGGCTTATTGTTTTTTATGTGTTTAGAGCTTT
```

-continued

```
GTTAAATGCGTATTATTTTCATCTTTTGGCALAGATTTTCTAAAGGGCGT
TATCATGCGATCGCTTATAAGGTTTTTTCTAAATTTTTAAATATTAATTA
TGAAAAATTTACTCAAAAAAATCAATCTGAAATTTTAAAGTCCATTACAG
GGIGAAGTTTATAATCTAAGCACTATGATTTCATCATTTTTACTTTTGAT
GAGTGAAATTTTTGTAGTACTTTTGCTTTATGCTTTAATGCTTTTGATTA
ATTATAAAATCACTTTGTTTTTAVAGTATTTTTATGGTGTTAAATGCCTT
TATTTTAGTGAAAATTTTAAGCCCTATCATTAAAAAAGCAGGAGTAAGAC
GCGAAGAAGCGATGAAAAATTTCTTTGAAATTTTAAATACAAATKTTAAA
TAATTTCAAATTTATTAAGCTTAAAACCAAAGAAGATGGAGTATTAAGTC
TTTTTAAAGCGCAAAGTGAAGCTTTTTCTAAAGCAAATATTACCAACGAA
AGCGTAGCTGCGGTGKCCTAGAATTTATCTTGAAGGAATAGGCTTTTGCG
TACTTGTTTTTATCGTGGTATTTTTGGTTTTGAAAAATGAAAGTGATATT
TCAGGTATTTTATCCACGATTTCTATTTTTGTTTTAVGCGCTTTATCGCT
TAATGCCAAGTGCAAATCGTATTATTACAAGTTATCATGATTTGCTTTAT
TATCATTCTTCTTTGGATATTATTTATCAAAATTTAAGACAAGAAGAAGA
AAATTTGYGGCGAGGAAAAATTAAGCTTTAATCAAGAGCTTAAAATTTGC
AATCTTAGCTTTGGTTATGAGGGAAAAAAATATTTATTTAAAAATCTTAA
CTTAAATATTAAAAAAGGCGAAAAAATCEGCTTTTATAGGGGAGAGTGGT
TGTGGAAAAAGTACCTTAGTAGATCTTATCATAGGACTTTTAAAACCAAA
AGAAGGGCAAATTTTAATTGATGAGCAAGAATTAAATGCAAATAATACAL
AAAAATTATCGCCAAAAAATAGGCTATATCCCGCAAAATATCTATCTTTT
TAATGACAGTATAGCTAAAAATATCACTTTTGGAGATGCGGTTGATGAAG
AAAAACTTAATAGGGTTATCIAAACAAGCAAATTTAGAGCATTTTATAAA
AAATTTACCTCAAGGAGTGCAAACAAAAGTGGGCGATGGGGGAGTAATT
TAAGCGGGGACAAAAACAACGCATAGCTATAGCAAGAGCTGTTATATTT
AGAGCCTGAAATGTTAGTGCTTGATGAAGCAACTTCTGCGCTTGATACTC
AAAGTGAAGCAAAAATTATGGATGAAATTTATAAAATTTCTAAAGATAAA
ACCATGATTATTSATCGCACATCGCCTTTCTACGATAACACAATGTGATA
AGGTTTATCGTTTAGAACACGGTAAGCTTAAAGAGGAGAAATGA
```

The amino acid sequence of the PglK protein encoded by the nucleic acid of SEQ ID NO: 49 is provided below:

```
(SEQ ID NO: 50)
MPFITLASDFSYFDRNKYLISLKEYLNIPVFEIIVYFGVGLIVFYVFRAL
LNAYYFHLLARFSKGRYHAIAYKVFSKFLNINYEKFTQKNQSEILKSITG
EVYNLSTMISSFLLLMSEIFVVLLLYALMLLINYKITLFLSIFMVLNAFI
LVKILSPIIKKAGVRREEAMKNFFEILNTNLNNFKFIKLKTKEDGVLSLF
KAQSEAFSKANITNESVAAVPRIYLEGIGFCVLVFIVVFLVLKNESDISG
ILSTISIFVLALYRLMPSANRIITSYHDLLYYHSSLDIIYQNLRQEEENL
GEEKLSFNQELKICNLSFGYEGKKYLFKNLNLNIKKGEKIAFIGESGCGK
STLVDLIIGLLKPKEGQILIDEQELNANNTKNYRQKIGYIPQNIYLFNDS
IAKNITFGDAVDEEKLNRVIKQANLEHFIKNLPQGVQTKVGDGGSNLSGG
QKQRIAIARALYLEPEMLVLDEATSALDTQSEAKIMDEIYKISKDKTMII
IAHRLSTITQCDKVYRLEHGKLKEEK.
```

In some embodiments, the nucleic acid comprises a *C. jejuni* pglK gene (provided as SEQ ID NO: 49). In some embodiments, the nucleic acid comprises a pglK gene, wherein the pglK gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 49. In some embodiments, the nucleic acid comprises a pglK gene, wherein the pglK gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 49.

In some embodiments, the nucleic acid comprises a nucleic acid sequence encoding a PglK protein, wherein said PglK protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 50. In some embodiments, the nucleic acid comprises a nucleic acid sequence encoding a PglK protein, wherein said PglK protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 50.

pglH—In some embodiments, the recombinant bacterium comprises a nucleic acid comprising a pglH gene (e.g., a *C. jejuni* pglH gene).

In some embodiments, the nucleic acid comprising a pglH gene is located on a plasmid in the bacterium. In some embodiments, the nucleic acid comprising a pglH gene is located on a chromosome of the bacterium.

The nucleic acid sequence of an exemplary *C. jejuni* pglH gene is provided below:

```
(SEQ ID NO: 51)
AAAATAAGCTTTATTATCGCAACTTTAAATTCAGGAGGTGCTGAGCGTGC
TTTAGTAACCTTAGCTAATGCACTTTGCAAAGAGCATGAAGTAAGTATTA
TTAAATTTCATGCAGGAGAATCTTTTTATAAGCTTGAAAATGAAGTTAAA
GTTACAAGTTTGGAACAATTTAGATTTGACACGCTTTATCATAAAATCGC
AAGTCGTTTTAAGAAATTTTTTGCTTTAAGAAAGGCTTTGAAAGAAAGTA
AGTCTGATGTTTTATTTCTTTTTTGGATACGACTAATATTGCTTGTATT
GCTGCGAAAATAGGGCTTAAAACTCCACTCATTATAAGTGAGCATAGCAA
TGAAGCGTATTTAAAACCTAAAATTTGGCGTTTTTTAAGAAGGGTAAGCT
```

-continued
```
ATCCTTTTTGTGATGCTTTAAGTGTGCTTGGAAGCAGTGATAAGGTGTAT

TATGAAAGATTTGTAAAAAGGGTTAAGCTTTTATTAAACCCTTGTCATTT

TAGCGATGAAATTTCTTTTGATTCTAGTTTTGAAAAGGAAAATTTGGTTC

TTTTTATAGGGCGTTTAGATCACAACAAAAACCCTGTAATGTTTTTAAAA

GCTATAGCGCATTTGGATAAAAATTTACAAGAAAATTATAAATTTGTTAT

AGCAGGAGATGGACAGTTAAGACAAGAACTTGAATATAAGGTAAAATCTT

TAGGAATAAAAGTTGATTTTTTAGGACGCGTTGAAAATGTCAAGGCTCTT

TATGAAAAAGCAAAAGTGCTTTGCCTTTGTTCTTTTGTAGAGGGTTTGCC

AACGGTTTTAATTGAAAGTTTGTATTTTGAGGTTTGTAGAATTTCAAGTT

CTTATTATAATGGTGCTAAGGATTTAATCAAAGATAATCATGATGGGCTT

TTGGTAGGTTGTGATGATGAAATAGCACTTGCTAAAAAACTTGAACTTGT

TTTAAATGATGAAAATTTTAGAAAAGAACTTGTAAATAATGCCAAACAAA

GGTGTAAAGACTTTGAAATTTCTCATATCAAAGAAGAATGGCTTAAGCTT

ATAGCCGAGGTT
```

The amino acid sequence of the PglH protein encoded by the nucleic acid of SEQ ID NO: 51 is provided below:

```
                                        (SEQ ID NO: 52)
KISFIIATLNSGGAERALVTLANALCKEHEVSIIKFHAGESFYKLENEVK

VTSLEQFRFDTLYHKIASRFKKFFALRKALKESKSDVFISFLDTTNIACI

AAKIGLKTPLIISEHSNEAYLKPKIWRFLRRVSYPFCDALSVLGSSDKVY

YERFVKRVKLLLNPCHFSDEISFDSSFEKENLVLFIGRLDHNKNPVMFLK

AIAHLDKNLQENYKFVIAGDGQLRQELEYKVKSLGIKVDFLGRVENVKAL

YEKAKVLCLCSFVEGLPTVLIESLYFEVCRISSSYYNGAKDLIKDNHDGL

LVGCDDEIALAKKLELVLNDENFRKELVNNAKQRCKDFEISHIKEEWLKL

IAEV
```

In some embodiments, the nucleic acid comprises a *C. jejuni* pglH gene (provided as SEQ ID NO: 51). In some embodiments, the nucleic acid comprises a pglH gene, wherein the pglH gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 51. In some embodiments, the nucleic acid comprises a pglH gene, wherein the pglH gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 51.

In some embodiments, the nucleic acid comprises a nucleic acid sequence encoding a PglH protein, wherein said PglH protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 52. In some embodiments, the nucleic acid comprises a nucleic acid sequence encoding a PglH protein, wherein said PglH protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 52.

pgII—In some embodiments, the recombinant bacterium comprises a nucleic acid comprising a pgII gene (e.g., a *C. jejuni* pgII gene).

In some embodiments, the nucleic acid comprising a pgII gene is located on a plasmid in the bacterium. In some embodiments, the nucleic acid comprising a pgII gene is located on a chromosome of the bacterium.

The nucleic acid sequence of an exemplary *C. jejuni* pgII gene is provided below:

```
                                        (SEQ ID NO: 53)
ATGCCTAAACTTTCTGTTATAGTACCAACTTTTAATCGTCAAGTTTTGTT

AGAAAAGGCTATTAAAAGCATACAAAATCAAGATTTTAAAGATTTAGAAA

TTATTGTAAGCGATGATAATTCTAGCGATGATACTAAAAGTGTGGTGCAA

AATTTACAAAAGATGATGATCGCATTAAGTATTTTTTAAATCAAAATTA

CAAACAAGGTCCAAATGGCAATAAAAACAATGGCTTAGATCAAGCAAGTG

GCGAGTTTGTAACTTTTTTAGATGATGATGATGAGCTTTTATCCGGGGCT

TTAAGTACCTTGATGCAAAAAGCAAATGAGGGTTATGCTCATGTTTTTGG

AAATTGTTTGATAGAAAAGAAGGAAATTTAAGCAAGGAATTTAGCGGCA

AGGGCTTGGAAAAAGATAGTGAAATTTCTAAAAAAGATTTTTTAATGGCT

AAATTTAGCGGAGAGTTTTTTCTGTTTTTAAAAAATCCCTACTTGAAAA

TAAGCGTTTTAATGAAGAATTTTATGGCAATGAAGCCACGCTTTGGGTAA

ATTTATACAAAGAAAAAGTTTTTATATCCATAAGGCTTTTAGGATTTAT

AGAATTTTTAGGCAAGATAGCGTGACTTTAGGGGCGAGTAAAAATGCTTA

TAGGGTGTATTTGGATATTTAGAGCTTGCTAAAATTTTAGAAAATGAACT

TAGAATGAGTAAGGATAAAGATTATAAAAAAACTTGTGCGAGTTATTATA

AAATGGCAGCTTATTATGCAAAACTTGCAAAAAATTATAAAGCCCTTTAT

AAATGTTTGTTTAAAAGCCTAAGTATAAAAATCAACGCTCCTGCTTTGAT

ATTACTCATTTTAAGTATAATTCCAAATAATATGATTGAAAAATTATCAA

AAATTCGGGTG
```

The amino acid sequence of the PglI protein encoded by the nucleic acid of SEQ ID NO: 53 is provided below:

```
                                        (SEQ ID NO: 54)
MPKLSVIVPTFNRQVLLEKAIKSIQNQDFKDLEIIVSDDNSSDDTKSVVQ

NLQKDDDRIKYFLNQNYKQGPNGNKNNGLDQASGEFVTFLDDDDELLSGA

LSTLMQKANEGYAHVFGNCLIEKEGNLSKEFSGKGLEKDSEISKKDFLMA

KFSGEFFSVFKKSLLENKRFNEEFYGNEATLWVNLYKEKSFYIHKAFRIY

RIFRQDSVTLGASKNAYRVYLGYLELAKILENELRMSKDKDYKKTCASYY
```

KMAAYYAKLAKNYKALYKCLFKSLSIKINAPALILLILSIIPNNMIEKLS

KIRV

In some embodiments, the nucleic acid comprises a *C. jejuni* pgII gene (provided as SEQ ID NO: 53). In some embodiments, the nucleic acid comprises a pgII gene, wherein the pgII gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 53. In some embodiments, the nucleic acid comprises a pgII gene, wherein the pgII gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 53.

In some embodiments, the nucleic acid comprises a nucleic acid sequence encoding a PgII protein, wherein said PgII protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 54. In some embodiments, the nucleic acid comprises a nucleic acid sequence encoding a PgII protein, wherein said PgII protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 54.

pglJ—In some embodiments, the recombinant bacterium comprises a nucleic acid comprising a pglJ gene (e.g., a *C. jejuni* pglJ gene).

In some embodiments, the nucleic acid comprising a pglJ gene is located on a plasmid in the bacterium. In some embodiments, the nucleic acid comprising a pglJ gene is located on a chromosome of the bacterium.

The nucleic acid sequence of an exemplary *C. jejuni* pglJ gene is provided below:

```
(SEQ ID NO: 55)
TTAGGCATTTTTATTTATTCTTTAGGAAGTGGTGGTGCTGAAAGAGTTGT

GGCGACTTTATTGCCTATTTTAAGTTTGAAATTTGAAGTGCATTTGATCT

TGATGAATGATAAAATTTCTTATGAAATTCCAGAGTGTCAAATTCATTTT

TTAGAATGTTCAAAACCTAGTGAAAATCCTATTTTGAAATTTTTAAAACT

ACCTTTTTTGGCTTTAAAATACAAAAAACTTTGCAGAAATTTAGGTATTG

ATACAGAATTTGTTTTTTAAATCGACCTAATTATATAGCTTTAATGGCA

AGAATGTTTGGAAACAAAACTCGCCTTGTGATCAATGAATGCACTACGCC

AAGTGTGATGTATATGAAAAATAATTTTAATTCTTTGGTAAATAAATTTT

TAATTTCTTTGCTTTACCCAAAAGCTGATTTAATCTTGCCTAATTCTAAG

GGAAATTTAGAAGATTTAGTGCAAAATTTTAGTATAAGTCCAAAAAAATG

TGAAATTTTATACAATGCCATCGATTTAGAAAACATAGGGCAAAAAGCCC

TTGAAGACATAGCTTTAAAAGATAAATTTATTTTAAGTGTAGGCAGGCTT

GATAAAGGTAAAAATCATGCTTTATTAATTCGTGCTTATGCGAGATTGAA

AACAGATTTAAAGCTTGTGATTTTAGGTGAAGGTGTGCTTAAGGATGAGC

TTTTAGCTTTGATTAAAGAATTAAATTTGGAAGAAAAGGTTTTGCTTTTA

GGATTTGATAATAATCCTTATAAATACATGGCTAAATGCGAATTTTTTGC

TTTTGCTTCTGTGTTTGAAGGTTTTTCAAATGTTTTAATCGAAAGTTTGG

CTTGTTCTTGTGCGGTGGTTTGCACTGATCATAAAAGTGGTGCAAGAGAG

CTTTTTGGCGATGATGAATTTGGACTTTTAGTAGAAGTAGATAATGAAAA

CTCTATGTTTCAGGGTTTAAAAACTATGCTTGAAGACGATAAATTAAGAA

AAGCGTATAAAAACAAAGCTAAAACTAGGGCTAAAGCCTTTGATAAAGTA

AAAATTGCACGCGATGCTTTGAAATATTTATTAGGATAA
```

The amino acid sequence of the PglJ protein encoded by the nucleic acid of SEQ ID NO: 55 is provided below:

```
(SEQ ID NO: 56)
LGIFIYSLGSGGAERVVATLLPILSLKFEVHLILMNDKISYEIPECQIHF

LECSKPSENPILKFLKLPFLALKYKKLCRNLGIDTEFVFLNRPNYIALMA

RMFGNKTRLVINECTTPSVMYMKNNFNSLVNKFLISLLYPKADLILPNSK

GNLEDLVQNFSISPKKCEILYNAIDLENIGQKALEDIALKDKFILSVGRL

DKGKNHALLIRAYARLKTDLKLVILGEGVLKDELLALIKELNLEEKVLLL

GFDNNPYKYMAKCEFFAFASVFEGFSNVLIESLACSCAVVCTDHKSGARE

LFGDDEFGLLVEVDNENSMFQGLKTMLEDDKLRKAYKNKAKTRAKAFDKV

KIARDALKYLLG
```

In some embodiments, the nucleic acid comprises a *C. jejuni* pglJ gene (provided as SEQ ID NO: 55). In some embodiments, the nucleic acid comprises a pglJ gene, wherein the pglJ gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 55. In some embodiments, the nucleic acid comprises a pglJ gene, wherein the pglJ gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 55.

In some embodiments, the nucleic acid comprises a nucleic acid sequence encoding a PglJ protein, wherein said PglJ protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 56. In some embodiments, the nucleic acid comprises a nucleic acid sequence encoding a PglJ protein, wherein said PglJ protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 56.

pglB—In some embodiments, the recombinant bacterium comprises a nucleic acid comprising a pglB gene (e.g., a *C. jejuni* pglB gene).

In some embodiments, the nucleic acid comprising a pglB gene is located on a plasmid in the bacterium. In some embodiments, the nucleic acid comprising a pglB gene is located on a chromosome of the bacterium.

The nucleic acid sequence of an exemplary *C. jejuni* pglB gene is provided below:

```
                                        (SEQ ID NO: 57)
ATGTTGAAAAAGAGTATTTAAAAAACCCTTATTTAGTTTTGTTTGCGAT

GATTGTATTAGCTTATGTTTTTAGTGTATTTTGCAGGTTTTATTGGGTTT

GGTGGGCAAGTGAGTTTAACGAGTATTTTTTCAATAATCAATTAATGATC

ATTTCAAACGATGGCTATGCTTTTGCTGAGGGCGAAGAGATATGATAGC

AGGTTTTCATCAGCCTAATGATTTGAGTTATTATGGATCTTCTTTATCTA

CGCTTACTTATTGGCTTTATAAAATCACACCTTTTTCTTTTGAAAGTATC

ATTTTATATATGAGTACTTTTTTATCTTCTTTGGTGGTGATTCCTATTAT

TTTACTAGCTAATGAATACAAACGCCCTTTAATGGGCTTTGTAGCTGCTC

TTTTAGCAAGTGTAGCAAACAGTTATTATAATCGCACTATGAGTGGGTAT

TATGATACGGATATGCTGGTAATTGTTTTACCTATGTTTATTTTATTTTT

TATGGTAAGAATGATTTTAAAAAAAGACTTTTTTTCATTGATTGCCTTGC

CATTATTTATAGGAATTTATCTTTGGTGGTATCCTTCAAGTTATACTTTA

AATGTAGCTTTAATTGGACTTTTTTTAATTTATACACTTATTTTTCATAG

AAAAGAAAAGATTTTTTATATAGCTGTGATTTTGTCTTCTCTTACTCTTT

CAAATATAGCATGGTTTTATCAAAGTGCCATTATAGTAATACTTTTTGCT

TTATTTGCTTTAGAGCAAAAACGCTTAAATTTTATGATTATAGGAATTTT

AGGTAGTGCAACTTTGATATTTTTGATTTTAAGTGGTGGGGTTGATCCCA

TACTTTATCAGCTTAAATTTTATATTTTTAGAAGCGATGAAAGTGCGAAT

TTAACACAGGGCTTTATGTATTTTAATGTTAATCAAACCATACAAGAAGT

TGAAAATGTAGATTTTAGCGAATTTATGCGAAGAATTAGTGGTAGTGAAA

TTGTTTTCTTGTTTTCTTTGTTTGGTTTTGTATGGCTTTTGAGAAAACAT

AAAAGTATGATTATGGCTTTACCTATATTGGTGCTTGGGTTTTTAGCCTT

AAAAGGAGGACTTAGATTTACCATTTATTCTGTACCTGTAATGGCTTTAG

GATTTGGTTTTTTATTGAGCGAGTTTAAGGCTATATTGGTTAAAAAATAT

AGCCAATTAACTTCAAATGTTTGTATTGTTTTTGCAACTATTTTGACTTT

GGCTCCAGTATTTATCCATATTTACAACTATAAAGCGCCAACAGTTTTTT

CTCAAAATGAAGCATCATTATTAAATCAATTAAAAAATATAGCCAATAGA

GAAGATTATGTGGTAACTTGGTGGGATTATGGTTATCCTGTGCGTTATTA

TAGCGATGTGAAAACTTTAGTAGATGGTGGAAAGCATTTAGGTAAGGATA

ATTTTTTCCCTTCTTTTTCTTTAAGTAAAGATGAACAAGCTGCAGCTAAT

ATGGCAAGACTTAGTGTAGAATATACAGAAAAAAGCTTTTATGCTCCGCA

AAATGATATTTTAAAATCAGACATTTTACAAGCCATGATGAAAGATTATA

ATCAAAGCAATGTGGATTTATTTCTAGCTTCATTATCAAAACCTGATTTT

AAAATCGATACACCAAAAACTCGTGATATTTATCTTTATATGCCCGCTAG

AATGTCTTTGATTTTTTCTACGGTGGCTAGTTTTTCTTTTATTAATTTAG

ATACAGGAGTTTTGGATAAACCTTTTACCTTTAGCACAGCTTATCCACTT

GATGTTAAAAATGGAGAAATTTATCTTAGCAACGGAGTGGTTTTAAGCGA

TGATTTTAGAAGTTTTAAAATAGGTGATAATGTGGTTTCTGTAAATAGTA

TCGTAGAGATTAATTCTATTAAACAAGGTGAATACAAAATCACTCCAATC

GATGATAAGGCTCAGTTTTATATTTTTATTTAAAGGATAGTGCTATTCC

TTACGCACAATTTATTTTAATGGATAAAACCATGTTTAATAGTGCTTATG

TGCAAATGTTTTTTTTGGGAAATTATGATAAGAATTTATTTGACTTGGTG

ATTAATTCTAGAGATGCTAAAGTTTTTAAACTTAAAATTTAA
```

The amino acid sequence of the PglB protein encoded by the nucleic acid of SEQ ID NO: 57 is provided below:

```
                                        (SEQ ID NO: 58)
MLKKEYLKNPYLVLFAMIVLAYVFSVFCRFYWVWWASEFNEYFFNNQLMI

ISNDGYAFAEGARDMIAGFHQPNDLSYYGSSLSTLTYWLYKITPFSFESI

ILYMSTFLSSLVVIPIILLANEYKRPLMGFVAALLASVANSYYNRTMSGY

YDTDMLVIVLPMFILFFMVRMILKKDFFSLIALPLFIGIYLWWYPSSYTL

NVALIGLFLIYTLIFHRKEKIFYIAVILSSLTLSNIAWFYQSAIIVILFA

LFALEQKRLNFMIIGILGSATLIFLILSGGVDPILYQLKFYIFRSDESAN

LTQGFMYFNVNQTIQEVENVDFSEFMRRISGSEIVFLFSLFGFVWLLRKH

KSMIMALPILVLGFLALKGGLRFTIYSVPVMALGFGFLLSEFKAILVKKY

SQLTSNVCIVFATILTLAPVFIHIYNYKAPTVFSQNEASLLNQLKNIANR

EDYVVTWWDYGYPVRYYSDVKTLVDGGKHLGKDNFFPSFSLSKDEQAANM

ARLSVEYTEKSFYAPQNDILKSDILQAMMKDYNQSNVDLFLASLSKPDFK

IDTPKTRDIYLYMPARMSLIFSTVASFSFINLDTGVLDKPFTFSTAYPLD

VKNGEIYLSNGVVLSDDFRSFKIGDNVVSVNSIVEINSIKQGEYKITPID

DKAQFYIFYLKDSAIPYAQFILMDKTMFNSAYVQMFFLGNYDKNLFDLVI

NSRDAKVFKLKI
```

In some embodiments, the nucleic acid comprises a *C. jejuni* pglB gene (provided as SEQ ID NO: 57). In some embodiments, the nucleic acid comprises a pglB gene, wherein the pglB gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 57. In some embodiments, the nucleic acid comprises a pglB gene, wherein the pglB gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 57.

In some embodiments, the nucleic acid comprises a nucleic acid sequence encoding a PglB protein, wherein said PglB protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 58. In some embodiments, the nucleic acid comprises a nucleic acid sequence encoding a PglB protein, wherein said PglB protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 58.

pglA—In some embodiments, the recombinant bacterium comprises a nucleic acid comprising a pglA gene (e.g., a *C. jejuni* pglA gene).

In some embodiments, the nucleic acid comprising a pglA gene is located on a plasmid in the bacterium. In some embodiments, the nucleic acid comprising a pglA gene is located on a chromosome of the bacterium.

The nucleic acid sequence of an exemplary *C. jejuni* pglA gene is provided below:

```
(SEQ ID NO: 59)
ATGAGAATAGGATTTTTATCACATGCAGGAGCGAGTATTTATCATTTTAG

AATGCCTATTATAAAAGCGTTAAAAGATAGAAAAGACGAAGTTTTTGTTA

TAGTGCCGCAAGATGAATACACGCAAAAACTTAGAGATCTTGGCTTAAAA

GTAATTGTTTATGAGTTTTCAAGAGCTAGTTTAAATCCTTTTGTGGTTTT

AAAGAATTTTTTTTATCTTGCTAAGGTTTTGAAAAATTTAAATCTTGATT

TTATTCAAAGTGCGGCACACAAAAGCAATACTTTTGGAATTTTAGCAGCA

AAATGGGCAAAAATTCCTTATCGTTTTGCCTTAGTAGAAGGCTTGGGATC

TTTTTATATAGATCAAGGTTTTAAGGCAAATTTAGTGCGTTTTGTTATTA

ATAGTCTTTATAAATTAAGTTTTAAATTTGCACACCAATTTATTTTTGTC

AATGAAAGTAATGCTGAGTTTATGCGGAATTTAGGACTTAAAGAAAATAA

AATTTGCGTGATAAAATCTGTAGGGATCAATTTAAAAAAATTTTTTCCTA

TTTATGTAGAATCGGAAAAAAAAGAGCTTTTTTGGAAAAATTTAAACATA

GATAAAAAACCCATTGTGCTTATGATAGCAAGAGCTTTATGGCATAAGGG

TGTAAAAGAATTTTATGAAAGTGCTACTATGCTAAAAGACAAAGCAAATT

TTGTTTTAGTTGGTGGAAGAGATGAAAATCCTTCTTGTGCAAGTTTGGAG

TTTTTAAACTCTGGCGCGGTGCATTATTTGGGTGCTAGAAGTGATATAGT

CGAGCTTTTGCAAAATTGTGATATTTTTGTTTTGCCAAGCTATAAAGAAG

GCTTTCCTGTAAGTGTTTTGGAGGCAAAAGCTTGCGGTAAGGCTATAGTG

GTGAGTGATTGTGAAGGTTGTGTGGAGGCTATTTCTAATGCTTATGATGG
```

-continued
```
ACTTTGGGCAAAAACAAAAAATGCTAAAGATTTAAGCGAAAAAATTTCAC

TTTTATTAGAAGATGAAAAATTAAGATTAAATTTAGCTAAAAATGCCGCC

CAAGATGCTTTACAATACGATGAAAATATAATCGCACAGCGTTATTTAAA

ACTTTATGATAGGGTAATTAAGAATGTA
```

The amino acid sequence of the PglA protein encoded by the nucleic acid of SEQ ID NO: 59 is provided below:

```
(SEQ ID NO: 60)
MRIGFLSHAGASIYHFRMPIIKALKDRKDEVFVIVPQDEYTQKLRDLGLK

VIVYEFSRASLNPFVVLKNFFYLAKVLKNLNLDFIQSAAHKSNTFGILAA

KWAKIPYRFALVEGLGSFYIDQGFKANLVRFVINSLYKLSFKFAHQFIFV

NESNAEFMRNLGLKENKICVIKSVGINLKKFFPIYVESEKKELFWKNLNI

DKKPIVLMIARALWHKGVKEFYESATMLKDKANFVLVGGRDENPSCASLE

FLNSGAVHYLGARSDIVELLQNCDIFVLPSYKEGFPVSVLEAKACGKAIV

VSDCEGCVEAISNAYDGLWAKTKNAKDLSEKISLLLEDEKLRLNLAKNAA

QDALQYDENIIAQRYLKLYDRVIKNV
```

In some embodiments, the nucleic acid comprises a *C. jejuni* pglA gene (provided as SEQ ID NO: 59). In some embodiments, the nucleic acid comprises a pglA gene, wherein the pglA gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 59. In some embodiments, the nucleic acid comprises a pglA gene, wherein the pglA gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 59.

In some embodiments, the nucleic acid comprises a nucleic acid sequence encoding a PglA protein, wherein said PglA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 60. In some embodiments, the nucleic acid comprises a nucleic acid sequence encoding a PglA protein, wherein said PglA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 60.

pglC—In some embodiments, the recombinant bacterium comprises a nucleic acid comprising a pglC gene (e.g., a *C. jejuni* pglC gene).

In some embodiments, the nucleic acid comprising a pglC gene is located on a plasmid in the bacterium. In some embodiments, the nucleic acid comprising a pglC gene is located on a chromosome of the bacterium.

The nucleic acid sequence of an exemplary *C. jejuni* pglC gene is provided below:

```
                                        (SEQ ID NO: 61)
GAAAAAGTTTTTAAAAGAATTTTTGATTTTATTTTATCTTTAGTGCTTTT

AGTGCTTTTTTCTCCGGTGATTTTAATCACTGCTTTACTTTTAAAAATCA

CTCAAGGAAGTGTGATTTTTACCCAAAATCGTCCCGGGTTAGATGAAAAA

ATTTTTAAAATTTATAAATTTAAAACCATGAGCGATGAAAGAGATGAAAA

GGGTGAGTTATTAAGCGATGAATTGCGTTTGAAAGCTTTTGGAAAAATCG

TTAGAAGCTTAAGTTTGGATGAGCTTTTGCAACTTTTTAATGTTTTAAAA

GGGGATATGAGTTTTGTTGGACCTAGACCTCTTTTGGTTGAGTATTTGCC

TCTTTACAATAAAGAGCAAAAATTGCGTCATAAAGTGCGTCCAGGTATAA

CAGGATGGGCGCAGGTAAATGGTAGAAATGCTATTTCTTGGCAGAAAAAA

TTCGAACTTGATGTGTATTATGTGAAAAATATTTCTTTTTTGCTTGATTT

AAAAATCATGTTTTTAACAGCTTTAAAGGTTTTAAAACGAAGTGGGGTAA

GCAAAGAAGGCCATGTTACAACAGAGAAATTTAATGGCAAGAACTGA
```

The amino acid sequence of the PglC protein encoded by the nucleic acid of SEQ ID NO: 61 is provided below:

```
                                        (SEQ ID NO: 62)
EKVFKRIFDFILSLVLLVLFSPVILITALLLKITQGSVIFTQNRPGLDEK

IFKIYKFKTMSDERDEKGELLSDELRLKAFGKIVRSLSLDELLQLFNVLK

GDMSFVGPRPLLVEYLPLYNKEQKLRHKVRPGITGWAQVNGRNAISWQKK

FELDVYYVKNISFLLDLKIMFLTALKVLKRSGVSKEGHVTTEKFNGKN
```

In some embodiments, the nucleic acid comprises a *C. jejuni* pglC gene (provided as SEQ ID NO: 61). In some embodiments, the nucleic acid comprises a pglC gene, wherein the pglC gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO:61. In some embodiments, the nucleic acid comprises a pglC gene, wherein the pglC gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 61. In some embodiments, the nucleic acid comprises a nucleic acid sequence encoding a PglC protein, wherein said PglC protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 62. In some embodiments, the nucleic acid comprises a nucleic acid sequence encoding a PglC protein, wherein said PglC protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 62.

pglD—In some embodiments, the recombinant bacterium comprises a nucleic acid comprising a pglD gene (e.g., a *C. jejuni* pglD gene).

In some embodiments, the nucleic acid comprising a pglD gene is located on a plasmid in the bacterium. In some embodiments, the nucleic acid comprising a pglD gene is located on a chromosome of the bacterium.

The nucleic acid sequence of an exemplary *C. jejuni* pglD gene is provided below:

```
                                        (SEQ ID NO: 63)
ATGGCAAGAACTGAAAAAATTTATATTTATGGTGCTAGTGGTCATGGGCT

TGTTTGTGAAGATGTGGCTAAAAATATGGGTTATAAAGAATGTATTTTTT

TAGATGATTTTAAAGGAATGAAATTTGAAAGTACCTTACCTAAATATGAT

TTTTTTATAGCCATAGGAAACAATGAAATTCGAAAAAAGATTTATCAAAA

AATTTCAGAAAATGGCTTTAAAATTGTCAATCTTATCCATAAAAGCGCGC

TTATAAGTCCTAGCGCAATCGTGGAAGAAAATGCAGGAATTTTAATCATG

CCTTATGTAGTGATTAACGCTAAAGCTAAAATAGAAAAAGGTGTGATTTT

AAATACTTCAAGCGTAATTGAGCATGAATGTGTGATAGGGGAATTTTCTC

ATGTGAGTGTGGGAGCTAAATGTGCGGGTAATGTAAAAATTGGTAAAAAT

TGTTTTTTAGGGATTAATTCTTGTGTTTTGCCTAATTTAAGTTTGGCAGA

TGATAGTATTTTAGGTGGTGGAGCAACTTTAGTTAAAAATCAAGATGAAA

AAGGTGTTTTTGTGGGAGTACCTGCAAAAAGGATGTAA
```

The amino acid sequence of the PglD protein encoded by the nucleic acid of SEQ ID NO: 63 is provided below:

```
                                        (SEQ ID NO: 64)
MARTEKIYIYGASGHGLVCEDVAKNMGYKECIFLDDFKGMKFESTLPKYD

FFIAIGNNEIRKKIYQKISENGFKIVNLIHKSALISPSAIVEENAGILIM

PYVVINAKAKIEKGVILNTSSVIEHECVIGEFSHVSVGAKCAGNVKIGKN

CFLGINSCVLPNLSLADDSILGGGATLVKNQDEKGVFVGVPAKRM
```

In some embodiments, the nucleic acid comprises a *C. jejuni* pglD gene (provided as SEQ ID NO: 63). In some embodiments, the nucleic acid comprises a pglD gene, wherein the pglD gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 63. In some embodiments, the nucleic acid comprises a pglD gene, wherein the pglD gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 63.

In some embodiments, the nucleic acid comprises a nucleic acid sequence encoding a PglD protein, wherein said PglD protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 64. In some embodiments, the nucleic acid comprises a nucleic acid sequence encoding a PglD protein, wherein said PglD protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 64.

pglE—In some embodiments, the recombinant bacterium comprises a nucleic acid comprising a pglE gene (e.g., a *C. jejuni* pglE gene).

In some embodiments, the nucleic acid comprising a pglE gene is located on a plasmid in the bacterium. In some embodiments, the nucleic acid comprising a pglE gene is located on a chromosome of the bacterium.

The nucleic acid sequence of an exemplary *C. jejuni* pglE gene is provided below:

(SEQ ID NO: 65)
ATGAGATTTTTTCTTTCTCCTCCGCATATGGGTGGTAATGAATTAAAATA

CATAGAAGAAGTTTTCAAAAGCAATTATATAGCACCTTTGGGTGAATTTG

TAAATCGCTTTGAACAAAGTGTCAAGGCTTACAGTAAAAGTGAAAATGCC

TTAGCTTTAAATTCAGCCACAGCGGCTTTGCATTTAGCTTTAAGGGTGGC

AGGGGTAAAACAAGATGATATTGTTTTGGCTTCTTCTTTTACTTTTATCG

CTTCAGTAGCACCTATTTGTTATCTTAAAGCAAAACCTGTATTTATAGAT

TGTGATGAAACTTATAATATCGATGTAGATTTATTAAAGCTTGCTATTAA

AGAATGTGAAAAAAACCAAAAGCATTGATTTTAACTCATCTTTATGGCA

ATGCGGCTAAAATGGATGAAATTGTTGAAATTTGCAAAGAAAATGAAATT

GTTTTAATCGAAGATGCTGCTGAAGCTTTAGGAAGTTTTTATAAGAATAA

AGCTTTAGGAACTTTTGGAGAATTTGGAGCTTATTCTTATAATGGCAATA

AAATTATCACCACTTCAGGTGGAGGTATGCTTATAGGAAAAAATAAAGAA

AAGATTGAAAAAGCAAGATTTTATAGCACTCAAGCTAGGGAAAATTGTTT

GCATTATGAACATTTAGATTATGGTTATAATTACCGCTTAAGCAATGTTT

TAGGAGCTATTGGCGTAGCGCAAATGGAGGTTTTAGAACAAAGAGTGCTT

AAAAAAAGAGAAATTTATGAGTGGTATAAAGAATTTTTAGGAGAGTGTTT

TAGCTTTTTAGATGAATTAGAAATTCAAGAAGCAATCGCTGGTTAAGTA

CAGCTTTGATTGATTTTGATAAAAATGAACTTAATTCTTGTCAAAAAGAT

ATAAATATCAGTCAAAAAAATATTACTTTGCATCCAAAAATTTCAAAACT

CATAGAAGATTTGAAAAATGAACAAATAGAAACAAGACCATTATGGAAAG

CTATGCACGCTCAAGAAGTATTTAAAGGAGCTAAGGCTTATCTTAATGGC

AATAGTGAGTTATTTTTCCAAAAAGGAATTTGTTTGCCAAGTGGCACGGC

-continued
GATGAGTAAAGATGATGTTTATGAAATTTCAAAACTGATCTTAAAGAGCA

TAAAGGCTTAA

The amino acid sequence of the PglE protein encoded by the nucleic acid of SEQ ID NO: 65 is provided below:

(SEQ ID NO: 66)
MRFFLSPPHMGGNELKYIEEVFKSNYIAPLGEFVNRFEQSVKAYSKSENA

LALNSATAALHLALRVAGVKQDDIVLASSFTFIASVAPICYLKAKPVFID

CDETYNIDVDLLKLAIKECEKKPKALILTHLYGNAAKMDEIVEICKENEI

VLIEDAAEALGSFYKNKALGTFGEFGAYSYNGNKIITTSGGGMLIGKNKE

KIEKARFYSTQARENCLHYEHLDYGYNYRLSNVLGAIGVAQMEVLEQRVL

KKREIYEWYKEFLGECFSFLDELENSRSNRWLSTALIDFDKNELNSCQKD

INISQKNITLHPKISKLIEDLKNEQIETRPLWKAMHAQEVFKGAKAYLNG

NSELFFQKGICLPSGTAMSKDDVYEISKLILKSIKA

In some embodiments, the nucleic acid comprises a *C. jejuni* pglE gene (provided as SEQ ID NO: 65). In some embodiments, the nucleic acid comprises a pglE gene, wherein the pglE gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 65. In some embodiments, the nucleic acid comprises a pglE gene, wherein the pglE gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 65.

In some embodiments, the nucleic acid comprises a nucleic acid sequence encoding a PglE protein, wherein said PglE protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 66. In some embodiments, the nucleic acid comprises a nucleic acid sequence encoding a PglE protein, wherein said PglE protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 66.

pglF—In some embodiments, the recombinant bacterium comprises a nucleic acid comprising a pglF gene (e.g., a *C. jejuni* pglF gene).

In some embodiments, the nucleic acid comprising a pglF gene is located on a plasmid in the bacterium. In some embodiments, the nucleic acid comprising a pglF gene is located on a chromosome of the bacterium.

The nucleic acid sequence of an exemplary *C. jejuni* pglF gene is provided below:

(SEQ ID NO: 67)
```
ATGATTTTTTATAAAAGCAAAAGATTAGCATTTTTTTTAACTTCAGATAT
TGTTTTAATTTTACTTAGCGTTTATCTGGCTTTTTCTTTGAGATTTAGTG
GAGATATTCCGAGTATTTTTTATCATGGTATGATGGTTTCTGCTATTATT
TTGCTTGTTTTAAAACTTTCATTTTTGTTTGTTTTTAGAATTTATAAAGT
AGCTTGGAGATTTTTTCTCTCAATGAAGCAAGAAAGATTTTTATCGCTT
TGCTTTTAGCTGAGTTTTGTTTTTTCTTATTTTTTATTTTTTAGTGAT
TTTTTTAATCCTTTTCCAAGAAGTGCTATTGTGATAGATTTTGTTCTTTC
TTATATGTTTATAGGTACTTTAAGAATTAGCAAAAGAATGCTTGTGGATT
TTAAACCTTCTAGAATGAAAGAAGAAGAAACTCCTTGTATTGTAGTAGGG
GCAACTTCTAAGGCTTTGCATTTGTTAAAAGGTGCAAAAGAAGGTTCTTT
AGGGCTTTTTCCTGTAGGCGTAGTTGATGCGAGAAAAGAGCTTATAGGGA
CTTATTGTGATAAATTTATTGTAGAAGAAAAAGAAAAAATAAAATCTTAT
GTAGAACAAGGGGTAAAAACTGCCATTATTGCTTTAAGACTTGAACAAGA
AGAGCTTAAAAAACTTTTTGAAGAACTTGTAGCTTATGGTATTTGCGATG
TAAAAATATTTTCTTTTACAAGAAACGAAGCAAGAGATATCAGTATAGAA
GACTTGCTTGCTAGAAAACCAAAAGATTTAGATGATAGTGCTGTGGCGGC
TTTTTTAAAAGATAAGGTAGTTTTGGTAAGTGGAGCAGGTGGAACTATAG
GCAGTGAACTTTGTAAGCAATGTATTAAATTTGGTGCTAAGCATCTTATC
ATGGTTGATCATAGTGAGTATAATCTTTATAAGATCAATGATGATTTAAA
TTTATATAAAGAAAAAATTACTCCTATTTTACTGAGTATTTTAGATAAGC
AAAGTTTAGATGAGGTATTAAAAACTTATAAACCCGAGCTTATTTTACAT
GCAGCCGCTTATAAACATGTGCCTCTTTGCGAACAAAATCCACATTCAGC
AGTAATCAATAATATTTTAGGAACTAAAATTTTATGCGACAGTGCTAAAG
AAAACAAAGTAGCTAAATTTGTGATGATAAGTACAGATAAAGCAGTACGA
CCAACAAATATTATGGGTTGCACTAAGAGAGTTTGCGAGCTTTATACTTT
AAGTATGAGTGATGAAAATTTTGAAGTTGCTTGTGTGCGTTTTGGTAATG
TTTTAGGTTCTAGTGGTAGTGTGATACCGAAATTTAAAGCACAAATTGCC
AATAATGAGCCTTTAACTTTAACGCACCCTGATATAGTGCGTTATTTTAT
GCTTGTGGCTGAGGCAGTGCAACTTGTTTTACAAGCTGGAGCTATCGCAA
AAGGGGGAGAACTTTTTGTTTTGGATATGGGTAAGCCTGTGAAAATCATA
GATTTAGCTAAAAAAATGCTTTTACTTTCTAATCGCAATGATTTAGAAAT
TAAAATCACAGGCTTAAGAAAAGGTGAGAAGCTTTATGAAGAGCTTTTGA
TTGATGAAAATGATGCTAAAACACAATATGAGAGTATTTTTGTAGCAAAG
AATGAGAAGGTTGATCTTGATTGGCTTAATAAAGAGATAGAAAATTTACA
AATATGTGAAGATATTTCAGAGGCTTTATTAAAGATTGTACCTGAATTTA
AACACAATAAAGAAGGTGTA
```

The amino acid sequence of the PglF protein encoded by the nucleic acid of SEQ ID NO: 67 is provided below:

(SEQ ID NO: 68)
```
MIFYKSKRLAFFLTSDIVLILLSVYLAFSLRFSGDIPSIFYHGMMVSAII
LLVLKLSFLFVFRIYKVAWRFFSLNEARKIFIALLLAEFCFFLIFYFFSD
FFNPFPRSAIVIDFVLSYMFIGTLRISKRMLVDFKPSRMKEEETPCIVVG
ATSKALHLLKGAKEGSLGLFPVGVVDARKELIGTYCDKFIVEEKEKIKSY
VEQGVKTAIIALRLEQEELKKLFEELVAYGICDVKIFSFTRNEARDISIE
DLLARKPKDLDDSAVAAFLKDKVVLVSGAGGTIGSELCKQCIKFGAKHLI
MVDHSEYNLYKINDDLNLYKEKITPILLSILDKQSLDEVLKTYKPELILH
AAAYKHVPLCEQNPHSAVINNILGTKILCDSAKENKVAKFVMISTDKAVR
PTNIMGCTKRVCELYTLSMSDENFEVACVRFGNVLGSSGSVIPKFKAQIA
NNEPLTLTHPDIVRYFMLVAEAVQLVLQAGAIAKGGELFVLDMGKPVKII
DLAKKMLLLSNRNDLEIKITGLRKGEKLYEELLIDENDAKTQYESIFVAK
NEKVDLDWLNKEIENLQICEDISEALLKIVPEFKHNKEGV.
```

In some embodiments, the nucleic acid comprises a *C. jejuni* pglF gene (provided as SEQ ID NO: 67). In some embodiments, the nucleic acid comprises a pglF gene, wherein the pglF gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 67. In some embodiments, the nucleic acid comprises a pglF gene, wherein the pglF gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 67.

In some embodiments, the nucleic acid comprises a nucleic acid sequence encoding a PglF protein, wherein said PglF protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:68. In some embodiments, the nucleic acid comprises a nucleic acid sequence encoding a PglF protein, wherein said PglF protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 68.

pglG—In some embodiments, the recombinant bacterium comprises a nucleic acid comprising a pglG gene (e.g., a *C. jejuni* pglG gene).

In some embodiments, the nucleic acid comprising a pglG gene is located on a plasmid in the bacterium. In some embodiments, the nucleic acid comprising an pglG gene is located on a chromosome of the bacterium.

The nucleic acid sequence of an exemplary *C. jejuni* pglG gene is provided below:

(SEQ ID NO: 69)
ATGTATATAAAAGATATACAAAGATTTGAAGATAATCGCTATCGTGCTAG

AGCTTATATGAGTTATATTTTAACAAGAAATCTGCCCAATAAACTTCCTG

ATATTCACCTTGAAACGATTAAAACAGCTTTGGATAAAATAGCTCATGAA

GTTGTTGTTTTTGATGCTTTGTATATTTTAGATATTTCAGGCATGCAAAT

AGAAAATGCGATTTCCTTAAATAAAGCTCATGAAATAGGGCAGGGTGAGG

ATAGAAGTACTCGTTCTTATTTTTATAGAGCTGTAAAATTAAGACGATGT

GTTTTGAGCGATCCTTATCCTTCGGTTTTAAATAATGAGCTTTGCGTGAC

AGCTTCTATGCCAATTTACGATGATAAAAATAACTTGCTTTTTGTTGTTT

GTATTGATATCAAGCTTGAAGATATTTTAAAGATTATTCAAGCAGGAAAA

TTTGAATTTGTTTTTACTCAGTTTAGTCGTTTGGTATATTTTTGCTTCGC

ACTGGTTTTATTTGTGATTACTTGTTTTTTATTTCAAAAAGGTTTTTTA

GTCTTTTTGATAATCAAGCTATAGGTATAGAACATATGTTTGAAAGTACC

ATCGCTATAACTTTGGCTTTAGCTATTTTTGATTGGCAAAAACTTTGAT

CGAACAAGAAGTATTAGGAAGGACGAAAAAAGAAGAAGGTGGAATTCAAA

AAACTATGGTGAGATTTTTGGGTTCTATTATCATTGCTTTAGCTATAGAA

GCTTTGATGTTGGTATTTAAACTTGCTATTGGTGATCTTTCTCAGATGAT

TTATGCGATTTATCTTATCGGTGGAGTGAGCTTGCTTCTTTTAGGTTTAA

GTGTATATTTATTTACGGTTAAGTATAAAAATAATAATATTTGA

The amino acid sequence of the PglG protein encoded by the nucleic acid of SEQ ID NO: 69 is provided below:

(SEQ ID NO: 70)
MYIKDIQRFEDNRYRARAYMSYILTRNLPNKLPDIHLETIKTALDKIAHE

VVVFDALYILDISGMQIENAISLNKAHEIGQGEDRSTRSYFYRAVKLRRC

VLSDPYPSVLNNELCVTASMPIYDDKNNLLFVVCIDIKLEDILKIIQAGK

FEFVFTQFSRLVYFCFALVLFVITCFLFQKGFFSLFDNQAIGIEHMFEST

IAITLALAIFDLAKTLIEQEVLGRTKKEEGGIQKTMVRFLGSIIIALAIE

ALMLVFKLAIGDLSQMIYAIYLIGGVSLLLLGLSVYLFTVKYKNNNI

In some embodiments, the nucleic acid comprises a C. jejuni pglG gene (provided as SEQ ID NO: 69). In some embodiments, the nucleic acid comprises a pglG gene, wherein the pglG gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 69. In some embodiments, the nucleic acid comprises a pglG gene, wherein the pglG gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 69.

In some embodiments, the nucleic acid comprises a nucleic acid sequence encoding a PglG protein, wherein said PglG protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 70. In some embodiments, the nucleic acid comprises a nucleic acid sequence encoding a PglG protein, wherein said PglG protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 70.

C. Attenuation

In some embodiments, the recombinant bacterium described herein is modified such that the expression of one or more genes can be regulated in a sugar-responsive manner. In some embodiments, one or more endogenous genes, e.g., virulence genes, are deleted from the bacterial chromosome. In some embodiments, the deletion is a partial deletion of the endogenous gene. In some embodiments, the deletion is a full-length deletion of the endogenous gene. In some embodiments, the gene is genetically-altered to prevent transcription and/or translation of the gene encoding the protein. In some embodiments, the endogenous gene is genetically altered to insert a transcriptional terminator in the open reading frame of the gene. In some embodiments, a regulatory region of the gene, e.g., virulence gene, is genetically-modified to alter (e.g., decrease) the expression of the gene. In some embodiments, the promoter of a gene, e.g., virulence gene, is altered to include one or more regulatory elements (e.g., a sugar-responsive promoter).

In some embodiments, the recombinant bacterium described herein is modified to comprise a nucleic acid comprising a gene. In some embodiments, the recombinant bacterium is modified to comprise a nucleic acid comprising a gene, whereby an endogenous copy of the gene in the bacterial chromosome has been altered and/or deleted. In some embodiments, the nucleic acid comprises a gene that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to an endogenous gene in the bacterial chromosome that has been deleted and/or altered. In some embodiments, the nucleic acid comprises a gene that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to an endogenous gene in the bacterial chromosome that has been deleted and/or altered. In some embodiments, the nucleic acid comprises a gene from a bacterial species, subspecies, serovar, or strain that is different than the bacterial species of the recombinant bacterium.

In some embodiments, the nucleic acid comprises a gene from a bacterial species, subspecies, serovar, or strain that is the same as the bacterial species of the recombinant bacterium. In some embodiments, the nucleic acid comprises a gene that is operably-linked to a regulatable promoter (e.g., a sugar-regulatable promoter). In some embodiments, the nucleic acid comprises a gene that is operably-linked to a rhamnose-regulatable promoter, a xylose-regulatable promoter, a galactose-regulatable promoter, an arabinose-regulatable promoter, a rhamnose-regulatable promoter, a mannose-regulatable promoter, or a maltose-regulatable promoter. In some embodiments, the nucleic acid comprising the gene is located in a plasmid in the bacterium. In some embodiments, the nucleic acid comprising the gene is located in the bacterial chromosome. In some embodiments, the nucleic acid comprising the gene is located at the chromosomal locus corresponding to the locus of an endogenous gene that has been deleted or altered in the bacterial chromosome. In some embodiments, the nucleic acid is codon-optimized (e.g., to improve expression of the nucleic acid in the recombinant bacterium).

GTP Pyrophosphokinase Genes

In some embodiments, the recombinant bacterium comprises a deletion in an endogenous relA gene, which encodes the GTP pyrophosphokinase RelA. The inclusion of a relA deletion in the recombinant bacterium uncouples the occurrence of growth-dependent lysis to the need for continued protein synthesis. In some embodiments, the deletion of the endogenous relA gene is a partial deletion. In some embodiments, the deletion of the endogenous relA gene is a full-length deletion.

Other Attenuation Methods

Other methods of attenuation are known in the art. For instance, attenuation may be accomplished by altering (e.g., deleting) native nucleic acid sequences found in the wild type bacterium. For instance, if the bacterium is *Salmonella*, non-limiting examples of nucleic acid sequences which may be used for attenuation include: a pab nucleic acid sequence, a pur nucleic acid sequence, an aro nucleic acid sequence, asd, a dap nucleic acid sequence, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, flgM, tonB, slyA, and any combination thereof. Exemplary attenuating mutations may be aroA, aroC, aroD, cdt, cya, crp, phoP, phoQ, ompR, galE, and htrA.

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant bacterium to induce disease symptoms.

D. Additional Mutations

In some embodiments, the recombinant bacterium comprises a deletion in an endogenous recF gene, which encodes the DNA replication and repair protein RecF. In some embodiments, the deletion of the endogenous recF gene is a partial deletion. In some embodiments, the deletion of the endogenous recF gene is a full-length deletion. In some embodiments, the endogenous recF gene is genetically altered to insert a transcriptional terminator in the open reading frame of the gene.

In some embodiments, the recombinant bacterium comprises a deletion in an endogenous recJ gene, which encodes the exonuclease RecJ. In some embodiments, the deletion of the endogenous recJ gene is a partial deletion. In some embodiments, the deletion of the endogenous recJ gene is a full-length deletion. In some embodiments, the endogenous recJ gene is genetically altered to insert a transcriptional terminator in the open reading frame of the gene.

The bacterium may also be modified to create a balanced-lethal host-vector system, although other types of systems may also be used (e.g., creating complementation heterozygotes). For the balanced-lethal host-vector system, the bacterium may be modified by manipulating its ability to synthesize various essential constituents needed for synthesis of the rigid peptidoglycan layer of its cell wall. In one example, the constituent is diaminopimelic acid (DAP) (see, for example, U.S. Pat. Nos. 5,672,345; 5,840,482; and 6,872,547, the entire contents of each of which are expressly incorporated herein by reference). Various enzymes are involved in the eventual synthesis of DAP.

In some embodiments, the recombinant bacterium comprises a deletion in an endogenous asd gene. In some embodiments, the deletion of the endogenous asd gene is a partial deletion. In some embodiments, the deletion of the endogenous asd gene is a full-length deletion. In some embodiments, the endogenous asd gene is genetically altered to insert a transcriptional terminator in the open reading frame of the gene. In some embodiments, the promoter of an endogenous asd gene is altered to include one or more regulatory elements (e.g., a sugar-responsive promoter). In one example, the bacterium is modified by using a ΔasdA mutation to eliminate the bacterium's ability to produce β-aspartate semialdehyde dehydrogenase, an enzyme essential for the synthesis of DAP. Other mutations that result in the abolition of the synthesis of DAP include, but are not limited to, dapA, dapB, dapC, dapD, dapE, dapF, and asd (see, e.g., U.S. Pat. No. 6,872,547, incorporated herein by reference). Other modifications that may be employed include modifications to a bacterium's ability to synthesize D-alanine or to synthesize D-glutamic acid (e.g., ΔmurI mutations), which are both unique constituents of the peptidoglycan layer of the bacterial cell wall.

Similarly, various embodiments may comprise the araC $P_{araBAD}$ c2 gene cassette inserted into the asd nucleic acid sequence that encodes aspartate semialdehyde dehydrogenase. Since the araC nucleic acid sequence is transcribed in a direction that could lead to interference in the expression of adjacent nucleic acid sequences and adversely affect vaccine strain performance, a transcription termination (TT) sequence is generally inserted 3' to the araC nucleic acid sequence. The chromosomal asd nucleic acid sequence is typically inactivated to enable use of plasmid vectors encoding the wild-type asd nucleic acid sequence in the balanced lethal host-vector system. This allows for stable maintenance of plasmids in vivo in the absence of any drug resistance attributes that are not permissible in live bacterial vaccines. In some of these embodiments, the wild-type asd nucleic acid sequence may be encoded by the vector described herein. The vector enables the regulated expression of an antigen encoding sequence through the repressible promoter.

Regulated Delayed Lysis In Vivo

In some embodiments, the recombinant bacterium may comprise deletions and/or deletion-insertion mutations to facilitate regulated delayed lysis in vivo that prevents bacterial persistence in vivo and survival if excreted (Table 3). These chromosomal mutations may include: Δ(wza-wcaM), $\Delta P_{murA}$::TT araC $P_{BAD}$ murA, and ΔasdA::TT araC $P_{BAD}$ c2. Δ(wza-wcaM) eliminates twenty enzymes needed to synthesize several exopolysaccharides that promote biofilm formation and for synthesis of GDP-fucose that is required for colonic acid synthesis 9194), which can protect cells from undergoing cell wall-less death from lysing (195). $\Delta P_{murA}$::TT araC $P_{BAD}$ murA, makes synthesis of MurA, the first enzyme in the synthesis of muramic acid, dependent on presence of arabinose in growth medium and ceases to be synthesized in vivo due to the absence of arabinose (142) (118). MurA decreases as a consequence of cell division in vivo to ultimately lead to cell lysis and death (166) (191). The murA defect is complemented by MurA$^+$ plasmid vectors (142) (118). With respect to the ΔasdA::TT araC P_{BAD} c2 mutations, the Asd enzyme is essential for the synthesis of diaminopimelic acid required for peptidoglycan synthesis (167) (192). The arabinose-dependent synthesis of the C2 repressor is to enable a regulated delayed expression of DNA sequences under the control of a promoter repressed by C2 (142) (118). The ΔasdA mutation is complemented by Asd⁺ plasmid vectors (157) (193).

The latter two mutations are typically complemented by a regulated delayed lysis plasmid vector that has an arabinose-dependent expression of asdA and murA genes. A recombinant bacterium comprising such mutations grows normally in the presence of arabinose. In vivo, however, the bacterium ceases to express any nucleic acids encoding the Asd and MurA enzymes, such that synthesis of the peptidoglycan cell wall layer ceases, ultimately resulting in the lysis of the bacterium. This lysis may result in the release of a bolus of antigen specific for an enteric pathogen, thereby serving as a means to enhance induction of immunity against that enteric pathogen while conferring biological containment.

Additional methods of delayed lysis are described in, for example, U.S. Pat. No. 9,481,888, the entire contents of which are expressly incorporated herein by reference.

sopB Mutation

To be safe for use as a vaccine, the bacterial enteric pathogen must be attenuated for virulence by deletion or regulated expression of a virulence gene. In the case of *Salmonella*, for instance, an effector molecule secreted by the type 3 secretion system, such as sopB, may be altered to achieve attenuation. The genes may be deleted or a regulatable promoter may be inserted in front of the gene to achieve regulated delayed attenuation. As used herein, "regulated delayed attenuation" refers to the ability of the microbe to colonize a host and then display an attenuation phenotype to avoid actually causing a symptomatic infection.

E. Repressor Regulatory Systems

In some embodiments, the recombinant bacterium comprises a nucleic acid (e.g., a gene) that is operably linked to a repressor-regulatable promoter to facilitate the regulatable expression of the gene. Thus, in some embodiments, the recombinant bacterium comprises a nucleic acid comprising a gene encoding a repressor. In some embodiments, the gene encoding the repressor is operably-linked to a regulatable promoter. Methods of chromosomally integrating a nucleic acid sequence encoding a repressor operably-linked to a regulatable promoter are known in the art and detailed in the examples. In some embodiments, the nucleic acid sequence encoding a repressor is not integrated into a chromosomal locus such that the ability of the bacterium to colonize a host cell is disrupted. In some embodiments, the recombinant bacterium comprises a nucleic acid encoding a repressor that is integrated into the relA locus of the bacterial chromosome. In some embodiments, the recombinant bacterium comprises a nucleic acid encoding a repressor that is integrated into the endA locus of the bacterial chromosome. In some embodiments, the recombinant bacterium comprises at least one nucleic acid sequence encoding a repressor. In some embodiments, the recombinant bacterium comprises at least two, at least three, at least four, at least five, at least six or more nucleic acids encoding a repressor. In some embodiments, the nucleic acid encoding the repressor is present on a plasmid in the bacterium. In some embodiments, the nucleic acid encoding the repressor is located in the bacterial chromosome. If there is more than one nucleic acid sequence encoding a repressor, each nucleic acid sequence encoding a repressor may be operably linked to a regulatable promoter, such that each promoter is regulated by the same compound or condition. Alternatively, each nucleic acid sequence encoding a repressor may be operably linked to a regulatable promoter, each of which is regulated by a different compound or condition.

As used herein, a "repressor" refers to a biomolecule that represses the transcriptional activity of a promoter. In some embodiments, the repressor is synthesized by the recombinant bacterium in high enough quantities during in vitro culture, such that the transcription of a nucleic acid that is operably linked to a repressor-regulatable promoter is repressed. This may be particularly advantageous if, for example, expression of the product encoded by said nucleic acid impedes the in vitro growth of the bacterium, and/or the ability of the bacterium to infect and/or colonize a subject. In some embodiments, the nucleic acid that is operably-linked to the repressor-regulatable promoter expresses an antigen of interest. In some embodiments, the concentration of the repressor within the cell gradually decreases with each cell division cycle after transcription of the gene encoding the repressor decreases or ceases (e.g., in vivo). The use of a particular repressor, as described herein, may depend, in part, on the species, subspecies, strain or serovar of the recombinant bacterium being used. In some embodiments, the repressor is derived from the same species (e.g., the same bacterial species or the same phage) from which the repressor-regulatable promoter is derived. In some embodiments the repressor is not derived from the same bacterial species as the bacterial species in which the repressor is expressed. For example, in some embodiments, the repressor is derived from *E. coli* if the recombinant bacterium is of the genus *Salmonella*. Other suitable repressors include repressors derived from a bacteriophage.

A nucleic acid sequence encoding a repressor and regulatable promoter detailed above may be modified so as to optimize the expression level of the nucleic acid sequence encoding the repressor. The optimal level of expression of the nucleic acid sequence encoding the repressor may be estimated, or may be determined by experimentation. Such a determination should take into consideration whether the repressor acts as a monomer, dimer, trimer, tetramer, or higher multiple, and should also take into consideration the copy number of the vector encoding the antigen of interest. In an exemplary embodiment, the level of expression is optimized so that the repressor is synthesized while in a permissive environment (i.e., in vitro growth) at a level that substantially inhibits the expression of the nucleic acid encoding an antigen of interest, and is substantially not synthesized in a non-permissive environment, thereby allowing expression of the nucleic acid encoding an antigen of interest.

In some embodiments, the recombinant bacterium described herein is modified to comprise a nucleic acid comprising a lacI gene, which encodes the LacI repressor protein. The expression of the lacI-encoded repressor in the recombinant bacterium described herein may be used to regulate the expression of an antigen of interest expressed by the bacterium. For example, in some embodiments, the expression of the lacI gene is regulated by a sugar-regulatable promoter (e.g., an arabinose-regulatable promoter). When cultured in the presence of arabinose, the recombinant bacterium will express the LacI repressor protein, which in turn will repress the expression of a gene encoding an antigen of interest that is operably-linked to a LacI-responsive promoter (e.g., $P_{trc}$, $P_{lac}$, $P_{T7lac}$ and $P_{tac}$). Upon administration to the subject and in the absence of a source of arabinose, the synthesis of LacI repressor ceases, leading to de-repression of the LacI-responsive promoter and the subsequence expression of the antigen of interest. The concentration of LacI in the cell decreases by about half at each cell division in vivo, leading to a gradual decreased level of repression and gradual increased synthesis of the antigen of interest.

In some embodiments, the nucleic acid comprising a lacI gene is located on a plasmid in the bacterium. In some embodiments, the nucleic acid comprising a lacI gene is located on a chromosome of the bacterium. In some embodiments, the nucleic acid comprising a lacI gene is located at the chromosomal locus corresponding to the locus of an endogenous a relA gene that has been deleted or altered in the bacterial chromosome. In some embodiments, the recombinant bacterium is modified to comprise a nucleic acid comprising a lacI gene, whereby an endogenous copy of the lacI gene in the bacterial chromosome has been altered and/or deleted.

In some embodiments, the nucleic acid comprises a *Escherichia coli* lacI gene. The nucleic acid sequence of the *E. coli* lacI gene is provided below:

(SEQ ID NO: 78)
gtgaaaccagtaacgttatacgatgtcgcagagtatgccggtgtctctta tcagaccgtttcccgcgtggtgaaccaggccagccacgtttctgcgaaaa cgcgggaaaaagtggaagcggcgatggcggagctgaattacattcccaac cgcgtggcacaacaactggcgggcaaacagtcgttgctgattggcgttgc cacctccagtctggccctgcacgcgccgtcgcaaattgtcgcggcgatta aatctcgcgccgatcaactgggtgccagcgtggtggtgtcgatggtagaa cgaagcggcgtcgaagcctgtaaagcggcggtgcacaatcttctcgcgca acgcgtcagtgggctgatcattaactatccgctggatgaccaggatgcca ttgctgtggaagctgcctgcactaatgttccggcgttatttcttgatgtc tctgaccagacacccatcaacagtattattttctcccatgaagacggtac gcgactgggcgtggagcatctggtcgcattgggtcaccagcaaatcgcgc tgttagcgggcccattaagttctgtctcggcgcgtctgcgtctggctggc tggcataaatatctcactcgcaatcaaattcagccgatagcggaacggga aggcgactggagtgccatgtccggttttcaacaaaccatgcaaatgctga atgagggcatcgttcccactgcgatgctggttgccaacgatcagatggcg ctgggcgcaatgcgcgccattaccgagtccgggctgcgcgttggtgcgga tatctcggtagtgggatacgacgataccgaagacagctcatgttatatcc cgccgttaaccaccatcaaacaggattttcgcctgctggggcaaaccagc gtggaccgcttgctgcaactctctcagggccaggcggtgaagggcaatca gctgttgcccgtctcactggtgaaagaaaaaccaccctggcgcccaata cgcaaaccgcctctccccgcgcgttggccgattcattaatgcagctggca cgacaggtttcccgactggaaagcgggcagtga The amino acid sequence of the *E. coli* LacI protein encoded by the nucleic acid of SEQ ID NO:78 is provided below:

(SEQ ID NO: 79)
MKPVTLYDVAEYAGVSYQTVSRVVNQASHVSAKTREKVEAAMAELNYIPN

RVAQQLAGKQSLLIGVATSSLALHAPSQIVAAIKSRADQLGASVVVSMVE

RSGVEACKAAVHNLLAQRVSGLIINYPLDDQDAIAVEAACTNVPALFLDV

SDQTPINSIIFSHEDGTRLGVEHLVALGHQQIALLAGPLSSVSARLRLAG

WHKYLTRNQIQPIAEREGDWSAMSGFQQTMQMLNEGIVPTAMLVANDQMA

LGAMRAITESGLRVGADISVVGYDDTEDSSCYIPPLTTIKQDFRLLGQTS

VDRLLQLSQGQAVKGNQLLPVSLVKRKTTLAPNTQTASPRALADSLMQLA

RQVSRLESGQ

In some embodiments, the nucleic acid comprises a lacI gene, wherein the lacI gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 78. In some embodiments, the nucleic acid comprises a lacI gene, wherein the lacI gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 78.

In some embodiments, the nucleic acid comprises a nucleic acid sequence encoding a LacI protein, wherein said LacI protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 79. In some embodiments, the nucleic acid comprises a nucleic acid sequence encoding a LacI protein, wherein said LacI protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 79.

In some embodiments, the nucleic acid comprises a lacI gene that is operably-linked to a regulatable promoter (e.g., a sugar-regulatable promoter). In some embodiments, the nucleic acid comprises a lacI gene that is operably-linked to a sugar-regulatable promoter. In some embodiments, the sugar regulatable promoter exhibits increased activity (e.g., increased transcription) in the presence of a specific sugar and decreased activity in the absence of a sugar. In some embodiments, the nucleic acid comprises a lacI gene that is operably-linked to a rhamnose-regulatable promoter (e.g., a sugar-regulatable promoter). In some embodiments, the nucleic acid comprises a lacI gene that is operably-linked to an arabinose-regulatable promoter. In some embodiments, the arabinose-regulatable promoter is $P_{araBAD}$. In some embodiments, the recombinant bacterium comprises the mutation ΔrelA::araC $P_{araBAD}$ lacI TT.

II. Pharmaceutical Compositions

A recombinant bacterium may be administered to a host as a pharmaceutical composition. In some embodiments, the pharmaceutical composition may be used as a vaccine to elicit an immune response to the recombinant bacterium, including any antigens that may be synthesized and delivered by the bacterium. In an exemplary embodiment, the immune response is protective. Immune responses to antigens are well studied and widely reported.

In some embodiments, the pharmaceutical composition comprises a recombinant bacterium described herein. In some embodiments, the pharmaceutical composition comprises a recombinant bacterium that synthesizes a *Salmonella* antigen of interest. In some embodiments, the pharmaceutical composition comprises a recombinant bacterium that synthesizes a *Campylobacter* antigen of interest. In some embodiments, the pharmaceutical composition comprises a recombinant bacterium that synthesizes a *Salmonella* antigen of interest and a recombinant bacterium that synthesizes a *Campylobacter* antigen of interest. In some embodiments, the pharmaceutical composition comprises a recombinant bacterium that synthesizes an antigen of interest comprising a *Campylobacter* N-glycan. In some embodiments, the pharmaceutical composition comprises at least one, at least two, at least three, at least four, at least five, at least six, at least seven, at least eight, at least nine or more recombinant bacterial strains, as described herein.

Pharmaceutical compositions may be administered to any host capable of mounting an immune response. Such hosts may include all vertebrates, for example, mammals, including domestic animals, agricultural animals, laboratory animals, and humans, and various species of birds, including domestic birds and birds of agricultural importance. Preferably, the host is a warm-blooded animal. In one embodiment, the host is a cow. In some embodiments, the host is an equine. In another embodiment, the host is an avian. In another embodiment, the host is a human.

The pharmaceutical composition can be administered to the subject as a prophylactic or for treatment purposes. In some embodiments, the pharmaceutical composition can be administered for the prophylaxis or treatment of *salmonellosis*. In some embodiments, the pharmaceutical composition can be administered for the prophylaxis or treatment of a *Campylobacter* infection. In some embodiments, the pharmaceutical composition can be administered for the prophylaxis or treatment of *salmonellosis* and/or a *Campylobacter* infection.

In some embodiments, the recombinant bacterium is alive when administered to a host in a pharmaceutical composition described herein. Suitable vaccine composition formulations and methods of administration are detailed below.

A pharmaceutical composition comprising a recombinant bacterium may optionally comprise one or more possible additives, such as carriers, preservatives, stabilizers, adjuvants, and other substances.

In one embodiment, the pharmaceutical composition comprises an adjuvant. Adjuvants are optionally added to increase the ability of the vaccine to trigger, enhance, or prolong an immune response. In exemplary embodiments, the use of a live attenuated recombinant bacterium may act as a natural adjuvant. In some embodiments, the recombinant bacterium synthesizes and secretes an immune modulator. Additional materials, such as cytokines, chemokines, and bacterial nucleic acid sequences naturally found in bacteria, like CpG, are also potential vaccine adjuvants.

In some embodiments, the pharmaceutical composition comprises buffered saline (e.g., phosphate-buffered saline (PBS)).

In some embodiments, the pharmaceutical composition comprises a food product.

In another embodiment, the pharmaceutical may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the bronchial tubes, the pharmaceutical composition is preferably presented in the form of an aerosol.

In some embodiments, the pharmaceutical composition is delivered to a farm animal (e.g., poultry). In some embodiments, the pharmaceutical composition is delivered as a course spray (e.g., for use in hatcheries for delivery to poultry). In some embodiments, the pharmaceutical composition is delivered in the drinking water.

Care should be taken when using additives so that the live recombinant bacterium is not killed, or have its ability to effectively colonize lymphoid tissues such as the GALT, NALT and BALT compromised by the use of additives. Stabilizers, such as lactose or monosodium glutamate (MSG), may be added to stabilize the pharmaceutical composition against a variety of conditions, such as temperature variations or a freeze-drying process. The recombinant bacterium may also be co-administered with glutamate and/or arginite as described herein.

The dosages of a pharmaceutical composition can and will vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. typical initial dosages of vaccine for oral administration could be about $1\times10^7$ to $1\times10^{10}$ CFU depending upon the age of the host to be immunized. Administering multiple dosages may also be used as needed to provide the desired level of protective immunity.

In order to stimulate a preferred response of the GALT, NALT or BALT cells, administration of the pharmaceutical composition directly into the gut, nasopharynx, or bronchus is preferred, such as by oral administration, intranasal administration, gastric intubation or in the form of aerosols, although other methods of administering the recombinant bacterium, such as intravenous, intramuscular, subcutaneous injection or intramammary, intrapenial, intrarectal, vaginal administration, or other parenteral routes, are possible, e.g., for anti-cancer applications.

In some embodiments, these compositions are formulated for administration by injection (e.g., intraperitoneally, intravenously, subcutaneously, intramuscularly, etc.).

In another embodiment, the disclosure provides a method for eliciting an immune response against an antigen in a host. The method comprises administering to the host an effective amount of a pharmaceutical composition comprising a recombinant bacterium described herein.

In still another embodiment, a recombinant bacterium may be used in a method for eliciting an immune response against a pathogen in an individual in need thereof. The method comprises administrating to the host an effective amount of a pharmaceutical composition comprising a recombinant bacterium as described herein. In a further embodiment, a recombinant bacterium described herein may be used in a method for ameliorating one or more symptoms of an infectious disease in a host in need thereof. The method comprises administering an effective amount of a pharmaceutical composition comprising a recombinant bacterium as described herein.

EXAMPLES

The present invention is further illustrated by the following examples, which should not be construed as limiting in any way. The contents of all cited references, including literature references, issued patents, and published patent applications, as cited throughout this application are hereby expressly incorporated herein by reference. It should further be understood that the contents of all the figures and tables attached hereto are also expressly incorporated herein by reference.

Example 1: Background and Overview

*Campylobacter* is a leading cause of bacterial foodborne gastroenteritis worldwide and is a major public health problem (21-23). A recent estimate by the CDC indicates that *C. jejuni* is not only among the most common causes of foodborne illnesses in humans (over 800,000 cases per year), but also is a leading cause of hospitalization (over 8,000 annually) (24). Patients infected with *C. jejuni* often experience watery/bloody diarrhea, abdominal cramps, nausea, and fever. Severe neurological sequelae, bacteremia and other extraintestinal complications may develop infrequently (25). *C. jejuni* is widespread in food-producing animals, especially in poultry. The majority of human *C. jejuni* infections are predominantly associated with poor handling of raw chicken or consumption of undercooked chicken (1, 2, 26-32). The predominant role of poultry in human campylobacteriosis is supported by high prevalence of *C. jejuni* in both live birds and on carcasses, findings from epidemiological studies, and detection of identical genotypes in both poultry and human infections (28-30, 33, 34).

Domestic poultry including chickens, turkeys, ducks, and geese, are frequently infected with *C. jejuni* and *C. coli* (3, 35-37). Despite extensive colonization in the intestinal tract, *Campylobacter* infection produces little or no clinical diseases in poultry (3, 35, 38, 39). Prevalence studies conducted in Europe and the U.S. have reported *C. jejuni*-positive flocks ranging from 2% to 100% (38, 40-42). typically, the prevalence of *C. jejuni* increases as the birds grow and reaches highest points at the slaughter age for broilers. Once a broiler flock is infected with *C. jejuni*, the majority of birds within the flock become colonized in (40, 43-46). The high numbers of *C. jejuni* in the intestinal tract results in contamination of poultry carcasses during slaughter such that *C. jejuni* on poultry carcasses at the end of the processing line (post-chill) is usually over 50% varying from 0 to 100% (33, 47-53). In the U.S., several studies reported that a large percentage of processed broiler carcasses were contaminated with high numbers of *C. jejuni* (47, 53-55). Carcass contamination by *C. jejuni* is attributable to the farm of origin as high prevalence on a farm is usually associated with high-level carcass contamination in processing plants (56-60).

*Salmonellosis* develops different syndromes, including gastroenteritis, enteric fever (typhoid fever), and bacteremia, and as asymptomatic carriage in animals and humans (61). It is the leading cause of foodborne illness in the U.S., with 35% of the hospitalizations and 28% of the deaths (24). There are approximately 1.03 million cases of non-typhoidal *Salmonella* each year in the U.S., costing an economic loss of approximately $3.31 billion due to premature mortality, disability, and medical and productivity costs, with an annual loss of 16,782 quality-adjusted life years (62). *Salmonella* has a broad host range and adapts to survive in a wide range of different environments, even up to 16 months in dry feed stored at 25° C. (63, 64). Although a large number of human infections are associated with food animal sources, infections also come from pets, reptiles, fruits, vegetables and other humans (65-67). Transmission of *Salmonella* to humans typically occurs when ingesting foods that are contaminated by animal feces or cross-contaminated by other sources (4). Among these sources, poultry and poultry-associated products are widely recognized as being among the most important vehicles for human *Salmonella* infections according to CDC reports (5, 67-74). With increasing consumption of poultry and poultry products, the number of *salmonellosis* associated with poultry continues to be a significant public health issue in the U.S.

There are over 2000 *Salmonella* serotypes. *S. enteritidis, S. heidelberg, S. kentucky* and *S. typhimurium* are commonly associated with chickens and to various extents with other food animal species and human infections. According to the CDC and USDA, *S. enteritidis* was the most common serovar implicated in human illness in the U.S. (74) and most commonly associated with chickens and eggs and to a much lesser extent with other food animal species (74-80). *S. heidelberg* is also found in most major food animal species, eggs, and retail meat samples and is among the top five most common serotypes associated with human disease (79, 81, 82). Although, *S. kentucky* rarely causes human infections in the United States, it is an emerging serovar in Europe and North Africa (83) and is prevalent in poultry (75, 84, 85).

Traditionally, antibiotics have been used to treat bacterial infections and for growth promotion in food animals. However, these uses of antibiotics contributed to increasing rates of antibiotic resistance (86), resulting in contamination of flocks and food products by antibiotic-resistant *Campylobacter, Salmonella, Enterococcus* and *Escherichia coli* and thereby increasing risks of human infections (87). Public concerns over the spread of antibiotic resistance in zoonotic bacterial pathogens, which poses a threat to the effectiveness of existing antibiotic therapy in both clinical medical and veterinary practice (88-97), led the European Union, in 1999, to ban use of most antibiotics for growth promotion to preserve the effectiveness of important human drugs (98). In 2004, the U.S. FDA banned enrofloxacin in food animals on the grounds that its use contributed to fluoroquinolone resistance in human pathogens. More recently, FDA and industry have agreed to cease use of growth promotion antimicrobials. However, there are concerns that reductions in antibiotic use in animal production may lead to an increase in foodborne pathogens on meat and other animal food. Besides management practices, it is necessary to develop other effective ways to mitigate emergence of antibiotic-resistant bacteria and to control foodborne pathogens. One of the best prevention strategies are development and use of vaccines.

Campylobacter Control:

Poultry houses can be contaminated by *Campylobacter* in many different ways from various environmental sources, making prevention of flock colonization by *Campylobacter* a very challenging task. In general, the on-farm control strategies examined for *Campylobacter* in poultry can be broadly divided into two approaches: 1) prevention of flock colonization by use of biosecurity-based interventions, and 2) prevention and/or reduction of *Campylobacter* colonization by non-biosecurity based measures such as vaccination, addition of bacteriocins, bacteriophages and feed additives, and competitive exclusion (42, 99-101). Improving biosecurity on farms apparently has a noticeable effect on lowering the overall flock prevalence. However, even the most stringent biosecurity measures do not always have a consistent and predictable effect on controlling *Campylobacter* and their effectiveness on flock prevalence is difficult to assess under commercial settings (42, 102-105). In addition, stringent biosecurity measures are cost-prohibitive, hard to maintain, and their effectiveness seems to vary with production systems (36, 42). Multiple non-biosecurity measures have been evaluated for control of *Campylobacter* in live birds. Currently, there are no commercially available competitive exclusion products, vaccines, bacteriocins, bacteriophages or feed/water additives for excluding *Campylobacter* from chickens under production conditions although some promising results obtained under laboratory conditions have recently been reported (99, 106-108).

Vaccination against *C. jejuni* is a promising strategy but requires optimization of the vaccination regimen (e.g., induction of mucosal and possibly cellular immunity and practical delivery systems) using protective antigens. *C. jejuni* is generally considered as a commensal of chickens even though systemic and mucosal humoral responses have been observed (109-111) and anti-*Campylobacter* antibodies are detectable in progenies as maternally-derived antibodies (112). However, lack of strong activation of innate/adaptive immune responses in chickens, unlike in humans, requires development of vaccine strategies that enhance the immune response to *C. jejuni* antigens. For *C. jejuni* vaccine antigens to be immunogenic, it is critical to deliver antigens to the regional lymph tissues and spleen to stimulate effective mucosal immunity and systemic antibody and cellular immune responses. Therefore, *S. typhimurium*-derived RASVs delivering *C. jejuni* protective antigens were constructed to control/reduce *C. jejuni* prevalence in poultry.

*Salmonella* Control.

Since contaminated poultry products are the major source of human *Salmonella* infection, vaccination of chickens is an important strategy to reduce the levels of *Salmonella* in poultry flocks, which will ultimately lead to lower rates of human *Salmonella* infection. Considering the whole life span of broilers as only 5-6 weeks, it is a challenge to develop a safe and effective *Salmonella* vaccine that could be cross-protective against different serovars. Currently, there are 3 types of vaccine, live attenuated, inactivated and subunit; only the former two are licensed for chickens. Live attenuated vaccines can be administered orally, delivering a bolus of antigens to the host and induce both antibody and cell-mediate immune responses. These live vaccines have used diverse attenuation strategies for strains of *S. typhimurium* (113-115) and *S. enteritidis* (115-121). However, variable efficacy and persistence, reversion to virulence, lack of cross protection and/or possible interference with *Salmonella* testing procedures are concerns (122-125). Killed vaccines are safe, but they must be delivered by costly injection and require adjuvants to increase efficacy (123-125). Thus, the need for a safe and improved live attenuated but highly immunogenic *Salmonella* vaccine still exists (125). *Salmonella* serotypes are defined by the immunologically heterogeneous LPS 0-antigen side chains and flagellar antigens. Therefore, induction of immune responses to these heterogeneous antigens will not serve well the purpose of inducing cross-protective immunity to the diversity of serotypes. On the other hand, *Salmonella* and other enteric bacterial pathogens possess a number of immunologically related cross-reactive antigens. These include the LPS core polysaccharide which is the same in most, if not all, *S. enterica* serotypes except for *S. enterica* serotype *Arizonae* (126). In addition, numerous outer membrane proteins (OMPs), although possessing micro-heterogeneity, nevertheless share antigenic determinants (127) as do the iron regulated outer membrane proteins (IROMPs) that are required for iron acquisition (128), an essential important function for pathogen success within an infected animal. Strategies for *Salmonella* vaccines have been developed to display wild-type surface antigenic determinants in vitro and during the initial phase of infection through mucosal surfaces in the orally immunized host and then cease to synthesize LPS O-antigen side chains and to constitutively synthesize iron-regulated outer membrane proteins (IROMPs) in internal organs (19, 129). Gradual elimination of LPS O-antigen side chains in vivo also better exposes the immunologically related cross-reactive OMPs and IROMPs for surveillance by and stimulation of the immune system. Immune responses to IROMPs are known to be effective in preventing septicemic infection with enteropathogens, especially *E. coli* causing colisepticemia in chickens and turkeys (130). Also, antibodies induced to IROMPs from one bacterial serotype can recognize IROMPs synthesized by other serotypes (131). The fur gene encodes a repressor that, in the presence of free iron, represses all genes encoding IROMPs (128). When iron concentrations become low, as is the case in animal host tissues beyond the intestinal wall barrier, the Fur ceases to be synthesized at a high level and one observes constitutive expression of IROMPs and other Fur-regulated genes needed to sequester iron away from the infected animal host (128). fur mutants are attenuated when fed orally, giving a two to three log higher $LD_{50}$ when administered either to mice (132) or day-of-hatch chicks (133). To achieve a high constitutive level of synthesis of all components for iron acquisition including IROMPs, the promoter of the fur gene ($P_{fur}$) was deleted and replaced with a tightly regulated araC $P_{BAD}$ activator-promoter so that expression of the fur gene is solely dependent on the presence of arabinose (129) and is blind to the concentration of iron. Growth of *S. typhimurium* vaccines with a $\Delta P_{fur}$::TT araC $P_{araBAD}$ fur deletion-insertion mutation in media with a low level of arabinose results in very good colonization of lymphoid tissues, total attenuation at doses of $10^9$ CFU and very high levels of induced protective immunity (129).

Genetically engineered *Salmonella* serovars typhimurium (134), Paratyphi A and typhi (135, 136) have been created as vaccines for regulated delayed attenuation in vivo (129, 134), regulated delayed in vivo synthesis of protective antigens specified by codon-optimized DNA sequences (137-140) and regulated delayed lysis in vivo (140-142) such that vaccines can be grown under conditions that enable them to display after course spray or oral immunization the capabilities of a wild-type strain to survive host defense stresses and efficiently colonize effector lymphoid tissues before manifesting attenuation to preclude disease symptoms and to synthesize protein antigens to induce protective immune responses. Strains have been engineered to eliminate or decrease synthesis of serotype-specific LPS O-antigen (18, 143) and flagellar antigens, to expose conserved LPS core (18, 19, 143) and over-express immunologically cross-reactive surface outer membrane protein antigens (19, 144) needed for the acquisition of essential iron and manganese ions, to diminish induction of gastroenteritis symptoms (145) while retaining abilities to recruit innate immunity, and to exhibit biological containment by cell lysis to preclude persistence in vivo or survival if excreted (140-142). Strains are totally safe at high doses to newborn (136, 146, 147), pregnant, protein malnourished and immunocompromised mice. Also neonatal pups (7 days old) born from mothers immunized with the same RASV strain develop better immune responses and exhibit higher levels of protective immunity to challenge than pups born from unimmunized mothers. A somewhat analogous result was observed years ago when chicks hatched from eggs laid by immunized hens displayed higher levels of protective immunity to the same attenuated *S. typhimurium* vaccine used to immunize the hens than chicks from eggs laid by unimmunized hens (148). These technologies have been used to develop vaccines to prevent infections of newborns with *Streptococcus pneumoniae* (147), *Mycobacterium tuberculosis* (140, 149), a diversity of enteric bacterial pathogens causing diarrheal diseases in humans and influenza virus (141). In a recent human trial of a *S. typhi* derived RASV, complete safety and shedding of zero viable vaccine cells in stools collected for 12 days was observed and with vaccine doses of up to $10^{10}$ CFU administered orally (150). Vaccines have also been developed using *S. typhimurium* RASVs against pathogens of agriculturally important animals, especially to pathogens of chickens such as *Eimeria* species causing coccidiosis (151, 152) and *Clostridium perfringens* causing necrotic enteritis (153, 154). In these regards, six studies (140-142, 154-156) have demonstrated that RASVs with the regulated delayed lysis in vivo phenotype gave superior levels of immune responses and protective immunity compared to RASVs that did not have this lysis phenotype.

To eliminate use of plasmid vectors with non-permitted drug resistance genes and to stabilize plasmid vectors in RASVs in vivo, (157) a balanced-lethal vector-host system was developed by deletion of the asd gene to impose an obligate requirement for diaminopimelic acid (DAP), an essential constituent of the rigid layer of the cell wall and a plasmid vector with the wild-type asd gene. It was also demonstrated that better immune responses to synthesized protective antigens could be achieved by having them secreted using T2SSs such as fusion to the N- and C-terminal β-lactamase sequences (158, 159), which has now been further optimized (154). Enhanced immunogenicity is partially due to enhanced formation of immunogenic outer membrane vesicles containing protective antigens (19, 160).

Plasmids were also constructed (118) and used that are required for the display of the regulated delayed lysis in vivo phenotype in conjunction with the derivatives of χ11730, χ11791 and χ12341. These strains have an araC $P_{araBAD}$ regulated expression of the murA gene encoding the first enzyme in muramic acid synthesis and the Δasd mutation blocking DAP synthesis in its chromosome. These lysis plasmids cause synthesis of protective antigens for delivery by cell lysis and have araC $P_{araBAD}$ regulated murA and asd genes with GTG start codons to decrease translation efficiency. The P22 $P_R$ located with opposite orientation to the transcription of the plasmid araC $P_{araBAD}$ GTG-murA GTG-asd genes is repressed by the C2 repressor made during growth of the strain in medium with arabinose (due to the ΔasdA::TT araC $P_{araBAD}$ c2 mutation). However, C2 concentration decreases due to cell division in vivo to cause $P_R$-directed synthesis of anti-sense mRNA to block translation of residual asdA and murA mRNA. Transcription terminators (TT) flank all plasmid domains for controlled lysis, replication and gene expression so that expression in one domain does not affect activities of another domain.

A. Protective Immunity Against *Eimeria* Infection in Chickens.

Figure 1A:
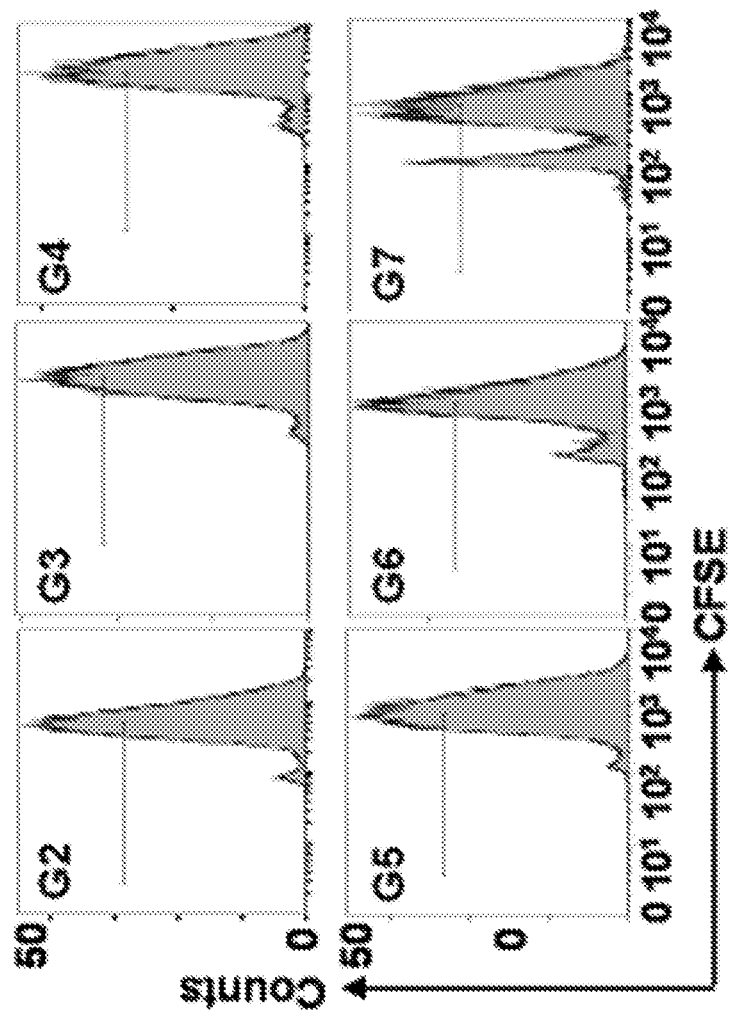
Figure 1C:
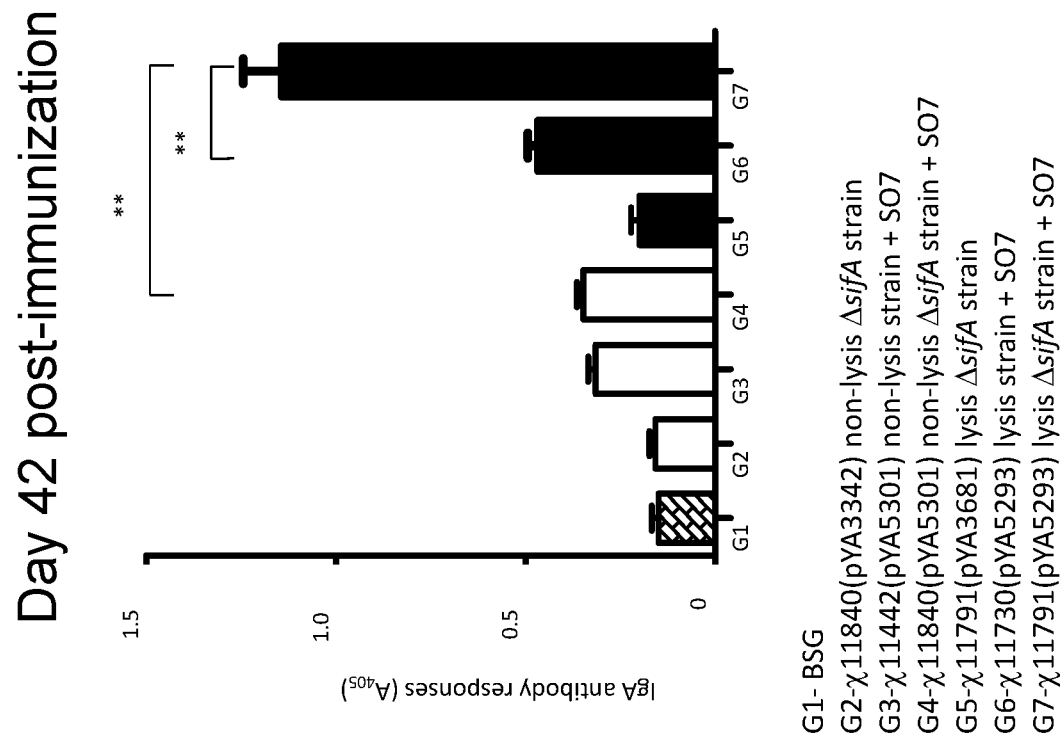
Figure 1D:
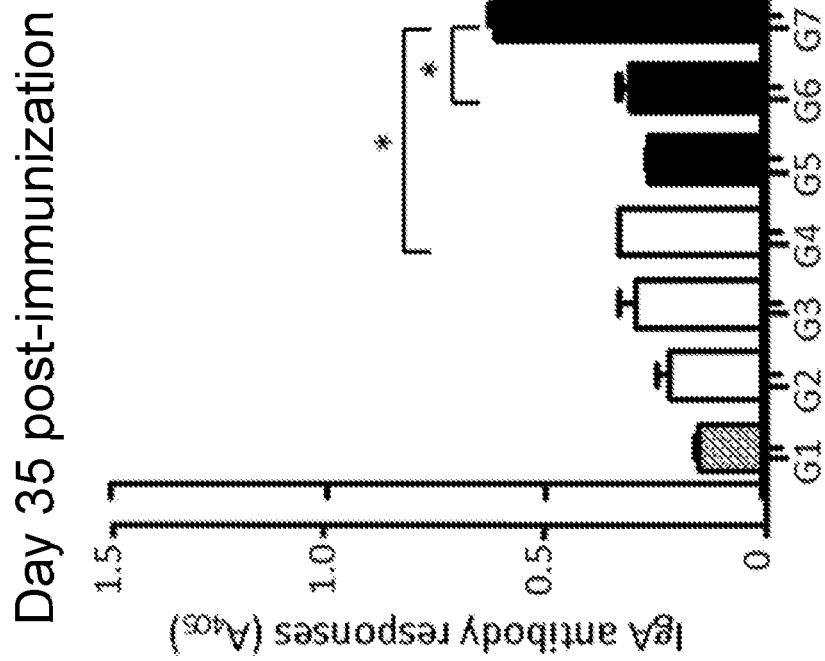

Protective responses in chickens against *E. acervulina* causing coccidiosis was demonstrated. FIGS. 1A and 1B show comparative data for immunization of chickens with non-lysis and lysis strains without and with the ΔsifA mutation for delivery of the *Eimeria* SO7 antigen. The ΔsifA mutation enables the RASV to escape from the *Salmonella* containing vesicle (SCV) so that lysis occurs in the cytosol to enhance induction of CD8-, CD17- and NKT-dependent cellular immunities. Clearly, the most extensive *Eimeria* SO7-specific lymphocyte proliferation was induced by RASV strains with the lysis phenotype and the ΔsifA mutation (Group 7). This same group gave the highest levels of antigen-specific IgA antibody responses (FIGS. 1C and 1D), CD8 cells (FIG. 2A), cytokine response (FIG. 2B), and weight gain after *Eimeria* oocyst challenge (Table 1). Based on these results, the ΔsifA mutation is included in the RASV vector strains to specify synthesis and delivery of *C. jejuni* protective antigens. These collective results demonstrate the efficacy in using these improved RASVs to develop vaccines that will confer protective immunity to *Salmonella* and *C. jejuni* strains in chickens. The use of RASVs that also exhibit complete biological containment with no persistence in vivo or survival if shed in feces, provides another important benefit.

TABLE 1

Immunization of broiler chickens with RASV strains and challenged with *E. tenella* oocysts

| Group | [a]Primary Immunization | Secondary Immunization | [b]Oocyst challenge | [c]Weight gain (mean ± SEM) | [d]Feed conversion ratio (FCR) |
|---|---|---|---|---|---|
| 1 | BSG | BSG | No | 576 ± 32 | 1.75 ± 0.17 |
| 2 | BSG | BSG | Yes | 510 ± 17 | 1.95 ± 0.06 |
| 3 | χ11791(pYA3681) | Yes | Yes | 491 ± 36 | 2.22 ± 0.47 |
| 4 | χ11442(pYA5301) | Yes | Yes | 502 ± 58 | 2.04 ± 0.17 |
| 5 | χ11840(pYA5301) | Yes | Yes | 433 ± 28 | 2.03 ± 0.19 |
| 6 | χ11730(pYA5293) | Yes | Yes | 558 ± 7 | 1.91 ± 0.08 |
| 7 | χ11791(pYA5293) | Yes | Yes | 598 ± 20 | 1.77 ± 0.00 |

[a]Chickens were orally vaccinated when 1 week old and again 1 week later.
[b]Three weeks later, groups G2 to G7 were inoculated with $10^5$ *E. tenella* oocysts. Group 3 = Empty Vector Control. Groups 3 & 4 = Non-Lysis RASVs delivering Eimeria S07 antigen. Groups 6 & 7 = Lysis RASVs delivering S07 antigen. Group 7 RASV also escapes from the *Salmonella*-containing vesicle for lysis in the cytosol to induce maximal systemic and cellular immunities.
[c]Weight gain in grams calculated over the infection period (6 days) between *E. tenella* challenge and termination.
[d]FCR, feed conversion ratio calculated as average amount of feed (g) consumed/average weight gain over the infection period (6 days) between *E. tenella* challenge and termination.

B. *S. typhimurium* Vaccine Vector Strains

*E. coli* host strains for construction of recombinant plasmid vectors and for conjugational transfer of suicide vectors for construction of *S. typhimurium* with improved properties with added mutational alterations are listed in Table 2. Strains used for the construction and evaluation of RASV strains synthesizing and delivering the *Eimeria* SO7 antigen and *C. jejuni* antigens are also listed in Table 2. The phenotypic attributes associated with the mutations in these strains are described in Table 3.

TABLE 2

Bacterial Strains

*E. coli* strains

χ6212(pYA232): φ80d lacZ ΔM15 deoR Δ(lacZYA-argF)U169 supE44 λ⁻ gyrA96 recA1 relA1 endA1 ΔasdA4 Δzhf-2::Tn10 hsdR17 (r⁻ m⁺), lacI$_q$ in pSC101 ori, Tc plasmid 10.2 kb
χ7213: thi-1 thr-1 leuB6 glnV44 fhuA21 lacY1 recA1 RP4-2-Tc::Mu [λ pir] ΔasdA4 Δzhf-2::Tn10

*S. Typhimurium* strains

χ11442: ΔasdA33 ΔrelA198::araC P$_{BAD}$ lacI TT ΔaraBAD23 Δpmi-2426
χ11730: ΔP$_{murA25}$::TT araC P$_{araBAD}$ murA ΔasdA27::TT araC P$_{araBAD}$ c2 Δ(wza-wcaM)-8 Δpmi-2426 ΔrelA198::araC P$_{araBAD}$ lacI TT
X11791: ΔP$_{murA25}$::TT araC P$_{araBAD}$ murA ΔasdA27::TT araC P$_{BAD}$ c2 Δ(wza-wcaM)-8 Δpmi-2426 ΔrelA198::araC P$_{araBAD}$ lacI TT ΔsifA26
χ11840: ΔasdA33 ΔrelA198::araC P$_{araBAD}$ lacI TT ΔaraBAD23 Δpmi-2426 ΔsifA26
χ12341: ΔP$_{murA25}$::TT araC P$_{araBAD}$ murA ΔasdA27::TT araC P$_{araBAD}$ c2 Δ(wza-wcaM)-8 Δpmi-2426 ΔrelA197::araC P$_{araBAD}$ lacI TT ΔrecF126 ΔsifA26 ΔwaaL46 ΔpagL64:TT rhaRS P$_{rhaBAD}$ waaL
χ12396: ΔP$_{murA25}$::TT araC P$_{araBAD}$ murA ΔasdA27::TT araC P$_{araBAD}$ c2 Δ(wza-wcaM)-8 Δpmi-2426 ΔrelA197:: araC P$_{araBAD}$ lacI TT ΔrecF126 ΔsifA26 ΔwaaL46 ΔpagL64::TT rhaRS P$_{rhaBAD}$ waaL ΔP$_{fur33}$::TT araC P$_{araBAD}$ fur
χ12445: ΔP$_{murA25}$::TT araC P$_{araBAD}$ murA ΔasdA27::TT araC P$_{araBAD}$ c2 Δ(wza-wcaM)-8 Δpmi- 2426 ΔrelA197:: araC P$_{araBAD}$ lacI TT ΔrecF126 ΔsifA26 ΔwbaP45 ΔpagL14::TT araC P$_{araBAD}$ wbaP
χ12452: ΔP$_{murA25}$::TT araC P$_{araBAD}$ murA ΔasdA27::TT araC P$_{araBAD}$ c2 Δ(wza-wcaM)-8 Δpmi-2426 ΔrelA197::araC P$_{araBAD}$ laI TT ΔrecF126 ΔsifA26 ΔwaaL46 ΔpagL64::TT rhaRS P$_{rhaBAD}$ waaL ΔompA11 ΔsopB1925

TABLE 3

Mutations and associated phenotypes used in *S. Typhimurium* vaccine strains[a]

| Genotype | Phenotype |
|---|---|
| A. Deletion and deletion-insertion mutations to confer a regulated delayed attenuation | |
| Δpmi | encodes phosphomannose isomerase needed for synthesis of GDP-mannose for LPS O-antigen and thus necessary for virulence (18). |
| ΔwaaL ΔpagL::TT rhaRS P$_{rhaBAD}$ waaL | regulates synthesis of enzyme responsible for attaching first subunit of LPS O-antigen to the LPS core (the deletion of the waaL gene is necessary to prevent impairment in expression of other rfb operon genes (161); the regulated expression cassette is therefore inserted into the pagL gene. |
| ΔP$_{fur}$::TT araC P$_{BAD}$ fur | makes synthesis of Fur dependent on presence of arabinose in growth medium and ceases to be synthesized in vivo due to the absence of arabinose (162) (104). Fur decreases as a consequence of cell division in vivo to lead to elevated synthesis of IROMPs and attenuation presumably due to an iron overload. |
| ΔP$_{mntR}$::TT araC P$_{BAD}$ mntR | R makes synthesis of MntR dependent on presence of arabinose in growth medium and ceases to be synthesized in vivo due to the absence of arabinose (162) (104). MntR decreases as a consequence of cell division in vivo to cause elevated synthesis of MnROMPs to enhance induction of cross-protective immunity. |
| B. Promoters and deletion-insertion mutations for regulated in vivo synthesis of antigens | |
| P$_{trc}$ | a promoter expressed at high level under both anaerobic and aerobic conditions and repressed by LacI (163). |
| ΔrelA::araC P$_{BAD}$ lacI TT | the relA mutation uncouples growth regulation from a dependence of protein synthesis, an important attribute in strains with regulated delayed lysis (164) (189). The arabinose-dependent synthesis of the LacI repressor is to enable a regulated delayed expression of DNA sequences under the control of P$_{trc}$ (137) (113). |
| Phage P22 P$_L$ and P$_R$ | these promoters are repressible by the arabinose-dependent synthesis of the C2 repressor (Vander Byl and Kropinski (190) (165). |
| C. Deletion and deletion-insertion mutations to facilitate regulated delayed lysis in vivo | |
| ΔP$_{murA}$::TT araC P$_{BAD}$ murA | makes synthesis of MurA, the first enzyme in the synthesis of muramic acid, dependent on presence of arabinose in growth medium and ceases to be synthesized in vivo due to the absence of arabinose (142) (118). MurA decreases as a consequence of cell division in vivo to ultimately lead to cell lysis and death (166) (191). The murA defect is complemented by MurA⁺ plasmid vectors (142) (118). |
| Δasd::TT araC P$_{BAD}$ c2 | the Asd enzyme is essential for the synthesis of diaminopimelic acid required for peptidoglycan synthesis (167) (192). The arabinose-dependent synthesis of the C2 repressor is to enable a regulated delayed expression of DNA sequences under the control of a promoter repressed |

TABLE 3-continued

Mutations and associated phenotypes used in *S. Typhimurium* vaccine strains[a]

| Genotype | Phenotype |
|---|---|
|  | by C2 (142) (118). The ΔasdA mutation is complemented by Asd+ plasmid vectors (157) (193). |
| Δ(wza-wcaM) | eliminates twenty enzymes needed to synthesize several exopolysaccharides that promote biofilm formation and for synthesis of GDP-fucose that is required for colanic acid synthesis (168) (194), which can protect cells undergoing cell wall-less death from lysing (169) (195). |
| D. Mutations needed to enhance effective delivery of protective T-cell epitope antigens | |
| ΔsifA | enables *Salmonella* to escape endosome = *Salmonella* containing vesicle (SCV) for lysis in cytosol (170) (196). |
| E. Other contributing mutations | |
| ΔrecF | eliminates recombinase that facilitates inter- and intra-plasmidic recombination (171-173) (197-199). |
| ΔsopB | eliminates excessive intestinal inflammation and enhances induction of mucosal immunity (145, 174-176)(122, 123) |
| ΔompA | eliminates a major outer membrane protein that is highly immunogenic (177) but does not contribute to protective immunity (178)with elimination due to mutation leading to enhanced induction of protective immunity to other outer membrane proteins |

[a]Δ = deletion; TT = transcription terminator; P = promoter

C. *Campylobacter jejuni* Putative and Demonstrated Protective Antigens.

Nineteen *C. jejuni* antigens were selected as known or probable protective antigens based on literature review and bioinformatics analyses. They are listed in Table 4 as likely to induce protective immune responses.

TABLE 4

Exemplary *Campylobacter jejuni* antigens

| Gene | Antigen | Function | GC contents | Signal peptide | bp/aa | Identity among *C. jejuni* seq |
|---|---|---|---|---|---|---|
| cj0034c | Cj0034c | putative periplasmic protein | 32.3% | 22/23 for euk | 702/233 | 96-100% |
| cj0113 | Omp18 | peptidoglycan associated lipoprotein | 33.9 | 21/22 for euk | 498/165 | 100% |
| cj0168c | Cj0168c | putative periplasmic protein | 33.3 | Yes 20/21 | 168/55 | 78-100% |
| cj0248 | Cj0248 | virulence factor and play a role in motility | 30.8 | No | 858/285 | 90-100% |
| cj0289c | Peb3 AcfC | major antigenic peptide PEB3 accessory colonization factor | 34.9 | Yes 20/21 | 753/250 | 100% |
| cj0365c | CmeC | outer membrane channel protein CmeC (multidrug efflux system CmeAB | 31.6 | 19/20 euk 23/24 gmN | 1479/492 | 98-100% |
| cj0404 | Cj0404 | putative transmembrane protein | 29.5 | No | 838/278 | 100% |
| cj0420 | Cj0420 | protein ycel precursor, polyisoprenoid-binding protein | 28.8 | 21/22 gmN and euk | 573/191 | 88-100% |
| cj0427 | Cj0427 | conserved hypothetical protein | 34.5 | No | 336/111 | 99-100% |
| cj0428 | Cj0428 | hypothetical protein | 33.1 | No | 384/127 | 82-100% |
| cj0588 | TlyA | putative haemolysin | 25.7 | No | 762/253 | 82-100% |
| cj0921c | Peb1 | bifunctional adhesin/ABC transporter aspartate/glutamate-binding protein | 31.7 | Yes 26/27 | 780/259 | 100% |
| cj0982c | CjaA | surface antigen/glutamine ABC transporter substrate-binding protein | 33.9 | 18/19 gmN/euk | 840/279 | 100% |
| cj0998c | Cj0998c | Hypothetical protein | 29.7 | 19/20 euk 20/21 gmN | 573/190 | 100% |
| cj1259 | Momp (PorA) | major outer membrane protein | 36.1 | Yes 22/23 | 1275/424 | 100% |
| cj1339c | FlaA | Flagellin A | 37.0 | No | 1719/572 | 100% |
| cj1478c | CadF | outer membrane fibronectin-binding protein | 31.8 | 16/17 euk very weak | 960/319 | 100% |

TABLE 4-continued

Exemplary *Campylobacter jejuni* antigens

| Gene | Antigen | Function | GC contents | Signal peptide | bp/aa | Identity among *C. jejuni* seq |
|---|---|---|---|---|---|---|
| cj1534c | Dps | DNA starvation/stationary phase protection protein, putative bacterioferritin | 32.0 | No | 450/149 | 93-100% |
| cj1656c | Cj1656c | putative motility protein | 38.3 | No | 183/60 | 80-100% | cj sequences are from *Campylobacter jejuni* NCTC 11168 (ATCC700819),
* Analyzed using Blast against *C. jejuni* NCTC 11168 (ATCC700819), 327, LMG23211, 84-25, H693-13, CG8486, LMG9872, S3, LMG23269, 414, ATCC33560, 2008-831, 1997-4, 260.94. CF93-6, M1, RM221 & 20 additional sequenced *C. jejuni* genomes
euk: in eukaryotic;
gmN: in gram negative These sequences are present in all 39 *C. jejuni* genomes analyzed and have 82% or more amino acid sequence identity in all these strains. These include cj0034c, cj0113 (Omp18), cj0168c, cj0248, cj0289 (Peb3), cj0365 (CmeC), cj0404, cj0420, cj0427, cj0428, cj0588 (TlyA), cj0921c (Peb1), cj0982c (CjaA), cj0998c, cj1259 (PorA), cj1339c (Fla), cj1478c (CadF), cj1534c (Dps) and cj1656c. Each of the 19 antigens were analyzed using a diversity of bioinformatic analyses to determine which antigens are present in all sequenced *C. jejuni* strains, which are highly conserved in amino acid sequence, have signal sequences for export and are cell surface localized. Ten of these were selected, including: Cj0113=Omp18 (Refs needed), Cj0289c=Peb3 (120-123), Cj0982c=CjaA (124-128), Cj1259=PorA (120, 121, 123, 126, 129-134), Cj1339c=FlaA (120, 121, 123, 135-144), Cj1478=CadF (120, 121, 129, 132, 144-147), Cj0588 TlyA (148-150), Cj0921c=Peb1 (121-123, 145, 151-157), Cj0998c (U.S. Pat. No. 9,328,148 (150) and Cj1534c=Dps (158, 159) to generate recombinant plasmids using the regulated lysis plasmids pYA4763 and/or pG8R17 depending on whether the antigens did or did not have signal sequences for their secretion from *C. jejuni* strains.

Figure 3A:
Figure 3B:
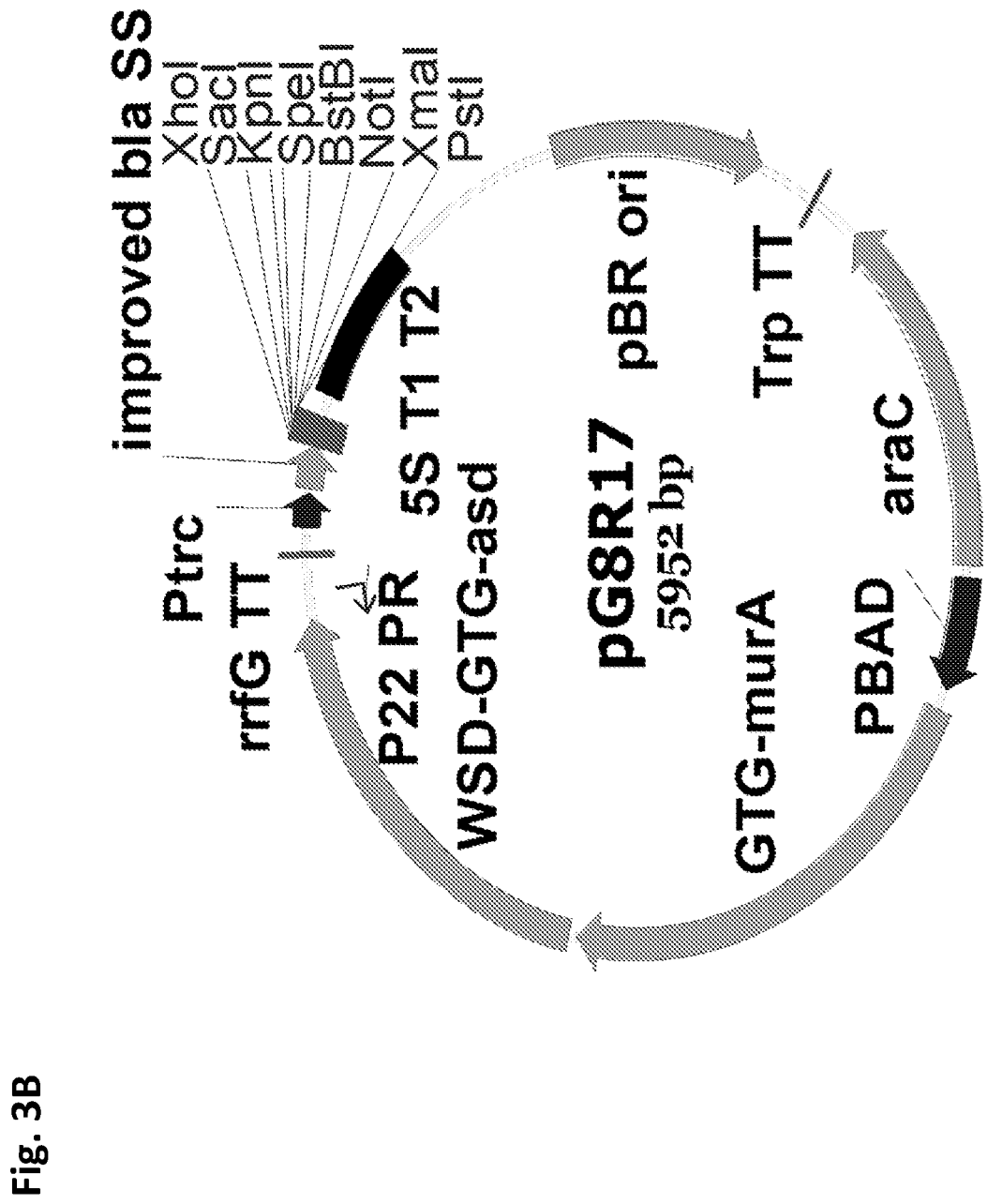

The encoding sequences were codon optimized to adjust GC contents and optimize expression in *Salmonella* and also eliminate potential sites in mRNA subject to cleavage by RNase E so as to prolong half-life of mRNA to also enhance level of antigen synthesis. The codon optimized sequences were modified to delete the native signal peptide encoding sequence (if present), add a sequence encoding a His-tag at the C-terminal end to facilitate protein purification and other sequences on the N- and C-terminal ends to specify the nucleotide sequences to be recognized by restriction enzymes to enable cloning into either pYA4763 (if the antigen was not to be secreted by the RASV) (FIG. 3A) or into pG8R17 (FIG. 3B) with the much improved β-lactamase signal sequence (154)(131) if the antigen was to be secreted. The sequences were also designed to enable excision of the His-tag sequence at a later date, if desired. These sequences were synthesized commercially and returned in promoterless pUC ori vectors. The sequences to be cloned were excised from these plasmids and inserted into either of the lysis plasmids that were then electroporated into the *E. coli* strain χ6212(pYA232) (Table 2). pYA232 encodes the lacI$^q$ gene that overproduces LacI to repress antigen synthesis by the recombinant strains in which the antigen-encoding sequences are under the control of P$_{trc}$ that is repressed by LacI. After selection of the recombinant clones by selection for Asd$^+$ and purification, viability is verified by ability of the *E. coli* recombinants to grow in the presence of IPTG to cause derepression and synthesis of the *C. jejuni* recombinant antigens. Desirably growth is unaltered by antigen synthesis although in some cases growth is slightly retarded due to the high-levels of *C. jejuni* antigen synthesis. The recombinant lysis plasmids were then isolated from the χ6212 host strain and electroporated into the *S. typhimurium* vaccine strain χ12341 (ΔP$_{murA25}$::TT araC P$_{BAD}$ murA ΔasdA27::TT araC P$_{BAD}$ c2 Δpmi-2426 ΔwaaL46 ΔpagL64::TT rhaRS P$_{rhaBAD}$ waaL Δ(wza-wcaNI)-8 ΔrelA197::araC P$_{BAD}$ lacI TT ΔrecF126 ΔsifA26)) (Table 2) again selecting for Asd$^+$. After purification, RASVs were tested for rate of growth and synthesis of *C. jejuni* antigens with and without IPTG, for synthesis of LPS O-antigen dependent on growth in the presence of both mannose and rhamnose and for stability of plasmid maintenance and antigen synthesis after 50 generations of growth under permissive growth in media supplemented with DAP.

FIGS. 4A-4B show western blot analyses of recombinant antigen synthesis in χ12341. The selected recombinant pG8R plasmid is indicated at the top of the Figure and also whether the plasmid was derived from pYA4763 or from pG8R17. Protein was detected using horse radish peroxidase tagged anti His-tag monoclonal antibodies. In some cases, such as with pG8R130 encoding the CadF antigen, the level of CadF protein is low indicating poor synthesis or degradation of the antigen. These problems are sometimes encountered and can be evaluated. Antigen synthesis is thus induced by exposure of RASV strains to IPTG for two hours and then adding 50 μg chloramphenicol; ml to block further protein synthesis. Samples are then taken every hour for four hours to measure antigen levels by western blot analyses. Maintenance of constant antigen levels rules out instability. If instability is observed the amino acid sequence is scrutinized with computer programs to indicate potential cleavage sites by proteases and then new constructs are made with nucleotide changes to eliminate such potential protease cleavage sites. If it appears that antigen synthesis is low, the sequence is examined and new constructs are made to fully establish the basis for the problem and ultimately generate recombinant clones with high-level stable synthesis of the recombinant antigens. In some cases this necessitates modification of the SD sequence to enhance ribosome binding or other alterations in the N-terminal coding sequence to enhance translation efficiency. Since the delivery of multiple recombinant *C. jejuni* antigens to poultry is examined to select those that reduce cecal titers of challenge strains by 100-fold or more, it is not likely that more than three or four antigens will be needed in the final vaccine. Thus, problems in getting high-level stable synthesis of all potential antigens might not be necessary.

In evaluating RASV constructs to induce protective immunity against *Salmonella* serotypes prevalent in poultry (Table 5), some of the recombinant plasmids encoding *C. jejuni* antigens were introduced into χ12452 that is a derivative of χ12341 with ΔsopB and ΔompA mutations. pG8R86 encoding CjaA, pG8R88 encoding Omp18, pG8R89 encoding Peb1, pG8R90 encoding Cj0998c, pG8R102 encoding Peb3, pG8R128 encoding Dps and pG8R129 encoding TlyA have thus been introduced. All of these constructs yield good levels of antigen synthesis as shown in FIG. 4. The relative abilities of the χ12341 constructs are compared versus the χ12452 constructs to protect against infection with the selected Salmonella serotype strains (Table 5). These constructs are also being evaluated for protection to challenge with the C. jejuni strains also listed in Table 5. In order to determine the best combination of C. jejuni antigens to result in the largest reductions in C. jejuni following challenge infection of non-immunized versus immunized chickens, different combinations of strains each delivering a separate C. jejuni antigen are evaluated for additive benefits in reducing cecal titers of challenge strains. In several studies with other RASVs, very similar, if not identical, levels of protective immunity have been found when immunizing with a mixture of two RASVs delivering two different protective antigens, as was observed when a single RASV delivered both antigens.

TABLE 5

Strains used for challenge studies

| Strain | Genotype or Phenotype | Reference |
|---|---|---|
| *Salmonella* | | |
| S. Typhimurium UK-1 χ3761 | Wild Type B, 1, 4, [5], 12: i: 1, 2 | (179) |
| S. Enteritidis χ3550 | Wild Type D1 1, 9, 12: g, m | (144) |
| S. Heidelberg χ3749 | Wild Type B 1, 4, [5], 12: r: 1, 2:- | (180) |
| S. Montevideo NR35 χ3217 | Wild Type C1 6, 7, 14, [54]: g, m, [p], s: [1, 2, 7] | (113) |
| S. Hadar NR14 χ3210 | Wild Type C2 6, 8: $Z_{10}$: e, n, x | (113) |
| S. Infantis NR29 χ3213 | Wild Type C1 6, 7, 14: r: 1, 5 | (113) |
| S. Newport NR90 χ3240 | Wild Type C2 6, 8, 20: e, h: 1, 2 | M. Rosenfeld, Borstel Institute |
| S. Kentucky χ11609 | Wild Type C3 8, 20: i: Z6 | John Maurer, U of Georgia |
| C. jejuni 81-176 | Human isolate, O:23/36 | (181) |
| C. jejuni NCTC11168 | Human isolate, serotype O:2 | (182) |
| C. jejuni 81116 (NCTC11828) | Human and Chicken, Lab strain O:6 | (183) |
| C. jejuni RM1221 | Chicken isolate HS:53 | (184, 185) |
| C. jejuni Chicken Isolate Mix | Chicken | (186) |

This research enhances food safety by immunization of poultry with multiple *S. typhimurium*-derived RASVs delivering multiple protective *C. jejuni* antigens to reduce colonization and persistence in chickens of *Salmonella* serotypes and *C. jejuni* strains to reduce their transmission through the food chain to humans. It is expected the selected vaccine will also enhance poultry farming productivity and decrease use of antibiotics contributing to improved economics of poultry production. Immunization of breeders as well as broiler chicks with these RASVs should reduce, if not eventually eliminate, transmission of *Salmonella* and *C. jejuni* through the food chain to humans.

D. Materials and Methods
  a. Bacterial Strains, Media and Bacterial Growth.
  Attenuated *S. typhimurium* UK-1 stain induces protective immunity to challenge with all *S. typhimurium* strains whereas other *S. typhimurium* strains attenuated with the same mutations often cannot induce protective immunity to other *S. typhimurium* strains, and definitely not to the highly virulent UK-1 strain (187). Therefore a strain that displays maximal ability to cause disease is used as the parental strains for all attenuated derivative vaccine strains. LB broth and agar is used as complex media for propagation and plating of *Salmonella* (see 163(188, 189)). Purple broth (Difco), which is devoid of arabinose, mannose and rhamnose, and minimal salts medium and agar are also used (190) (164). Chrome azurol S (CAS) plates is used to evaluate synthesis of Fe acquisition siderophores. MacConkey agar with 0.5% lactose (Lac) and 0.1% arabinose (Ara), when necessary, is used to enumerate bacteria from chickens. Tetrathionate or selenite broth, with or without supplements, is used to enrich for *Salmonella* from cecal and intestinal contents, the bursa of Fabricius, liver and spleen. Bacterial growth is monitored spectrophotometrically and by plating for colony counts. Sequenced and well-characterized *C. jejuni* strains NCTC11168, 81-176, 81116 and RM221 and *C. jejuni* isolates from chickens (Table 5) are used in challenge studies. These strains are cultured microaerophilically (85% $N_2$, 10% $CO_2$, 5% $O_2$) on Mueller-Hinton (MH) medium at 42° C. for 24 h. For *C. jejuni* isolation from chicken feces and organs, MH agar plates are supplemented with *Campylobacter* selective supplement (SR117E; Oxoid, Lenexa, Kans.). Bacterial strains for the challenge studies are listed in Table 5.
  b. Molecular and Genetic Procedures.
  Methods for DNA isolation, restriction enzyme digestion, DNA cloning and use of PCR for construction and verification of vectors are standard (see 172 (191)). DNA sequence analyses were performed at the University of Florida Interdisciplinary Center for Biotechnology Research (ICBR). All oligonucleotide and/or gene segment syntheses were performed using codon optimization to enhance translational efficiency in *Salmonella* and stabilize mRNA by eliminating RNase E cleavage sites to prolong mRNA half-life (192-194) (173-175). Since live vaccines cannot display antibiotic resistance, defined unmarked deletion mutations are generated with and without insertions using suicide vector technologies (see 176-181 Edwards et al. (1998) *Gene* 207: 149-57(195); Kaniga et al. (1998) *Infect. Immun.* 66: 5599-606(196); Maloy and Nunn (1981) *J. Bacteriol.* 145: 1110-2(197); Miller and Mekalanos (1988) *J. Bacteriol.* 170: 2575-83(198); Ried and Collmer (1987) *Gene* 57: 239-46(199); and Roland et al. (1999) *Avian Dis.* 43: 429-41)(200)). Suicide vectors having flanking sequences derived from the *S. typhimurium* parent χ3761 for generation of all defined mutations listed in Table 3 have been used. These mutations can be introduced using either phage P22HTint transduction (201, 202) (182, 183) of suicide vectors integrated into the deletion mutation in the parental *S. typhimurium* strain followed by selection for sucrose resistance or by conjugational transfer of suicide vectors using standard methods (201, 202) (195, 203) (176, 185) with the suicide vector donor strains χ7213 (181). All strains constructed are given Chi numbers and stored at −80° C. Plasmid constructs will be evaluated by DNA sequencing and the ability to specify synthesis of *C. jejuni* proteins using gel electrophoresis and western blot analyses.
  c. RASV Strain Characterization.
  Vaccine strains have been fully characterized at each step in their construction and after introducing plasmids encoding *C. jejuni* antigens. Initially, the *C. jejuni* antigens Peb1 and Omp18 will be evaluated to enable comparative analyses of the different RASV vector strains χ12341 and χ12452. Then, we will evaluate different combinations of two strains to establish a rank order in giving the largest decrease in cecal titers of the *C. jejuni* challenge strains. Prior to commencing immunization studies, RASVs have been compared with vector control strains for stability of plasmid maintenance, integrity, and antigen synthesis ability when grown in the presence of arabinose and DAP for 50 generations. For constitutive synthesis of the *C. jejuni* antigens, strains are grown in the presence of IPTG to determine whether it results in poor growth and/or genetic instability. Molecular genetic attributes have been confirmed by PCR and/or Southern blot analyses. Measurement of LPS core and O-antigen has been performed after electrophoresis using silver-stained gels (204) (186). This analysis is performed after every step in any strain construction to eliminate rough variants should they arise. Motility tests and use of specific antisera for flagellar antigens are used to determine the presence of flagella. Final RASVs have been assessed for bile sensitivity, acid tolerance, and the ability to survive in sera with and without complement inactivation (104,111). Complete sensitivity of the RASVs to antibiotics will also be evaluated. Metabolic attributes of vaccine strains are evaluated using API-20E tests.

d. Animal Experimentation.

Testing of RASV strains: Studies on RASVs will be conducted in SPAFAS white leghorn chicks and in Cobb and/or Ross broiler chicks obtained from a commercial hatchery. Newly hatched white leghorn chicks will be immunized orally after which food and water will be provided ad libitum. Broiler chicks will be similarly orally immunized one day after receipt from the hatchery to enable them to acclimate but before feeding. Food will be provided after immunization. Vaccine strains to be evaluated (as well as *Salmonella* challenge strains) will be grown in LB broth to an $OD_{600}$ of ~0.9, sedimented by centrifugation at room temperatures and suspended in PBS at densities of $5 \times 10^{10}$ CFU/ml to enable oral doses of up to $1 \times 10^9$ CFU to be administered in 20 µl into chicks. Final RASVs will be evaluated for induction of immune responses that diminish tissue (bursa, liver and spleen) and cecal titers of *Salmonella* serotype challenge strains and cecal titers of *C. jejuni* challenge strains. RASVs will be quantitatively enumerated in various tissues as a function of time after oral inoculation.

The NIH RAC and the UF IBC reclassified the RASV strains with the regulated lysis phenotype and complete biological containment for use at level 1 containment, in commercial settings and in outpatients, with initial immunizations in chicks housed in batteries or on litter. However, for challenge with *Salmonella* serotypes, birds are housed in Federal Design Molded Isolators. All experimental work is conducted in compliance with the regulations and policies of the Animal Welfare Act and the Public Health Service Policy on Humane Care and Use of Laboratory Animals and approved by the UF IACUC.

e. Statistical Analysis.

All results are analyzed using the most appropriate statistical test from the SAS program to evaluate the relative significance or lack thereof of results obtained. In specific cases, the staff at the Clinical Translational Science Institute at UF is consulted to provide help with experimental design and statistical analyses services for animal and human studies and trials. Using ten chickens/treatment group will yield a statistical power >0.80. In previous studies it was found that n=10 is an adequate number of birds to obtain statistically significant differences between treatment groups. However, the best RASVs will be evaluated multiple times at two institutions to substantiate conclusions.

Example 2. Construction of RASV Strains

The starting strain for the development of derivative strains was *S. typhimurium* χ12341 ($\Delta P_{murA25}$::TT araC $P_{BAD}$ murA ΔasdA27::TT araC $P_{BAD}$ c2 Δpmi-2426 ΔwaaL46 ΔpagL64::TT rhaRS $P_{rhaBAD}$ waaL Δ(wzawcaM)-8 ΔrelA197::araC $P_{BAD}$ lacI TT ΔrecF126 ΔsifA2). This strain was derived in many steps from the *S. typhimurium* UK-1 parent strain χ3761. Since live vaccines cannot display antibiotic resistance, defined unmarked deletion mutations were generated using suicide vector technologies (see Edwards et al. (1998) *Gene* 207: 149-57(195); Kaniga et al. (1998) *Infect. Immun.* 66: 5599-606(196); Maloy and Nunn (1981) *J. Bacteriol.* 145: 1110-2(197); Miller and Mekalanos (1988) *J. Bacteriol.* 170: 2575-83(198); Ried and Collmer (1987) *Gene* 57: 239-46(199); and Roland et al. (1999) *Avian Dis.* 43: 429-41(200). Precise deletion and deletion-insertion mutations without interference on adjacent gene functions and without leaving repetitive scars that can contribute to genetic instability can be generated using a combination of molecular genetics, suicide vectors and phage P22-mediated transduction (Kang et al. (2002) *J. Bacteriol.* 184: 307-12)(205). These procedures were used to introduce the deletion and deletion-insertion mutations listed in Table 3 to construct the strains listed in Table 2 as well as the derivatives described herein into *S. typhimurium* χ12341. Suicide vectors derived from either pRE112 or pMEG-375 have been and are constructed, as necessary. To prevent an adverse effect by an inserted sequence on the expression of any adjacent genes, strong transcription terminator (TT) isolated from a bacteriophage genome can be inserted in appropriate locations to block such undesirable effects. These sequences can be inserted into the suicide vectors as appropriate for the individual constructions. Upon construction of suicide vectors and creating deletion and deletion-insertion mutations, allele numbers and Chi numbers are assigned to enable distinction. Strains are stored at –80° C.

Construction of RASV Displaying the Conserved *C. jejuni* N-Glycan.

In this case, the 14 gene *C. jejuni* pgl operon encoding for synthesis of the highly conserved, cross-protective N-glycan (15, 206) also possessing adjuvant properties that is ligated to and transported by the universal UndPP carrier with attachment to the LPS core will be inserted into a deletion of the cysG gene which is dispensable and a very useful site for insertion of foreign genes. Expression of the pgl operon will be driven by fusion to a LacI-regulatable $P_{trc}$ modified by inclusion of a 35 bp sequence found in promoters of operons encoding many genes involved in polysaccharide synthesis (207, 208), which enables synthesis of long mRNA transcripts. This insertion into ΔcysG will be introduced into the χ12341 derivative χ12445 (Table 2) in which the ΔwaaL46 ΔpagL64::TT rhaRS $P_{rhaBAD}$ waaL mutations have been eliminated since the activity of WaaL is needed to cause ligation and transport of the *C. jejuni* N-glycan (209, 210). Since regulated cessation of the LPS O-antigen in vivo is desired to better display protective surface antigens, a deletion of the wbaP gene that encodes the enzyme that couples the first sugar galactose of the O-antigen repeat onto the LPS core and an araC $P_{araBAD}$ wbaP into the pagL gene are present in χ12445. Thus, the waaL gene is expressed continuously and the WaaL enzyme will be able to ligate the *C. jejuni* N-glycan onto the LPS core, the synthesized Cj1433c protein and any *C. jejuni* or RASV surface proteins such as OmpC and OmpD with the D/E-$X_1$-N-$X_2$-T/S sequences that serve as the receptor sequence for N-glycosylation.

This χ12445 strain is further modified by insertion of all or part of the cj1433c gene (209) into a deletion of the ompA gene to generate a fusion of the Cj1433c protein, which has nine repeats of a DLNNT sequence for N-glycan binding, with the ompA-encoded signal sequence. It should be noted that the OmpA protein is one of the most abundant *Salmonella* surface antigens, is totally unnecessary for colonization and virulence and yet is one of the most immunogenic *Salmonella* proteins but unable to afford any protective immunity.

Example 3: RASV Displaying *C. jejuni* N-glycan

One RASV currently being constructed will display the conserved *C. jejuni*-specific N-glycan antigen and synthesize a *C. jejuni* outer membrane protein with multiple targets for N-glycosylation. This will be achieved by expression of the 14-gene pgl operon from *C. jejuni* that encodes the enzymes to synthesize the immuno-protective N-linked glycan attached to many *C. jejuni* surface proteins on a balanced-lethal plasmid or after insertion into the chromosome and inserting sequences encoding the canonical bacterial N-glycosylation sequence D/E-X-N-Y-T/S in genes encoding RASV surface antigens. This RASV can be further modified to cause in vivo display of conserved cross-reactive antigens for iron and manganese uptake to yield a RASV that will induce cross protective immunity to most *Salmonella* serotypes while also delivering multiple *C. jejuni* protein antigens to induce superior protective immunity against *C. jejuni.*

Construction of RASV Encoding the *C. jejuni* Pgl Operon.

*C. jejuni* possesses a 14-gene pgl operon encoding enzymes for the synthesis and placement of a highly conserved, cross-protective N-glycan (15, 206). FIG. 7 depicts the pgl operon. The N-glycan possesses adjuvant properties when ligated to and transported by the universal UndPP carrier for attachment to the LPS core. Due to the length of the pgl operon nucleotide sequence, no attempt has yet been made to optimize codons for expression in *Salmonella* since this would require codon-optimization and synthesis of segments that would then need to be reassembled into a full-length operon. Although this is possible, the native *C. jejuni* sequence has been initially cloned and inserted into a modified derivative (pG8R160) of the low copy number $Asd^+$ plasmid pYA3337 (pSC101 ori) that possesses the Lad repressible $P_{trc}$ promotor modified by insertion of a 35 bp insertion that enhances complete transcription of long operons (206, 207). Since the pglB gene encodes an oligo polysaccharide transferase, it has a duplicate competing activity to the *Salmonella* WaaL enzyme and deletion of the pglB gene enabled better addition of the N-glycan to the LPS core (see FIG. 5) to enable its transfer to D/E-X-N-Y-T/S sequences in proteins. The pglB gene in the pG8R160-derived construct pG8R161 was therefore deleted. The inserted pgl operon sequence, which follows, has a ~30% GC content and still contains codons infrequently used in highly-expressed *Salmonella* genes. However, this may be beneficial for the well-being of the RASV derivative of χ12445 (Δ$P_{murA25}$::TT araC $P_{araBAD}$ murA ΔasdA27::TT araC $P_{araBAD}$ c2 Δpmi-2426 Δ(wza-wcaNI)-8 ΔrelA197::araC $P_{araBAD}$ lacI TT ΔrecF126 ΔsifA26 ΔwbaP45 ΔpagL14::TT araC $P_{araBAD}$ wbaP) since over expression of genes even on a low copy number plasmid can result in decreased growth. Thus lower levels of gene expression are likely beneficial.

Construction of RASV Displaying the Conserved *C. jejuni* N-Glycan.

The pgl operon has been inserted into the low copy number pYA3337 (pSC101 ori) $Asd^+$ plasmid pG8R161 (see above) and will be inserted into a deletion of the cysG gene, which is dispensable, and a very useful site for insertion of foreign genes. Expression of the pgl operon is driven by fusion to a LacI-regulatable $P_{trc}$ promoter modified by inclusion of a 35 bp sequence found in promoters of operons encoding many genes involved in polysaccharide synthesis (207, 208). This enables synthesis of long mRNA transcripts. The insertion into ΔcysG will be introduced into χ12445 (Table 2) in which the ΔwaaL46 ΔpagL64::TT rhaRS $P_{rhaBAD}$ waaL mutations have been eliminated since the activity of WaaL is needed to cause ligation and transport of the *C. jejuni* N-glycan (209, 210). Since regulated cessation of LPS O-antigen synthesis in vivo to better display protective surface antigens, is desired, a deletion of the wbaP gene that encodes the enzyme that couples the first sugar galactose of the O-antigen repeat onto the LPS core was inserted, and an araC $P_{araBAD}$ wbaP was inserted into the pagL gene. The resulting strain derived in multiple steps from χ12341 is χ12445 (Δ$P_{murA25}$::TT araC $P_{araBAD}$ murA ΔasdA27::TT araC $P_{araBAD}$ c2 Δpmi-2426 Δ(wza-wcaM)-8 ΔrelA 197::araC $P_{araBAD}$ lacI TT ΔrecF126 ΔsifA26 ΔwbaP45 ΔpagL14::TT araC $P_{araBAD}$ wbaP). In this strain either with a plasmid or the cysG insertion of the pgl operon, the waaL gene is expressed continuously and the WaaL enzyme will ligate the *C. jejuni* N-glycan onto the LPS core, the synthesized Cj1433c protein fusion (see below) and any *C. jejuni* or RASV surface proteins such as OmpC and OmpD with the D/E-$X_1$-N-$X_2$-T/S sequence that serves as the receptor sequence for N-glycosylation. χ12445 is further modified by insertion of the Cj1433c gene (209) into a partial deletion of the ompA gene to generate a fusion of the Cj1433c protein, which has nine repeats of a DLNNT sequence for N-glycan binding, with the ompA-encoded signal sequence. It should be noted that the OmpA protein is one of the most abundant *Salmonella* surface antigens, is totally unnecessary for colonization and virulence and yet is one of the most immunogenic *Salmonella* proteins but unable to afford any protective immunity. If desired, the Δ$P_{fur}$::TT araC $P_{BAD}$ fur and Δ$P_{mntR}$::TT araC $P_{BAD}$ mntR deletion-insertion mutations can be added to χ12445 to lead to the up-regulation in vivo of all genes needed for iron and manganese uptake. Since immune responses to IROMPs are cross reactive in the Enterobacteriaceae, this strain, as LPS O-antigen synthesis ceases in vivo (due to the pmi mutation and absence of mannose and the araC $P_{araBAD}$ regulated shutoff of the wbaP gene) to better expose surface protein antigens, will induce enhanced cross-protective immunity to *Salmonella* serotypes and other enteric bacteria.

Construction of Cj1433c-OmpA Fusion and Insertion into the ΔompA11 Mutation in χ12445.

The genome of *C. jejuni* is AT rich, which causes problems in transcription fidelity in *S. typhimurium*. The Cj1433c gene is particularly ‘bad’ in that it has a GC content of only 26.4%. Two successive codon optimizations to improve faithful expression of this gene or parts of it in RASV strains were performed. The original and improved nucleotide sequences for Cj14433c gene are given below with indication of the sequences specifying N-glycosylation sites in the protein.
Cj1433c 1107 bp (368 aa) No signal peptide, GC of 26.4% Identity among various *C. jejuni*; low (31%-100%) many sequences aligned only with partial sequence 1st line; original (26.4%)
2nd line; best optimized (45.9%)
3rd lime; modified for higher GC (49.1%) serine, valine, glycine (S, V and G) modified
The N-glycan addition sites are underlined

```
            TATAATATTTTTGGCAGTTTGTTTTAA AGGATGTTTTA
1/1                                 31/11
ATG CAG CGA TTT AAA AAA TGG TTT TTG TCT ATC ATA AAA AAT TTC AAG CAA CAT GAA AAA
ATG CAG CGT TTC AAA AAA TGG TTC CTG TCT ATC ATC AAA AAC TTC AAA CAG CAC GAA AAA
ATG CAG CGT TTC AAA AAA TGG TTC CTG TCC ATC ATC AAA AAC TTC AAA CAG CAC GAA AAA
 M   Q   R   F   K   K   W   F   L   S   I   I   K   N   F   K   Q   H   E   K

61/21                               91/31
ATT AAG ATA GAT CTT AAT AAT ACA AAG ATA GAT CTT AAT AAT ACA AAG ATA GAT CTT AAT
ATC AAA ATC GAC CTG AAC AAC ACC AAA ATC GAC CTG AAC AAC ACC AAA ATC GAC CTG AAC
ATC AAA ATC GAC CTG AAC AAC ACC AAA ATC GAC CTG AAC AAC ACC AAA ATC GAC CTG AAC
 I   K   I   D   L   N   N   T   K   I   D   L   N   N   T   K   I   D   L   N

121/41                              151/51
AAT ACA AAG ATA GAT CTT AAT AAT ACA AAG ATA GAT CTT AAT AAT ACA AAG ATA GAT CTT
AAC ACC AAA ATC GAC CTG AAC AAC ACC AAA ATC GAC CTG AAC AAC ACC AAA ATC GAC CTG
AAC ACC AAA ATC GAC CTG AAC AAC ACC AAA ATC GAC CTG AAC AAC ACC AAA ATC GAC CTG
 N   T   K   I   D   L   N   N   T   K   I   D   L   N   N   T   K   I   D   L

181/61                              211/71
AAT AAT ACA AAG ATA GAT CTT AAT AAT ACA AAG ATA GAT CTT AAT AAT ACA AAG ATA GAT
AAC AAC ACC AAA ATC GAC CTG AAC AAC ACC AAA ATC GAC CTG AAC AAC ACC AAA ATC GAC
AAC AAC ACC AAA ATC GAC CTG AAC AAC ACC AAA ATC GAC CTG AAC AAC ACC AAA ATC GAC
 N   N   T   K   I   D   L   N   N   T   K   I   D   L   N   N   T   K   I   D

241/81                              271/91
CTT AAT AAT ACA AAG ATA GAA TTA TCG CAA TTA AAA AAA GAG CAC TAT AAA GTA TTA GAT
CTG AAC AAC ACC AAA ATC GAA CTG TCT CAG CTG AAA AAA GAA CAC TAC AAA GTT CTG GAC
CTG AAC AAC ACC AAA ATC GAA CTG TCC CAG CTG AAA AAA GAA CAC TAC AAA GTG CTG GAC
 L   N   N   T   K   I   E   L   S   Q   L   K   K   E   H   Y   K   V   L   D

301/101                             331/111
TTT CAT TTA AGA AAA ATT ACA CCT CAA GCT TTT TTA GAG ATT GTT GAA ATT CAT TTA GCC
TTC CAC CTG CGT AAA ATC ACC CCG CAG GCG TTC CTG GAA ATC GTT GAA ATC CAC CTG GCG
TTC CAC CTG CGT AAA ATC ACC CCG CAG GCG TTC CTG GAA ATC GTG GAA ATC CAC CTG GCG
 F   H   L   R   K   I   T   P   Q   A   F   L   E   I   V   E   I   H   L   A

361/121                             391/131
GAA TCA TGT AAT TTA AAT TGT TTT GGT TGT AAT CAT TTT TCA CAA ATA GCT GAA AAA GAA
GAA TCT TGC AAC CTG AAC TGC TTC GGT TGC AAC CAC TTC TCT CAG ATC GCG GAA AAA GAA
GAA TCC TGC AAC CTG AAC TGC TTC GGC TGC AAC CAC TTC TCC CAG ATC GCG GAA AAA GAA
 E   S   C   N   L   N   C   F   G   C   N   H   F   S   Q   I   A   E   K   E

421/141                             451/151
TTT CCA GAT ATA GAA ATT TTT AAA AAA GAT ATG CAA AGA CTT TCA GAA ATA TCT AAA GGT
TTC CCG GAC ATC GAA ATC TTC AAA AAA GAC ATG CAG CGT CTG TCT GAA ATC TCT AAA GGT
TTC CCG GAC ATC GAA ATC TTC AAA AAA GAC ATG CAG CGT CTG TCC GAA ATC TCT AAA GGC
 F   P   D   I   E   I   F   K   K   D   M   Q   R   L   S   E   I   S   K   G

481/161                             511/171
ATT GTC GGA ACT TTT AGA TTG ATG GGT GGC GAA CCT CTT TTA AAT CCC AAT TGT ATA CAG
ATC GTT GGT ACC TTC CGT CTG ATG GGT GGT GAA CCG CTG CTG AAC CCG AAC TGC ATC CAG
ATC GTG GGC ACC TTC CGT CTG ATG GGC GGC GAA CCG CTG CTG AAC CCG AAC TGC ATC CAG
 I   V   G   T   F   R   L   M   G   G   E   P   L   L   N   P   N   C   I   Q

541/181                             571/191
TTT TTT GAC ATT ACA AGA TAT TTT TTT CCA AAA AGT GCC ATT TGG TTG GTA ACT AAT GGT
TTC TTC GAC ATC ACC CGT TAC TTC TTC CCG AAA TCT GCG ATC TGG CTG GTT ACC AAC GGT
TTC TTC GAC ATC ACC CGT TAC TTC TTC CCG AAA TCC GCG ATC TGG CTG GTG ACC AAC GGC
 F   F   D   I   T   R   Y   F   F   P   K   S   A   I   W   L   V   T   N   G

601/201                             631/211
ATT TTA CTT GAT AAG CAA AAT GAG GAT TTT TGG AAT TCA TGC CAA AGG AAT AAA ATG CAA
ATC CTG CTG GAC AAA CAG AAC GAA GAC TTC TGG AAC TCT TGC CAG CGT AAC AAA ATG CAG
ATC CTG CTG GAC AAA CAG AAC GAA GAC TTC TGG AAC TCC TGC CAG CGT AAC AAA ATG CAG
 I   L   L   D   K   Q   N   E   D   F   W   N   S   C   Q   R   N   K   M   Q

661/221                             691/231
ATT CGT CCA ACA AAG TAT CCT ATA AAA ATT AAT TGG GAT TTG ATT AAA GAT AAG TGT GAT
ATC CGT CCG ACC AAA TAC CCG ATC AAA ATC AAC TGG GAC CTG ATC AAA GAC AAA TGC GAC
ATC CGT CCG ACC AAA TAC CCG ATC AAA ATC AAC TGG GAC CTG ATC AAA GAC AAA TGC GAC
 I   R   P   T   K   Y   P   I   K   I   N   W   D   L   I   K   D   K   C   D
```

```
721/241                                751/251
CAA TAT GAT ATC CCC TTG ATA TTT TTT AAC AAT GGA GAG TTG GAA AAA ACT TCT TGG AAA
CAG TAC GAC ATC CCG CTG ATC TTC TTC AAC AAC GGT GAA CTG GAA AAA ACC TCT TGG AAA
CAG TAC GAC ATC CCG CTG ATC TTC TTC AAC AAC GGC GAA CTG GAA AAA ACC TCC TGG AAA
 Q   Y   D   I   P   L   I   F   F   N   N   G   E   L   E   K   T   S   W   K

781/261                                811/271
TTT TCT CTA GAT CCT TCT GGA AAT TGT GAT AAT TAC CAT AGT TTT ACA AAT TGT AGT ATG
TTC TCT CTG GAC CCG TCT GGT AAC TGC GAC AAC TAC CAC TCT TTC ACC AAC TGC TCT ATG
TTC TCC CTG GAC CCG TCC GGC AAC TGC GAC AAC TAC CAC TCC TTC ACC AAC TGC TCC ATG
 F   S   L   D   P   S   G   N   C   D   N   Y   H   S   F   T   N   C   S   M

841/281                                871/291
GCA AAT CAC TGT GTT CAG TTT AAA GAT GGA AAG CTA TTT ACT TGT ACC TTT CCT GCA CAT
GCG AAC CAC TGC GTT CAG TTC AAA GAC GGT AAA CTG TTC ACC TGC ACC TTC CCG GCG CAC
GCG AAC CAC TGC GTG CAG TTC AAA GAC GGC AAA CTG TTC ACC TGC ACC TTC CCG GCG CAC
 A   N   H   C   V   Q   F   K   D   G   K   L   F   T   C   T   F   P   A   H

901/301                                931/311
GTA CAG CAT TTT AAT AAA AAG TAT GGA AAT CAT TTT GAA GTT TGC GAA TTT GAC TTT ATT
GTT CAG CAC TTC AAC AAA AAA TAC GGT AAC CAC TTC GAA GTT TGC GAA TTC GAC TTC ATC
GTG CAG CAC TTC AAC AAA AAA TAC GGC AAC CAC TTC GAA GTG TGC GAA TTC GAC TTC ATC
 V   Q   H   F   N   K   K   Y   G   N   H   F   E   V   C   E   F   D   F   I

961/321                                991/331
GAT ATT TAT AAA GCC AAG GAT TAT CAA GAA ATT TTA TTT TTT CTT TCT AAG CCT ATT CCT
GAC ATC TAC AAA GCG AAA GAC TAC CAG GAA ATC CTG TTC TTC CTG TCT AAA CCG ATC CCG
GAC ATC TAC AAA GCG AAA GAC TAC CAG GAA ATC CTG TTC TTC CTG TCC AAA CCG ATC CCG
 D   I   Y   K   A   K   D   Y   Q   E   I   L   F   F   L   S   K   P   I   P

1021/341                               1051/351
TTT TGT AGA TAT TGC AAG GTA TCA CAA TGG GCA GAA ATT GGA AAA TGG CGT TCT AGC AAT
TTC TGC CGA TAC TGC AAA GTT TCT CAG TGG GCG GAA ATC GGT AAA TGG CGT TCT TCT AAC
TTC TGC CGA TAC TGC AAA GTG TCC CAG TGG GCG GAA ATC GGC AAA TGG CGT TCC TCC AAC
 F   C   R   Y   C   K   V   S   Q   W   A   E   I   G   K   W   R   S   S   N

1081/361
AAA ACA AAA CAT GAA TAT TTA ATT TGA (SEQ ID NO: 71)
AAA ACC AAA CAC GAA TAC CTG ATC TGA (SEQ ID NO: 72)
AAA ACC AAA CAC GAA TAC CTG ATC TGA (SEQ ID NO: 73)
 K   T   K   H   E   Y   L   I   (SEQ ID NO: 74)
```

The topology of the OmpA protein indicating all 16 transmembrane sequences was diagramed by Reusch et al., Int. J. Mol. Sci. 2013, 14(6): 10727-10748 (213)(214, 215), the entire contents of which are expressly incorporated herein by reference. Based on bioinformatic analyses, a portion of the *C. jejuni* Cj1433c gene encoding the repeats of the N-glycosylation sites (amino acids 21 to 86) was inserted as a substitute for the loop spanning and including the 3 and 4 transmembrane sequences (amino acids 70 to 107) of OmpA.

Encoding Sequence for Modified OmpA with Insertion of Portion of Cj1433c Sequence Beta loops 3 and 4 of OmpA (aa 70-107) are deleted and 66 aa (aa21 to 86) of Cj1433c are inserted that specify the nine repeats for N-glycosylation.

```
1/1                                    31/11
ATG AAA AAG ACA GCT ATC GCG ATT GCA GTG GCA CTG GCT GGT TTC GCT ACC GTA GCG CAG
 M   K   K   T   A   I   A   I   A   V   A   L   A   G   F   A   T   V   A   Q

61/21                                  91/31
GCC GCT CCG AAA GAT AAC ACC TGG TAC GCT GGT GCT AAA CTG GGC TGG TCT CAG TAC CAT
 A   A   P   K   D   N   T   W   Y   A   G   A   K   L   G   W   S   Q   Y   H

121/41                                 151/51
GAC ACC GGC TTC ATT CAC AAT GAT GGC CCG ACT CAT GAA AAC CAA CTG GGC GCA GGT GCT
 D   T   G   F   I   H   N   D   G   P   T   H   E   N   Q   L   G   A   G   A

181/61                                 211/71
TTT GGT GGT TAC CAG GTT AAC CCG TAT gtc gac ATC AAA ATC GAC CTG AAC AAC ACC AAA
 F   G   G   Y   Q   V   N   P   Y   V   D   I   K   I   D   L   N   N   T   K
                                    OmpA aa69                    Cj1433 aa21-86

241/81                                 271/91
ATC GAC CTG AAC AAC ACC AAA ATC GAC CTG AAC AAC ACC AAA ATC GAC CTG AAC AAC ACC
 I   D   L   N   N   T   K   I   D   L   N   N   T   K   I   D   L   N   N   T

301/101                                331/111
AAA ATC GAC CTG AAC AAC ACC AAA ATC GAC CTG AAC AAC ACC AAA ATC GAC CTG AAC AAC
 K   I   D   L   N   N   T   K   I   D   L   N   N   T   K   I   D   L   N   N
```

-continued

```
361/121                            391/131
ACC AAA ATC GAC CTG AAC AAC ACC AAA ATC GAC CTG AAC AAC ACC AAA ATC ctg cag ATC
 T   K   I   D   L   N   N   T   K   I   D   L   N   N   T   K   I   L   Q   I
                                                                       OmpA aa108

421/141                            451/151
ACT GAC GAT CTG GAC GTT TAT ACC CGT CTG GGT GGT ATG GTA TGG CGT GCA GAC ACC AAG
 T   D   D   L   D   V   Y   T   R   L   G   G   M   V   W   R   A   D   T   K

481/161                            511/171
TCT AAC GTC CCT GGC GGC CCG TCT ACT AAA GAC CAC GAC ACC GGC GTT TCC CCG GTA TTC

541/181                            571/191
 S   N   V   P   G   G   P   S   T   K   D   H   D   T   G   V   S   P   V   F
GCG GGC GGT ATC GAG TAT GCT ATC ACC CCT GAA ATC GCA ACC CGT CTG GAA TAC CAG TGG
 A   G   G   I   E   Y   A   I   T   P   E   I   A   T   R   L   E   Y   Q   W

601/201                            631/211
ACT AAC AAC ATC GGT GAT GCC AAC ACC ATC GGC ACC CGT CCG GAC AAC GGC CTG CTG AGC
 T   N   N   I   G   D   A   N   T   I   G   T   R   P   D   N   G   L   L   S

661/221                            691/231
GTA GGT GTT TCC TAC CGT TTC GGC CAG CAA GAA GCT GCT CCG GTA GTA GCT CCG GCA CCA
 V   G   V   S   Y   R   F   G   Q   Q   E   A   A   P   V   V   A   P   A   P

721/241                            751/251
GCT CCG GCT CCG GAA GTA CAG ACC AAG CAC TTC ACT CTG AAG TCT GAC GTA CTG TTC AAC
 A   P   A   P   E   V   Q   T   K   H   F   T   L   K   S   D   V   L   F   N

781/261                            811/271
TTC AAC AAA TCT ACC CTG AAG CCG GAA GGC CAG CAG GCT CTG GAT CAG CTG TAC AGC CAG
 F   N   K   S   T   L   K   P   E   G   Q   Q   A   L   D   Q   L   Y   S   Q

841/281                            871/291
CTG AGC AAC CTG GAT CCG AAA GAC GGT TCC GTT GTC GTT CTG GGC TTC ACT GAC CGT ATC
 L   S   N   L   D   P   K   D   G   S   V   V   V   L   G   F   T   D   R   I

901/301                            931/311
GGT TCT GAC GCT TAC AAC CAG GGT CTG TCC GAG AAA CGT GCT CAG TCT GTT GTT GAT TAC
 G   S   D   A   Y   N   Q   G   L   S   E   K   R   A   Q   S   V   V   D   Y

961/321                            991/331
CTG ATC TCC AAA GGT ATT CCG TCT GAC AAA ATC TCC GCA CGT GGT ATG GGC GAA TCT AAC
 L   I   S   K   G   I   P   S   D   K   I   S   A   R   G   M   G   E   S   N

1021/341                           1051/351
CCG GTT ACC GGC AAC ACC TGT GAC AAC GTG AAA CCT CGC GCT GCC CTG ATC GAT TGC CTG
 P   V   T   G   N   T   C   D   N   V   K   P   R   A   A   L   I   D   C   L

1081/361                           1111/371
GCT CCG GAT CGT CGC GTA GAG ATC GAA GTT AAA GGC GTT AAA GAC GTG GTA ACT CAG CCG
 A   P   D   R   R   V   E   I   E   V   K   G   V   K   D   V   V   T   Q   P

1141/381
CAG GCT TAA (SEQ ID NO: 75)
 Q   A   *   (SEQ ID NO: 76)
```

OmpA Δ70-107::Cj1433 aa21-86

ATGAAAAAGACAGCTATCGCGATTGCAGTGGCACTGGCTGGTTTCGCTACCGTAGCGCAGGCCGCTCCGAAAGAT

AACACCTGGTACGCTGGTGCTAAACTGGGCTGGTCTCAGTACCATGACACCGGCTTCATTCACAATGATGGCCCG

ACTCATGAAAACCAACTGGGCGCAGGTGCTTTTGGTGGTTACCAGGTTAACCCGTATGTCGACATCAAAATCGAC

CTGAACAACACCAAAATCGACCTGAACAACACCAAAATCGACCTGAACAACACCAAAATCGACCTGAACAACACC

AAAATCGACCTGAACAACACCAAAATCGACCTGAACAACACCAAAATCGACCTGAACAACACCAAAATCGACCTG

AACAACACCAAAATCGACCTGAACAACACCAAAATCCTGCAGATCACTGACGATCTGGACGTTTATACCCGTCTG

GGTGGTATGGTATGGCGTGCAGACACCAAGTCTAACGTCCCTGGCGGCCCGTCTACTAAAGACCACGACACCGGC

GTTTCCCCGGTATTCGCGGGCGGTATCGAGTATGCTATCACCCCTGAAATCGCAACCCGTCTGGAATACCAGTGG

ACTAACAACATCGGTGATGCCAACACCATCGGCACCCGTCCGGACAACGGCCTGCTGAGCGTAGGTGTTTCCTAC

CGTTTCGGCCAGCAAGAAGCTGCTCCGGTAGTAGCTCCGGCACCAGCTCCGGCTCCGGAAGTACAGACCAAGCAC

TTCACTCTGAAGTCTGACGTACTGTTCAACTTCAACAAATCTACCCTGAAGCCGGAAGGCCAGCAGGCTCTGGAT

CAGCTGTACAGCCAGCTGAGCAACCTGGATCCGAAAGACGGTTCCGTTGTCGTTCTGGGCTTCACTGACCGTATC

```
GGTTCTGACGCTTACAACCAGGGTCTGTCCGAGAAACGTGCTCAGTCTGTTGTTGATTACCTGATCTCCAAAGGT

ATTCCGTCTGACAAAATCTCCGCACGTGGTATGGGCGAATCTAACCCGGTTACCGGCAACACCTGTGACAACGTG

AAACCTCGCGCTGCCCTGATCGATTGCCTGGCTCCGGATCGTCGCGTAGAGATCGAAGTTAAAGGCGTTAAAGAC

GTGGTAACTCAGCCGCAGGCTTAA (SEQ ID NO: 77)
```

FIGS. 8A-8B depict the structural aspects of the modified S. typhimurium OmpA protein with the insertion of the Cj1433c gene encoded sequences specifying the nine repeats to which the C. jejuni conserved N-glycan is attached as a consequence of the C. jejuni pgl operon and the activity of the Salmonella WaaL enzyme. The resulting construct is currently being introduced into a suicide vector that will be used to introduce the sequence encoding this Cj14433c-OmpA fusion into the χ12445 chromosome in place of the wild-type ompA gene. This strain will then be further modified to deliver a lysis plasmid encoding the C. jejuni antigens found in earlier studies to be maximally effective in reducing cecal titers of C. jejuni challenge strains. Experiments as described above by immunization of white leghorn and broiler chicks will be repeated.

Production of IROMPS and MnOMPs to Enhance Protective Immunity Against Salmonella Serotypes and Other Enteric Bacteria.

The $\Delta P_{fur}$::TT araC $P_{BAD}$ fur mutation was inserted into χ12341 to yield χ12396 (Table 2) and the $\Delta P_{mntR}$::TT araC $P_{BAD}$ mntR deletion-insertion mutation (Table 3) will also be inserted to lead to the up-regulation in vivo of all genes needed for iron and manganese uptake. Since immune responses to IROMPs are cross reactive in the Enterobacteriaceae, this strain, as LPS O-antigen synthesis ceases in vivo (due to the pmi mutation and absence of mannose and the araC $P_{araBAD}$ regulated shutoff of the waaL gene) to better expose surface protein antigens, will induce enhanced cross-protective immunity to Salmonella serotypes and other enterics.

Example 4: Evaluation of RASV-Cj Strains in White Leghorn Chickens

Evaluation of Ability to Induce Cross-Protective Immunity to Salmonella Serotypes, to Prevent Organ Colonization, and to Reduce Cecal Titers.

RASV-Cj will be evaluated delivering CjaA specified by the pG8R17 T2SS vector pG8R86 (FIG. 8) comparing χ12341 with the derivative of χ12396 described in Example 2. The protocol described by Hassan and Curtiss (113) will be followed. The CjaA antigen is selected for these comparative studies since in an unpublished study with one of the new RASV strains there was a 3- to 4-log reduction in cecal titers of the C. jejuni challenge strain. In addition, CjaA, which has been evaluated in some 23 prior studies, contains a sequence that should permit glycosylation with the C. jejuni N-glycan in the RASV-Cj strain. Day-of-hatch white leghorn chicks will be orally immunized and provided a second immunization at 10 days. At six weeks of age, ten immunized chicks and ten unimmunized chicks will each be challenged with 1×10⁶ CFU of each of the eight serotypes of Salmonella listed in Table 5 (typhimurium, Enteritidis, Heidelberg, Montevideo, Hadar, Infantis, Newport and Kentucky). Four and eleven days after challenge, five birds in each group will be euthanized by $CO_2$ asphyxiation and titers of challenge and vaccine strains in liver, spleen, ovary (if present), bursa of Fabricius and cecum quantitated by direct plating on SS agar and by selenite-cysteine broth enrichment (113). The enrichment broth will detect bacterial titers as low as 5 per gram of tissue or contents. The biological containment features of the RASVs will preclude their detection.

Second Stage Studies.

These studies are repeated with a mixture of the two RASVs each delivering two or three validated protective C. jejuni antigens. The same immunization protocol described above will be used. This will serve as an independent repeat of the first experiment and establish the level of repeatability of the initial results. Titers of S. typhimurium and S. enteritidis challenge strains will also be evaluated 10, 20 and 30 days after challenge by immunizing with a combination of the two RASVs each delivering multiple C. jejuni protein antigens. Another small study will be directed at determining whether a single immunization is sufficient and determining how soon after primary immunization protective immunity to Salmonella serotypes is detectable in challenge studies.

Example 5: Evaluation of RASV-Cj Strains in Broiler Chickens

Figure 5:
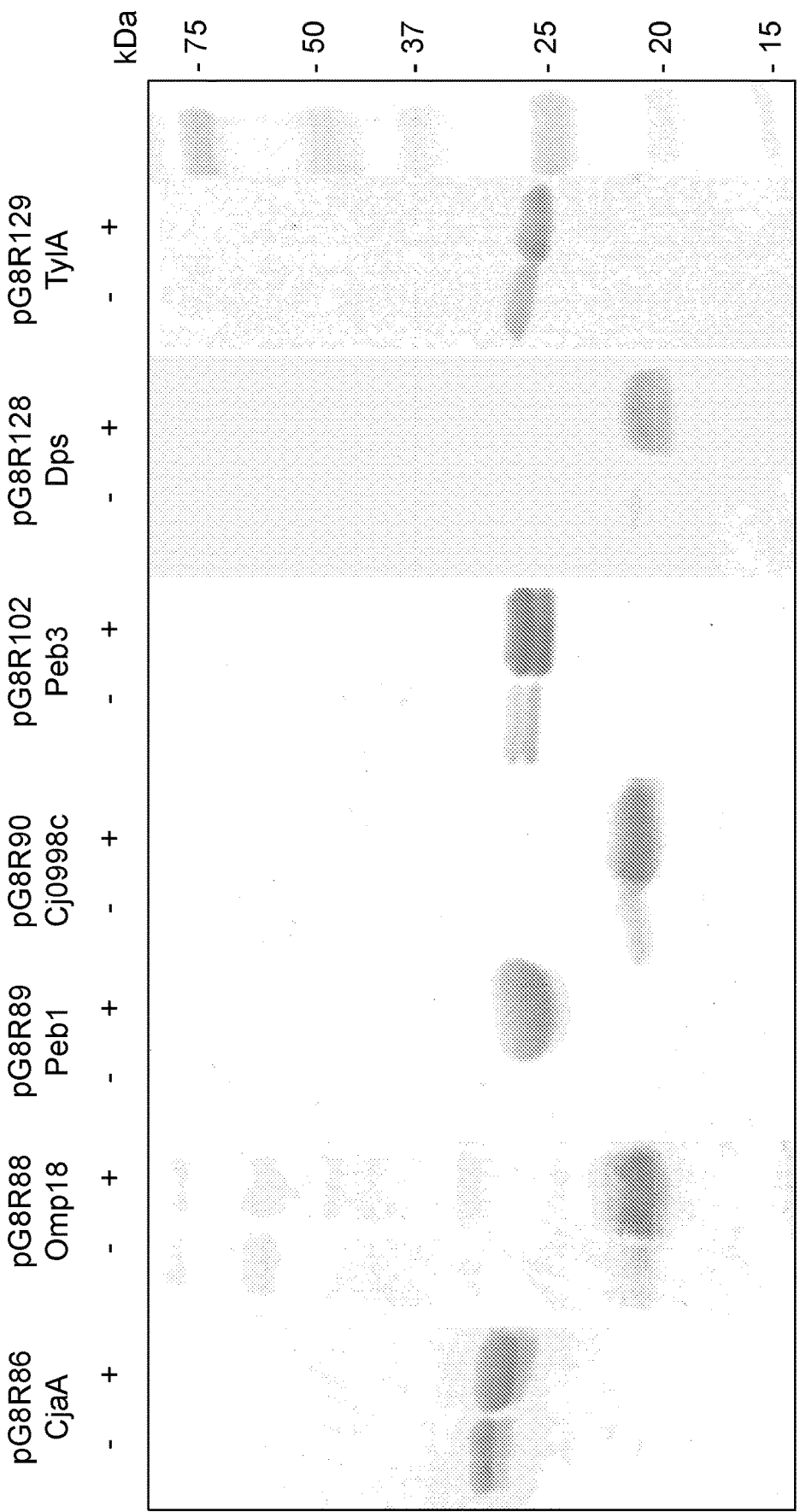

RASV-Cj strains comprising lysis plasmids encoding each of the C. jejuni antigens listed in Table 4 will be evaluated to determine the level of protection against C. jejuni colonization and persistence. Initial tests will evaluate whether χ12341 (FIGS. 4A and 4B) or χ12452 (FIG. 5) delivery of the CjaA antigen gives the best results. The best delivery strain will then be used in subsequent evaluations. Protection will be assessed by measuring CFU in cecal contents and the results correlated with antibody responses in both serum and feces. Plasmids encoding C. jejuni antigens resulting in the greatest levels of protection will be used to evaluate protection against heterologous challenge using well characterized C. jejuni strains, as well as to a cocktail of chicken isolates that are frequently isolated from poultry in the US (listed in Table 5).

Newly hatched day-old broiler chicks will be obtained from hatcheries, and prior to use, chicks will be confirmed negative for Campylobacter by culturing cloacal swabs on MH agar plates and by PCR 6 groups of 3-day old broiler chickens (n=10/group) will be immunized with 1×10⁹ CFU/chick orally with different RASV-Cj strains delivering C. jejuni antigens (Table 4). Control groups of 10 birds will be inoculated with RASV-Cj with an empty plasmid or be non-vaccinated. Chicks will be re-inoculated with RASVs 10 days after the first inoculation. Two weeks after the boost, chicks will be challenged with C. jejuni strain 81-176 orally (1×10⁵ CFU/chick in 200 µl of PBS). Our previous work using 81-176 and a chicken C. jejuni cocktail indicated that this dose results in 100% colonization (186, 211). One week following challenge, chickens will be killed, cecal contents collected, homogenized in PBS, and plated on MH agar+CSS plates. Plates will be incubated at 42° C. microaerobically for 3 days and CFU/g of cecal contents determined to assess protection against *C. jejuni* challenge comparing titers from the vaccinated groups compared to the non-vaccinated control groups. It is expected that several RASV-Cj constructs will lead to over a 100-fold reduction in cecal *C. jejuni* colonization titers.

Blood, bile and fecal samples will be collected, IgY responses in serum and IgA responses in feces will be measured by indirect ELISA as previously described (212). Briefly, microtiter plates will be coated with purified recombinant *C. jejuni* proteins, washed, blocked with Sea Block blocking buffer (Pierce, Rockford, Ill.). Test samples (serum, bile or feces) will be added, the plates washed and anti-*C. jejuni* antibodies detected with biotinylated goat anti-chicken IgG or IgA antibody (Bethyl Laboratories, Montgomery, Tex.). Plates will be washed and streptavidin-horseradish peroxidase solution (Southern Biotech, Birmingham, Ala.) will be added. Color development will be detected using ABTS (Sigma, St. Louis, Mo.) containing 0.03% $H_2O_2$ in citrate buffer, pH 4.35. After color development, the reaction will be stopped with 1% SDS solution and $OD_{405}$ measured using a microplate reader (Molecular Devices, Sunnyvale, Calif.).

Delivery of multiple *C. jejuni* antigens found to confer reduced challenge titers following immunization are tested. Plasmids encoding the multiple antigens will be constructed and introduced into the RASV-Cj strains. Studies will involve comparing one RASV versus a mixture of the two delivering the same or even different *C. jejuni* antigens. Immunizing with one versus two doses will be compared. If results with a single dose give satisfactory results, lower oral doses will be investigated. Ability of these RASVs to confer protection against *C. jejuni* cecal colonization will be assessed as described above. The protective response will also be correlated with antibody response in sera and feces as above. Control groups of chickens inoculated with a RASV carrying an empty plasmid and challenged and non-vaccinated unchallenged chickens will be used.

RASVs selected from the above studies are tested for whether they confer protection against challenge with heterologous *C. jejuni* strains. RASV-immunized chickens will be challenged with commonly used well-characterized *C. jejuni* strains (NC11168, 81116, RM221 and 81-176). In addition, chickens will be challenged with a cocktail of *C. jejuni* isolates of poultry origin (5 isolates that are frequently isolated from poultry). Chickens (n=10/group) will be vaccinated with selected RASVs ($1\times10^9$ CFU/chicken orally) by the best means as established by the studies described above and challenged with $1\times10^5$ CFU/chick in 200 µl of PBS of *C. jejuni* strains. For the cocktail, equal concentrations of each strain ($1\times10^5$) will be mixed in PBS for challenge. Following challenge, protection against cecal colonization and antibody responses in serum and feces will be assessed as above. Groups of chickens inoculated with RASVs carrying an empty plasmid and challenged with *C. jejuni* as well as a group of non-vaccinated non-challenged chickens will be used as controls.

In regard to safety and utility, multiple mutations in all *S. typhimurium* strains are included that preclude biofilm formation and inability to colonize gallstones in presence of bile. These same mutations decrease ability for persistence in the intestinal tracts of mice and chickens. *S. typhi* strains with some of the same mutations in the proposed *S. typhimurium* RASVs were unable to cause bacteremia in humans and were not shed in a viable cultivatable form in stools following oral administration of up to $10^{10}$ CFU (150). *S. typhimurium* strains of the same genotype were safe in newborn (146, 147), pregnant, malnourished and immuno-compromised mice. In addition, most of the strains undergo regulated delayed lysis which precludes persistence in vivo and viability if shed in feces (142). Also, infectivity and full virulence of these RASVs requires the presence of the sugars arabinose, mannose and rhamnose and thus inability if shed to infect or immunize animals or humans. New means to evaluate and demonstrate safety and efficacy of RASVs are continually devised, often with productive input from APHIS and FDA. Studies on survival of RASVs in water (with and without chlorination), as a consequence of desiccation, in sewage, in feces, in whole blood, in sera with and without complement inactivation, and in monocyte-derived macrophages have been performed. Such testing of *S. typhimurium* RASVs and in chicken feces, body fluids and cells will ultimately be done.

While *Salmonella* is a category 2 pathogen with research conducted using BSL2 laboratory facilities and procedures and animal studies in ABSL2 facilities, the NIH RAC has reviewed the safety properties of our RASVs and is permitting conduct of all studies with immunization to be done under level 1 containment, in commercial agricultural settings and in outpatient human volunteers. This approval was contingent upon concurrence by the Institutional Biosafety Committee and the UF IBC has given such approval. However, challenge of immunized animals must still be conducted under the level of containment needed for that particular pathogen.

REFERENCES

1. Altekruse S F, Stern N J, Fields P I, Swerdlow D L. 1999. *Campylobacter jejuni*—an emerging foodborne pathogen. Emerg Infect Dis 5:28-35.
2. DuPont H L. 2007. The growing threat of foodborne bacterial enteropathogens of animal origin. Clin Infect Dis 45:1353-1361.
3. Lee M D, Newell D G. 2006. *Campylobacter* in poultry: filling an ecological niche. Avian Dis 50:1-9.
4. Gantois I, Ducatelle R, Pasmans F, Haesebrouck F, Gast R, Humphrey T J, Van Immerseel F. 2009. Mechanisms of egg contamination by *Salmonella Enteritidis*. FEMS Microbiol Rev 33:718-738.
5. Braden C R. 2006. *Salmonella enterica* serotype Enteritidis and eggs: a national epidemic in the United States. Clin Infect Dis 43:512-517.
6. Bhaysar A P, Zhao X, Brown E D. 2001. Development and characterization of a xylose-dependent system for expression of cloned genes in *Bacillus subtilis*: conditional complementation of a teichoic acid mutant. Appl Environ Microbiol 67:403-410.
7. Walder R Y, Walder J A. 1986. Oligodeoxynucleotide-directed mutagenesis using the yeast transformation system. Gene 42:133-139.
8. Bauer C E, Hesse S D, Waechter-Brulla D A, Lynn S P, Gumport R I, Gardner J F. 1985. A genetic enrichment for mutations constructed by oligodeoxynucleotide-directed mutagenesis. Gene 37:73-81.
9. Craik C S. 1985. Use Of Oligonucleotides For Site-specific Mutagenesis BIOTECHNIQUES 3:12-19.
10. Smith M, Gillam S. 1981. Constructed Mutants Using Synthetic Oligodeoxyribonucleotides as Site-Specific Mutagens, p 1-32. In Setlow J K, Hollaender A (ed), Genetic Engineering: Principles and Methods Volume 3 doi:10.1007/978-1-4615-7075-2_1. Springer U S, Boston, Mass.
11. Mark D F, Lin L S, Lu S Y. May 21, 1985 1985. Human recombinant interleukin-2 muteins.

12. Mark D F, Lin L S, Lu S D Y. 1988. Structural genes, plasmids and transformed cells for producing cysteine depleted muteins of interferon-β patent U.S. Pat. No. 4,737,462
13. Nothaft H, Scott N E, Vinogradov E, Liu X, Hu R, Beadle B, Fodor C, Miller W G, Li J, Cordwell S J, Szymanski C M. 2012. Diversity in the protein N-glycosylation pathways within the *Campylobacter* genus. Mol Cell Proteomics 11:1203-1219.
14. Szymanski C M, Michael F S, Jarrell H C, Li J, Gilbert M, Larocque S, Vinogradov E, Brisson J R. 2003. Detection of conserved N-linked glycans and phase-variable lipooligosaccharides and capsules from *campylobacter* cells by mass spectrometry and high resolution magic angle spinning NMR spectroscopy. J Biol Chem 278:24509-24520.
15. Wacker M, Linton D, Hitchen P G, Nita-Lazar M, Haslam S M, North S J, Panico M, Morris H R, Dell A, Wren B W, Aebi M. 2002. N-linked glycosylation in *Campylobacter jejuni* and its functional transfer into *E. coli*. Science 298:1790-1793.
16. Elhenawy W, Bording-Jorgensen M, Valguarnera E, Haurat M F, Wine E, Feldman M F. 2016. LPS Remodeling Triggers Formation of Outer Membrane Vesicles in *Salmonella*. MBio 7:e00940-00916.
17. Man S M, Hopkins L J, Nugent E, Cox S, Gluck I M, Tourlomousis P, Wright J A, Cicuta P, Monie T P, Bryant C E. 2014. Inflammasome activation causes dual recruitment of NLRC4 and NLRP3 to the same macromolecular complex. Proc Natl Acad Sci USA 111:7403-7408.
18. Collins L V, Attridge S, Hackett J. 1991. Mutations at rfc or pmi attenuate *Salmonella typhimurium* virulence for mice. Infect Immun 59:1079-1085.
19. Curtiss R, Ill., Zhang X, Wanda S Y, Kang H Y, Konjufca V, Li Y, Gunn B, Wang S, Scarpellini G, Lee I S. 2007. Induction of host immune responses using *Salmonella*-vectored vaccines, p 297-313. In Brogden K A, Minion F C, Cornick N, Stanton T B, Zhang Q, Nolan L K, Wannemuehler M J (ed), Virulence mechanisms of bacterial pathogens, 4th ed. ASM Press, Washington D.C.
20. Cascales E, Buchanan S K, Duche D, Kleanthous C, Lloubes R, Postle K, Riley M, Slatin S, Cavard D. 2007. Colicin biology. Microbiol Mol Biol Rev 71:158-229.
21. Adak G K, Meakins S M, Yip H, Lopman B A, O'Brien S J. 2005. Disease risks from foods, England and Wales, 1996-2000. Emerg Infect Dis 11:365-372.
22. Allos B M, Moore M R, Griffin P M, Tauxe R V. 2004. Surveillance for sporadic foodborne disease in the 21st century: the FoodNet perspective. Clin Infect Dis 38 Suppl 3:S115-120.
23. Mead P S, Slutsker L, Dietz V, McCaig L F, Bresee J S, Shapiro C, Griffin P M, Tauxe R V. 1999. Food-related illness and death in the United States. Emerg Infect Dis 5:607-625.
24. Scallan E, Hoekstra R M, Angulo F J, Tauxe R V, Widdowson M A, Roy S L, Jones J L, Griffin P M. 2011. Foodborne illness acquired in the United States—major pathogens. Emerg Infect Dis 17:7-15.
25. Nachamkin I, Allos B M, Ho T. 1998. *Campylobacter* species and Guillain-Barre syndrome. Clin Microbiol Rev 11:555-567.
26. Doorduyn Y, Van Den Brandhof W E, Van Duynhoven Y T, Breukink B J, Wagenaar J A, Van Pelt W. 2010. Risk factors for indigenous *Campylobacter jejuni* and *Campylobacter coli* infections in The Netherlands: a case-control study. Epidemiol Infect 138:1391-1404.
27. Ge B, Girard W, Zhao S, Friedman S, Gaines S A, Meng J. 2006. Genotyping of *Campylobacter* spp. from retail meats by pulsed-field gel electrophoresis and ribotyping. J Appl Microbiol 100:175-184.
28. Mullner P, Collins-Emerson J M, Midwinter A C, Carter P, Spencer S E, van der Logt P, Hathaway S, French N P. 2010. Molecular epidemiology of Campylobacterjejuni in a geographically isolated country with a uniquely structured poultry industry. Appl Environ Microbiol 76:2145-2154.
29. Mullner P, Shadbolt T, Collins-Emerson J M, Midwinter A C, Spencer S E, Marshall J, Carter P E, Campbell D M, Wilson D J, Hathaway S, Pirie R, French N P. 2010. Molecular and spatial epidemiology of human campylobacteriosis: source association and genotype-related risk factors. Epidemiol Infect 138:1372-1383.
30. Wilson D J, Gabriel E, Leatherbarrow A J, Cheesbrough J, Gee S, Bolton E, Fox A, Fearnhead P, Hart C A, Diggle P J. 2008. Tracing the source of campylobacteriosis. PLoS Genet 4:e1000203.
31. Friedman C R, Hoekstra R M, Samuel M, Marcus R, Bender J, Shiferaw B, Reddy S, Ahuja S D, Helfrick D L, Hardnett F, Carter M, Anderson B, Tauxe R V, Emerging Infections Program FoodNet Working G. 2004. Risk factors for sporadic *Campylobacter* infection in the United States: A case-control study in FoodNet sites. Clin Infect Dis 38 Suppl 3:S285-296.
32. Friedman C R, Niemann J, Wegener H C, Tauxe R V. 2000. Epidemiology of Campylobacterjejuni infections in the United States and other industrialized nations, p 121-138. In Nachamkin I, Blaser M J (ed), *Campylobacter*, 2nd ed. ASM Press, Washington, D C.
33. Guerin M T, Sir C, Sargeant J M, Waddell L, O'Connor A M, Wills R W, Bailey R H, Byrd J A. 2010. The change in prevalence of *Campylobacter* on chicken carcasses during processing: a systematic review. Poult Sci 89:1070-1084.
34. Strachan N J, Gormley F J, Rotariu O, Ogden I D, Miller G, Dunn G M, Sheppard S K, Dallas J F, Reid T M, Howie H, Maiden M C, Forbes K J. 2009. Attribution of *Campylobacter* infections in northeast Scotland to specific sources by use of multilocus sequence typing. J Infect Dis 199:1205-1208.
35. Corry J E, Atabay H I. 2001. Poultry as a source of *Campylobacter* and related organisms. Symp Ser Soc Appl Microbiol:96S-114S.
36. Sahin O, Kobalka P, Zhang Q. 2003. Detection and survival of *Campylobacter* in chicken eggs. J Appl Microbiol 95:1070-1079.
37. Shane S M. 1992. The significance of Campylobacterjejuni infection in poultry: a review. Avian Pathol 21:189-213.
38. Newell D G, Fearnley C. 2003. Sources of *Campylobacter* colonization in broiler chickens. Appl Environ Microbiol 69:4343-4351.
39. Zhang Q, P. P. 2008. Mechanisms of antibiotic resistance in *Campylobacter*, p 263-276. In Nachamkin I, Szymanski C M, Blaser M J (ed), *Campylobacter* vol III. ASM Press; Washington D.C., USA.
40. Stern N J, Fedorka-Cray P, Bailey J S, Cox N A, Craven S E, Hiett K L, Musgrove M T, Ladely S, Cosby D, Mead G C. 2001. Distribution of *Campylobacter* spp. in selected U.S. poultry production and processing operations. J Food Prot 64:1705-1710.
41. Luangtongkum T, Morishita T Y, Ison A J, Huang S, McDermott P F, Zhang Q. 2006. Effect of conventional and organic production practices on the prevalence and antimicrobial resistance of *Campylobacter* spp. in poultry. Appl Environ Microbiol 72:3600-3607.
42. Food Standards Agency U K. 2008. A critical review of interventions and strategies (both biosecurity and non-biosecurity) to reduce *Campylobacter* on the poultry farm. B15025
43. Gregory E, Barnhart H, Dreesen D W, Stern N J, Corn J L. 1997. Epidemiological study of *Campylobacter* spp. in broilers: source, time of colonization, and prevalence. Avian Dis 41:890-898.
44. Cardinale E, Tall F, Gueye E F, Cisse M, Salvat G. 2004. Risk factors for *Campylobacter* spp. infection in Senegalese broiler-chicken flocks. Prev Vet Med 64:15-25.
45. Berndtson E, Danielsson-Tham M L, Engvall A. 1996. *Campylobacter* incidence on a chicken farm and the spread of *Campylobacter* during the slaughter process. Int J Food Microbiol 32:35-47.
46. Barrios P R, Reiersen J, Lowman R, Bisaillon J R, Michel P, Fridriksdottir V, Gunnarsson E, Stern N, Berke O, McEwen S, Martin W. 2006. Risk factors for *Campylobacter* spp. colonization in broiler flocks in Iceland. Prev Vet Med 74:264-278.
47. Stern N J, Pretanik S. 2006. Counts of *Campylobacter* spp. on U.S. broiler carcasses. J Food Prot 69:1034-1039.
48. Wempe J M, Genigeorgis C A, Farver T B, Yusufu H I. 1983. Prevalence of Campylobacterjejuni in two California chicken processing plants. Appl Environ Microbiol 45:355-359.
49. Richardson L J, Cox N A, Bailey J S, Berrang M E, Cox J M, Buhr R J, Fedorka-Cray P J, Harrison M A. 2009. Evaluation of TECRA broth, Bolton broth, and direct plating for recovery of *Campylobacter* spp, from broiler carcass rinsates from commercial processing plants. J Food Prot 72:972-977.
50. Logue C M, Sherwood J S, Elijah L M, Olah P A, Dockter M R. 2003. The incidence of *Campylobacter* spp. on processed turkey from processing plants in the midwestern United States. J Appl Microbiol 95:234-241.
51. Hue O, Le Bouquin S, Laisney M J, Allain V, Lalande F, Petetin I, Rouxel S, Quesne S, Gloaguen P Y, Picherot M, Santolini J, Salvat G, Bougeard S, Chemaly M. 2010. Prevalence of and risk factors for *Campylobacter* spp. contamination of broiler chicken carcasses at the slaughterhouse. Food Microbiol 27:992-999.
52. EFSA. 2011. Annual report 2011.
53. Berrang M E, Bailey J S, Altekruse S F, Patel B, Shaw W K, Jr., Meinersmann R J, Fedorka-Cray P J. 2007. Prevalence and numbers of *Campylobacter* on broiler carcasses collected at rehang and postchill in 20 U.S. processing plants. J Food Prot 70:1556-1560.
54. Nannapaneni R, Story R, Wiggins K C, Johnson M G. 2005. Concurrent quantitation of total *campylobacter* and total ciprofloxacin-resistant *campylobacter* loads in rinses from retail raw chicken carcasses from 2001 to 2003 by direct plating at 42 degrees C. Appl Environ Microbiol 71:4510-4515.
55. Byrd J A, Sams A R, Hargis B M, Caldwell D J. 2011. Effect of selected modified atmosphere packaging on *Campylobacter* survival in raw poultry. Poult Sci 90:1324-1328.
56. Rosenquist H, Sommer H M, Nielsen N L, Christensen B B. 2006. The effect of slaughter operations on the contamination of chicken carcasses with thermotolerant *Campylobacter*. Int J Food Microbiol 108:226-232.
57. Jeon B, Muraoka W T, Zhang Q. 2010. Advances in *Campylobacter* biology and implications for biotechnological applications. Microb Biotechnol 3:242-258.
58. Hue O, Allain V, Laisney M J, Le Bouquin S, Lalande F, Petetin I, Rouxel S, Quesne S, Gloaguen P Y, Picherot M, Santolini J, Bougeard S, Salvat G, Chemaly M. 2011. *Campylobacter* contamination of broiler caeca and carcasses at the slaughterhouse and correlation with *Salmonella* contamination. Food Microbiol 28:862-868.
59. Berrang M E, Smith D P, Windham W R, Feldner P W. 2004. Effect of intestinal content contamination on broiler carcass *Campylobacter* counts. J Food Prot 67:235-238.
60. Allen V M, Bull S A, Corry J E, Domingue G, Jorgensen F, Frost J A, Whyte R, Gonzalez A, Elviss N, Humphrey T J. 2007. *Campylobacter* spp. contamination of chicken carcasses during processing in relation to flock colonisation. Int J Food Microbiol 113:54-61.
61. Andrews-Polymenis H L, Baumler A J, McCormick B A, Fang F C. 2010. Taming the elephant: *Salmonella* biology, pathogenesis, and prevention. Infect Immun 78:2356-2369.
62. Hoffmann S, Batz M B, Morris J G, Jr. 2012. Annual cost of illness and quality-adjusted life year losses in the United States due to 14 foodborne pathogens. J Food Prot 75:1292-1302.
63. Schleifer J H, Juven B J, Beard C W, Cox N A. 1984. The susceptibility of chicks to *Salmonella* montevideo in artificially contaminated poultry feed. Avian Dis 28:497-503.
64. Williams J E, Benson S T. 1978. Survival of *Salmonella typhimurium* in poultry feed and litter at three temperatures. Avian Dis 22:742-747.
65. CDC. 1997. *Salmonella* serotype Montevideo infections associated with chicks—Idaho, Washington, and Oregon, spring 1995 and 1996. MMWR Morb Mortal Wkly Rep 46:237-239.
66. Batz M B, Doyle M P, Morris G, Jr., Painter J, Singh R, Tauxe R V, Taylor M R, Lo Fo Wong D M, Food Attribution Working G. 2005. Attributing illness to food. Emerg Infect Dis 11:993-999.
67. Morris Jr J G, Hoffmann S, Batz B. 2011. Ranking the Risks: The 10 Pathogen-Food Combinations With the Greatest Burden on Public Health.
68. Batz M B, Hoffmann S, Morris Jr J G. 2012. Ranking the disease burden of 14 pathogens in food sources in the United States using attribution data from outbreak investigations and expert elicitation. Journal of Food Protection 75:1278-1291.
69. CDC. 2009. Multistate outbreaks of *Salmonella* infections associated with live poultry—United States, 2007. MMWR Morb Mortal Wkly Rep 58:25-29.
70. CDC. 2007. Three outbreaks of *salmonellosis* associated with baby poultry from three hatcheries—United States, 2006. MMWR Morb Mortal Wkly Rep 56:273-276.
71. Altekruse S F, Bauer N, Chanlongbutra A, DeSagun R, Naugle A, Schlosser W, Umholtz R, White P. 2006. *Salmonella enteritidis* in broiler chickens, United States, 2000-2005. Emerg Infect Dis 12:1848-1852.
72. Patrick M E, Adcock P M, Gomez T M, Altekruse S F, Holland B H, Tauxe R V, Swerdlow D L. 2004. *Salmonella enteritidis* infections, United States, 1985-1999. Emerg Infect Dis 10:1-7.
73. Linam W M, Gerber M A. 2007. Changing epidemiology and prevention of *Salmonella* infections. Pediatr Infect Dis J 26:747-748.
74. CDC. 2014. Foodborne Diseases Active Surveillance Network (FoodNet): FoodNet Surveillance Report for 2012. (Final Report). U.S. Department of Health and Human Services, CDC., Atlanta, Ga.

75. CDC. 2016. National Enteric Disease Surveillance: *Salmonella* Annual Report, 2013. U.S. Department of Health and Human Services, CDC., Atlanta, Ga.
76. CDC. 2012. Foodborne Diseases Active Surveillance Network (FoodNet): FoodNet Surveillance Report for 2011 (Final Report). U.S. Department of Health and Human Services, CDC., Atlanta, Ga.:
77. Roy P, Dhillon A S, Lauerman L H, Schaberg D M, Bandli D, Johnson S. 2002. Results of *Salmonella* isolation from poultry products, poultry, poultry environment, and other characteristics. Avian Dis 46:17-24.
78. Kuehn B M. 2010. *Salmonella* cases traced to egg producers: findings trigger recall of more than 500 million eggs. JAMA 304:1316.
79. Hennessy T W, Cheng L H, Kassenborg H, Ahuja S D, Mohle-Boetani J, Marcus R, Shiferaw B, Angulo F J, Emerging Infections Program FoodNet Working G. 2004. Egg consumption is the principal risk factor for sporadic *Salmonella* serotype Heidelberg infections: a case-control study in FoodNet sites. Clin Infect Dis 38 Suppl 3:S237-243.
80. Elson R, Little C L, Mitchell R T. 2005. *Salmonella* and raw shell eggs: results of a cross-sectional study of contamination rates and egg safety practices in the United Kingdom catering sector in 2003. J Food Prot 68:256-264.
81. Hennessy T W, Hedberg C W, Slutsker L, White K E, Besser-Wiek J M, Moen M E, Feldman J, Coleman W W, Edmonson L M, MacDonald K L, Osterholm M T. 1996. A national outbreak of *Salmonella enteritidis* infections from ice cream. The Investigation Team. N Engl J Med 334:1281-1286.
82. Han J, David D E, Deck J, Lynne A M, Kaldhone P, Nayak R, Stefanova R, Foley S L. 2011. Comparison of *Salmonella enterica* serovar Heidelberg isolates from human patients with those from animal and food sources. J Clin Microbiol 49:1130-1133.
83. Le Hello S, Hendriksen R S, Doublet B, Fisher I, Nielsen E M, Whichard J M, Bouchrif B, Fashae K, Granier S A, Jourdan-Da Silva N, Cloeckaert A, Threlfall E J, Angulo F J, Aarestrup F M, Wain J, Weill F X. 2011. International spread of an epidemic population of *Salmonella enterica* serotype Kentucky ST198 resistant to ciprofloxacin. J Infect Dis 204:675-684.
84. Ladely S R, Meinersmann R J, Ball T A, Fedorka-Cray P J. 2016. Antimicrobial Susceptibility and Plasmid Replicon typing of *Salmonella enterica* Serovar Kentucky Isolates Recovered from Broilers. Foodborne Pathog Dis 13:309-315.
85. Jones D R, Guard J, Gast R K, Buhr R J, Fedorka-Cray P J, Abdo Z, Plumblee J R, Bourassa D V, Cox N A, Rigsby L L, Robison C I, Regmi P, Karcher D M. 2016. Influence of commercial laying hen housing systems on the incidence and identification of *Salmonella* and *Campylobacter*. Poult Sci 95:1116-1124.
86. Bailar J C, 3rd, Travers K. 2002. Review of assessments of the human health risk associated with the use of antimicrobial agents in agriculture. Clin Infect Dis 34 Suppl 3:S135-143.
87. Cohen M L, Tauxe R V. 1986. Drug-resistant *Salmonella* in the United States: an epidemiologic perspective. Science 234:964-969.
88. Kumarasamy K K, Toleman M A, Walsh T R, Bagaria J, Butt F, Balakrishnan R, Chaudhury U, Doumith M, Giske C G, Irfan S, Krishnan P, Kumar A V, Maharjan S, Mushtaq S, Noorie T, Paterson D L, Pearson A, Perry C, Pike R, Rao B, Ray U, Sarma J B, Sharma M, Sheridan E, Thirunarayan M A, Turton J, Upadhyay S, Warner M, Welfare W, Livermore D M, Woodford N. 2010. Emergence of a new antibiotic resistance mechanism in India, Pakistan, and the U K: a molecular, biological, and epidemiological study. Lancet Infect Dis 10:597-602.
89. Bebell L M, Muiru A N. 2014. Antibiotic use and emerging resistance: how can resource-limited countries turn the tide? Glob Heart 9:347-358.
90. Founou L L, Founou R C, Essack S Y. 2016. Antibiotic Resistance in the Food Chain: A Developing Country-Perspective. Front Microbiol 7:1881.
91. Founou R C, Founou L L, Essack S Y. 2017. Clinical and economic impact of antibiotic resistance in developing countries: A systematic review and meta-analysis. PLoS One 12:e0189621.
92. Prestinaci F, Pezzotti P, Pantosti A. 2015. Antimicrobial resistance: a global multifaceted phenomenon. Pathog Glob Health 109:309-318.
93. O'Brien T F. 1997. The global epidemic nature of antimicrobial resistance and the need to monitor and manage it locally. Clin Infect Dis 24 Suppl 1:S2-8.
94. Centres for Disease Control and Prevention UDoHaHS. 2013. Antibiotic resistance threats in the United States. https://www.cdc.gov/drugresistance/pdf/ar-threats-2013-508.pdf. Accessed
95. Organization W H. 2001. WHO global strategy for containment of antimicrobial resistance. Accessed
96. Organization W H. 2012. The evolving threat of antimicrobial resistance. Options for action. Accessed
97. Organization W H. 2014. Antimicrobial resistance: global report on surveillance 2014. Accessed
98. Casewell M, Friis C, Marco E, McMullin P, Phillips I. 2003. The European ban on growth-promoting antibiotics and emerging consequences for human and animal health. J Antimicrob Chemother 52:159-161.
99. Lin J. 2009. Novel approaches for *Campylobacter* control in poultry. Foodborne Pathog Dis 6:755-765.
100. Hermans D, Van Deun K, Messens W, Martel A, Van Immerseel F, Haesebrouck F, Rasschaert G, Heyndrickx M, Pasmans F. 2011. *Campylobacter* control in poultry by current intervention measures ineffective: urgent need for intensified fundamental research. Vet Microbiol 152:219-228.
101. Doyle M P, Erickson M C. 2006. Reducing the carriage of foodborne pathogens in livestock and poultry. Poult Sci 85:960-973.
102. Ridley A M, Morris V K, Cawthraw S A, Ellis-Iversen J, Harris J A, Kennedy E M, Newell D G, Allen V M. 2011. Longitudinal molecular epidemiological study of thermophilic campylobacters on one conventional broiler chicken farm. Appl Environ Microbiol 77:98-107.
103. Ridley A, Morris V, Gittins J, Cawthraw S, Harris J, Edge S, Allen V. 2011. Potential sources of *Campylobacter* infection on chicken farms: contamination and control of broiler-harvesting equipment, vehicles and personnel. J Appl Microbiol 111:233-244.
104. Arsenault J, Letellier A, Quessy S, Normand V, Boulianne M. 2007. Prevalence and risk factors for *Salmonella* spp. and *Campylobacter* spp. caecal colonization in broiler chicken and turkey flocks slaughtered in Quebec, Canada. Prev Vet Med 81:250-264.
105. Nather G, Alter T, Martin A, Ellerbroek L. 2009. Analysis of risk factors for *Campylobacter* species infection in broiler flocks. Poult Sci 88:1299-1305.
106. Hermans D, Van Deun K, Martel A, Van Immerseel F, Messens W, Heyndrickx M, Haesebrouck F, Pasmans F. 2011. Colonization factors of Campylobacterjejuni in the chicken gut. Vet Res 42:82.

107. Layton S L, Morgan M J, Cole K, Kwon Y M, Donoghue D J, Hargis B M, Pumford N R. 2011. Evaluation of *Salmonella*-vectored *Campylobacter* peptide epitopes for reduction of Campylobacterjejuni in broiler chickens. Clin Vaccine Immunol 18:449-454.

108. Buckley A M, Wang J, Hudson D L, Grant A J, Jones M A, Maskell D J, Stevens M P. 2010. Evaluation of live-attenuated *Salmonella* vaccines expressing *Campylobacter* antigens for control of *C. jejuni* in poultry. Vaccine 28:1094-1105.

109. Cawthraw S, Ayling R, Nuijten P, Wassenaar T, Newell D G. 1994. Isotype, specificity, and kinetics of systemic and mucosal antibodies to *Campylobacter jejuni* antigens, including flagellin, during experimental oral infections of chickens. Avian Dis 38:341-349.

110. Myszewski M A, Stern N J. 1990. Influence of Campylobacterjejuni cecal colonization on immunoglobulin response in chickens. Avian Dis 34:588-594.

111. Noor S M, Husband A J, Widders P R. 1995. In ovo oral vaccination with Campylobacterjejuni establishes early development of intestinal immunity in chickens. Br Poult Sci 36:563-573.

112. Sahin O, Zhang Q, Meitzler J C, Harr B S, Morishita T Y, Mohan R. 2001. Prevalence, antigenic specificity, and bactericidal activity of poultry anti-*Campylobacter* maternal antibodies. Appl Environ Microbiol 67:3951-3957.

113. Hassan J O, Curtiss R, III. 1994. Development and evaluation of an experimental vaccination program using a live avirulent *Salmonella typhimurium* strain to protect immunized chickens against challenge with homologous and heterologous *Salmonella* serotypes. Infect Immun 62:5519-5527.

114. Dorea F C, Cole D J, Hofacre C, Zamperini K, Mathis D, Doyle M P, Lee M D, Maurer J J. 2010. Effect of *Salmonella* vaccination of breeder chickens on contamination of broiler chicken carcasses in integrated poultry operations. Appl Environ Microbiol 76:7820-7825.

115. Gantois I, Ducatelle R, Timbermont L, Boyen F, Bohez L, Haesebrouck F, Pasmans F, van Immerseel F. 2006. Oral immunisation of laying hens with the live vaccine strains of TAD *Salmonella* Vac® E and TAD *Salmonella* Vac® T reduces internal egg contamination with *Salmonella Enteritidis*. Vaccine 24:6250-6255.

116. Cooper G L, Venables L M, Woodward M J, Hormaeche C E. 1994. Vaccination of chickens with strain CVL30, a genetically defined *Salmonella enteritidis* aroA live oral vaccine candidate. Infect Immun 62:4747-4754.

117. Cerquetti M C, Gherardi M M. 2000. Vaccination of chickens with a temperature-sensitive mutant of *Salmonella enteritidis*. Vaccine 18:1140-1145.

118. Springer S, Lindner T, Ahrens M, Woitow G, Prandini F, Selbitz H J. 2011. Duration of immunity induced in chickens by an attenuated live *Salmonella enteritidis* vaccine and an inactivated *Salmonella enteritidis/typhimurium* vaccine. Berl Munch Tierarztl Wochenschr 124:89-93.

119. Methner U, Barrow P A, Berndt A, Rychlik I. 2011. *Salmonella Enteritidis* with double deletion in phoP-fliC—a potential live *Salmonella* vaccine candidate with novel characteristics for use in chickens. Vaccine 29:3248-3253.

120. Nandre R M, Matsuda K, Chaudhari A A, Kim B, Lee J H. 2012. A genetically engineered derivative of *Salmonella Enteritidis* as a novel live vaccine candidate for salmonellosis in chickens. Res Vet Sci 93:596-603.

121. Matulova M, Havlickova H, Sisak F, Rychlik I. 2012. Vaccination of chickens with *Salmonella* Pathogenicity Island (SPI) 1 and SPI2 defective mutants of *Salmonella enterica* serovar Enteritidis. Vaccine 30:2090-2097.

122. Tan S, Gyles C L, Wilkie B N. 1997. Evaluation of an aroA mutant *Salmonella typhimurium* vaccine in chickens using modified semisolid Rappaport Vassiliadis medium to monitor faecal shedding. Vet Microbiol 54:247-254.

123. Barrow P A. 2007. *Salmonella* infections: immune and non-immune protection with vaccines. Avian Pathol 36:1-13.

124. Gast R K. 2007. Serotype-specific and serotype-independent strategies for preharvest control of food-borne *Salmonella* in poultry. Avian Dis 51:817-828.

125. Desin T S, Koster W, Potter A A. 2013. *Salmonella* vaccines in poultry: past, present and future. Expert Rev Vaccines 12:87-96.

126. Kaniuk N A, Monteiro M A, Parker C T, Whitfield C. 2002. Molecular diversity of the genetic loci responsible for lipopolysaccharide core oligosaccharide assembly within the genus *Salmonella*. Mol Microbiol 46:1305-1318.

127. Malik M, Butchaiah G, Bansal M P, Siddiqui M Z, Bakshi C S, Singh R K. 2002. Antigenic relationships within the genus *Salmonella* as revealed by anti-*Salmonella enteritidis* monoclonal antibodies. Vet Res Commun 26:179-188.

128. Earhart C F. 1996. Uptake and metabolism of iron and molybdenum, p 1075-1090. In Neidhardt F C, Curtiss III R, Ingraham J L, Lin E C C, Low K B, Magasanik B, Reznikoff W S, Riley M, Schaechter M, Umbarger H E (ed), *Escherichia coli* and *Salmonella* Cellular and Molecular Biology, 2nd ed, vol 1. ASM Press, Washington, D.C.

129. Curtiss R, III., Wanda S Y, Gunn B M, Zhang X, Tinge S A, Ananthnarayan V, Mo H, Wang S, Kong W. 2009. *Salmonella enterica* serovar typhimurium strains with regulated delayed attenuation in vivo. Infect Immun 77:1071-1082.

130. Bolin C A, Jensen A E. 1987. Passive immunization with antibodies against iron-regulated outer membrane proteins protects turkeys from *Escherichia coli* septicemia. Infect Immun 55:1239-1242.

131. Lin J, Hogan J S, Smith K L. 1999. Antigenic homology of the inducible ferric citrate receptor (FecA) of coliform bacteria isolated from herds with naturally occurring bovine intramammary infections. Clin Diagn Lab Immunol 6:966-969.

132. Wilmes-Riesenberg M R, Bearson B, Foster J W, Curtiss III R. 1996. Role of the acid tolerance response in virulence of *Salmonella typhimurium*. Infect Immun 64:1085-1092.

133. taniewski P, Mitra A, Karaca K, Khan A, Prasad R, Curtiss R, III, Roland K L. 2014. Evaluation of protective efficacy of live attenuated *Salmonella enterica* serovar *Gallinarum* vaccine strains against fowl typhoid in chickens. Clin Vaccine Immunol 21:1267-1276.

134. Li Y, Wang S, Scarpellini G, Gunn B, Xin W, Wanda S Y, Roland K L, Curtiss R, III. 2009. Evaluation of new generation *Salmonella enterica* serovar typhimurium vaccines with regulated delayed attenuation to induce immune responses against PspA. Proc Natl Acad Sci USA 106:593-598.

135. Shi H, Santander J, Brenneman K E, Wanda S Y, Wang S, Senechal P, Sun W, Roland K L, Curtiss R, III. 2010. Live recombinant *Salmonella typhi* vaccines constructed 136. Shi H, Wang S, Curtiss R, III. 2013. Evaluation of regulated delayed attenuation strategies for *Salmonella enterica* serovar typhi vaccine vectors in neonatal and infant mice. Clin Vaccine Immunol 20:931-944.
137. Wang S, Li Y, Scarpellini G, Kong W, Shi H, Baek C H, Gunn B, Wanda S Y, Roland K L, Zhang X, Senechal-Willis P, Curtiss R, III. 2010. *Salmonella* vaccine vectors displaying delayed antigen synthesis in vivo to enhance immunogenicity. Infect Immun 78:3969-3980.
138. Wang S, Li Y, Shi H, Sun W, Roland K L, Curtiss R, III. 2011. Comparison of a regulated delayed antigen synthesis system with in vivo-inducible promoters for antigen delivery by live attenuated *Salmonella* vaccines. Infect Immun 79:937-949.
139. Xin W, Wanda S Y, Li Y, Wang S, Mo H, Curtiss R, III. 2008. Analysis of type II secretion of recombinant pneumococcal PspA and PspC in a *Salmonella enterica* serovar typhimurium vaccine with regulated delayed antigen synthesis. Infect Immun 76:3241-3254.
140. Juarez-Rodriguez M D, Yang J, Kader R, Alamuri P, Curtiss R, Ill, Clark-Curtiss J E. 2012. Live attenuated *Salmonella* vaccines displaying regulated delayed lysis and delayed antigen synthesis to confer protection against *Mycobacterium tuberculosis*. Infect Immun 80:815-831.
141. Kong W, Brovold M, Koeneman B A, Clark-Curtiss J, Curtiss R, III. 2012. Turning self-destructing *Salmonella* into a universal DNA vaccine delivery platform. Proc Natl Acad Sci USA 109:19414-19419.
142. Kong W, Wanda S Y, Zhang X, Bollen W, Tinge S A, Roland K L, Curtiss R, III. 2008. Regulated programmed lysis of recombinant *Salmonella* in host tissues to release protective antigens and confer biological containment. Proc Natl Acad Sci USA 105:9361-9366.
143. Germanier R, Furer E. 1971. Immunity in experimental *salmonellosis*. II. Basis for the avirulence and protective capacity of gal E mutants of *Salmonella typhimurium*. Infect Immun 4:663-673.
144. Kong Q, Liu Q, Roland K L, Curtiss R, III. 2009. Regulated delayed expression of rfaH in an attenuated *Salmonella enterica* serovar typhimurium vaccine enhances immunogenicity of outer membrane proteins and a heterologous antigen. Infect Immun 77:5572-5582.
145. Li Y, Wang S, Xin W, Scarpellini G, Shi Z, Gunn B, Roland K L, Curtiss R, III. 2008. A sopB deletion mutation enhances the immunogenicity and protective efficacy of a heterologous antigen delivered by live attenuated *Salmonella enterica* vaccines. Infect Immun 76:5238-5246.
146. Gunn B M, Wanda S Y, Burshell D, Wang C, Curtiss R, III. 2010. Construction of recombinant attenuated *Salmonella enterica* serovar typhimurium vaccine vector strains for safety in newborn and infant mice. Clin Vaccine Immunol 17:354-362.
147. Shi H, Wang S, Roland K L, Gunn B M, Curtiss R, III. 2010. Immunogenicity of a live recombinant *Salmonella enterica* serovar typhimurium vaccine expressing pspA in neonates and infant mice born from naive and immunized mothers. Clin Vaccine Immunol 17:363-371.
148. Hassan J O, Curtiss R, III. 1996. Effect of vaccination of hens with an avirulent strain of *Salmonella typhimurium* on immunity of progeny challenged with wild-type *Salmonella* strains. Infection and Immunity 64:938-944.
149. Juarez-Rodriguez M D, Arteaga-Cortes L T, Kader R, Curtiss R, III, Clark-Curtiss J E. 2012. Live attenuated *Salmonella* vaccines against *Mycobacterium tuberculosis* with antigen delivery via the type III secretion system. Infect Immun 80:798-814.
150. Frey S E, Lottenbach K R, Hill H, Blevins T P, Yu Y, Zhang Y, Brenneman K E, Kelly-Aehle S M, McDonald C, Jansen A, Curtiss R, III. 2013. A Phase I, dose-escalation trial in adults of three recombinant attenuated *Salmonella typhi* vaccine vectors producing *Streptococcus pneumoniae* surface protein antigen PspA. Vaccine 31:4874-4880.
151. Konjufca V, Jenkins M, Wang S, Juarez-Rodriguez M D, Curtiss R, Ill. 2008. Immunogenicity of recombinant attenuated *Salmonella enterica* serovar typhimurium vaccine strains carrying a gene that encodes *Eimeria tenella* antigen SO7. Infect Immun 76:5745-5753.
152. Konjufca V, Wanda S Y, Jenkins M C, Curtiss R, III. 2006. A recombinant attenuated *Salmonella enterica* serovar typhimurium vaccine encoding *Eimeria acervulina* antigen offers protection against *E. acervulina* challenge. Infect Immun 74:6785-6796.
153. Zekarias B, Mo H, Curtiss R, III. 2008. Recombinant attenuated *Salmonella enterica* serovar *typhimurium* expressing the carboxy-terminal domain of alpha toxin from *Clostridium perfringens* induces protective responses against necrotic enteritis in chickens. Clin Vaccine Immunol 15:805-816.
154. Jiang Y, Mo H, Willingham C, Wang S, Park J Y, Kong W, Roland K L, Curtiss R, III. 2015. Protection Against Necrotic Enteritis in Broiler Chickens by Regulated Delayed Lysis *Salmonella* Vaccines. Avian Dis 59:475-485.
155. Ashraf S, Kong W, Wang S, Yang J, Curtiss R, III. 2011. Protective cellular responses elicited by vaccination with influenza nucleoprotein delivered by a live recombinant attenuated *Salmonella* vaccine. Vaccine 29:3990-4002.
156. Ameiss K, Ashraf S, Kong W, Pekosz A, Wu W H, Milich D, Billaud J N, Curtiss R, III. 2010. Delivery of woodchuck hepatitis virus-like particle presented influenza M2e by recombinant attenuated *Salmonella* displaying a delayed lysis phenotype. Vaccine 28:6704-6713.
157. Nakayama K, Kelly S M, Curtiss R, III 1988. Construction of an Asd$^+$ expression-cloning Vector: stable maintenance and high level expression of cloned genes in a *Salmonella* vaccine strain. Nat Biotech 6:693-697.
158. Branger C G, Sun W, Torres-Escobar A, Perry R, Roland K L, Fetherston J, Curtiss R, III. 2010. Evaluation of Psn, HmuR and a modified LcrV protein delivered to mice by live attenuated *Salmonella* as a vaccine against bubonic and pneumonic *Yersinia pestis* challenge. Vaccine 29:274-282.
159. Kang H Y, Srinivasan J, Curtiss R, III. 2002. Immune responses to recombinant pneumococcal PspA antigen delivered by live attenuated *Salmonella enterica* serovar typhimurium vaccine. Infect Immun 70:1739-1749.
160. Muralinath M, Kuehn M J, Roland K L, Curtiss R, III. 2011. Immunization with *Salmonella enterica* serovar typhimurium-derived outer membrane vesicles delivering the pneumococcal protein PspA confers protection against challenge with *Streptococcus pneumoniae*. Infect Immun 79:887-894.
161. Kaniuk N A, Vinogradov E, Whitfield C. 2004. Investigation of the structural requirements in the lipopolysaccharide core acceptor for ligation of 0 antigens in the genus *Salmonella*: WaaL "ligase" is not the sole determinant of acceptor specificity. J Biol Chem 279:36470-36480.

162. Curtiss R, III, Wanda S Y, Gunn B M, Zhang X, Tinge S A, Ananthnarayan V, Mo H, Wang S, Kong W. 2009. *Salmonella enterica* serovar typhimurium strains with regulated delayed attenuation in vivo. Infect Immun 77:1071-1082.

163. Brosius J, Erfle M, Storella J. 1985. Spacing of the −10 and −35 regions in the tac promoter. Effect on its in vivo activity. J Biol Chem 260:3539-3541.

164. Pizarro-Cerda J, Tedin K. 2004. The bacterial signal molecule, ppGpp, regulates *Salmonella* virulence gene expression. Mol Microbiol 52:1827-1844.

165. Vander Byl C, Kropinski A M. 2000. Sequence of the genome of *Salmonella* bacteriophage P22. J Bacteriol 182:6472-6481.

166. Brown E D, Vivas E I, Walsh C T, Kolter R. 1995. MurA (MurZ), the enzyme that catalyzes the first committed step in peptidoglycan biosynthesis, is essential in *Escherichia coli*. J Bacteriol 177:4194-4197.

167. Black S, Wright N G. 1955. Aspartic β-semialdehyde dehydrogenase and aspartic β-semialdehyde. J Biol Chem 213:39-50.

168. Stevenson G, Andrianopoulos K, Hobbs M, Reeves P R. 1996. Organization of the *Escherichia coli* K-12 gene cluster responsible for production of the extracellular polysaccharide colanic acid. J Bacteriol 178:4885-4893.

169. Whitfield C. 2006. Biosynthesis and assembly of capsular polysaccharides in *Escherichia coli*. Annu Rev Biochem 75:39-68.

170. Beuzón C R, Méresse S, Unsworth K E, Ruiz-Albert J, Garvis S, Waterman S R, Ryder T A, Boucrot E, Holden D W. 2000. *Salmonella* maintains the integrity of its intracellular vacuole through the action of SifA. EMBO J 19:3235-3249.

171. Cohen A, Laban A. 1983. Plasmidic recombination in *Escherichia coli* K-12: the role of recF gene function. Mol Gen Genet 189:471-474.

172. Kolodner R, Fishel R A, Howard M. 1985. Genetic recombination of bacterial plasmid DNA: effect of RecF pathway mutations on plasmid recombination in *Escherichia coli*. J Bacteriol 163:1060-1066.

173. Zhang X, Wanda S Y, Brenneman K, Kong W, Roland K, Curtiss R, III. 2011. Improving *Salmonella* vector with rec mutation to stabilize the DNA cargoes. BMC Microbiol 11:31.

174. Link C, Ebensen T, Standner L, Dejosez M, Reinhard E, Rharbaoui F, Guzman C A. 2006. An SopB-mediated immune escape mechanism of *Salmonella enterica* can be subverted to optimize the performance of live attenuated vaccine carrier strains. Microbes Infect 8:2262-2269.

175. Norris F A, Wilson M P, Wallis T S, Galyov E E, Majerus P W. 1998. SopB, a protein required for virulence of *Salmonella* dublin, is an inositol phosphate phosphatase. Proc Natl Acad Sci USA 95:14057-14059.

176. Reis B P, Zhang S, Tsolis R M, Baumler A J, Adams L G, Santos R L. 2003. The attenuated sopB mutant of *Salmonella enterica* serovar typhimurium has the same tissue distribution and host chemokine response as the wild type in bovine Peyer's patches. Vet Microbiol 97:269-277.

177. Singh S P, Williams Y U, Miller S, Nikaido H. 2003. The C-terminal domain of *Salmonella enterica* serovar typhimurium OmpA is an immunodominant antigen in mice but appears to be only partially exposed on the bacterial cell surface. Infect Immun 71:3937-3946.

178. Chart H, Rowe B. 1991. Antibodies to lipopolysaccharide and outer membrane proteins of *Salmonella enteritidis* PT4 are not involved in protection from experimental infection. FEMS Microbiol Lett 68:345-350.

179. Curtiss R, III., S. B. Porter, M. Munson, S. A. Tinge, J. O. Hassan, C. Gentry-Weeks, Kelly. S M. 1991. Nonrecombinant and recombinant avirulent *Salmonella* live vaccines for poultry, p 169-198. In L. C. Blankenship, J.H.S. Bailey, N. A. Cox, Stern N J, Meinersmann R J (ed), Colonization control of human bacterial enteropathogens in poultry. Academic Press New York 180. Poppe C, Gyles C L. 1987. Relation of plasm ids to virulence and other properties of salmonellae from avian sources. Avian Dis 31:844-854.

181. Black R E, Levine M M, Clements M L, Hughes T P, Blaser M J. 1988. Experimental *Campylobacter-Jejuni* Infection in Humans. Journal of Infectious Diseases 157: 472-479.

182. Parkhill J, Wren B W, Mungall K, Ketley J M, Churcher C, Basham D, Chillingworth T, Davies R M, Feltwell T, Holroyd S, Jagels K, Karlyshev A V, Moule S, Pallen M J, Penn C W, Quail M A, Rajandream M A, Rutherford K M, van Vliet A H, Whitehead S, Barrell B G. 2000. The genome sequence of the food-borne pathogen Campylobacterjejuni reveals hypervariable sequences. Nature 403: 665-668.

183. Pearson B M, Gaskin D J, Segers R P, Wells J M, Nuijten P J, van Vliet A H. 2007. The complete genome sequence of Campylobacterjejuni strain 81116 (NCTC11828). J Bacteriol 189:8402-8403.

184. Fouts D E, Mongodin E F, Mandrell R E, Miller W G, Rasko D A, Ravel J, Brinkac L M, DeBoy R T, Parker C T, Daugherty S C, Dodson R J, Durkin A S, Madupu R, Sullivan S A, Shetty J U, Ayodeji M A, Shvartsbeyn A, Schatz M C, Badger J H, Fraser C M, Nelson K E. 2005. Major structural differences and novel potential virulence mechanisms from the genomes of multiple *campylobacter* species. PLoS Biol 3:e15.

185. Parker C T, Quinones B, Miller W G, Horn S T, Mandrell R E. 2006. Comparative genomic analysis of *Campylobacter jejuni* strains reveals diversity due to genomic elements similar to those present in *C. jejuni* strain RM1221. J Clin Microbiol 44:4125-4135.

186. Issmat I. Kassem, Gbenga K, Kumar A, Chandrashekhar K, Pina-Mimbela R, Rajashekara G. 2014. An evaluation of the impact of litter chemical amendments on reducing *Campylobacter jejuni* in broilers, abstr Conference of research workers in animal disease (CRWAD), Chicago, Ill., December 6-8.

187. Zhang X, Kelly S M, Bollen W S, Curtiss R, III. 1997. Characterization and immunogenicity of *Salmonella typhimurium* SL1344 and UK-1 Δcrp and Δcdt deletion mutants. Infect Immun 65:5381-5387.

188. Kong Q, Liu Q, Jansen A, Curtiss R, III. 2010. Regulated delayed expression of rfc enhances the immunogenicity and protective efficacy of a heterologous antigen delivered by live attenuated *Salmonella enterica* vaccines. Vaccine 28:6094-6103.

189. Bertani G. 1951. Studies on lysogenesis. I. The mode of phage liberation by lysogenic *Escherichia coli*. J Bacteriol 62:293-300.

190. Pardee A B, Jacob F, Monod J. 1959. The genetic control and cytoplasmic expression of "Inducibility" in the synthesis of β-galactosidase by *E. coli*. Journal of Molecular Biology 1:165-178.

191. Sambrook J, Russell D W. 2001. Molecular cloning: a laboratory manual, 3rd ed. Cold Spring Harbor Laboratory Press, Cold Spring Harbor, N.Y.

192. Ehretsmann C P, Carpousis A J, Krisch H M. 1992. Specificity of *Escherichia coli* endoribonuclease RNase E: in vivo and in vitro analysis of mutants in a bacteriophage T4 mRNA processing site. Genes Dev 6:149-159.
193. McDowall K J, Kaberdin V R, Wu S W, Cohen S N, Lin-Chao S. 1995. Site-specific RNase E cleavage of oligonucleotides and inhibition by stem-loops. Nature 374:287-290.
194. Lin-Chao S, Wong T T, McDowall K J, Cohen S N. 1994. Effects of nucleotide sequence on the specificity of rne-dependent and RNase E-mediated cleavages of RNA I encoded by the pBR322 plasmid. J Biol Chem 269: 10797-10803.
195. Edwards R A, Keller L H, Schifferli D M. 1998. Improved allelic exchange vectors and their use to analyze 987P fimbria gene expression. Gene 207:149-157.
196. Kaniga K, Compton M S, Curtiss R, Ill., Sundaram P. 1998. Molecular and functional characterization of *Salmonella enterica* serovar typhimurium poxA gene: effect on attenuation of virulence and protection. Infect Immun 66:5599-5606.
197. Maloy S R, and W. D. Nunn. 1981. Selection for loss of tetracycline resistance by *Escherichia coli*. J Bacteriol 145:1110-1112.
198. Miller V L, and J. J. Mekalanos. 1988. A novel suicide vector and its use in construction of insertion mutations: osmoregulation of outer membrane proteins and virulence determinants in *Vibrio cholerae* requires toxR. J Bacteriol 170:2575-2583.
199. Ried J, and A. Collmer. 1987. An nptl-sacB-sacR cartridge for constructing directed unmarked mutations in gram-negative bacteria by marker exchange-eviction mutagenesis. Gene 57:239-246.
200. Roland K, Curtiss R, III., Sizemore D. 1999. Construction and evaluation of a Δcya Δcrp *Salmonella typhimurium* strain expressing avian pathogenic *Escherichia coli* 078 LPS as a vaccine to prevent airsacculitis in chickens. Avian Dis 43:429-441.
201. Schmieger H. 1972. Phage P22-mutants with increased or decreased transduction abilities. Mol Gen Genet 119: 75-88.
202. Schmieger H, Backhaus H. 1976. Altered cotransduction frequencies exhibited by H T-mutants of Salmonella-phage P22. Mol Gen Genet 143:307-309.
203. Quandt J, Hynes M F. 1993. Versatile suicide vectors which allow direct selection for gene replacement in gram-negative bacteria. Gene 127:15-21.
204. Hitchcock P J, Brown T M. 1983. Morphological heterogeneity among *Salmonella* lipopolysaccharide chemotypes in silver-stained polyacrylamide gels. J Bacteriol 154:269-277.
205. Kang H Y, Dozois C M, Tinge S A, Lee T H, Curtiss R, III. 2002. Transduction-mediated transfer of unmarked deletion and point mutations through use of counterselectable suicide vectors. J Bacteriol 184:307-312.
206. Young N M, Brisson J R, Kelly J, Watson D C, Tessier L, Lanthier P H, Jarrell H C, Cadotte N, St Michael F, Aberg E, Szymanski C M. 2002. Structure of the N-linked glycan present on multiple glycoproteins in the Gram-negative bacterium, Campylobacterjejuni. J Biol Chem 277:42530-42539.
207. Hobbs M, Reeves P R. 1994. The JUMPstart sequence: a 39 bp element common to several polysaccharide gene clusters. Mol Microbiol 12:855-856.
208. Nieto J M, Bailey M J, Hughes C, Koronakis V. 1996. Suppression of transcription polarity in the *Escherichia coli* haemolysin operon by a short upstream element shared by polysaccharide and DNA transfer determinants. Mol Microbiol 19:705-713.
209. Nothaft H, Davis B, Lock Y Y, Perez-Munoz M E, Vinogradov E, Walter J, Coros C, Szymanski C M. 2016. Engineering the Campylobacterjejuni N-glycan to create an effective chicken vaccine. Sci Rep 6:26511.
210. Price N L, Goyette-Desjardins G, Nothaft H, Valguarnera E, Szymanski C M, Segura M, Feldman M F. 2016. Glycoengineered Outer Membrane Vesicles: A Novel Platform for Bacterial Vaccines. Sci Rep 6:24931.
211. Gangaiah D, Liu Z, Arcos J, Kassem, I I, Sanad Y, Torrelles J B, Rajashekara G. 2010. Polyphosphate kinase 2: a novel determinant of stress responses and pathogenesis in Campylobacterjejuni. PLoS One 5:e12142.
212. Annamalai T, Pina-Mimbela R, Kumar A, Binjawadagi B, Liu Z, Renukaradhya G J, Rajashekara G. 2013. Evaluation of nanoparticle-encapsulated outer membrane proteins for the control of Campylobacterjejuni colonization in chickens. Poult Sci 92:2201-2211.
213. Reusch R N. 2013. The role of short-chain conjugated poly-(R)-3-hydroxybutyrate (cPHB) in protein folding. Int J Mol Sci 14:10727-10748.
214. Pautsch A, Schulz G E. 1998. Structure of the outer membrane protein A transmembrane domain. Nat Struct Biol 5:1013-1017.
215. Vogel H, Jahnig F. 1986. Models for the structure of outer-membrane proteins of *Escherichia coli* derived from raman spectroscopy and prediction methods. J Mol Biol 190:191-199.

What is claimed is:

1. A recombinant derivative of a *Salmonella enterica* pathogenic bacterium comprising:
   (a) a regulated-delayed attenuation conferred by a Δpmi mutation;
   (b) a regulated-delayed expression of an antigen of interest conferred by a ΔrelA::araC $P_{BAD}$ lacI TT deletion-insertion mutation;
   (c) a regulated-delayed lysis in vivo phenotype conferred by a $\Delta P_{murA}$::TT araC $P_{BAD}$ murA deletion-insertion mutation and a ΔasdA::TT araC $P_{BAD}$ c2 deletion-insertion mutation; and
   (d) a nucleic acid sequence encoding one or more protein antigens of *Campylobacter jejuni* selected from the group consisting of Peb1, CjaA, Dps, TlyA, Omp18, Cj0998c, Cj0034c, Cj0168c, Cj0248, Peb3, CmeC, Cj0404, Cj0420, Cj0427, Cj0428, PorA, FlaA, CadF, and Cj1656c.

2. The bacterium of claim 1, wherein the bacterium further comprises a ΔsifA mutation.

3. The recombinant bacterium of claim 2, wherein the ΔsifA mutation is ΔsifA26.

4. A pharmaceutical composition comprising the recombinant bacterium of claim 1, and a pharmaceutically acceptable carrier.

5. The pharmaceutical composition of claim 4, further comprising a second recombinant derivative of a pathogenic bacterium, wherein said bacterium comprises a nucleic acid encoding a second antigen of interest.

6. The pharmaceutical composition of claim 5, wherein the second antigen of interest is a *Salmonella* antigen.

7. A method for inducing protective immunity in an avian, the method comprising administering to the avian an effective amount of a pharmaceutical composition of claim 4.

8. The recombinant bacterium of claim 1, wherein the Δpmi mutation is Δpmi-2426.

9. The recombinant bacterium of claim 1, wherein the ΔrelA::araC $P_{BAD}$ lacI TT deletion-insertion mutation is ΔrelA197::araC $P_{BAD}$ lacI TT or ΔrelA198::araC $P_{BAD}$ lacI TT.

10. The recombinant bacterium of claim 1, wherein the araC $P_{BAD}$ murA deletion-insertion mutation is $\Delta P_{murA25}$::TT araC $P_{BAD}$ murA.

11. The recombinant bacterium of claim 1, wherein the ΔasdA::TT araC $P_{BAD}$ c2 deletion-insertion mutation is ΔasdA27::TT araC $P_{BAD}$ c2.

12. The recombinant bacterium of claim 1, where in the bacterium comprises
   (a) Δpmi-2426, $\Delta P_{murA25}$::TT araC $P_{BAD}$ murA, ΔasdA27::TT araC $P_{BAD}$ c2 and ΔrelA197 araC $P_{BAD}$ lacI TT;
   (b) Δpmi-2426, $\Delta P_{murA25}$::TT araC $P_{BAD}$ murA, ΔasdA27::TT araC $P_{BAD}$ c2 and ΔrelA198 araC $P_{BAD}$ lacI TT;
   (c) Δpmi-2426, $\Delta P_{murA25}$::TT araC $P_{BAD}$ murA, ΔasdA27::TT araC $P_{BAD}$ c2, ΔrelA197:: araC $P_{BAD}$ lacI TT, and ΔsifA26; or
   (d) Δpmi-2426, $\Delta P_{murA25}$::TT araC $P_{BAD}$ murA, ΔasdA27::TT araC $P_{BAD}$ c2, ΔrelA198 araC $P_{BAD}$ lacI TT, and ΔsifA26.

13. The recombinant bacterium of claim 1, wherein the bacterium further comprises a deletion of the wbaP gene.

14. The bacterium of claim 13, wherein the bacterium further comprises a pgl operon, with or without a deletion of a pglB gene.

15. The recombinant bacterium of claim 14, wherein a *C. jejuni* N-glycan is attached to the one or more protein antigens of *Campylobacter jejuni*.

16. The recombinant bacterium of claim 14, wherein a *C. jejuni* N-glycan is attached to one or more *Salmonella* proteins or LPS core antigens.

17. The bacterium of claim 14, wherein the bacterium comprises insertion of all or part of the cj1433c gene into a deletion of the ompA gene to generate a fusion of the Cj1433c protein.

* * * * *